(12) United States Patent
Jessen et al.

(10) Patent No.: US 9,181,563 B2
(45) Date of Patent: Nov. 10, 2015

(54) COMPOSITIONS AND METHODS FOR INCREASED ETHANOL PRODUCTION FROM BIOMASS

(75) Inventors: Holly J. Jessen, Chanhassen, MN (US); Jian Yi, Carlsbad, CA (US); Joshua Lundorff, Minneapolis, MN (US); Hans Liao, Superior, CO (US); Ana Negrete-Raymond, Roseville, MN (US); Pirkko Suominen, Maple Grove, MN (US); Aristos Aristidou, Highlands Ranch, CO (US)

(73) Assignee: Cargill, Incorporated, Wayzata, MN (US)

( * ) Notice: Subject to any disclaimer, the term of this patent is extended or adjusted under 35 U.S.C. 154(b) by 84 days.

(21) Appl. No.: 14/111,415

(22) PCT Filed: Apr. 11, 2012

(86) PCT No.: PCT/US2012/033030
§ 371 (c)(1),
(2), (4) Date: Oct. 11, 2013

(87) PCT Pub. No.: WO2012/142094
PCT Pub. Date: Oct. 18, 2012

(65) Prior Publication Data
US 2014/0038253 A1 Feb. 6, 2014

Related U.S. Application Data

(60) Provisional application No. 61/474,035, filed on Apr. 11, 2011.

(51) Int. Cl.
| | | |
|---|---|---|
| *C12N 1/00* | (2006.01) | |
| *C12N 1/19* | (2006.01) | |
| *C12N 1/22* | (2006.01) | |
| *C12P 7/06* | (2006.01) | |
| *C07K 14/39* | (2006.01) | |
| *C12N 9/04* | (2006.01) | |
| *C12N 9/10* | (2006.01) | |
| *C12N 9/12* | (2006.01) | |
| *C12N 9/90* | (2006.01) | |
| *C12N 9/92* | (2006.01) | |
| *C12P 7/10* | (2006.01) | |
| *C12N 15/81* | (2006.01) | |

(52) U.S. Cl.
CPC . *C12P 7/06* (2013.01); *C07K 14/39* (2013.01); *C12N 9/0006* (2013.01); *C12N 9/1022* (2013.01); *C12N 9/1205* (2013.01); *C12N 9/90* (2013.01); *C12N 9/92* (2013.01); *C12N 15/815* (2013.01); *C12P 7/10* (2013.01); *C12Y 101/0101* (2013.01); *C12Y 101/01009* (2013.01); *C12Y 202/01001* (2013.01); *C12Y 202/01002* (2013.01); *C12Y 207/01016* (2013.01); *C12Y 207/01017* (2013.01); *C12Y 501/03001* (2013.01); *C12Y 501/03004* (2013.01); *C12Y 503/01003* (2013.01); *C12Y 503/01005* (2013.01); *C12Y 503/01006* (2013.01); *Y02E 50/16* (2013.01); *Y02E 50/17* (2013.01)

(58) Field of Classification Search
CPC ............... C12N 1/00; C12N 1/16; C12N 1/22
USPC ........................................................ 435/255.1
See application file for complete search history.

(56) References Cited

U.S. PATENT DOCUMENTS

| | | |
|---|---|---|
| 7,846,712 B2 | 12/2010 | Zhang et al. |
| 7,943,366 B2 | 5/2011 | Rajgarhia et al. |
| 8,431,360 B2 | 4/2013 | Glass et al. |

FOREIGN PATENT DOCUMENTS

| | | |
|---|---|---|
| WO | 2009011591 A2 | 1/2009 |
| WO | 2011041426 A2 | 4/2011 |
| WO | 2011131674 A1 | 10/2011 |

OTHER PUBLICATIONS

Database Geneseq (Online), "Crop improvement related protein homolog sequence, SEQ ID 14837.", XP002737344, Mar. 1, 2012.
Van Vleet J et al., "Yeast metabolic engineering for hemicellulosic ethanol production", Current opinion in Biotechnology, London, GB, vol. 20, No. 3, Jun. 1, 2009, pp. 300-306, XP026283532, ISSN: 0958-1669.
Becker et al., "A Modified *Saccharomyces cerevisiae* Strain That Consumes L-Arabinose and Produces Ethanol," Appl Environ Microbiol, Jul. 2003, vol. 69, No. 7, pp. 4144-4150.
Bera et al., "Establishment of L-arabinose fermentation in glucose/xylose co-fermenting recombinant *Saccharomyces cerevisiae* 424A (LNH-ST) by genetic engineering," Appl Microbiol Biotechnol, 2010, vol. 87, pp. 1803-1811.
Burma et al., "Pentose Fermentation by *Lactobacillus plantarum*," J Biol Chem, Sep. 11, 1957, pp. 1039-1051.
Chu et al., "Genetic improvement of *Saccharomyces cerevisiae* for xylose fermentation," Biotechnol Adv, 2007, vol. 25, pp. 425-441.
Dujon et al., "Genome evolution in yeasts," Nature, Jul. 1, 2004, vol. 430, pp. 35-44.
Gárdonyi et al., "High capacity xylose transport in *Candida intermedia* PYCC 4715," FEMS Yeast Research, 2003, vol. 3, pp. 45-52.
Jeffries, "Engineering yeasts for xylose metabolism," Curr Opin Biotechnol, 2006, vol. 17, pp. 320-326.
Karhumaa et al., "Comparison of the xylose reductase-xylitol dehydrogenase and the xylose isomerase pathways for xylose fermentation by recombinant *Saccharomyces cerevisiae*," Microb Cell Fact, 2007, vol. 6, No. 5, pp. 1-10.
Leandro et al., "Two glucose/xylose transporter genes from the yeast *Candida intermedia*: first molecular characterization of a yeast xylose-H+ symporter," Biochem J, 2006, vol. 395, pp. 543-549.
Nonklang et al., "High-Temperature Ethanol Fermentation and Transformation with Linear DNA in the Thermotolerant Yeast *Kluyveromyces marxianus* DMKU3-1042," Appl Environ Microbiol, Dec. 2008, vol. 74, No. 24, pp. 7514-7521.

(Continued)

*Primary Examiner* — Maryam Monshipouri

(57) ABSTRACT

The present application discloses the identification of the novel *K. marxianus* xylose transporter genes KHT105 and RAG4, as well as the identification of a novel set of *I. orientalis* pentose phosphate pathway genes The present application further discloses a series of genetically modified yeast cells comprising various combinations of arabinose fermentation pathways, xylose fermentation pathways, pentose phosphate pathways, and/or xylose transporter genes, and methods of culturing these cells to produce ethanol in fermentation media containing xylose.

15 Claims, 35 Drawing Sheets

(56) References Cited

OTHER PUBLICATIONS

Rhimi et al., "The acid tolerant L-arabinose isomerase from the food grade *Lactobacillus sakei* 23K is an attractive D-tagatose producer," Bioresour Technol, 2010, vol. 101, pp. 9171-9177.

Richard et al., "The role of xylulokinase in *Saccharomyces cerevisiae* xylulose catabolism," FEMS Microbiol Lett, 2000, vol. 190, pp. 39-43.

Rodrussamee et al., "Growth and ethanol fermentation ability on hexose and pentose sugars and glucose effect under various conditions in thermotolerant yeast *Kluyveromyces marxianus*," Appl Microbiol Biotechnol, Apr. 8, 2011, vol. 90, pp. 1573-1586.

Runquist et al., "Comparison of heterologous xylose transporters in recombinant *Saccharomyces cerevisiae*," Biotechnol Biofuels, 2010, vol. 3, No. 5, pp. 1-7.

Saint-Prix et al., "Functional analysis of the ALD gene family of *Saccharomyces cerevisiae* during anaerobic growth on glucose: the NADP+-dependent Ald6p and Ald5p isoforms play a major role in acetate formation," Microbiology, 2004, vol. 150, pp. 2209-2220.

Saloheimo et al., "Xylose transport studies with xylose-utilizing *Saccharomyces cerevisiae* strains expressing heterologous and homologous permeases," Appl Microbiol Biotechnol, Dec. 19, 2006, vol. 74, pp. 1041-1052.

Schneider, "Conversion of Pentoses to Ethanol by Yeasts and Fungi," Crit Rev Biotechnol, 1989, vol. 9, Issue 1, 40 pgs.

Stambuk et al., "D-Xylose Transport by *Candida succiphila* and *Kluyveromyces marxianus*," Appl Biochem Biotechnol, 2003, vol. 105-108, 11 pgs.

Toivari, "Engineering the pentose phosphate pathway of *Saccharomyces cerevisiae* for production of ethanol and xylitol," VTT Publications 641, Espoo 2007, 121 pgs.

Toivari et al., "Conversion of Xylose to Ethanol by Recombinant *Saccharomyces cerevisiae*: Importance of Xylulokinase (XKS1) and Oxygen Availability," Metab Eng, 2001, vol. 3, pp. 236-249.

Toivari et al., "Endogenous Xylose Pathway in *Saccharomyces cerevisiae*," Appl Environ Microbiol, Jun. 2004, vol. 70, No. 6, pp. 3681-3686.

Toivari et al., "Metabolic engineering of *Saccharomyces cerevisiae*, for conversion of D-glucose to xylitol and other five-carbon sugars and sugar alcohols," Appl Environ Microbiol, Sep. 2007, vol. 73, No. 17, 5471-5476.

Träff et al., "Putative xylose and arabinose reductases in *Saccharomyces cerevisiae*," Yeast, 2002, vol. 19, pp. 1233-1241.

Wisselink et al., "Engineering of *Saccharomyces cerevisiae* for Efficient Anaerobic Alcoholic Fermentation of L-Arabinose," Appl Environ Microbiol, Aug. 2007, vol. 73, No. 15, pp. 4881-4891.

COMPOSITIONS AND METHODS FOR INCREASED ETHANOL PRODUCTION FROM BIOMASS

PRIORITY CLAIM

The present application is a section 371 national stage application of International Application No. PCT/US2012/033030, filed Apr. 11, 2012, which claims priority to U.S. Provisional Application No. 61/474,035, filed Apr. 11, 2011, the disclosures of which are incorporated by reference herein in their entirety.

BACKGROUND

A great deal of work has been performed in recent years to develop cost-effective methods for generating ethanol from biomass. The use of biomass to generate ethanol for fuel presents several advantages over the use of more traditional feedstock sources. The potential raw materials are abundant and diverse, the use of these feedstocks does not divert from the food supply, and they potentially exhibit a smaller carbon footprint.

Although biomass provides an attractive substrate for ethanol production, it also presents several challenges. First, biomass contains both cellulose, which can be broken down into hexose sugars such as glucose, and hemicellulose, which can be broken down into pentose sugars such as arabinose and xylose. Many of the microorganisms traditionally used in ethanol fermentation are incapable of fermenting both hexose and pentose sugars to ethanol. Second, unlike more traditional sources of ethanol feedstock (e.g., corn, cane sugar), biomass includes structural components from plant sources. Because the source material is structural and more difficult to break down, biomass requires more processing to generate the sugar monomers that function as a fermentation substrate. Third, hydrolysate resulting from pre-treatment of biomass presents a harsh environment for fermenting microorganisms.

Several bacterial species are capable of fermenting pentose sugars to ethanol, but these species generally produce a mixture of products rather than a single product. Often one or more of these products are harmful to the bacteria. Further, bacteria can exhibit drastically reduced fermentation rates in the harsh environment of plant matter hydrolysate.

Yeast are generally considered to be more attractive candidates for industrial-scale ethanol fermentation than bacteria. However, very few yeast are capable of fermenting pentose sugars to ethanol. Various genetic modifications have been introduced into different yeast species in an attempt to overcome this problem, but none of these previously developed modified strains have proven entirely satisfactory for large-scale ethanol production from biomass. Therefore, there is a need in the art for new genetically modified yeast strains capable of fermenting biomass to ethanol.

SUMMARY

Provided herein in certain embodiments are isolated KHT105 and RAG4 polynucleotides. In certain of these embodiments, the polynucleotides encode a polypeptide with the amino acid sequence of SEQ ID NOs:2 (KHT105) or 4 (RAG4), or a polypeptide comprising an amino acid sequence with at least 90% sequence identity to the amino acid sequence of SEQ ID NOs:2 or 4. In certain embodiments, the polynucleotides comprise the nucleotide sequence of SEQ ID NOs:1 or 3, or a nucleotide sequence with at least 90% sequence identity to the nucleotide sequence of SEQ ID NOs:1 or 3. In other embodiments, the polynucleotides encode a polypeptide comprising an amino acid sequence with at least 70% sequence identity to the amino acid sequence of SEQ ID NOs:2 or 4, where the encoded polypeptide is capable of transporting xylose into a yeast cell. In certain of these embodiments, a yeast cell overexpressing the polynucleotide consumes a greater amount of xylose relative to glucose than an identical yeast cell that does not overexpress the polynucleotide. In certain embodiments, the polynucleotides comprise a nucleotide sequence with at least 70% sequence identity to the nucleotide sequence of SEQ ID NOs:1 or 3.

Provided herein in certain embodiments are isolated KHT105 and RAG4 polypeptides. In certain of these embodiments, the polypeptides comprise the amino acid sequence of SEQ ID NOs:2 (KHT105) or 4 (RAG4), or an amino acid sequence with at least 90% sequence identity to SEQ ID NOs:2 or 4. In other embodiments, the polypeptides comprise an amino acid sequence with at least 70% sequence identity to the amino acid sequence of SEQ ID NOs:2 or 4 and are capable of transporting xylose into a yeast cell. In certain of these embodiments, a yeast cell overexpressing the polypeptide consumes a greater amount of xylose relative to glucose than an identical yeast cell that does not overexpress the polypeptide.

Provided herein in certain embodiments are isolated RPE, RKI, TKL, and TAL polynucleotides. In certain of these embodiments, the polynucleotides encode a polypeptide with the amino acid sequence of SEQ ID NOs:34 (RPE), 40 (RKI), 46 (TKL), or 52 (TAL), or a polypeptide comprising an amino acid sequence with at least 80% sequence identity to SEQ ID NOs:34, 40, 46, or 52. In certain embodiments, the polynucleotides comprise the nucleotide sequence of SEQ ID NOs:33, 39, 45, or 51, or a nucleotide sequence with at least 80% sequence identity to the nucleotide sequence of SEQ ID NOs: 33, 39, 45, or 51.

Provided herein in certain embodiments are isolated RPE, RKI, TKL, and TAL polypeptides. In certain of these embodiments, the polypeptides comprise the amino acid sequence of SEQ ID NOs:34 (RPE), 40 (RKI), 46 (TKL), or 52 (TAL), or an amino acid sequence with at least 80% sequence identity to SEQ ID NOs:34, 40, 46, or 52.

Provided herein in certain embodiments are genetically modified yeast cells that overexpress one or more xylose transporter genes. In certain of these embodiments, the overexpressed xylose transporter gene is a KHT105 or RAG4 gene encoding a polypeptide with at least 90% sequence identity to SEQ ID NO:2 or SEQ ID NO:4, respectively. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that comprise an active arabinose pathway for converting arabinose to xylulose 5-phosphate, wherein the cells comprise one or more exogenous arabinose fermentation pathway genes selected from the group consisting of AI, RK, and RE genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes and comprise an active arabinose pathway for converting arabinose to xylulose 5-phosphate, wherein the cells comprise one or more exogenous arabinose fermentation pathway genes selected from the group consisting of AI, RK, and RE genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes and comprise an active xylose fermentation pathway for converting xylose to xylulose 5-phosphate, wherein the cells comprise one or more exogenous xylose fermentation pathway genes selected from the group consisting of XR, XDH, and XK genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that comprise an active arabinose pathway for converting arabinose to xylulose 5-phosphate and an active xylose fermentation pathway for converting xylose to xylulose 5-phosphate, wherein the cells comprise one or more exogenous arabinose fermentation pathway genes selected from the group consisting of AI, RK, and RE genes and one or more exogenous xylose fermentation pathway genes selected from the group consisting of XR, XDH, and XK genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes and comprise an active arabinose pathway for converting arabinose to xylulose 5-phosphate and an active xylose fermentation pathway for converting xylose to xylulose 5-phosphate, wherein the cells comprise one or more exogenous arabinose fermentation pathway genes selected from the group consisting of AI, RK, and RE genes and one or more exogenous xylose fermentation pathway genes selected from the group consisting of XR, XDH, and XK genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes and comprise an active xylose fermentation pathway for converting xylose to xylulose 5-phosphate, wherein the cells comprise one or more exogenous xylose fermentation pathway genes selected from the group consisting of XI and XK genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that comprise an active arabinose pathway for converting arabinose to xylulose 5-phosphate and an active xylose fermentation pathway for converting xylose to xylulose 5-phosphate, wherein the cells comprise one or more exogenous arabinose fermentation pathway genes selected from the group consisting of AI, RK, and RE genes and one or more exogenous xylose fermentation pathway genes selected from the group consisting of XI and XK genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes and comprise an active arabinose pathway for converting arabinose to xylulose 5-phosphate and an active xylose fermentation pathway for converting xylose to xylulose 5-phosphate, wherein the cells comprise one or more exogenous arabinose fermentation pathway genes selected from the group consisting of AI, RK, and RE genes and one or more exogenous xylose fermentation pathway genes selected from the group consisting of XI and XK genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that comprise an active arabinose pathway for converting arabinose to xylulose 5-phosphate and an active non-oxidative pentose phosphate pathway for converting xylulose 5-phosphate plus ribose 5-phosphate to F6P and G3P, wherein the cells comprise one or more exogenous arabinose fermentation pathway genes selected from the group consisting of AI, RK, or RE genes and one or more exogenous non-oxidative pentose phosphate pathway genes selected from the group consisting of TKL and TAL genes. In certain embodiments, the cells further comprise one or more exogenous non-oxidative pentose phosphate pathway genes selected from the group consisting of RPE and RKI genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes, comprise an active arabinose pathway for converting arabinose to xylulose 5-phosphate, and comprise an active non-oxidative pentose phosphate pathway for converting xylulose 5-phosphate plus ribose 5-phosphate to F6P and G3P, wherein the cells comprise one or more exogenous arabinose fermentation pathway genes selected from the group consisting of AI, RK, or RE genes and one or more exogenous non-oxidative pentose phosphate pathway genes selected from the group consisting of TKL and TAL genes. In certain embodiments, the cells further comprise one or more exogenous non-oxidative pentose phosphate pathway genes selected from the group consisting of RPE and RKI genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes, comprise an active xylose fermentation pathway for converting xylose to xylulose 5-phosphate, and comprise an active non-oxidative pentose phosphate pathway for converting xylulose 5-phosphate plus ribose 5-phosphate to F6P and G3P, wherein the cells comprise one or more exogenous arabinose fermentation pathway genes selected from the group consisting of AI, RK, or RE genes, one or more exogenous xylose fermentation pathway genes selected from the group consisting of XR, XDH, and XK genes, and one or more exogenous non-oxidative pentose phosphate pathway genes selected from the group consisting of TKL and TAL genes. In certain embodiments, the cells further comprise one or more exogenous non-oxidative pentose phosphate pathway genes selected from the group consisting of RPE and RKI genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that comprise an active arabinose pathway for converting arabinose to xylulose 5-phosphate, an active xylose fermentation pathway for converting xylose to xylulose 5-phosphate, and an active non-oxidative pentose phosphate pathway for converting xylulose 5-phosphate plus ribose 5-phosphate to F6P and G3P, wherein the cells comprise one or more exogenous arabinose fermentation pathway genes selected from the group consisting of AI, RK, or RE genes, one or more exogenous xylose fermentation genes selected from the group consisting of XR, XDH, and XK genes, and one or more exogenous non-oxidative pentose phosphate pathway genes selected from the group consisting of TKL and TAL genes. In certain embodiments, the cells further comprise one or more exogenous non-oxidative pentose phosphate pathway genes selected from the group consisting of RPE and RKI genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes, comprise an active arabinose pathway for converting arabinose to xylulose 5-phosphate, comprise an active xylose fermentation pathway for converting xylose to xylulose 5-phosphate, and comprise an active non-oxidative pentose phosphate pathway for converting xylulose 5-phosphate plus ribose 5-phosphate to F6P and G3P, wherein the cells comprise one or more exogenous arabinose fermentation pathway genes selected from the group consisting of AI, RK, or RE genes, one or more exogenous xylose fermentation pathway genes selected from the group consisting of XR, XDH, and XK genes, and one or more exogenous non-oxidative pentose phosphate pathway genes selected from the group consisting of TKL and TAL genes. In certain embodiments, the cells further comprise one or more exogenous non-oxidative pentose phosphate pathway genes selected from the group consisting of RPE and RKI genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes, comprise an active xylose fermentation pathway for converting xylose to xylulose 5-phosphate, and comprise an active non-oxidative pentose phosphate pathway for converting xylulose 5-phosphate plus ribose 5-phosphate to F6P and G3P, wherein the cells comprise one or more exogenous arabinose fermentation pathway genes selected from the group consisting of AI, RK, or RE genes, one or more exogenous xylose fermentation pathway genes selected from the group consisting of XI and XK genes, and one or more exogenous non-oxidative pentose phosphate pathway genes selected from the group consisting of TKL and TAL genes. In certain embodiments, the cells further comprise one or more exogenous non-oxidative pentose phosphate pathway genes selected from the group consisting of RPE and RKI genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that comprise an active arabinose pathway for converting arabinose to xylulose 5-phosphate, an active xylose fermentation pathway for converting xylose to xylulose 5-phosphate, and an active non-oxidative pentose phosphate pathway for converting xylulose 5-phosphate plus ribose 5-phosphate to F6P and G3P, wherein the cells comprise one or more exogenous arabinose fermentation pathway genes selected from the group consisting of AI, RK, or RE genes, one or more exogenous xylose fermentation pathway genes selected from the group consisting of XI and XK genes, and one or more exogenous non-oxidative pentose phosphate pathway genes selected from the group consisting of TKL and TAL genes. In certain embodiments, the cells further comprise one or more exogenous non-oxidative pentose phosphate pathway genes selected from the group consisting of RPE and RKI genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes, comprise an active arabinose pathway for converting arabinose to xylulose 5-phosphate, comprise an active xylose fermentation pathway for converting xylose to xylulose 5-phosphate, comprise an active non-oxidative pentose phosphate pathway for converting xylulose 5-phosphate plus ribose 5-phosphate to F6P and G3P, wherein the cells comprise one or more exogenous arabinose fermentation pathway genes selected from the group consisting of AI, RK, or RE genes, one or more exogenous xylose fermentation pathway genes selected from the group consisting of XI and XK genes, and one or more exogenous non-oxidative pentose phosphate pathway genes selected from the group consisting of TKL and TAL genes. In certain embodiments, the cells further comprise one or more exogenous non-oxidative pentose phosphate pathway genes selected from the group consisting of RPE and RKI genes. In certain embodiments, the genetically modified yeast cells belong to the *I. orientalis/P. fermentans* clade, and in certain of these embodiments the cells are *I. orientalis*.

Provided herein in certain embodiments are genetically modified yeast cells that overexpress one or more xylose transporter genes, comprise an active arabinose pathway for converting arabinose to xylulose 5-phosphate, comprise an active xylose fermentation pathway for converting xylose to xylulose 5-phosphate, and/or comprise an active non-oxidative pentose phosphate pathway for converting xylulose 5-phosphate plus ribose 5-phosphate to F6P and G3P, wherein the cells further comprise a deletion or disruption of one or more genes encoding enzymes involved in an active xylose fermentation pathway that converts xylose to xylulose 5-phosphate via xylitol and D-xylulose intermediates. In certain embodiments, the cells comprise a deletion or disruption of one or more AR/XR, arabitol 4-dehydrogenase, xylulose reductase, or XDH genes. In certain embodiments, the deleted or disrupted AR/XR gene encodes a polypeptide with at least 50% sequence identity to the amino acid sequence of SEQ ID NOs:64, 66, 68, 69, or 71, and/or comprises a nucleotide sequence with at least 50% sequence identity to the coding region of the nucleotides sequence of SEQ ID NOs: 63, 65, 67, or 70. In certain embodiments, the deleted or disrupted xylulose reductase gene encodes a polypeptide with at least 50% sequence identity to the amino acid sequence of SEQ ID NO:58 and/or comprises a nucleotide sequence with at least 50% sequence identity to the coding region of the nucleotide sequence of SEQ ID NO:57. In certain embodiments, the deleted or disrupted XDH gene encodes a polypeptide with at least 50% sequence identity to the amino acid sequence of SEQ ID NOs:60 or 62 and/or comprises a nucleotide sequence with at least 50% sequence identity to the coding region of the nucleotide sequence set forth in SEQ ID NOs:59 or 61.

Provided herein in certain embodiments are genetically modified yeast cells that overexpress one or more xylose transporter genes, comprise an active arabinose pathway for converting arabinose to xylulose 5-phosphate, comprise an active xylose fermentation pathway for converting xylose to xylulose 5-phosphate, and/or comprise an active non-oxidative pentose phosphate pathway for converting xylulose 5-phosphate plus ribose 5-phosphate to F6P and G3P, wherein the cells further comprise a deletion or disruption of one or more ALD or ADH genes. In certain embodiments, the deleted or disrupted ALD gene encodes a polypeptide with at least 50% sequence identity to the amino acid sequence of SEQ ID NO:73 and/or comprises a nucleotide sequence with at least 50% sequence identity to the coding region of the nucleotide sequence of SEQ ID NO:72. In certain embodiments, the deleted or disrupted ADH gene encodes a polypeptide with at least 50% sequence identity to the amino acid sequence of SEQ ID NOs:75 or 85 and/or comprises a nucleotide sequence with at least 50% sequence identity to the coding region of the nucleotide sequence set forth in SEQ ID NOs:74 or 84.

Provided herein in certain embodiments are fermentation methods that utilize one or more of the genetically modified yeast cells provided herein. In certain embodiments, the fermentation media contains xylose. In certain of these embodiments, the media contains at least 10 g/L xylose from a plant biomass hydrolysate, and in certain embodiments xylose is the most abundant sugar in the media.

Provided herein in certain embodiments are methods of producing ethanol using one or more of the genetically modified yeast cells provided herein. In certain embodiments, the cells are cultured in a media containing xylose. In certain of these embodiments, the media contains at least 10 g/L xylose from a plant biomass hydrolysate, and in certain embodiments xylose is the most abundant sugar in the media.

DETAILED DESCRIPTION

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

Unless otherwise indicated, all numbers expressing concentrations of components, fermentation conditions, fermentation performance, and so forth used in the specification are to be understood as being modified in all instances by the term "about." Accordingly, unless indicated to the contrary, the numerical parameters set forth in the specification are approximations that may vary depending at least upon the specific analytical technique. Any numerical value inherently contains certain errors necessarily resulting from the standard deviation found in their respective testing measurements.

All references cited herein are incorporated by reference in their entirety.

Abbreviations

ADH, alcohol dehydrogenase; AI/araA, arabinose isomerase; ALD, aldehyde dehydrogenase; AR, aldose reductase; CYB2, L-(+)-lactate-cytochrome c oxidoreductase; CYC, iso-2-cytochrome c; DHAP, dihydroxyacetone P; ENO1, enolase 1; E4P, erythrose 4-phosphate; F6P, fructose 6-phosphate; GALE, cysteine aminopeptidase; GAPDH, glyceraldehyde-3-phosphate dehydrogenase 3; G3P, glyceraldehyde 3-phosphate; G3PDH, glycerol-3-phosphate dehydrogenase; PDC1, pyruvate decarboxylase 1; PGK, phosphoglycerate kinase; PPP, pentose phosphate pathway; RE/araD, ribulose 5-phosphate 4-epimerase; RK/araB, ribulokinase; RKI, ribose 5-phosphate ketol-isomerase; RPE, ribulose 5-phosphate 3-epimerase; S7P, sedoheptulose 7-phosphate; TAL, transaldolase; TDH3, glyceraldehye-3-phosphate dehydrogenase; TEF1, translation elongation factor-1; TEF2, translation elongation factor-2; TKL, transketolase; TPI, triosephosphate isomerase; URA3, orotidine 5'-phosphate decarboxylase; XDH, xylitol dehydrogenase; XI, xylose isomerase; XK, xylulokinase; XR, xylose reductase.

Provided herein are genetically modified yeast cells for the production of ethanol, methods of making these yeast cells, and methods of using these cells to produce ethanol.

The ideal yeast species for industrial-scale ethanol production from biomass should exhibit resistance to low pH environments, the ability to ferment both hexose and pentose sugars to ethanol, and resistance to inhibitory compounds present in plant matter hydrolysate and arising from fermentation, including acetate, HMF, furfural, phenolics, aldehydes, ketones, and ethanol itself.

Figure 1:
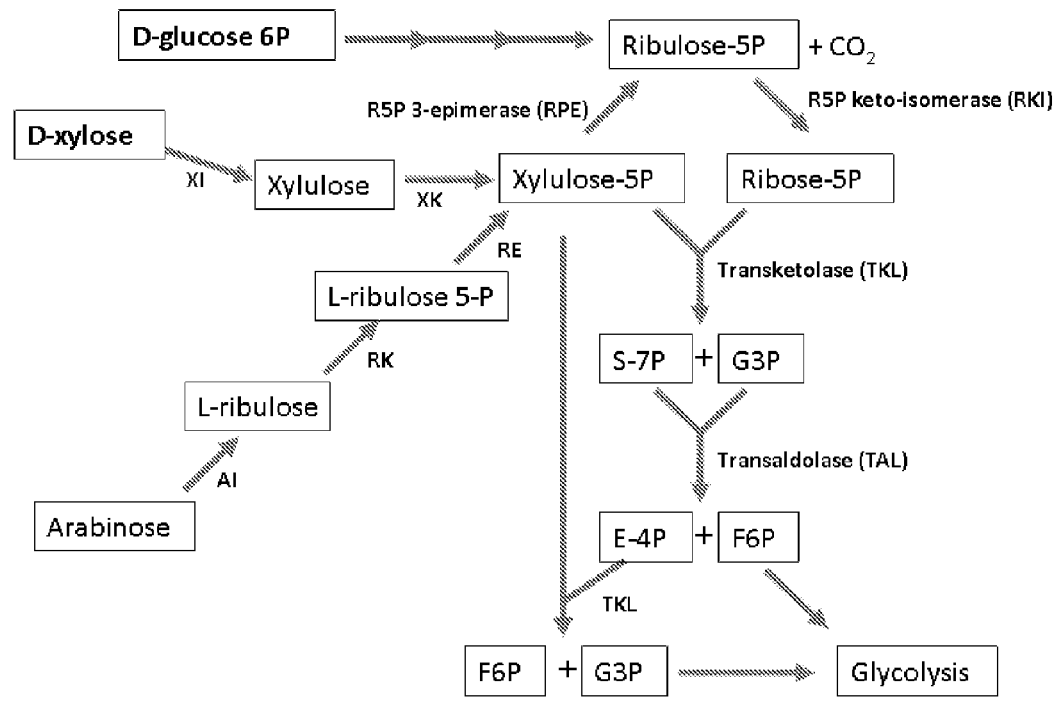
FIG. 1: Yeast pathways for xylose and arabinose metabolism.

*Saccharomyces cerevisiae* and most other yeast species are capable of fermenting hexose sugars to ethanol. However, the majority of yeast species are incapable of fermenting pentose sugars such as arabinose and xylose. Those yeast species that are capable of metabolizing pentose sugars do so via a complex pathway. The conventional yeast pathways for xylose and arabinose metabolism (the two most common pentose sugars in cellulosic biomass) utilize a xylitol intermediate. D-xylose is reduced to xylitol by xylose reductase (XR). Arabinose is converted to xylitol via a three step process. L-arabinose is reduced to L-arabitol by aldose reductase (AR), L-arabitol is converted to L-xylulose by L-arabitol 4-dehydrogenase, and L-xylulose is converted to xylitol by L-xylulose reductase. In both pathways, xylitol is oxidized to D-xylose by xylitol dehydrogenase (XDH), and D-xylose is phosphorylated by xylulokinase (XK) to produce D-xylulose 5-P. The resultant D-xylulose 5-P enters the pentose phosphate pathway (PPP), which generates fructose 6-phosphate (F6P) and glyceraldehyde 3-phosphate (G3P), both of which enter the glycolytic cycle. This pathway is illustrated in FIG. 1. Pyruvate arising from glycolysis is converted to acetaldehyde and $CO_2$ by pyruvate decarboxylase, and acetaldehyde is reduced to ethanol by alcohol dehydrogenase (ADH).

Since the reductases of the fungal arabinose utilization pathway utilize NADPH as the reductant and the dehydrogenases are specific to $NAD^+$, a cofactor imbalance results in slow anaerobic growth on L-arabinose and low levels of ethanol production even though the process is redox neutral.

Unlike yeast, bacteria do not utilize a xylitol intermediate when metabolizing arabinose. In bacteria, L-arabinose is converted to L-ribulose by L-arabinose isomerase (AI). L-ribulose is converted to L-ribulose 5-phosphate by L-ribulokinase (RK), which is then converted to D-xylulose 5-phosphate by L-ribulose-phosphate 4-epimerase (RE). None of these enzymatic steps require an NAD or NADH cofactor, meaning that the bacterial arabinose pathway does not have complicating cofactor imbalance issues. Previous attempts have been made to utilize the bacterial arabinose pathway in yeast. AI, RK, and RE genes from bacterial sources were incorporated into *S. cerevisiae*, and the resultant genetically modified yeast strain exhibited the ability to ferment arabinose to ethanol (Becker and Boles Appl. Environ Microbiol 69:4144 (2003)). However, *S. cerevisiae* has limited tolerance to free acetate and other common inhibitors in hydrolysates.

Previous attempts have been made to generate additional yeast species that are capable of fermenting pentose sugars and tolerant to hydrolysate inhibitors. An *I. orientalis* strain was generated that contained a knockout of the putative ADH genes ADHa and ADHb and also overexpressed a putative ADH1 gene. The resultant yeast strain showed an increased ability to ferment xylose to ethanol. However, it was incapable of fermenting arabinose.

As disclosed herein, bacterial arabinose pathway AI (araA), RK (araB), and RE (araD) genes from *Bacteroides thetaiotaomicron, Escherichia coli, Lactobacillus plantarum*, and *Bacillus licheniformis* were incorporated into an *Issatchenkia orientalis* strain in various combinations (Example 1). The bacterial genes were typically, but not always, codon optimized for *I. orientalis*. Each of the resultant strains exhibited appropriate AI, RK, and/or RE activity (Example 2). Several strains containing a complete set of bacterial arabinose pathway genes (i.e., at least one copy each of AI, RK, and RE genes) were tested for their ability to ferment arabinose. These strains exhibited both arabinose consumption and ethanol production from arabinose (Example 3). The results disclosed herein confirm that bacterial arabinose pathway genes are active when expressed in *I. orientalis*.

A complete set of *B. thetaiotaomicron* arabinose pathway genes was incorporated into an *I. orientalis* strain that had previously been engineered to ferment xylose to ethanol in order to create a dual pathway strain capable of fermenting both xylose and arabinose (Example 4). The resultant dual pathway strains exhibited the ability to ferment both arabinose and xylose to ethanol, and both produced more ethanol than control strains containing only xylose or only arabinose pathway genes (Example 5). However, xylose utilization was decreased in the dual pathway strains versus the xylose-only strain, even in media lacking arabinose. Further, arabinose consumption did not begin until both dextrose and xylose were mostly depleted. Additional *I. orientalis* strains were generated that contained non-codon optimized *B. thetaiotaomicron* and *L. citreum* araB genes (Example 6). These strains exhibited improved xylose utilization and ethanol production versus a strain containing the codon optimized *B. thetaiotaomicron* gene.

As disclosed herein, the *K. marxianus* genome was screened to identify potential sugar transporters (Example 7). Two putative *K. marxianus* sugar transporter genes, KHT105 and RAG4, were characterized. Both genes were integrated into *I. orientalis* strains that had previously been engineered to contain a basic xylose pathway (XI, XK) in order to evaluate the effect of putative transporter expression on xylose utilization (Example 8). The resultant strains exhibited increased co-consumption of glucose and xylose, so a second copy of each transporter gene was integrated into the cells. Cells containing two copies of the KHT105 gene exhibited higher xylose utilization and ethanol production than the parent strain or strains containing two copies of the RAG4 gene.

The effects of KHT105 expression were further tested by integrating two copies of the gene into an *I. orientalis* strain containing more advanced xylose engineering, including overexpression of the non-oxidative pentose pathway genes transaldolase (TAL), ribose 5-phosphate ketol-isomerase (RKI), and ribulose 5-phosphate 3-epimerase (RPE) (Example 9). In fermentors with hydrolysate media, the strain expressing KHT105 exhibited an 80% increase xylose consumption and ethanol production versus a control strain.

To evaluate the effect of KHT105 expression on arabinose consumption, a single copy of the gene was integrated into the S141 G4546 locus of an *I. orientalis* strain containing arabinose pathway genes (Example 10). S141G4546 is a homolog of butanediol dehydrogenase and xylitol dehydrogenase. The resultant strain exhibited a slight increase in arabinose consumption and ethanol production versus a parent strain.

Based on data showing that the KHT105 transporter increased both xylose and arabinose consumption, two copies of the KHT105 gene were integrated into the S141G4546 locus of the dual-pathway *I. orientalis* strains described above (Example 11). Strains containing the KHT105 transporter exhibited greater ethanol production and xylose and arabinose consumption than the parent strain (Example 12). The benefits of KHT105 expression were particularly apparent in media containing higher levels of sugar.

To evaluate additional methods for improving ethanol production in *I. orientalis*, an aldehyde dehydrogenase (ALD) knockout strain was developed. *I. orientalis* has three main homologs to the *S. cerevisiae* ALD4, ALD5, and ALD6 genes: S141G5680 ("ALD5680"), S141G9161 ("ALD9161"), and S141G6502 ("ALD6502"). The knockouts targeted ALD5680, which exhibits increased expression when cells are grown on xylose. Both copies of ALD5680 were knocked out in an *I. orientalis* strain that had previously been engineered to ferment xylose to ethanol (Example 13). The ALD5680 knockout strain exhibited increased xylose consumption and ethanol production and decreased acetate production under certain conditions, but results were partially dependent on the precise fermentation conditions used (Example 14).

Additional copies of the *K. marxianus* KHT105 gene were integrated into an *I. orientalis* strain that had previously been engineered to contain two copies of KHT105 at the S141G9091 (ADH homolog) locus (Example 15). The additional copies of KHT105 were integrated at the S141G456 or ALD5680 loci, and the effect of increased KHT105 copy number and S141G4546/ALD5680 knockout on sugar consumption and ethanol production in hydrolysate media was evaluated. Among both the S141G4546 and ALD5680 knockout strains, the presence of a fourth copy of the KHT105 gene increased xylose consumption and ethanol production versus strains containing only three copies of the gene, with ALD knockout strains exhibiting slightly better results than S141G4546 knockout strains.

The effects of KHT105 overexpression and/or ALD5680 knockout were next evaluated in an ethanol resistant *I. orientalis* strain. KHT105 overexpression resulted in a significant increase in ethanol production and xylose consumption in low dextrose defined medium, but only had a slight effect in high dextrose medium (Example 16).

*Bifidobacterium animalis* and *Lactococcus lactis* araD genes (Example 17) and *Lactobacillus sakei* and alternate *B. thetaiotaomicron* araA genes (Example 18) were integrated into dual pathway *I. orientalis* strains overexpressing KHT105 to evaluate their effect on arabinose fermentation. These strains exhibited increased arabinose consumption versus parent strains.

As disclosed herein, novel *I. orientalis* TAL, RKI, TKL, and RPE gene sequences were identified. Exogenous copies of these genes were integrated into *I. orientalis* to evaluate the effect of their overexpression on xylose consumption and ethanol production (Examples 19-21). The resultant strains exhibited increased xylose utilization and ethanol production versus parental strains.

Provided herein in certain embodiments are isolated KHT105 and RAG4 transporter polynucleotides. In certain embodiments, these isolated polynucleotides comprise a coding region encoding a polypeptide having the amino acid sequence set forth in SEQ ID NOs:2 or 4, respectively. In certain of these embodiments, the polynucleotides comprise the coding region of the nucleotide sequence set forth in SEQ ID NOs:1 or 3. In other embodiments, the polynucleotides comprise a nucleotide sequence with at least 90% sequence identity to the coding region of the nucleotide sequence set forth in SEQ ID NOs:1 or 3. In certain of these embodiments, the polynucleotides comprise a nucleotide sequence having at least 95%, at least 96%, at least 97%, at least 98%, at least 99%, or at least 99.5% sequence identity to the coding region of the nucleotide sequence set forth in SEQ ID NOs:1 or 3.

In certain embodiments, the isolated KHT105 and RAG4 polynucleotides provided herein comprise a coding region encoding a polypeptide that comprises an amino acid sequence with at least 90% sequence identity to the amino acid sequence set forth in SEQ ID NOs:2 or 4, respectively. In certain of these embodiments, the encoded polypeptide comprises an amino acid sequence with at least 95%, at least 96%, at least 97%, at least 98%, at least 99%, or at least 99.5% sequence identity to the amino acid sequence set forth in SEQ ID NOs:2 or 4. In certain embodiments, the isolated polynucleotides comprise a nucleotide sequence with at least 90% sequence identity to the coding region of the nucleotide sequence set forth in SEQ ID NOs:1 or 3. In certain of these embodiments, the isolated polynucleotides comprise a nucleotide sequence having at least 95%, at least 96%, at least 97%, at least 98%, at least 99%, or at least 99.5% sequence identity to the coding region of the nucleotide sequence set forth in SEQ ID NOs:1 or 3.

In certain embodiments, the isolated KHT105 and RAG4 polynucleotides provided herein comprise a coding region encoding a polypeptide with 70% or greater sequence identity to the amino acid sequence set forth in SEQ ID NOs:2 or 4, wherein a yeast cell overexpressing the polynucleotide consumes a greater amount of xylose relative to glucose than an identical cell that does not overexpress the polynucleotide. Similarly, in certain embodiments the polynucleotides provided herein comprise a coding region encoding a polypeptide with 70% or greater sequence identity to the amino acid sequence set forth in SEQ ID NOs:2 or 4, wherein the encoded polypeptide is capable of transporting xylose into a yeast cell. In certain of these embodiments, the polynucleotides comprise a coding region encoding a polypeptide with at least 70%, at least 75%, at least 80%, at least 85%, or at least 90% sequence identity to the amino acid sequence set forth in SEQ ID NOs:2 or 4. In certain of these embodiments, the polynucleotides comprise a nucleotide sequence with at least 70%, at least 75%, at least 80%, at least 85%, or at least 90% sequence identity to the coding region of the nucleotide sequence set forth in SEQ ID NOs:1 or 3.

Provided herein in certain embodiments are isolated *I. orientalis* RPE, RKI, TKL, and TAL polynucleotides. In certain embodiments, these isolated polynucleotides comprise a coding region encoding a polypeptide having the amino acid sequence set forth in SEQ ID NOs:34, 40, 46, or 52, respectively. In certain of these embodiments, the polynucleotides comprise the coding region of the nucleotide sequence set forth in SEQ ID NOs:33, 39, 45, or 51. In other embodiments, the polynucleotides comprise a nucleotide sequence with at least 80% sequence identity to the coding region of the nucleotide sequence set forth in SEQ ID NOs:33, 39, 45, or 51. In certain of these embodiments, the polynucleotides comprise a nucleotide sequence having at least 85%, at least 90%, at least 95%, at least 96%, at least 97%, at least 98%, at least 99%, or at least 99.5% sequence identity to the coding region of the nucleotide sequence set forth in SEQ ID NOs:33, 39, 45, or 51.

In certain embodiments, the isolated *I. orientalis* RKI, TKL, and TAL polynucleotides provided herein comprise a coding region encoding a polypeptide that comprises an amino acid sequence with at least 80% sequence identity to the amino acid sequence set forth in SEQ ID NOs:34, 40, 46, or 52, respectively. In certain of these embodiments, the encoded polypeptide comprises an amino acid sequence with at least 85%, at least 90%, at least 95%, at least 96%, at least 97%, at least 98%, at least 99%, or at least 99.5% sequence identity to the amino acid sequence set forth in SEQ ID NOs:34, 40, 46, or 52. In certain embodiments, the isolated polynucleotides comprise a nucleotide sequence with at least 80% sequence identity to the coding region of the nucleotide sequence set forth in SEQ ID NOs:33, 39, 45, or 51. In certain of these embodiments, the isolated polynucleotides comprise a nucleotide sequence having at least 85%, at least 90%, at least 95%, at least 96%, at least 97%, at least 98%, at least 99%, or at least 99.5% sequence identity to the coding region of the nucleotide sequence set forth in SEQ ID NOs:33, 39, 45, or 51.

Provided herein in certain embodiments are constructs comprising one or more of the isolated KHT105, RAG4, *I. orientalis* RKI, *I. orientalis* TKL, and/or *I. orientalis* TAL polynucleotides provided herein. The term "construct" as used herein refers to a DNA sequence that is used to transform a cell. The construct may be, for example, a circular plasmid or vector, a portion of a circular plasmid or vector (such as a restriction enzyme digestion product), a linearized plasmid or vector, or a PCR product prepared using a plasmid or genomic DNA as a template. In addition to one or more of the polynucleotides provided herein, a construct may comprise one or more regulatory elements (e.g., promoters, terminators) operatively linked to the polynucleotide sequence. As used herein, the term "promoter" refers to an untranslated sequence located upstream (i.e., 5') to the translation start codon of a gene (generally within about 1 to 1000 base pairs (bp), preferably within about 1 to 500 bp) which controls the start of transcription of the gene. The term "terminator" as used herein refers to an untranslated sequence located downstream (i.e., 3') to the translation finish codon of a gene (generally within about 1 to 1000 bp, preferably within about 1 to 500 bp, and especially within about 1 to 100 bp) which controls the end of transcription of the gene. A promoter or terminator is "operatively linked" to a gene if its position in the genome relative to that of the gene is such that the promoter or terminator, as the case may be, performs its transcriptional control function. Suitable promoters and terminators are described, for example, in WO99/14335, WO00/71738, WO02/42471, WO03/102201, WO03/102152 and WO03/049525 (all incorporated by reference herein in their entirety). A construct may further comprise one or more additional components, including for example one or more restriction sites and/or one or more selection marker genes, optionally linked to one or more regulatory elements. A "selection marker gene" is a gene that encodes a protein needed for the survival and/or growth of the transformed cell in a selective culture medium, and therefore can be used to apply selection pressure to the cell.

Provided herein in certain embodiments are isolated KHT105 and RAG4 polypeptides. In certain embodiments, these polypeptides comprise the amino acid sequence set forth in SEQ ID NOs:2 or 4. In other embodiments, the polypeptides comprise an amino acid sequence with at least 90% sequence identity to the amino acid sequence set forth in SEQ ID NOs:2 or 4. In certain of these embodiments, the polypeptides comprise an amino acid sequence with at least 95%, at least 96%, at least 97%, at least 98%, at least 99%, or at least 99.5% sequence identity to the amino acid sequence set forth in SEQ ID NOs:2 or 4. In still other embodiments, the polypeptides comprise an amino acid sequence with at least 70% sequence identity to the amino acid sequence set forth in SEQ ID NOs:2 or 4 and are capable of transporting xylose into a yeast cell. Similarly, in certain embodiments the polypeptides provided herein comprise an amino acid sequence with at least 70% sequence identity to the amino acid sequence set forth in SEQ ID NOs:2 and 4, and a yeast cell overexpressing the polypeptide consumes a greater amount of xylose relative to glucose than an identical cell that does not overexpress the polypeptide. In certain of these embodiments, the polypeptides comprise an amino acid sequence with at least 75%, at least 80%, at least 85%, or at least 90% sequence identity to the amino acid sequence set forth in SEQ ID NOs:2 or 4.

Provided herein in certain embodiments are isolated *I. orientalis* RPE, RKI, TKL, and TAL polypeptides. In certain embodiments, these polypeptides comprise the amino acid sequence set forth in SEQ ID NOs:34, 40, 46, or 52, respectively. In other embodiments, the polypeptides comprise an amino acid sequence with at least 80% sequence identity to the amino acid sequence set forth in SEQ ID NOs:34, 40, 46, or 52. In certain of these embodiments, the polypeptides comprise an amino acid sequence with at least 80%, at least 85%, at least 95%, at least 96%, at least 97%, at least 98%, at least 99%, or at least 99.5% sequence identity to the amino acid sequence set forth in SEQ ID NOs:34, 40, 46, or 52.

Sequence identity percentages for nucleotide or amino acid sequences can be calculated by methods known in the art, such as for example using BLAST (National Center for Biological Information (NCBI) Basic Local Alignment Search Tool) version 2.2.1 software with default parameters. Sequences having an identity score of at least 90%, using the BLAST version 2.2.1 algorithm with default parameters are considered to have at least 90% sequence identity. The BLAST software is available from the NCBI, Bethesda, Md.

Provided herein in certain embodiments are genetically modified yeast cells comprising one or more KHT105 and/or RAG4 genes. In certain embodiments, these genes comprise the nucleotide sequence of the KHT105 and/or RAG4 polynucleotides disclosed herein. Similarly, in certain embodiments the xylose transporter genes encode a xylose transporter comprising the amino acid sequence of the KHT105 and/or RAG4 polypeptides disclosed herein. In certain embodiments, the genetically modified cells exhibit a higher degree of xylose transport than corresponding wild-type cells.

Provided herein in certain embodiments are genetically modified yeast cells having at least one active arabinose fermentation pathway for converting arabinose to xylulose 5-phosphate. A yeast cell having an "active arabinose fermentation pathway" as used herein produces active enzymes necessary to catalyze each reaction in an arabinose fermentation pathway, and therefore is capable of converting arabinose to xylulose 5-phosphate when cultured under fermentation conditions in the presence of arabinose. A yeast cell having an active arabinose fermentation pathway comprises one or more arabinose fermentation pathway genes. An "arabinose fermentation pathway gene" as used herein refers to the coding region of a nucleotide sequence that encodes an enzyme involved in an active arabinose fermentation pathway. In certain embodiments, the yeast cells provided herein have an active arabinose fermentation pathway that converts arabinose to xylulose 5-phosphate without proceeding through an arabitol, xylulose, xylitol, or xylulose intermediate. In certain of these embodiments, the yeast cells have an active arabinose fermentation pathway that converts arabinose to xylulose 5-phosphate via ribulose and ribulose 5-phosphate intermediates. In these embodiments, the yeast cells comprise at least one copy each of the arabinose fermentation pathway genes AI, RK, and RE.

Provided herein in certain embodiments are genetically modified yeast cells that have at least one active arabinose fermentation pathway for converting arabinose to xylulose 5-phosphate, and which further comprise one or more xylose transporter genes. In certain embodiments, the active arabinose fermentation pathway converts arabinose to xylulose 5-phosphate via ribulose and ribulose 5-phosphate intermediates, and in these embodiments the cells comprise at least one copy each of the arabinose fermentation pathway genes AI, RK, and RE. In certain embodiments, the xylose transporter genes comprise the nucleotide sequence of one or more of the KHT105 and/or RAG4 polynucleotides disclosed herein. Similarly, in certain embodiments the xylose transporter genes encode a xylose transporter comprising the amino acid sequence of one or more of the KHT105 and/or RAG4 polypeptides disclosed herein.

In certain embodiments, the genetically modified yeast cells provided herein comprise an active xylose fermentation pathway for converting xylose to xylulose 5-phosphate. A yeast cell having an "active xylose fermentation pathway" as used herein produces active enzymes necessary to catalyze each reaction in a xylose fermentation pathway, and therefore is capable of converting xylose to xylulose 5-phosphate when cultured under fermentation conditions in the presence of xylose. A yeast cell having an active xylose fermentation pathway comprises one or more xylose fermentation pathway genes. A "xylose fermentation pathway gene" as used herein refers to the coding region of a nucleotide sequence that encodes an enzyme involved in an active xylose fermentation pathway. In certain embodiments, an active xylose fermentation pathway converts xylose to xylulose 5-phosphate via xylitol and xylulose intermediates. In these embodiments, the yeast cells comprise at least one copy each of the xylose fermentation pathway genes XR, XDH, and XK. In other embodiments, an active xylose fermentation pathway converts xylose to xylulose 5-phosphate via a xylulose intermediate only. In these embodiments, the yeast cells comprise at least one copy each of the xylose fermentation pathway genes xylose isomerase (XI) and XK.

Provided herein in certain embodiments are genetically modified yeast cells that have at least one active xylose fermentation pathway for converting xylose to xylulose 5-phosphate, and which further comprise one or more xylose transporter genes. In certain embodiments, the active xylose fermentation pathway converts xylose to xylulose 5-phosphate via xylitol and xylulose intermediates, and in certain of these embodiments the cells comprise at least one copy each of the xylose fermentation pathway genes XR, XDH, and XK. In other embodiments, the active xylose fermentation pathway converts xylose to xylulose 5-phosphate via a xylulose intermediate only, and in certain of these embodiments the cells comprise at least one copy each of the xylose fermentation pathway genes XI and XK. In certain embodiments, the xylose transporter genes comprise the nucleotide sequence of one or more of the KHT105 and/or RAG4 polynucleotides disclosed herein. Similarly, in certain embodiments the xylose transporter genes encode a xylose transporter comprising the amino acid sequence of one or more of the KHT105 and/or RAG4 polypeptides disclosed herein.

Provided herein in certain embodiments are genetically modified yeast cells that have at least one active xylose fermentation pathway for converting xylose to xylulose 5-phosphate, and which further comprise an active arabinose fermentation pathway for converting arabinose to xylulose 5-phosphate. In certain embodiments, the active xylose fermentation pathway converts xylose to xylulose 5-phosphate via xylitol and xylulose intermediates, and in certain of these embodiments the cells comprise at least one copy each of the xylose fermentation pathway genes XR, XDH, and XK. In other embodiments, the active xylose fermentation pathway converts xylose to xylulose 5-phosphate via a xylulose intermediate only, and in certain of these embodiments the cells comprise at least one copy each of the xylose fermentation pathway genes XI and XK. In certain embodiments, the active arabinose fermentation pathway converts arabinose to xylulose 5-phosphate via ribulose and ribulose 5-phosphate intermediates, and in these embodiments the cells comprise at least one copy each of the arabinose fermentation pathway genes AI, RK, and RE.

Provided herein in certain embodiments are genetically modified yeast cells that have at least one active xylose fermentation pathway for converting xylose to xylulose 5-phosphate, and which further comprise one or more xylose transporter genes and an active arabinose fermentation pathway for converting arabinose to xylulose 5-phosphate. In certain embodiments, the active xylose fermentation pathway converts xylose to xylulose 5-phosphate via xylitol and xylulose intermediates, and in certain of these embodiments the cells comprise at least one copy each of the xylose fermentation pathway genes XR, XDH, and XK. In other embodiments, the active xylose fermentation pathway converts xylose to xylulose 5-phosphate via a xylulose intermediate only, and in certain of these embodiments the cells comprise at least one copy each of the xylose fermentation pathway genes XI and XK. In certain embodiments, the xylose transporter genes comprise the nucleotide sequence of one or more of the KHT105 and/or RAG4 polynucleotides disclosed herein. Similarly, in certain embodiments the xylose transporter genes encode a xylose transporter comprising the amino acid sequence of one or more of the KHT105 and/or RAG4 polypeptides disclosed herein. In certain embodiments, the active arabinose fermentation pathway converts arabinose to xylulose 5-phosphate via ribulose and ribulose 5-phosphate intermediates, and in these embodiments the cells comprise at least one copy each of the arabinose fermentation pathway genes AI, RK, and RE.

In certain embodiments, the genetically modified yeast cells provided herein comprise an active non-oxidative pentose phosphate pathway. A yeast cell having an "active non-oxidative pentose phosphate pathway" as used herein produces active enzymes necessary to convert xylulose 5-phosphate plus ribose 5-phosphate to F6P and G3P. A yeast cell having an active non-oxidative pentose phosphate pathway comprises one or more non-oxidative pentose phosphate pathway genes. A "non-oxidative pentose phosphate pathway gene" as used herein refers to the coding region of a nucleotide sequence that encodes an enzyme involved in an active non-oxidative pentose phosphate pathway. In certain embodiments, a yeast cell having an active non-oxidative pentose phosphate pathway comprises at least one copy each of the non-oxidative pentose phosphate pathway genes TKL and TAL. In certain of these embodiments, the yeast cell further comprises one or more copies of the non-oxidative pentose phosphate pathway genes RPE and RKI. In certain embodiments, a yeast cell having an active non-oxidative pentose phosphate pathway comprises at least one copy of an *I. orientalis* RPE, RKI, TKL, and/or TAL gene, and in certain embodiments these genes comprise the DNA sequence of the RPE, RKI, TKL, and/or TAL polynucleotides disclosed herein and/or encode a polypeptide that comprises the amino acid sequence of the RPE, RKI, TKL, and/or TAL polypeptides disclosed herein.

Provided herein in certain embodiments are genetically modified yeast cells that have at least one active non-oxidative pentose phosphate pathway for converting xylulose 5-phosphate plus ribose 5-phosphate to F6P and G3P, and which further comprise an active arabinose fermentation pathway for converting arabinose to xylulose 5-phosphate. In certain embodiments, the cells comprise at least one copy of the non-oxidative pentose phosphate pathway genes TKL and TAL, and in certain embodiments the cells further comprise at least one copy of the non-oxidative pentose phosphate pathway genes RPE and RKI. In certain embodiments, the TKL, TAL, RPE, and RKI genes comprise the nucleotide sequence of one or more of the TKL, TAL, RPE, and/or RKI polynucleotides disclosed herein. Similarly, in certain embodiments the TKL, TAL, RPE, and RKI genes encode polypeptides comprising the amino acid sequence of one or more of the TKL, TAL, RPE, and/or RKI polypeptides disclosed herein. In certain embodiments, the active arabinose fermentation pathway converts arabinose to xylulose 5-phosphate via ribulose and ribulose 5-phosphate intermediates, and in these embodiments the cells comprise at least one copy each of the arabinose fermentation pathway genes AI, RK, and RE.

Provided herein in certain embodiments are genetically modified yeast cells that have at least one active non-oxidative pentose phosphate pathway for converting xylulose 5-phosphate plus ribose 5-phosphate to F6P and G3P, and which further comprise one or more xylose transporter genes and an active arabinose fermentation pathway for converting arabinose to xylulose 5-phosphate. In certain embodiments, the cells comprise at least one copy of the non-oxidative pentose phosphate pathway genes TKL and TAL, and in certain embodiments the cells further comprise at least one copy of the non-oxidative pentose phosphate pathway genes RPE and RKI. In certain embodiments, the TKL, TAL, RPE, and RKI genes comprise the nucleotide sequence of one or more of the TKL, TAL, RPE, and/or RKI polynucleotides disclosed herein. Similarly, in certain embodiments the TKL, TAL, RPE, and RKI genes encode polypeptides comprising the amino acid sequence of one or more of the TKL, TAL, RPE, and/or RKI polypeptides disclosed herein. In certain embodiments, the xylose transporter genes comprise the nucleotide sequence of one or more of the KHT105 and/or RAG4 polynucleotides disclosed herein. Similarly, in certain embodiments the xylose transporter genes encode a xylose transporter comprising the amino acid sequence of one or more of the KHT105 and/or RAG4 polypeptides disclosed herein. In certain embodiments, the active arabinose fermentation pathway converts arabinose to xylulose 5-phosphate via ribulose and ribulose 5-phosphate intermediates, and in these embodiments the cells comprise at least one copy each of the arabinose fermentation pathway genes AI, RK, and RE.

Provided herein in certain embodiments are genetically modified yeast cells that have at least one active non-oxidative pentose phosphate pathway for converting xylulose 5-phosphate plus ribose 5-phosphate to F6P and G3P, and which further comprise one or more xylose transporter genes and an active xylose fermentation pathway for converting xylose to xylulose 5-phosphate. In certain embodiments, the cells comprise at least one copy of the non-oxidative pentose phosphate pathway genes TKL and TAL, and in certain embodiments the cells further comprise at least one copy of the non-oxidative pentose phosphate pathway genes RPE and RKI. In certain embodiments, the TKL, TAL, RPE, and RKI genes comprise the nucleotide sequence of one or more of the TKL, TAL, RPE, and/or RKI polynucleotides disclosed herein. Similarly, in certain embodiments the TKL, TAL, RPE, and RKI genes encode polypeptides comprising the amino acid sequence of one or more of the TKL, TAL, RPE, and/or RKI polypeptides disclosed herein. In certain embodiments, the active xylose fermentation pathway converts xylose to xylulose 5-phosphate via xylitol and xylulose intermediates, and in certain of these embodiments the cells comprise at least one copy each of the xylose fermentation pathway genes XR, XDH, and XK. In other embodiments, the active xylose fermentation pathway converts xylose to xylulose 5-phosphate via a xylulose intermediate only, and in certain of these embodiments the cells comprise at least one copy each of the xylose fermentation pathway genes XI and XK. In certain embodiments, the xylose transporter genes comprise the nucleotide sequence of one or more of the KHT105 and/or RAG4 polynucleotides disclosed herein. Similarly, in certain embodiments the xylose transporter genes encode a xylose transporter comprising the amino acid sequence of one or more of the KHT105 and/or RAG4 polypeptides disclosed herein.

Provided herein in certain embodiments are genetically modified yeast cells that have at least one active non-oxidative pentose phosphate pathway for converting xylulose 5-phosphate plus ribose 5-phosphate to F6P and G3P, and which further comprise an active arabinose fermentation pathway for converting arabinose to xylulose 5-phosphate and an active xylose fermentation pathway for converting xylose to xylulose 5-phosphate. In certain embodiments, the cells comprise at least one copy of the non-oxidative pentose phosphate pathway genes TKL and TAL, and in certain embodiments the cells further comprise at least one copy of the non-oxidative pentose phosphate pathway genes RPE and RKI. In certain embodiments, the TKL, TAL, RPE, and RKI genes comprise the nucleotide sequence of one or more of the TKL, TAL, RPE, and/or RKI polynucleotides disclosed herein. Similarly, in certain embodiments the TKL, TAL, RPE, and RKI genes encode polypeptides comprising the amino acid sequence of one or more of the TKL, TAL, RPE, and/or RKI polypeptides disclosed herein. In certain embodiments, the active arabinose fermentation pathway converts arabinose to xylulose 5-phosphate via ribulose and ribulose 5-phosphate intermediates, and in these embodiments the cells comprise at least one copy each of the arabinose fermentation pathway genes AI, RK, and RE. In certain embodiments, the active xylose fermentation pathway converts xylose to xylulose 5-phosphate via xylitol and xylulose intermediates, and in certain of these embodiments the cells comprise at least one copy each of the xylose fermentation pathway genes XR, XDH, and XK. In other embodiments, the active xylose fermentation pathway converts xylose to xylulose 5-phosphate via a xylulose intermediate only, and in certain of these embodiments the cells comprise at least one copy each of the xylose fermentation pathway genes XI and XK.

Provided herein in certain embodiments are genetically modified yeast cells that have at least one active non-oxidative pentose phosphate pathway for converting xylulose 5-phosphate plus ribose 5-phosphate to F6P and G3P, and which further comprise one or more xylose transporter genes, an active arabinose fermentation pathway for converting arabinose to xylulose 5-phosphate, and an active xylose fermentation pathway for converting xylose to xylulose 5-phosphate. In certain embodiments, the cells comprise at least one copy of the non-oxidative pentose phosphate pathway genes TKL and TAL, and in certain embodiments the cells further comprise at least one copy of the non-oxidative pentose phosphate pathway genes RPE and RKI. In certain embodiments, the TKL, TAL, RPE, and RKI genes comprise the nucleotide sequence of one or more of the TKL, TAL, RPE, and/or RKI polynucleotides disclosed herein. Similarly, in certain embodiments the TKL, TAL, RPE, and RKI genes encode polypeptides comprising the amino acid sequence of one or more of the TKL, TAL, RPE, and/or RKI polypeptides disclosed herein. In certain embodiments, the xylose transporter genes comprise the nucleotide sequence of one or more of the KHT105 and/or RAG4 polynucleotides disclosed herein. Similarly, in certain embodiments the xylose transporter genes encode a xylose transporter comprising the amino acid sequence of one or more of the KHT105 and/or RAG4 polypeptides disclosed herein. In certain embodiments, the active arabinose fermentation pathway converts arabinose to xylulose 5-phosphate via ribulose and ribulose 5-phosphate intermediates, and in these embodiments the cells comprise at least one copy each of the arabinose fermentation pathway genes AI, RK, and RE. In certain embodiments, the active xylose fermentation pathway converts xylose to xylulose 5-phosphate via xylitol and xylulose intermediates, and in certain of these embodiments the cells comprise at least one copy each of the xylose fermentation pathway genes XR, XDH, and XK. In other embodiments, the active xylose fermentation pathway converts xylose to xylulose 5-phosphate via a xylulose intermediate only, and in certain of these embodiments the cells comprise at least one copy each of the xylose fermentation pathway genes XI and XK.

The arabinose fermentation pathway, xylose transporter, xylose fermentation pathway, and non-oxidative pentose phosphate pathway genes in the genetically modified yeast cells provided herein may be endogenous or exogenous. "Endogenous" as used herein with regard to genetic components such as genes, promoters, and terminator sequences means that the genetic component is present at a particular location in the genome of a native form of a particular yeast cell. "Exogenous" as used herein with regard to genetic components means that the genetic component is not present at a particular location in the genome of a native form of a particular yeast cell. "Native" as used herein with regard to a yeast cell refers to a wild-type yeast cell of a particular yeast species. "Native" as used herein with regard to a metabolic pathway refers to a metabolic pathway that exists and is active in a native yeast cell.

An exogenous genetic component may have either a native or non-native sequence. An exogenous genetic component with a native sequence comprises a sequence identical to (apart from individual-to-individual mutations which do not affect function) a genetic component that is present in the genome of a native cell (i.e., the exogenous genetic component is identical to an endogenous genetic component). However, the exogenous component is present at a different location in the host cell genome than the endogenous component. For example, an exogenous XI gene that is identical to an endogenous XI gene may be inserted into a yeast cell, resulting in a modified cell with a non-native (increased) number of XI gene copies. An exogenous genetic component with a non-native sequence comprises a sequence that is not found in the genome of a native cell. For example, an exogenous XI gene from a particular species may be inserted into a yeast cell of another species. An exogenous gene is preferably integrated into the host cell genome in a functional manner, meaning that it is capable of producing an active protein in the host cell. However, in certain embodiments the exogenous gene may be introduced into the cell as part of a vector that is stably maintained in the host cytoplasm.

In certain embodiments, the yeast cells provided herein comprise one or more exogenous arabinose fermentation pathway, xylose transporter, xylose fermentation pathway, or non-oxidative pentose phosphate pathway genes. In certain embodiments, the genetically modified yeast cells disclosed herein comprise a single exogenous gene. In other embodiments, the yeast cells comprise multiple exogenous genes. In these embodiments, the yeast cells may comprise multiple copies of a single exogenous gene and/or copies of two or more different exogenous genes. Yeast cells comprising multiple exogenous genes may comprise any number of exogenous genes. For example, these yeast cells may comprise 1 to 20 exogenous genes, and in certain preferred embodiments they may comprise 1 to 7 exogenous genes. Multiple copies of an exogenous gene may be integrated at a single locus such that they are adjacent to one another. Alternatively, they may be integrated at several loci within the host cell's genome. A yeast cell as provided herein may comprise only one type of exogenous gene or exogenous genes from only one pathway. For example, the exogenous genes in a yeast cell may be limited to arabinose fermentation pathway genes or to xylose transporter genes. Alternatively, a yeast cell may comprise exogenous genes from two or more pathways or from one or more pathways in combination with an exogenous xylose transporter gene. For example, a yeast cell may comprise one or more exogenous arabinose fermentation pathway genes and one or more exogenous xylose transporter genes.

In certain embodiments, the yeast cells provided herein comprise one or more endogenous arabinose fermentation pathway, xylose transporter, xylose fermentation pathway, and non-oxidative pentose phosphate pathway genes. In certain of these embodiments, the cells may be engineered to overexpress one or more of these endogenous genes, meaning that the modified cells express the endogenous gene at a higher level than a native cell under at least some conditions. In certain of these embodiments, the endogenous gene being overexpressed may be operatively linked to one or more exogenous regulatory elements. For example, one or more native or non-native exogenous strong promoters may be introduced into a cell such that they are operatively linked to one or more endogenous genes.

Arabinose fermentation pathway, xylose transporter, xylose fermentation pathway, and/or non-oxidative pentose phosphate pathway genes in the genetically modified yeast cells provided herein may be operatively linked to one or more regulatory elements such as a promoter or terminator. As used herein, the term "promoter" refers to an untranslated sequence located upstream (i.e., 5') to the translation start codon of a gene (generally within about 1 to 1000 base pairs (bp), preferably within about 1 to 500 bp) which controls the start of transcription of the gene. The term "terminator" as used herein refers to an untranslated sequence located downstream (i.e., 3') to the translation finish codon of a gene (generally within about 1 to 1000 bp, preferably within about 1 to 500 bp, and especially within about 1 to 100 bp) which controls the end of transcription of the gene. A promoter or terminator is "operatively linked" to a gene if its position in the genome relative to that of the gene is such that the promoter or terminator, as the case may be, performs its transcriptional control function. Suitable promoters and terminators are described, for example, in WO99/14335, WO00/71738, WO02/42471, WO03/102201, WO03/102152 and WO03/049525 (all incorporated by reference herein in their entirety).

Regulatory elements linked to arabinose fermentation pathway, xylose transporter, xylose fermentation pathway, or non-oxidative pentose phosphate pathway genes in the yeast cells provided herein may be endogenous or exogenous. For example, an exogenous arabinose fermentation pathway or xylose transporter gene may be inserted into a yeast cell such that it is under the transcriptional control of an endogenous promoter and/or terminator. Alternatively, the exogenous arabinose fermentation pathway or xylose transporter gene may be linked to one or more exogenous regulatory elements. For example, an exogenous gene may be introduced into the cell as part of a gene expression construct that comprises one or more exogenous regulatory elements. In certain embodiments, exogenous regulatory elements, or at least the functional portions of exogenous regulatory elements, may comprise native sequences. In other embodiments, exogenous regulatory elements may comprise non-native sequences. In these embodiments, the exogenous regulatory elements may comprise a sequence with a relatively high degree of sequence identity to a native regulatory element. For example, an exogenous gene may be linked to an exogenous promoter or terminator having at least 50%, at least 60%, at least 70%, at least 80%, or at least 90% sequence identity to a native promoter or terminator. Sequence identity percentages for nucleotide or amino acid sequences can be calculated by methods known in the art, such as for example using BLAST (National Center for Biological Information (NCBI) Basic Local Alignment Search Tool) version 2.2.1 software with default parameters. For example, a sequence having an identity score of at least 90% using the BLAST version 2.2.1 algorithm with default parameters is considered to have at least 90% sequence identity. The BLAST software is available from the NCBI, Bethesda, Md. In those embodiments wherein multiple exogenous genes are inserted into a host cell, each exogenous gene may be under the control of a different regulatory element, or two or more exogenous genes may be under the control of the same regulatory elements. For example, where a first exogenous gene is linked to a first regulatory element, a second exogenous gene may also be linked to the first regulatory element, or it may be linked to a second regulatory element. The first and second regulatory elements may be identical or share a high degree of sequence identity, or they be wholly unrelated.

Examples of promoters that may be linked to one or more arabinose fermentation pathway, xylose transporter, xylose fermentation pathway, or non-oxidative pentose phosphate pathway genes in the yeast cells provided herein include, but are not limited to, promoters for pyruvate decarboxylase 1 (PDC1), enolase 1 (ENO1), translation elongation factor-1 or -2 (TEF1, TEF2), phosphoglycerate kinase (PGK), XR, XDH, L-(+)-lactate-cytochrome c oxidoreductase (CYB2), glyceraldehyde-3-phosphate dehydrogenase 3 (GAPDH/TDH3), and orotidine 5'-phosphate decarboxylase (URA3) genes. In these examples, the genes may be linked to endogenous or exogenous promoters for PDC1, PGK, XR, XDH, CYB2, TEF1, TEF2, ENO1, TDH3, or URA3 genes. Where the promoters are exogenous, they may be identical to or share a high degree of sequence identity (i.e., at least about 80%, at least about 85%, at least about 90%, at least about 95%, or at least about 99%) with native promoters for PDC1, ENO1, TEF1, TEF2, PGK, XR, XDH, CYB2, TDH3, or URA3 genes.

Examples of terminators that may be linked to one or more arabinose fermentation pathway, xylose transporter, xylose fermentation pathway, or non-oxidative pentose phosphate pathway genes in the yeast cells provided herein include, but are not limited to, terminators for PDC1, XR, XDH, TAL, TKL, RKI, CYB2, or iso-2-cytochrome c (CYC) genes or the galactose family of genes (especially the GAL10 terminator). In these examples, the genes may be linked to endogenous or exogenous terminators for PDC1, XR, XDH, TAL, TKL, RKI, CYB2, or CYC genes or galactose family genes. Where the terminators are exogenous, they may be identical to or share a high degree of sequence identity (i.e., at least about 80%, at least about 85%, at least about 90%, at least about 95%, or at least about 99%) with native terminators for PDC1, XR, XDH, TAL, TKL, RKI, CYB2, or CYC genes or galactose family genes. In certain embodiments, genes are linked to a terminator that comprises a functional portion of a native GAL10 gene native to the host cell or a sequence that shares at least 80%, at least 85%, at least 90%, or at least 95% sequence identity with a native GAL10 terminator.

Exogenous genes may be inserted into a yeast host cell via any method known in the art. In preferred embodiments, the genes are integrated into the host cell genome. Exogenous genes may be integrated into the genome in a targeted or a random manner. In those embodiments where the gene is integrated in a targeted manner, it may be integrated into the loci for a particular gene, such that integration of the exogenous gene is coupled to deletion or disruption of a native gene. For example, introduction of an exogenous arabinose fermentation pathway, xylose transport, xylose fermentation pathway, or non-oxidative pentose phosphate pathway gene may be coupled to deletion or disruption of one or more genes encoding enzymes involved other fermentation product pathways. Alternatively, the exogenous gene may be integrated into a portion of the genome that does not correspond to a gene.

Targeted integration and/or deletion may utilize an integration construct. The term "construct" as used herein refers to a DNA sequence that is used to transform a cell. The construct may be, for example, a circular plasmid or vector, a portion of a circular plasmid or vector (such as a restriction enzyme digestion product), a linearized plasmid or vector, or a PCR product prepared using a plasmid or genomic DNA as a template. Methods for transforming a yeast cell with an exogenous construct are described in, for example, WO99/14335, WO00/71738, WO02/42471, WO03/102201, WO03/102152, and WO03/049525. An integration construct can be assembled using two cloned target DNA sequences from an insertion site target. The two target DNA sequences may be contiguous or non-contiguous in the native host genome. In this context, "non-contiguous" means that the DNA sequences are not immediately adjacent to one another in the native genome, but are instead are separated by a region that is to be deleted. "Contiguous" sequences as used herein are directly adjacent to one another in the native genome. Where targeted integration is to be coupled to deletion or disruption of a target gene, the integration construct may also be referred to as a deletion construct. In a deletion construct, one of the target sequences may include a region 5' to the promoter of the target gene, all or a portion of the promoter region, all or a portion of the target gene coding sequence, or some combination thereof. The other target sequence may include a region 3' to the terminator of the target gene, all or a portion of the terminator region, and/or all or a portion of the target gene coding sequence. Where targeted integration is not to be coupled to deletion or disruption of a native gene, the target sequences are selected such that insertion of an intervening sequence will not disrupt native gene expression. An integration or deletion construct is prepared such that the two target sequences are oriented in the same direction in relation to one another as they natively appear in the genome of the host cell. Where an integration or deletion construct is used to introduce an exogenous gene into a host cell, a gene expression cassette is cloned into the construct between the two target gene sequences to allow for expression of the exogenous gene. The gene expression cassette contains the exogenous gene, and may further include one or more regulatory sequences such as promoters or terminators operatively linked to the exogenous gene. Deletion constructs can also be constructed that do not contain a gene expression cassette. Such constructs are designed to delete or disrupt a gene sequence without the insertion of an exogenous gene.

An integration or deletion construct may comprise one or more selection marker cassettes cloned into the construct between the two target gene sequences. The selection marker cassette contains at least one selection marker gene that allows for selection of transformants. Successful transformants will contain the selection marker gene, which imparts to the successfully transformed cell at least one characteristic that provides a basis for selection. Typical selection marker genes encode proteins that (a) confer resistance to antibiotics or other toxins (e.g., resistance to bleomycin or zeomycin (e.g., *Streptoalloteichus hindustanus* ble gene), aminoglycosides such as G418 or kanamycin (e.g., kanamycin resistance gene from transposon Tn903), or hygromycin (e.g., aminoglycoside antibiotic resistance gene from *E. coli*)), (b) complement auxotrophic deficiencies of the cell (e.g., deficiencies in leucine (e.g., *K. marxianus* LEU2 gene), uracil (e.g., *K. marxianus, S. cerevisiae*, or *I. orientalis* URA3 gene), or tryptophan (e.g., *K. marxianus, S. cerevisiae*, or *I. orientalis* TRP gene)), (c) enable the cell to synthesize critical nutrients not available from simple media, or (d) confer the ability for the cell to grow on a particular carbon source (e.g., MEL5 gene from *S. cerevisiae*, which encodes the alpha-galactosidase (melibiose) enzyme and confers the ability to grow on melibiose as the sole carbon source). Preferred selection markers include the URA3 gene, zeocin resistance gene, G418 resistance gene, MEL5 gene, and hygromycin resistance gene. Another preferred selection marker is a CYB2 gene cassette, provided that the host cell either natively lacks such a gene or that its native CYB2 gene(s) are first deleted or disrupted. A selection marker gene is operatively linked to one or more promoter and/or terminator sequences that are operable in the host cell. In certain embodiments, these promoter and/or terminator sequences are exogenous promoter and/or terminator sequences that are included in the selection marker cassette. Suitable promoters and terminators are as described above.

In other embodiments, an integration or deletion construct may not contain a selection marker cassette, but may nonetheless allow for selection of transformants based on overexpression of an exogenous gene (in the case of insertion constructs) or deletion of an endogenous gene (in the case of deletion constructs). For example, where an integration construct comprises one or more exogenous arabinose fermentation pathway gene, transformants may be selected based on their ability to grow on arabinose.

An integration or deletion construct is used to transform the host cell. Transformation may be accomplished using, for example, electroporation and/or chemical transformation (e.g., calcium chloride, lithium acetate-based, etc.) methods. Selection or screening based on the presence or absence of the selection marker may be performed to identify successful transformants. In successful transformants, a homologous recombination event at the locus of the target site results in the disruption or the deletion of the target site sequence. Where the construct targets a native gene for deletion or disruption, all or a portion of the native target gene, its promoter, and/or its terminator may be deleted during this recombination event. The expression cassette, selection marker cassette, and any other genetic material between the target sequences in the integration construct is inserted into the host genome at the locus corresponding to the target sequences. Analysis by PCR or Southern analysis can be performed to confirm that the desired insertion/deletion has taken place.

In some embodiments, cell transformation may be performed using DNA from two or more constructs, PCR products, or a combination thereof, rather than a single construct or PCR product. In these embodiments, the 3' end of one integration fragment overlaps with the 5' end of another integration fragment. In one example, one construct will contain the first sequence from the locus of the target sequence and a non-functional part of the marker gene cassette, while the other will contain the second sequence from the locus of the target sequence and a second non-functional part of the marker gene cassette. The parts of the marker gene cassette are selected such that they can be combined to form a complete cassette. The cell is transformed with these pieces simultaneously, resulting in the formation of a complete, functional marker or structural gene cassette. Successful transformants can be selected for on the basis of the characteristic imparted by the selection marker. In another example, the selection marker resides on one fragment but the target sequences are on separate fragments, so that the integration fragments have a high probability of integrating at the site of interest. In other embodiments, transformation from three linear DNAs can be used to integrate exogenous genetic material. In these embodiments, one fragment overlaps on the 5' end with a second fragment and on the 3' end with a third fragment.

An integration or deletion construct may be designed such that the selection marker gene and some or all of its regulatory elements can become spontaneously deleted as a result of a subsequent homologous recombination event. A convenient way of accomplishing this is to design the construct such that the selection marker gene and/or regulatory elements are flanked by repeat sequences. Repeat sequences are identical DNA sequences, native or non-native to the host cell, and oriented on the construct in the same direction with respect to one another. The repeat sequences are advantageously about 25 to 1500 bp in length, and do not have to encode for anything. Inclusion of the repeat sequences permits a homologous recombination event to occur, which results in deletion of the selection marker gene and one of the repeat sequences. Since homologous recombination occurs with relatively low frequency, it may be necessary to grow transformants for several rounds on nonselective media to allow for the spontaneous homologous recombination to occur in some of the cells. Cells in which the selection marker gene has become spontaneously deleted can be selected or screened on the basis of their loss of the selection characteristic imparted by the selection marker gene. In certain cases, expression of a recombinase enzyme may enhance recombination between the repeated sites.

An exogenous arabinose fermentation pathway, xylose transporter, xylose fermentation pathway, or non-oxidative pentose phosphate pathway gene in the modified yeast cells provided herein may be derived from a source gene from any suitable source organism. For example, an exogenous gene may be derived from a yeast, fungal, bacterial, plant, insect, or mammalian source. As used herein, an exogenous gene that is "derived from" a native source gene encodes a polypeptide that 1) is identical to a polypeptide encoded by the native gene, 2) shares at least 50%, at least 60%, at least 70%, at least 80%, at least 85%, at least 90%, at least 95%, at least 97%, or at least 99% sequence identity with a polypeptide encoded by the native gene, and/or 3) has the same function in an arabinose fermentation pathway, xylose fermentation pathway, or non-oxidative pentose phosphate pathway or in xylose transport as the polypeptide encoded by the native gene. For example, a xylose transporter gene that is derived from a *K. marxianus* KHT105 gene may encode a polypeptide comprising the amino acid sequence of SEQ ID NO:2, a polypeptide with at least 50%, at least 60%, at least 70%, at least 80%, at least 85%, at least 90%, at least 95%, at least 97%, or at least 99% sequence identity to the amino acid sequence of SEQ ID NO:2, and/or a polypeptide that has the ability to transport xylose into a yeast cell. A gene derived from a native gene may comprise a nucleotide sequence with at least 50%, at least 60%, at least 70%, at least 80%, at least 85%, at least 90%, at least 95%, at least 97%, or at least 99% sequence identity to the coding region of the native gene. In certain embodiments, a gene derived from a native gene may comprise a nucleotide sequence that is identical to the coding region of the source gene. For example, a xylose transporter gene that is derived from a *K. marxianus* KHT105 gene may comprise the nucleotide sequence of SEQ ID NO:1 or a nucleotide sequence with at least 50%, at least 60%, at least 70%, at least 80%, at least 85%, at least 90%, at least 95%, at least 97%, or at least 99% sequence identity to the nucleotide sequence of SEQ ID NO:1.

In certain embodiments of the modified yeast cells provided herein, an exogenous arabinose fermentation pathway, xylose transporter, xylose fermentation pathway, or non-oxidative pentose phosphate pathway gene may be derived from the host yeast species. For example, where the host cell is *I. orientalis*, an exogenous gene may be derived from an *I. orientalis* gene. In these embodiments, the exogenous gene may comprise a nucleotide sequence identical to the coding region of the native gene, such that incorporation of the exogenous gene into the host cell increases the copy number of a native gene sequence and/or changes the regulation or expression level of the gene if under the control of a promoter that is different from the promoter that drives expression of the gene in a wild-type cell. In other embodiments, the exogenous gene may comprise a nucleotide sequence that differs from the coding region of a native gene, but nonetheless encodes a polypeptide that is identical to the polypeptide encoded by the native gene. In still other embodiments, the exogenous gene may comprise a nucleotide sequence that encodes a polypeptide with at least 50%, at least 60%, at least 70%, at least 80%, at least 85%, at least 90%, at least 95%, at least 97%, or at least 99% sequence identity to a polypeptide encoded by one or more native genes. In certain of these embodiments, the exogenous gene comprises a nucleotide sequence with at least 50%, at least 60%, at least 70%, at least 80%, at least 85%, at least 90%, at least 95%, at least 97%, or at least 99% sequence identity to the coding region of one or more native genes. In still other embodiments, the exogenous arabinose fermentation pathway, xylose transporter, xylose fermentation pathway, or non-oxidative pentose phosphate pathway gene may encode a polypeptide that has less than 50% sequence identity to a polypeptide encoded by a native arabinose fermentation pathway, xylose transporter, xylose fermentation pathway, or non-oxidative pentose phosphate pathway gene but which nonetheless has the same function as the native polypeptide in an arabinose fermentation, xylose fermentation, or non-oxidative pentose phosphate pathway (i.e., the ability to catalyze the same reaction between reaction intermediates) or in xylose transport (i.e., the ability to transport xylose into a cell).

In other embodiments, an exogenous arabinose fermentation pathway, xylose transporter, xylose fermentation pathway, or non-oxidative pentose phosphate pathway gene may be derived from a species that is different than that of the host yeast cell. In certain of these embodiments, the exogenous gene may be derived from a different yeast species than the host cell. For example, where the host cell is *I. orientalis*, the exogenous gene may be derived from *S. cerevisiae*. In other embodiments, the exogenous gene may be derived from a fungal, bacterial, plant, insect, or mammalian source. For example, where the host cell is *I. orientalis*, the exogenous gene may be derived from a bacterial source such as *E. coli*. In those embodiments where the exogenous gene is derived from a non-yeast source, the exogenous gene sequence may be codon optimized for expression in a yeast host cell.

In those embodiments where the exogenous arabinose fermentation pathway, xylose transporter, xylose fermentation pathway, or non-oxidative pentose phosphate pathway gene is derived from a species other than the host cell species, the exogenous gene may encode a polypeptide identical to a polypeptide encoded by a native gene from the source organism. In certain of these embodiments, the exogenous gene may be identical to a native gene from the source organism. In other embodiments, the exogenous gene may share at least 50%, at least 60%, at least 70%, at least 80%, at least 85%, at least 90%, at least 95%, at least 97%, or at least 99% sequence identity to the coding region of a native gene from the source organism. In other embodiments, the exogenous gene may encode a polypeptide that shares at least 50%, at least 60%, at least 70%, at least 80%, at least 85%, at least 90%, at least 95%, at least 97%, or at least 99% sequence identity with a polypeptide encoded by a native gene from the source organism. In certain of these embodiments, the exogenous gene may comprise a nucleotide sequence with at least 50%, at least 60%, at least 70%, at least 80%, at least 85%, at least 90%, at least 95%, at least 97%, or at least 99% sequence identity to the coding region of one or more native genes from the source organism. In still other embodiments, the exogenous gene may encode a polypeptide that has less than 50% sequence identity to a polypeptide encoded by a native gene from the source organism, but which nonetheless has the same function as the native polypeptide from the source organism in a native arabinose fermentation pathway, xylose fermentation pathway, or non-oxidative pentose phosphate pathway or in xylose transport. An exogenous source gene may be subjected to mutagenesis if necessary to provide a coding sequence starting with the usual eukaryotic starting codon (ATG), or for other purposes.

An "arabinose isomerase gene," "AI gene," or "araA gene" as used herein refers to any gene that encodes a polypeptide with arabinose isomerase activity, meaning the ability to catalyze the conversion of arabinose to ribulose. In certain embodiments, an AI gene may be derived from a bacterial source. For example, an AI gene may be derived from a *B.*

*thetaiotaomicron* araA1 gene encoding the amino acid sequence set forth in SEQ ID NO:6, a *B. thetaiotaomicron* araA2 gene encoding the amino acid sequence set forth in SEQ ID NO:8, a *L. sakei* AI gene encoding the amino acid sequence set forth in SEQ ID NO:10, a *L. plantarum* AI gene encoding the amino acid sequence set forth in SEQ ID NO:81, or a *B. licheniformis* AI gene encoding the amino acid sequence set forth in SEQ ID NO:83. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:6, 8, 10, 81, or 83. In certain embodiments, a *B. thetaiotaomicron, L. sakei, L. plantarum,* or *B. licheniformis*-derived AI gene may comprise the nucleotide sequence set forth in SEQ ID NOs:5, 7, 9, 80, or 82, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs: 5, 7, 9, 80, or 82.

A "ribulokinase gene," "RK gene," or "araB gene" as used herein refers to any gene that encodes a polypeptide with ribulokinase activity, meaning the ability to catalyze the conversion of ribulose to ribulose 5-phosphate. In certain embodiments, an RK gene may be derived from a bacterial source. For example, an RK gene may be derived from a *B. thetaiotaomicron* RK gene encoding the amino acid sequence set forth in SEQ ID NO:12 or a *Leuconostoc citreum* RK gene encoding the amino acid sequence set forth in SEQ ID NO:14. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:12 or 14. In certain embodiments, a *B. thetaiotaomicron* or *L. citreum*-derived RK gene may comprise the nucleotide sequence set forth in SEQ ID NOs:11, 86, or 13, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:11, 86, or 13.

A "ribulose-phosphate 4-epimerase," "RE gene," or "araD gene" as used herein refers to any gene that encodes a polypeptide with ribulose-phosphate 4-epimerase activity, meaning the ability to catalyze the conversion of ribulose 5-phosphate to xylulose 5-phosphate. In certain embodiments, an RE gene may be derived from a bacterial source. For example, an RE gene may be derived from a *B. thetaiotaomicron* RE gene encoding the amino acid sequence set forth in SEQ ID NO:16, a *B. animalis* RE gene encoding the amino acid sequence set forth in SEQ ID NO:18, a *L. lactis* RE gene encoding the amino acid sequence set forth in SEQ ID NO:20, an *E. coli* RE gene encoding the amino acid sequence set forth in SEQ ID NO:77, or an *L. plantarum* RE gene encoding the amino acid sequence set forth in SEQ ID NO:79. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:16, 18, 20, 77, or 79. In certain embodiments, a *B. thetaiotaomicron, B. animalis, L. lactis, E. coli,* or *L. plantarum*-derived RE gene may comprise the nucleotide sequence set forth in SEQ ID NOs:15, 17, 19, 76, or 78, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:15, 17, 19, 76, or 78.

A "xylose isomerase gene" or "XI gene" as used herein refers to any gene that encodes a polypeptide with xylose isomerase activity, meaning the ability to catalyze the conversion of xylose to xylulose. In certain embodiments, an XI gene may be derived from a bacterial source. For example, an XI gene may be derived from a *B. thetaiotaomicron* XI gene encoding the amino acid sequence set forth in SEQ ID NO:22. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NO:22. In certain embodiments, a *B. thetaiotaomicron*-derived XI gene may comprise the nucleotide sequence set forth in SEQ ID NO:21, or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NO:21.

A "xylulokinase gene" or "XK gene" as used herein refers to any gene that encodes a polypeptide with xylulokinase activity, meaning the ability to catalyze the conversion of xylulose to xylulose 5-phosphate. In certain embodiments, an XK gene may be derived from a yeast source. For example, the XK gene may be derived from an *I. orientalis* XK gene encoding the amino acid sequence set forth in SEQ ID NO:24, an *S. cerevisiae* XK gene encoding the amino acid sequence set forth in SEQ ID NO:26, or a *K. marxianus* XK gene encoding the amino acid sequence set forth in SEQ ID NO:28. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:24, 26, or 28. In certain embodiments, an *I. orientalis, S. cerevisiae,* or *K. marxianus*-derived XK gene may comprise the nucleotide sequence set forth in SEQ ID NOs:23, 25, or 27 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs: 23, 25, or 27.

A "xylose reductase gene" or "XR gene" as used herein refers to any gene that encodes a polypeptide with xylose reductase activity, meaning the ability to catalyze the conversion of xylose to xylitol. In certain embodiments, an XR gene may be derived from a yeast source. For example, the XR gene may be derived from an *I. orientalis* XR/AR homolog encoding the amino acid sequence set forth in SEQ ID NO:71 or a *Pichia stipitis* XR gene encoding the amino acid sequence set forth in SEQ ID NO:30. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:71 or 30. In certain embodiments, an *I. orientalis* or *P. stipitis*-derived XR gene may comprise the nucleotide sequence set forth in SEQ ID NOs:70 or 29 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs: 70 or 29.

A "xylitol dehydrogenase gene" or "XDH gene" as used herein refers to any gene that encodes a polypeptide with xylitol dehydrogenase activity, meaning the ability to catalyze the conversion of xylitol to xylulose. In certain embodiments, an XDH gene may be derived from a yeast source. For example, the XDH gene may be derived from an *I. orientalis* XDH homolog encoding the amino acid sequence set forth in SEQ ID NO:60 or a *P. stipitis* XDH gene encoding the amino acid sequence set forth in SEQ ID NO:32. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:60 or 32. In certain embodiments, an *I. orientalis* or *P. stipitis*-derived XDH gene may comprise the nucleotide sequence set forth in SEQ ID NOs:59 or 31 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:59 or 31.

A "ribulose 5-phosphate 3-epimerase gene" or "RPE gene" as used herein refers to any gene that encodes a polypeptide with ribulose 5-phosphate 3-epimerase activity, meaning the ability to catalyze the conversion of xylulose 5-phosphate to ribulose 5-phosphate. In certain embodiments, an RPE gene may be derived from a yeast source. For example, the RPE gene may be derived from an *I. orientalis* RPE gene encoding the amino acid sequence set forth in SEQ ID NO:34, an *S. cerevisiae* RPE gene encoding the amino acid sequence set forth in SEQ ID NO:36, or a *K. marxianus* RPE gene encoding the amino acid sequence set forth in SEQ ID NO:38. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:34, 36, or 38. In certain embodiments, an *I. orientalis*, *S. cerevisiae*, or *K. marxianus*-derived RPE gene may comprise the nucleotide sequence set forth in SEQ ID NOs:33, 35, or 37 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs: 33, 35, or 37.

A "ribose 5-phosphate ketol-isomerase gene" or "RKI gene" as used herein refers to any gene that encodes a polypeptide with ribose 5-phosphate ketol-isomerase activity, meaning the ability to catalyze the conversion of ribulose 5-phosphate to ribose 5-phosphate. In certain embodiments, an RKI gene may be derived from a yeast source. For example, the RKI gene may be derived from an *I. orientalis* RKI gene encoding the amino acid sequence set forth in SEQ ID NO:40, an *S. cerevisiae* RKI gene encoding the amino acid sequence set forth in SEQ ID NO:42, or a *K. marxianus* RKI gene encoding the amino acid sequence set forth in SEQ ID NO:44. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:40, 42, or 44. In certain embodiments, an *I. orientalis*, *S. cerevisiae*, or *K. marxianus*-derived RKI gene may comprise the nucleotide sequence set forth in SEQ ID NOs:39, 41, or 43 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:39, 41, or 43.

A "transketolase gene" or "TKL gene" as used herein refers to any gene that encodes a polypeptide with transketolase activity, meaning the ability to catalyze the conversion of xylulose 5-phosphate and ribose 5-phosphate to G3P and sedoheptulose 7-phosphate (S7P) and the conversion of xylulose 5-phosphate and erythrose 4-phosphate to F6P and G3P. In certain embodiments, a TKL gene may be derived from a yeast source. For example, the TKL gene may be derived from an *I. orientalis* TKL gene encoding the amino acid sequence set forth in SEQ ID NO:46, an *S. cerevisiae* TKL gene encoding the amino acid sequence set forth in SEQ ID NO:48, or a *K. marxianus* TKL gene encoding the amino acid sequence set forth in SEQ ID NO:50. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:46, 48, or 50. In certain embodiments, an *I. orientalis*, *S. cerevisiae*, or *K. marxianus*-derived TKL gene may comprise the nucleotide sequence set forth in SEQ ID NOs:45, 47, or 49 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:45, 47, or 49.

A "transaldolase gene" or "TAL gene" as used herein refers to any gene that encodes a polypeptide with transaldolase activity, meaning the ability to catalyze the conversion of G3P and S7P to erythrose 4-phosphate (E4P) and F6P. In certain embodiments, a TAL gene may be derived from a yeast source. For example, the TAL gene may be derived from an *I. orientalis* TAL gene encoding the amino acid sequence set forth in SEQ ID NO:52, an *S. cerevisiae* TAL gene encoding the amino acid sequence set forth in SEQ ID NO:54, or a *K. marxianus* TAL gene encoding the amino acid sequence set forth in SEQ ID NO:56. In other embodiments, the gene may encode an amino acid sequence with at least 50%, at least 60%, at least 70%, at least 80%, at least 85%, at least 90%, at least 95%, at least 97%, or at least 99% sequence identity to the amino acid sequence of SEQ ID NOs:52, 54, or 56. In certain embodiments, an *I. orientalis*, *S. cerevisiae*, or *K. marxianus*-derived TAL gene may comprise the nucleotide sequence set forth in SEQ ID NOs:51, 53, or 55 or a nucleotide sequence with at least 50%, at least 60%, at least 70%, at least 80%, at least 85%, at least 90%, at least 95%, at least 97%, or at least 99% sequence identity to the nucleotide sequence set forth in SEQ ID NOs:51, 53, or 55.

In certain embodiments, the genetically modified yeast cells provided herein further comprise a deletion or disruption of one or more native genes. "Deletion or disruption" with regard to a native gene means that either the entire coding region of the gene is eliminated (deletion) or the coding region of the gene, its promoter, and/or its terminator region is modified (such as by deletion, insertion, or mutation) such that the gene no longer produces an active enzyme, produces a severely reduced quantity (at least 75% reduction, preferably at least 90% reduction) of an active enzyme, or produces an enzyme with severely reduced (at least 75% reduced, preferably at least 90% reduced) activity.

In certain embodiments, deletion or disruption of one or more native genes results in a deletion or disruption of one or more native metabolic pathways. "Deletion or disruption" with regard to a metabolic pathway means that the pathway is either inoperative or else exhibits activity that is reduced by at least 75%, at least 85%, or at least 95% relative to the native pathway.

In certain embodiments, deletion or disruption of native gene can be accomplished by forced evolution, mutagenesis, or genetic engineering methods, followed by appropriate selection or screening to identify the desired mutants. In certain embodiments, deletion or disruption of a native host cell gene may be coupled to the incorporation of one or more exogenous genes into the host cell, i.e., the exogenous genes may be incorporated using a gene expression integration construct that is also a deletion construct. In other embodiments, deletion or disruption may be accomplished using a deletion construct that does not contain an exogenous gene or by other methods known in the art.

In certain embodiments, the genetically modified yeast cells provided herein comprise a deletion or disruption of one or more native genes encoding an enzyme involved in an active arabinose fermentation pathway that converts arabinose to xylulose 5-phosphate via arabitol, xylulose, xylitol, and xylulose intermediates. In these embodiments, the cells may comprise a deletion or disruption of one or more native AR, arabitol 4-dehydrogenase, xylulose reductase, or XDH genes. In those embodiments wherein the cells have an active arabinose fermentation pathway that converts arabinose to xylulose 5-phosphate via ribulose and ribulose 5-phosphate intermediates, deletion or disruption of one or more AR, arabitol 4-dehydrogenase, xylulose reductase, or XDH genes results in an increase in the amount of arabinose entering the ribulose/ribulose 5-phosphate intermediate pathway. In certain embodiments wherein the modified yeast cell is *I. orientalis*, the cells may comprise a deletion or disruption of a xylulose reductase gene homolog encoding the amino acid sequence of SEQ ID NO:58, an XDH gene homolog encoding the amino acid sequence of SEQ ID NOs:60 or 62, and/or an XR/AR gene homolog encoding the amino acid sequence of SEQ ID NOs:64, 66, 68, 69, or 71. In certain embodiments wherein the cells comprise a deletion or disruption of a xylulose reductase gene homolog, the gene is located at locus S141G8160 and/or comprises the nucleotide sequence of SEQ ID NO:57 or a nucleotide sequence with at least 50%, at least 60%, at least 70%, at least 80%, at least 85%, at least 90%, at least 95%, at least 97%, or at least 99% sequence identity to SEQ ID NO:57. In certain embodiments wherein the cells comprise a deletion or disruption of an XDH gene homolog, the gene is located at locus S141G4546 or S141G7675 and/or comprises the nucleotide sequence of SEQ ID NOs:59 or 61 or a nucleotide sequence with at least 50%, at least 60%, at least 70%, at least 80%, at least 85%, at least 90%, at least 95%, at least 97%, or at least 99% sequence identity to SEQ ID NOs:59 or 61. In certain embodiments wherein the cells comprise a deletion or disruption of an AR/XR gene homolog, the gene is located at locus S141G725, S141G4738, or S141G1158-1159, or S141G8885 and/or comprises the nucleotide sequence of SEQ ID NOs:63, 65, 67, or 70 or a nucleotide sequence with at least 50%, at least 60%, at least 70%, at least 80%, at least 85%, at least 90%, at least 95%, at least 97%, or at least 99% sequence identity to SEQ ID NOs: 63, 65, 67, or 70.

In certain embodiments, the genetically modified yeast cells provided herein comprise a deletion or disruption of one or more native genes encoding an enzyme involved in an active xylose fermentation pathway that converts xylose to xylulose 5-phosphate via xylitol and D-xylulose intermediates. In these embodiments, the cells may comprise a deletion or disruption of one or more native XDH or XR genes. In those embodiments wherein the cells have an active xylose fermentation pathway that converts xylose to xylulose 5-phosphate without a xylitol intermediate (i.e., by converting xylose directly to xylulose), deletion or disruption of one or more XDH or XR genes results in an increase in the amount of xylose entering the xylulose-only intermediate pathway. In certain embodiments wherein the modified yeast cell is *I. orientalis*, the cells comprise a deletion or disruption of an XDH gene homolog encoding the amino acid sequence of SEQ ID NOs:60 or 62 and/or an AR/XR gene homolog encoding the amino acid sequence of SEQ ID NO:64, 66, 68, 69, or 71. In certain embodiments wherein the cells comprise a deletion or disruption of an XDH gene homolog, the gene is located at locus S141G7675 or S141G4546 and/or comprises the nucleotide sequence of SEQ ID NOs:59 or 61 or a nucleotide sequence with at least 50%, at least 60%, at least 70%, at least 80%, at least 85%, at least 90%, at least 95%, at least 97%, or at least 99% sequence identity to SEQ ID NOs:59 or 61. In certain embodiments wherein the cells comprise a deletion or disruption of an AR/XR gene homolog, the gene is located at locus S141G725, S141G4738, S141G1158-1159, or S141G8885 and/or comprises the nucleotide sequence of SEQ ID NOs:63, 65, 67, or 70 or a nucleotide sequence with at least 50%, at least 60%, at least 70%, at least 80%, at least 85%, at least 90%, at least 95%, at least 97%, or at least 99% sequence identity to SEQ ID NOs:63, 65, 67, or 70.

In certain embodiments, the genetically modified yeast cells provided herein comprise a deletion or disruption of one or more native genes encoding an enzyme that diverts carbon away from ethanol production. In these embodiments, the cells may comprise a deletion or disruption of one or more ALD or ADH genes. In certain embodiments wherein the modified yeast cell is *I. orientalis*, the cells comprise a deletion or disruption of an ALD gene encoding the amino acid sequence of SEQ ID NO:73 (ALD5680) and/or an ADH gene encoding the amino acid sequence of SEQ ID NOs:75 or 85. In certain embodiments wherein the cells comprise a deletion or disruption of an ALD gene, the ALD gene is located at locus S141G5680 and/or comprises the nucleotide sequence of SEQ ID NO:72 or a nucleotide sequence with at least 50%, at least 60%, at least 70%, at least 80%, at least 85%, at least 90%, at least 95%, at least 97%, or at least 99% sequence identity to SEQ ID NO:72. In certain embodiments wherein the cells comprise a deletion or disruption of an ADH gene, the ADH gene is located at locus S141G9091 or S141G1202 and/or comprises the nucleotide sequence of SEQ ID NOs:74 or 84 or a nucleotide sequence with at least 50%, at least 60%, at least 70%, at least 80%, at least 85%, at least 90%, at least 95%, at least 97%, or at least 99% sequence identity to SEQ ID NOs:74 or 84.

The genetically modified yeast cells provided herein may be selected from a variety of yeast species. In certain embodiments, the genetically modified yeast cells provided herein are non-*Saccharomyces* yeast cells. In certain of these embodiments, the yeast cells are Crabtree-negative yeast cells, and in certain of these embodiments the yeast cells belong to the *I. orientalis*/*Pichia fermentans* clade. The *I. orientalis*/*P. fermentans* clade is the most terminal clade that contains at least the species *I. orientalis*, *Pichia galeiformis*, *Pichia* sp. YB-4149 (NRRL designation), *Candida ethanolica*, *Pichia deserticola*, *Pichia membranifaciens*, and *Pichia fermentans*. Members of the *I. orientalis*/*P. fermentans* clade are identified by analysis of the variable D1/D2 domain of the 26S ribosomal DNA of yeast species, using the method described by Kurtzman and Robnett in "Identification and Phylogeny of Ascomycetous Yeasts from Analysis of Nuclear Large Subunit (26S) Ribosomal DNA Partial Sequences," *Antonie van Leeuwenhoek* 73:331-371, 1998, incorporated herein by reference (see especially p. 349). Analysis of the variable D1/D2 domain of the 26S ribosomal DNA from hundreds of ascomycetes has revealed that the *I. orientalis*/*P. fermentans* clade contains very closely related species. Members of the *I. orientalis*/*P. fermentans* clade exhibit greater similarity in the variable D1/D2 domain of the 26S ribosomal DNA to other members of the clade than to yeast species outside of the clade. Therefore, other members of the *I. orientalis*/*P. fermentans* clade can be identified by comparison of the D1/D2 domains of their respective ribosomal DNA and comparing to that of other members of the clade and closely related species outside of the clade, using Kurtzman and Robnett's methods. In certain embodiments, the genetically modified yeast cells provided herein belong to the genus *Issatchenkia*, and in certain of these embodiments the yeast cells are *I. orientalis*. When first characterized, the species *I. orientalis* was assigned the name *Pichia kudriavzevii*. The anamorph (asexual form) of *I. orientalis* is known as *Candida krusei*. Numerous additional synonyms for the species *I. orientalis* have been listed elsewhere (Kurtzman and Fell, The Yeasts, a Taxonomic Study. Section 35. *Issatchenkia Kudryavtsev*, pp 222-223 (1998)). *I. orientalis* and other members of the *I. orientalis/P. fermentans* clade exhibit certain characteristics that make them ideal for ethanol fermentation from biomass, including tolerance to low pH, ethanol, high temperature (40° C. or greater), and various inhibitors present in hydrolysate.

In certain embodiments, fermentation processes are provided wherein a genetically modified yeast cell as provided herein is cultured under fermentation conditions. In certain of these embodiments, the fermentation process results in the production of ethanol. Accordingly, provide herein in certain embodiments are methods for producing ethanol by culturing a genetically modified yeast cell as provided herein with one or more pentose and/or hexose sugars.

In certain embodiments of the processes and methods provided herein, the media used for culturing the genetically modified yeast cells provided herein comprises one or more non-glucose sugars that are fermentable by the cells. In certain of these embodiments, the non-glucose sugars may be xylose, xylan, another oligomer of xylose, and/or arabinose. These non-glucose sugars may be hydrolysates of a hemicellulose-containing biomass such as a plant biomass hydrolysate. The media may further comprise glucose and/or oligomers or polymers of glucose. Where multimeric sugars are present, it may be necessary to add enzymes to the fermentation broth to digest these sugars to the corresponding monomeric sugar.

In certain embodiments of the process and methods provided herein, the media used for culturing the genetically modified yeast cells provided herein is a xylose-containing medium, and in certain of these embodiments the xylose is derived from a plant biomass hydrolysate. In certain embodiments, xylose may be present in the medium at a concentration of about 0 to about 150 g/L at the outset of fermentation (i.e., at or before the point at which the cells are added to the medium) and/or at various timepoints during the fermentation process. In certain of these embodiments, xylose may be present in the medium at a concentration of at least about 10 g/L, 20 g/L, 30 g/L, 40 g/L, 50 g/L, 75 g/L, 100 g/L, or 125 g/L. In certain embodiments, the media may comprise one or more sugars in addition to xylose, including one or more pentose and/or hexose sugars. In certain of these embodiments, xylose may make up about 10 to about 95% of the total sugar content of the medium at the outset of fermentation and/or at various timepoints during the fermentation process. In certain of these embodiments, xylose may make up at least about 10%, 20%, 30%, 40%, 50%, 60%, 70%, 80%, or 90% of the total sugar content of the medium. In certain embodiments, the genetically modified yeast cells may ferment one or more of the additional sugars present in the media to ethanol.

In certain embodiments of the process and methods provided herein, the media is a synthetic media such as a yeast extract/peptone media, and in certain of these embodiments the media may contain acetate. In other embodiments, the media is a defined synthetic media, and in certain of these embodiments the media may contain acetate. In certain embodiments, the media comprises some percentage of biomass hydrolysate, such as corn stover hydrolysate. In these embodiments, hydrolysate may be present in the medium at anywhere from about 10% to 100% of the total medium volume. In certain of these embodiments, the hydrolysate may have been pre-treated. For example, the hydrolysate may have been pre-treated with one or more acids or enzymes in order to partially break down the feedstock. In certain embodiments, the hydrolysate is undetoxified hydrolysate. In those embodiments wherein the medium comprises hydrolysate at less than 100%, the remainder of the medium may comprise one or more diluting agents including synthetic medium or water.

In certain embodiments, culturing of the cells provided herein to produce ethanol may be divided up into phases. For example, the cell culture process may be divided into a cultivation phase, a production phase, and a recovery phase. One of ordinary skill in the art will recognize that these conditions may be varied based on factors such as the species of yeast being used, the specific fermentation pathway utilized by the yeast, the desired yield, or other factors.

In certain embodiments of the processes and methods provided herein, cells are cultured at a temperature of about 20° C. to about 60° C. In certain of these embodiments, fermentation takes place at a temperature ranging from about 30° C. to about 50° C., and in certain of these embodiments fermentation takes place at a temperature from about 35° C. to about 45° C. Temperature may be varied throughout the fermentation process.

The fermentation may be conducted aerobically, microaerobically, substantially anaerobically, or anaerobically. If desired, oxygen uptake rate can be varied throughout fermentation as a process control (see, e.g., WO03/102200). In certain preferred embodiments, fermentation may take place under microaerobic conditions, which are characterized by an oxygen uptake rate from about 2 to about 25 mmol/L/h.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Integration of *B. thetaiotaomicron*, *L. plantarum*, *E. coli*, and *B. licheniformis* Arabinose Pathway Genes into *I. Orientalis*

Wild-type or codon optimized AI (araA), RK (araB), and RE (araD) genes from *B. thetaiotaomicron*, *L. plantarum*, *E. coli*, and *B. licheniformis* were incorporated into *I. orientalis* strain 1822 (a lactic acid-resistant strain) to determine whether they conferred the ability to utilize arabinose.

Example 1A

Integration of *B. thetaiotaomicron* araB into an XR Locus of *I. orientalis*

The *B. thetaiotaomicron* araB gene was codon optimized for expression in *I. orientalis* using an *I. orientalis* codon usage table for back translation (SEQ ID NO:12). The codon optimized araB gene was synthesized so that it contained an XbaI restriction site on the 5' end and a PacI restriction site on the 3' end. The PCR product was gel purified and cloned into TOPO PCR2.1 vector. Sequencing of inserts for multiple clones resulted in the identification of a clone with the desired DNA sequence.

The *B. thetaiotaomicron* araB gene under the control of the *I. orientalis* ENO1 promoter was cloned into a plasmid containing an *I. orientalis* PDC terminator, a first URA3 selection marker cassette (URA3 promoter/gene/terminator), and a second copy of the URA3 promoter downstream of the terminator to generate plasmid pHJJ2.

Regions upstream and downstream of the *I. orientalis* XYL1 gene (XR) locus were cloned contiguously, separated by a NotI restriction site, into a cloning vector to form plasmid pHJJ1. A NotI fragment from pHJJ2 containing the ENO1 promoter, araB gene, and URA3 selection cassette was ligated into pHJJ1 to form pHJJ3 (orientation 1) and pHJJ18 (orientation 2).

pHJJ3 and pHJJ18 were linearized by sequential digest with ApaI and SacI. The linearized DNA was transformed into *I. orientalis* strain 2762 (ura3Δ ura3Δ), and the cells were plated onto ScD-ura media. Transformed colonies were purified on ScD-ura media, and integration at the XYL1 location was confirmed by PCR. Strain 2762 transformed with pHJJ3 formed the strain yHJJ1 (2903), while strain 2762 transformed with pHJJ18 formed the strain yHJJ2 (2902).

Strains 2902 and 2903 were grown overnight in YPD media and plated on ScD-FOA media to select for strains in which the URA3 marker had been looped out through recombination between the URA3 promoter regions. Resulting colonies were purified on YPD media and tested on ScD-ura media to confirm loss of URA3. The colonies were also confirmed by colony PCR. The ura- derivative of strain 2902 was named strain yHJJ3 (2904) and the ura- derivative of strain 2903 was named strain yHJJ4 (2905).

Expression of the araB gene was confirmed using qPCR. RNA was purified from the parent strain and from strain 2902 using a ZymoResearch RNA kit. An Epicentre MasterAmp RT-PCR kit was used with araB and actin primers for amplification from RNA. The araB integrants showed Cts of approximately 14 versus approximately 34 for strain 1822 and 18 for actin.

Example 1B

Integration of *B. thetaiotaomicron* araD into an AR Locus of *I. orientalis*

The *B. thetaiotaomicron* araD gene was codon optimized for expression in *I. orientalis* (SEQ ID NO:15) and cloned into PCR2.1-TOPO as described above in Example 1A except using the ClonTech Genome Advantage2 PCR system rather than rTth DNA polymerase. Because all six clones sequenced had at least one nucleotide error, the error-free 5' end (XbaI/PstI fragment) of one clone was joined with the error-free 3' end (PstI/PacI fragment) of a second clone through digestion and ligation. The resulting gene was digested with XbaI and PacI and ligated into similarly cut pHJJ3, creating vector pHJJ5. pHJJ5 contained the ENO1 promoter, araD gene, and PDC terminator. A NotI fragment containing the ENO1 promoter, araD gene, PDC terminator, and URA3 locus from pHJJ5 was ligated into vector pHJJ4 to generate vectors pHJJ9 (orientation 1) and pHJJ10 (orientation 2). pHJJ4 contained upstream and downstream regions of the *I. orientalis* S141G725 locus (AR, "AXR1").

pHJJ9 was linearized by sequential digest with SacI and ApaI, releasing a fragment that contained the ENO1 promoter, araD gene, PDC terminator, URA3 cassette, and AXR1 targeting sequences. The integration fragments were transformed into *I. orientalis* strain 2904 as described above in Example 1A. Transformed colonies were purified on ScD-ura media, and PCR was performed to confirm integration at the AXR1 locus. Strain 2904 transformed with linearized pHJJ9 produced strains yHJJ7 (2908) and yHJJ8 (2909), each having one copy of araB and one copy of araD from *B. thetaiotaomicron*.

Strain 2908 was grown overnight in YPD media and plated on ScD-FOA media to select for strains in which the URA3 marker had been looped out. Resulting colonies were purified on YPD media and tested on ScD-ura media to confirm uracil auxotrophy. The colonies were also confirmed by colony PCR. Ura- derivatives of strain 2908 were strains yHJJ13 (3009) and yHJJ14 (3010).

pHJJ10 was linearized by sequential digest with SacI and ApaI, releasing a fragment that contained the ENO1 promoter, araD gene, PDC terminator, URA3 cassette, and AXR1 targeting sequences. The integration fragments were transformed into *I. orientalis* strain 3009. Transformed colonies were purified on ScD-ura media, and PCR was performed to confirm integration at the AXR1 locus. Strain 3009 transformed with linearized pHJJ10 produced strain yHJJ15 (3011), having one copy of araB and two copies of araD from *B. thetaiotaomicron*.

Expression of araD was confirmed using qPCR. RNA was purified from strains 2908 (araB/araD) and 2904 (araB) using an acid phenol extraction. Genomic DNA was eliminated using a ZymoResearch DNA-free RNA kit, and cDNA was made from 4 μg of RNA using Promega Reverse Transcriptase. Genomic DNA from strain 2908 for use as a standard was isolated using a ZymoResearch YeaStar genomic DNA kit. QPCR was run using Applied Biosystems SYBR Green PCR Master Mix and araD and actin primers. The araD integrants showed approximately six times as much araD expression as actin expression, versus no expression in the araB control strain.

The URA3 marker from yHJ15 (3011) was looped out by growing cells overnight in YPD media and plating on ScD-FOA plates. Colonies were screened by colony PCR to identify colonies that lost the selection marker but retained the rest of the araD insertion, and one such colony was named yJY21. It was later confirmed that the copy of *B. thetaiotaomicron* araB was lost during the loopout event, so that strain yJY21 only had the two copies of araD.

Example 1C

Integration of *B. thetaiotaomicron* araA into an XDH Locus of *I. orientalis*

The *B. thetaiotaomicron* araA gene was codon optimized for expression in *I. orientalis* as described above in Example 1A (SEQ ID NO:5) and synthesized. Site-directed mutagenesis was used to correct nucleotide errors in the assembled gene. A clone carrying the vector with the desired gene sequence was named pJY13.

A three-piece ligation was performed using a XbaI/PacI fragment containing the *B. thetaiotaomicron* araA gene, an XhoI/PacI fragment of a cloning vector containing XYL2 (XDH) targeting sequences, a PDC terminator, and a URA3 selection cassette, and an XhoI/XbaI fragment containing the *I. orientalis* TDH3 promoter. The resulting plasmid pJY15 contained the TDH3 promoter, *B. thetaiotaomicron* araA gene, PDC terminator, and URA3 marker cassette flanked by XYL2 targeting sequences.

Plasmid pJY15 was digested with ApaI and KpnI to release the integration fragment, and linearized DNA was transformed into strain 2904 from Example 1A (contains *B. thetaiotaomicron* araB gene in the XYL1 locus). Ura+ colonies were screened by colony PCR to identify colonies with integration at the desired locus, and one such strain was named yJY16. Strain yJY16 contained one copy each of the *B. thetaiotaomicron* araB and araA genes, and was used to test AI activity relative to other sources of the araA gene.

The linearized integration fragment from pJY15 was also transformed into strain yJY21 from Example 1B (contains two copies of the *B. thetaiotaomicron* araD gene in the S141G725 locus). Ura+ colonies were screened by colony PCR to identify colonies with integration at the XYL2 locus, and one such strain was named yJY22. Strain yJY22 contained one copy of the *B. thetaiotaomicron* araA gene and two copies of the *B. thetaiotaomicron* araD gene.

The URA3 marker in yJY22 was looped out by plating on ScD-FOA plates. Colonies were screened by PCR to identify colonies that lost the selection marker but retained the rest of the araA insertion, and one such colony was named yJY23.

Strain yJY23 was transformed with the ApaI/KpnI integration fragment from pJY15, and ura+ colonies were screened by PCR to identify colonies with integration at the desired locus. One such strain was named yJY24, which had two copies each of the *B. thetaiotaomicron* araA and araD genes.

The URA3 marker from strain yJY24 was looped out by plating cells on ScD-FOA plates. Colonies were screened by PCR to identify colonies that lost the selection marker but retained the rest of the insertion, and one such colony was named yJY29.

Plasmid pHJJ3 (Example 1A) was digested with ApaI and SacI to release the integration fragment containing the *B. thetaiotaomicron* araB gene, and linearized DNA was transformed into strain yJY29. Ura+ colonies were screened by PCR to identify colonies with integration at the XYL1 site, and one such strain was named yJY30 (3409). Strain 3409 had two copies each of the *B. thetaiotaomicron* araA and araD genes and one copy of the araB gene.

The URA3 marker from strain 3409 was looped out by plating cells on ScD-FOA plates. Colonies were screened by PCR to identify colonies that lost the selection marker but retained the rest of the insertion, and one such colony was named yJY31. The linearized integration fragment from pHJJ3 was transformed into strain yJY31 in order to insert a second copy of the araB gene at the XYL1 site. Ura+ colonies was screened by PCR to identify colonies with integration at the desired locus, and one such strain was named strain yJY33 (3410).

A region of DNA containing the TEF1 promoter was amplified from *I. orientalis* genomic DNA so that the 5' end contained an XhoI restriction site and the 3' end contained an XbaI site. XhoI/XbaI cut PCR product was ligated into plasmids pHJJ3 and pHJJ18 (Example 1A) that had been similarly digested to release the ENO1 promoter. Colonies transformed with the ligation were screened by PCR for the desired insert and confirmed by sequencing. These vectors, which contained the *B. thetaiotaomicron* araB gene under the control of the ENO1 promoter, were named pHJJ33 (pHJJ3 derivative) and pHJJ35 (pHJJ18 derivative).

Plasmid pHJJ33 was digested with ApaI and SacI to release the integration fragment, and the linearized DNA was transformed into strain yJY29. Ura+ colonies were screened by PCR to identify colonies with integration at the XYL1 site, and one such strain was named yHJJ40 (3406). Strain 3406 contained two copies of the *B. thetaiotaomicron* araA and araD genes and one copy of the araB under control of the TEF1 promoter.

The URA3 marker from 3406 was looped out by growing cells overnight in YPD and plating on ScD-FOA plates. Colonies were screened by PCR to identify colonies that lost the selection marker but retained the rest of the insertion. One such colony was named yHJJ44. Plasmid pHJJ35 was digested with ApaI and SacI to release the integration fragment, and the linearized DNA was transformed into strain yHJJ44 to insert TEF1:araB at a second XYL1 locus. Ura+ colonies was screened by PCR to identify colonies with correct integration, and one such strain was named strain yHJJ47 (3408). Strain 3408 contained two copies each of the *B. thetaiotaomicron* araA, araD, and araB genes, with araB under control of the TEF1 promoter.

Example 1D

Integration of *E. coli* araD into AR Locus of *I. orientalis* Strain Containing *B. thetaiotaomicron* araB The *E. coli* araD gene (SEQ ID NO:76) was amplified from genomic DNA of strain MG1655 so that the 5' end of the gene contained an XbaI restriction site and the 3' end contained a PacI restriction site. PCR product was gel purified and digested with XbaI and PacI. The resultant fragment was ligated into pHJJ18 (Example 1A) from which the *B. thetaiotaomicron* araB gene had been digested out with XbaI and PacI. Colonies having the desired *E. coli* araD insert were confirmed by PCR, and plasmid DNA was isolated (pHJJ12). The fragment containing the ENO1 promoter, *E. coli* araD gene, PDC terminator, and URA3 marker cassette was digested from pHJJ12 with NotI and ligated into NotI-digested pHJJ4 (AXR1 targeting sequences separated by a NotI site) to obtain vectors pHJJ14 (orientation 1) and pHJJ19 (orientation 2).

Plasmid pHJJ14 was digested with ApaI and SacI to release the integration fragment, and the linearized DNA was transformed into strain 2904 (Example 1A). Ura+ colonies were screened by PCR to identify colonies with integration at the desired locus, and one such strain was named yHJJ9 (3005).

Example 1E

Integration of *L. plantarum* araD into AR Locus of *I. orientalis* Strain Containing *B. thetaiotaomicron* araB The *L. plantarum* araD gene was codon optimized for expression in *I. orientalis* using an *I. orientalis* codon usage table for back translation and synthesized so that it contained an XbaI restriction site on the 5' end and a PacI restriction site on the 3' end (SEQ ID NO:78). *L. plantarum* araD PCR product was gel purified and digested with XbaI and PacI. The resultant fragments were ligated into pHJJ18 (Example 1A) from which the *B. thetaiotaomicron* araB gene had been digested out with XbaI and PacI. Colonies having the desired *L. plantarum* araD insert were confirmed by PCR, and plasmid DNA was isolated (pHJJ13). The fragment containing the ENO1 promoter, *L. plantarum* araD, PDC terminator, and URA3 marker cassette was digested from pHJJ13 with NotI and ligated into NotI-digested pHJJ4 (AXR1 targeting sequences separated by a NotI site) to obtain vectors pHJJ15 (orientation 1) and pHJJ20 (orientation 2).

Plasmid pHJJ15 was digested with ApaI and SacI to release the integration fragment, and the linearized DNA was transformed into strain 2904 (Example 1A). Ura+ colonies were screened by PCR to identify colonies with integration at the AXR1 locus, and one such strain was named yHJJ11 (3007).

Example 1F

Integration of *L. plantarum* araA into XDH Locus of *I. orientalis* Strain Containing *B. thetaiotaomicron* araB The *L. plantarum* araA gene was codon optimized for expression in *I. orientalis* using an *I. orientalis* codon usage table for back translation and synthesized so that it contained an XbaI restriction site on the 5' end and a PacI restriction site on the 3' end (SEQ ID NO:80). The DNA was TOPO-cloned and plasmid with the desired sequence was named pJY14.

A three-piece ligation was performed using a XbaI/PacI fragment from pJY14 containing the *L. plantarum* araA gene, a XhoI/PacI fragment containing XYL2 (XDH) targeting sequences, an *I. orientalis* PDC terminator, and a URA3 selection cassette, and a XhoI/XbaI fragment containing the *I. orientalis* TDH3 promoter. The resulting plasmid pJY17 contained the TDH3 promoter, *L. plantarum* araA gene, PDC terminator, and URA3 marker cassette flanked by XYL2 targeting sequences.

Plasmid pJY17 was digested with ApaI and KpnI to release the integration fragment, and the linearized DNA was transformed into strain 2904 (Example 1A). Ura+ colonies were screened by PCR to identify colonies with integration at the XYL2 locus, and one such strain was named yJY17.

Example 1G

Integration of *B. licheniformis* araA into XDH Locus of *I. orientalis* Strain Containing *B. thetaiotaomicron* araB The 1.5 Kb *B. licheniformis* araA gene was codon optimized for expression in *I. orientalis* using an *I. orientalis* codon usage table for back translation and constructed so that it contained an XbaI restriction site on the 5' end and a PacI restriction site on the 3' end (SEQ ID NO:82). The PCR product was cloned into a TOPO vector, and directed mutagenesis was used to correct three nucleotide errors. The resulting plasmid pJY23 contained the correct codon optimized *B. licheniformis* araA gene.

A three-piece ligation was performed using a XbaI/PacI fragment of pJY23 containing *B. licheniformis* araA, a XhoI/PacI fragment of a cloning vector containing XYL2 (XDH) targeting sequences, a PDC terminator, and a URA3 selection cassette, and a XhoI/XbaI fragment containing the *I. orientalis* TDH3 promoter. The resulting plasmid pJY24 contained the TDH3 promoter, *B. licheniformis* araA gene, PDC terminator, and URA3 marker cassette flanked by XYL2 targeting sequences.

Plasmid pJY24 was digested with ApaI and KpnI to release the integration fragment, and the linearized DNA was transformed into strain 2904 (Example 1A). Ura+ colonies were screened by PCR to identify colonies with integration at the XYL2 locus, and one such strain was named yJY18.

Genetically modified *I. orientalis* strains generated in Examples 1A to 1G are summarized in Table 1.

TABLE 1

| Strain name | | araA | araB | araD |
|---|---|---|---|---|
| 2762 | Source | — | — | — |
| (parent strain) | # of copies | 0 | 0 | 0 |
| | Promoter | — | — | — |
| | Location | — | — | — |
| yHJJ2/2902 (ura+), | Source | — | *B. thetaiotaomicron* | — |
| yHJJ3/2904 (ura−) | # of copies | — | 1 | — |
| | Promoter | — | ENO1 | — |
| | Location | — | XYL1 locus | — |
| yHJJ1/2903 (ura+), | Source | — | *B. thetaiotaomicron* | — |
| yHJJ4/2905 (ura−) | # of copies | 0 | 1 | 0 |
| | Promoter | — | ENO1 | — |
| | Location | — | XYL1 locus | — |
| yHJJ7/2908 (ura+), | Source | — | *B. thetaiotaomicron* | *B. thetaiotaomicron* |
| yHJJ8/2909 (ura+), | | | | |
| yHJJ13/3009 (ura−), | # of copies | 0 | 1 | 1 |
| yHJJ14/3010 (ura−) | Promoter | — | ENO1 | ENO1 |
| | Location | — | XYL1 locus | AXR1 locus |
| yHJJ9/3005 | Source | — | *B. thetaiotaomicron* | *E. coli* |
| | # of copies | 0 | 1 | 1 |
| | Promoter | — | ENO1 | ENO1 |
| | Location | — | XYL1 locus | AXR1 locus |
| yHJJ11/3007 | Source | — | *B. thetaiotaomicron* | *L. plantarum* |
| | # of copies | 0 | 1 | 1 |
| | Promoter | — | ENO1 | ENO1 |
| | Location | — | XYL1 locus | AXR1 locus |
| yHJJ15/3011 | Source | — | *B. thetaiotaomicron* | *B. thetaiotaomicron* |
| | # of copies | 0 | 1 | 2 |
| | Promoter | — | ENO1 | ENO1 |
| | Location | — | XYL1 locus | AXR1 locus |

TABLE 1-continued

| Strain name | | araA | araB | araD |
|---|---|---|---|---|
| yJY16 | Source | *B. thetaiotaomicron* | *B. thetaiotaomicron* | — |
| | # of copies | 1 | 1 | 0 |
| | Promoter | TDH3 | ENO1 | — |
| | Location | XYL2 locus | XYL1 locus | — |
| yJY17 | Source | *L. plantarum* | *B. thetaiotaomicron* | — |
| | # of copies | 1 | 1 | 0 |
| | Promoter | TDH3 | ENO1 | — |
| | Location | XYL2 locus | XYL1 locus | — |
| yJY18 | Source | *B. licheniformis* | *B. thetaiotaomicron* | — |
| | # of copies | 1 | 1 | 0 |
| | Promoter | TDH3 | ENO1 | — |
| | Location | XYL2 locus | XYL1 locus | — |
| yJY21 | Source | — | — | *B. thetaiotaomicron* |
| | # of copies | 0 | 0 | 2 |
| | Promoter | — | — | ENO1 |
| | Location | — | — | AXR1 locus |
| yJY22 (ura+), yJY23 (ura−) | Source | *B. thetaiotaomicron* | — | *B. thetaiotaomicron* |
| | # of copies | 1 | 0 | 2 |
| | Promoter | TDH3 | — | ENO1 |
| | Location | XYL2 locus | — | AXR1 locus |
| yJY24 (ura+), yJY29 (ura−) | Source | *B. thetaiotaomicron* | — | *B. thetaiotaomicron* |
| | # of copies | 2 | 0 | 2 |
| | Promoter | TDH3 | — | ENO1 |
| | Location | XYL2 locus | — | AXR1 locus |
| yHJJ40/3406 (ura+), yHJJ44 (ura−) | Source | *B. thetaiotaomicron* | *B. thetaiotaomicron* | *B. thetaiotaomicron* |
| | # of copies | 2 | 1 | 2 |
| | Promoter | TDH3 | TEF1 | ENO1 |
| | Location | XYL2 locus | XYL1 locus | AXR1 locus |
| yHJJ47/3408 | Source | *B. thetaiotaomicron* | *B. thetaiotaomicron* | *B. thetaiotaomicron* |
| | # of copies | 2 | 2 | 2 |
| | Promoter | TDH3 | TEF1 | ENO1 |
| | Location | XYL2 locus | XYL1 locus | AXR1 locus |
| yJY30/3409 (ura+), yJY31 (ura−) | Source | *B. thetaiotaomicron* | *B. thetaiotaomicron* | *B. thetaiotaomicron* |
| | # of copies | 2 | 1 | 2 |
| | Promoter | TDH3 | ENO1 | ENO1 |
| | Location | XYL2 locus | XYL1 locus | AXR1 locus |
| yJY33/3410 | Source | *B. thetaiotaomicron* | *B. thetaiotaomicron* | *B. thetaiotaomicron* |
| | # of copies | 2 | 2 | 2 |
| | Promoter | TDH3 | ENO1 | ENO1 |
| | Location | XYL2 locus | XYL1 locus | AXR1 locus |

Example 2

Analysis of RK, RE, and AI Activity in *I. orientalis* Strains Containing Bacterial araA, araB, and/or araD Genes Strains generated in Example 1 were tested for RK, RE, and AI activity.

Example 2A

Analysis of RK Activity

RK catalyzes the ATP-dependent conversion of L-ribulose to L-ribulose 5-phosphate, producing ADP. RK activity is followed by regeneration of ATP with PEP catalyzed by pyruvate kinase. This reaction produces pyruvate, which is reduced to lactate with NADH and lactate dehydrogenase.

Assays contained 30 mM Tris HCl, pH 7.5, 3.3 mM $MgCl_2$, 0.3 mM EDTA, 1.7 mM PEP, 0.7 mM ATP, >4 U/mL each pyruvate kinase and lactate dehydrogenase (premixed PK+LDH from Sigma), 2 mM ribulose, 0.5 mM NADH, and cell extract. In initial assays, D-ribulose was used as a substrate. In later assays, L-ribulose (ZuChem) was used. Due to the generally high expression level of this enzyme, extracts were diluted 10-fold in 50 mM NaTES, pH 7.0, 100 mM NaCl, 0.1 mM $MnCl_2$, 0.01% (v/v) Tween 20. The reaction was carried out at room temperature, and the change in absorbance at 340 nm was monitored over 10 minutes at 15 second intervals. Assays were carried out in microtiter wells with a final assay volume of 200 µL. The reaction was initiated by addition of NADH alone or with L-ribulose. The measured $\Delta A_{340}$ was converted to mM using an effective path length of 0.576 cm (determined by measuring the absorbance of a solution of NADH under these conditions versus that measured in a 1-cm cuvette, and applying Beer's law).

In assays with D-ribulose as substrate, a net specific activity of 1.0 units/mg protein was measured in crude extracts of strain 2902 (1 copy of *B. thetaiotaomicron* araB). In assays with L-ribulose as substrate, the RK specific activity in extracts of strain 3409 (1 copy of *B. thetaiotaomicron* araB, 2 copies each of *B. thetaiotaomicron* araA and araD genes) was 1.4 units/mg protein.

Because the RK assay measures the production of ADP which may arise from any kinase activity, it has a high background activity in the absence of L-ribulose (approximately ⅓ as much as in the presence of L-ribulose). This background activity is present in the parent strain, and does not increase when L-ribulose is added to assays with extracts from these cells. The background activity is not substantially decreased in dialyzed extracts, suggesting that the kinases utilize macromolecular substrates such as proteins or nucleic acids. In the specific activities listed above, background activity in the absence of substrate is subtracted from the activity measured in the presence of L-ribulose.

Example 2B

Analysis of RE Activity

RE interconverts L-ribulose 5-P and D-xylulose 5-P. L-ribulose 5-P is not commercially available, and thus needs to be made either in a separate reaction or in a coupled reaction by RK. Since RK from *B. thetaiotaomicron* is highly expressed and/or active in *I. orientalis*, extracts from cells with RK generally have excess RK over RE activity, meaning that they produce an excess of L-ribulose 5-P from L-ribulose and ATP.

D-xylulose 5-P is detected in a coupled reaction scheme by adding D-ribose 5-P and TKL plus thiamine PP to generate S7P plus G3P; converting the G3P to dihydroxyacetone P (DHAP) with triosephosphate isomerase (TPI); and reducing DHAP to glycerol 3-P with NADH-dependent glycerol 3-P dehydrogenase (G3PDH). Activity of RE is thus coupled to the oxidation of the NADH. Coupling enzymes are added exogenously, but are likely be present in the extract as well, which should not affect results as they should all be in excess over RE activity.

Assays contained 50 mM Tris HCl, pH 7.5, 3.3 mM $MgCl_2$, 2 mM ATP, 0.1 mM TPP, 1 mM D-ribose 5-P, 0.05 U/mL transketolase, 4.5 U/mL TPI, 1.5 U/mL G3PDH, 4 mM L-ribulose, and 0.5 mM NADH. The reaction was carried out at room temperature, and the change in absorbance at 340 nm monitored over 10 minutes at 15 second intervals. Assays were carried out in microtiter wells with a final assay volume of 200 µl. The reaction was initiated by the addition of NADH alone or with L-ribulose. The measured $\Delta A_{340}$ was converted to mM using an effective path length of 0.576 cm (determined by measuring the absorbance of a solution of NADH under these conditions versus that measured in a 1-cm cuvette, and applying Beer's law).

After background activity was subtracted, *I. orientalis* strain 2908, which contained single copies of the *B. thetaiotaomicron* araB and araD genes, had 0.022 U/mg RE activity. Strain 3005, which contained *E. coli* araD and *B. thetaiotaomicron* araB, had activity similar to strain 2908. Strain 3007, which contained *L. plantarum* araD and *B. thetaiotaomicron* araB, had approximately half the specific activity of the other two strains.

Example 2C

Analysis of AI Activity

AI assays contained 100 mM Na TES, pH 7.0, 0.3 mM $MnCl_2$, 37.5 units/mL sorbitol dehydrogenase (SIGMA S3764), 0.5 mM NADH, 66.7 mM L-arabinose, and cell extract. The reaction was carried out at room temperature, and the change in absorbance at 340 nm monitored over 10 minutes at 15 second intervals. Assays were carried out in microtiter wells at a final assay volume of 200 µL. The reaction was initiated by the addition of NADH alone or with L-arabinose. The measured $\Delta A_{340}$ was converted to mM using an effective path length of 0.576 cm (determined by measuring the absorbance of a solution of NADH under these conditions versus that measured in a 1-cm cuvette, and applying Beers law).

Strain yJY16 (1 copy each of *B. thetaiotaomicron* araA and araB) exhibited a specific activity of 0.045 units/mg, while yJY17 (one copy each of *L. plantarum* araA and *B. thetaiotaomicron* araB) and yJY18 (one copy each of *B. licheniformis* araA and *B. thetaiotaomicron* araB) exhibited specific activities of 0.012 and 0.010 units/mg, respectively. Significantly higher specific activities were measured in extracts from cells carrying two copies of *B. thetaiotaomicron* araA (yJY24 and 3409), which may be a reflection of the instability of heterochromosomes in *I. orientalis*.

AI activity in extracts of strain 3409 carrying the complete arabinose pathway was 0.24 U/mg. This number was higher than measured in preliminary experiment for several reasons: this strain carried two copies of the integrated *B. thetaiotaomicron* araA gene instead of one; the amount of coupling enzyme sorbitol dehydrogenase was optimized; and cell growth and protein extraction was improved.

Example 3

Figure 2:
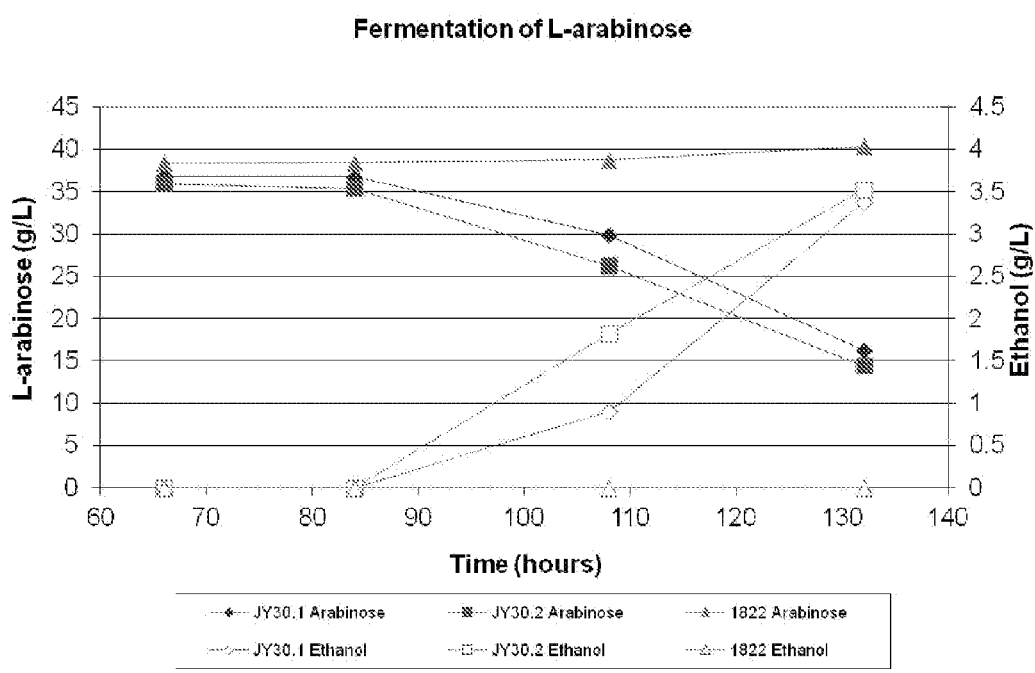
FIG. 2: Fermentation of L-arabinose to ethanol by strains 1822, JY30.1, and JY30.2.

Characterization of *I. orientalis* Strains Containing *B. thetaiotaomicron* Arabinose Pathway Genes Two sister strains of 3409 (yJY30.1 and yJY30.2) and strain 1822 (parent strain) were tested for their ability to ferment arabinose to ethanol. Strains yJY30.1 and JY30.2 contained copies of all three *B. thetaiotaomicron* arabinose pathway genes (two copies each of araA and araD, one copy of araB). Cells were grown in YP plus 40 g/L arabinose at 37° C. and 100 rpm. After 132 hours, both *B. thetaiotaomicron* arabinose pathway strains consumed about 22 g/L arabinose while producing about 4 g/L ethanol (FIG. 2).

Example 4

Integration Of *B. thetaiotaomicron* Arabinose Pathway genes into *I. orientalis* Strain Engineered to Utilize Xylose

*I. orientalis* strain 3489 had previously been engineered to ferment xylose to ethanol. Strain 3489 contained four copies of an exogenous gene encoding *B. thetaiotaomicron* XI, two copies of a native exogenous gene encoding XK, two copies each of native exogenous non-oxidative pentose phosphate pathway genes TAL, RKI, and RPE, and two copies of a native exogenous ADH1 gene, all under the control of strong native exogenous glycolytic promoters. Construction of this strain also included gene deletions for XR, XDH, S141G725, S141G4738, S141G1158-1159, S141G8160, and GALE. Strain 3489 was incapable of fermenting arabinose to ethanol. Therefore, *B. thetaiotaomicron* araA and araD genes were inserted into strain 3489 at the site of a putative *L. orientalis* ADH homolog (SEQ ID NO:74, locus S141G9091), and the *B. thetaiotaomicron* araB gene was inserted at the site of a second ADH homolog (SEQ ID NO:84, locus S141G1202).

Example 4A

Construction of *B. thetaiotaomicron* araA and araD Insertion Vector

To generate an insertion vector with the *B. thetaiotaomicron* araA gene linked to the *I. orientalis* TDH3 promoter and TAL terminator, a XhoI/PacI fragment from vector pJY39 containing the TAL terminator, XYL1 targeting sites, and a URA3 selection cassette was ligated to a XhoI/PacI fragment from pJY15 (Example 1C) containing the *I. orientalis* TDH3 promoter and *B. thetaiotaomicron* araA gene. Plasmids from colonies transformed with the ligation mix were screened by restriction enzyme digests with HindIII and SphI, and the correct plasm id was named pLUN111.

To combine the araA and araD genes into a single plasmid, an AscI/ApaI fragment from pLUN111 containing the *I. orientalis* TDH3 promoter, *B. thetaiotaomicron* araA gene, *I. orientalis* TAL terminator, URA3 selection cassette, and downstream targeting sequence was ligated to an AscI/ApaI fragment of pJY33, which contained the vector backbone, upstream targeting sequence, *I. orientalis* ENO1 promoter, *B. thetaiotaomicron* araD gene, and *I. orientalis* PDC terminator. Plasmids from colonies transformed with the ligation were screened for the desired insertion by restriction digest. The resulting plasmid, pLUN112, contained the B. thetaiotaomicron araA gene under the control of the TDH3 promoter and the *B. thetaiotaomicron* araD gene under the control of the ENO1 promoter.

A NotI fragment from pLUN112 containing the araA and araD genes and their regulatory elements, as well as the URA3 selection cassette, was ligated into NotI-cut pHJJ22 vector. pHJJ22 contained the regions upstream and downstream of the 9091 gene separated by a NotI site. Thus, the ligation inserted araA/araD between the 9091 flanking sequences. Colonies resulting from transformation of the ligation were screened for the presence of the desired insert by colony PCR. Plasmids were isolated for clones having the expected PCR products, and the isolated plasmids were screened for orientation of the araA/araD insert using a SphI restriction digest. Plasmids were named pLUN113 (orientation 1) and pLUN114 (orientation 2).

Example 4B

Construction of *B. thetaiotaomicron* araB Insertion Vector

To generate an insertion vector with the *B. thetaiotaomicron* araB gene linked to the ENO1 promoter between 1202 gene flanking regions, NotI-cut pHJJ74, a vector containing the upstream and downstream target sequences separated by a NotI site, was ligated to the NotI insert from pHJJ2 (Example 1A), which contained the *I. orientalis* ENO1 promoter, *B. thetaiotaomicron* araB gene, *I. orientalis* PDC terminator, and URA3 selection cassette. Plasmid DNA was isolated from colonies transformed with the ligation and screened by digestion with SphI and XhoI. Plasmids were named pLUN125 (orientation 1) and pLUN126 (orientation 2).

To generate an insertion vector with the araB gene linked to the TEF1 promoter between 1202 gene flanking regions, NotI-cut pHJJ74 was ligated to the NotI insert from pHJJ33 (Example 1C), which contained the *I. orientalis* TEF1 promoter, *B. thetaiotaomicron* araB gene, *I. orientalis* PDC terminator, and URA3 selection cassette. Plasmid DNA was isolated from colonies transformed with the ligation and screened by digestion with SphI and XhoI. Plasmids were named pLUN127 (orientation 1) and pLUN128 (orientation 2).

Example 4C

Integration of *B. thetaiotaomicron* araA and araD into *I. orientalis* Strain 3514

*I. orientalis* strain yHJJ84 (3514), a ura– derivative of strain 3489, was transformed with ApaI/SacI linearized pLUN113 (Example 4A) and plated on ScD-ura media. Genomic DNA from purified transformants was screened by PCR and clones identified as having a correctly inserted araA/araD cassette were named yARA21.

The URA3 marker gene from yARA21 was looped out by growing cells overnight in YPD and plating on ScD-FOA plates. Genomic DNA prepared from loopout colonies was screened by PCR across both integration junctions and one colony (yARA22) was identified as having retained the integration but lost the URA3 gene. This colony was plated on ScD-ura plates to verify lack of growth without uracil supplementation.

The second araA/araD integration cassette was added to yARA22 by transforming with ApaI/SacI linearized pLUN114 (Example 4A). Transformants were selected on ScD-ura plates and single colony purified. The two junctions for each locus were screened in separate PCR reactions. Clones identified as having both copies of araA/araD correctly inserted were named yARA25.

The URA3 marker gene from yARA25 was looped out by growing cells overnight in YPD and plating on ScD-FOA plates. Loopout colonies were screened in two separate PCR reactions to identify colonies that retained the desired integration. These clones were plated on ScD-ura to verify lack of growth without uracil supplementation. The correct loopout clones were named yARA26.

Example 4D

Integration of *B. thetaiotaomicron* araB into *I. orientalis* Strain yARA26

To integrate the first copy of the *B. thetaiotaomicron* araB gene linked to the ENO1 promoter, *I. orientalis* strain yARA26 (Example 4C) was transformed with ApaI/SacI linearized pLUN125 (Example 4B). Transformants were selected on ScD-ura plates and screened by PCR across both integration junctions. Clones identified as having the EN01:araB fragment inserted at the 1202 locus were named yARA29.

To integrate the first copy of the *B. thetaiotaomicron* araB gene linked to the TEF1 promoter, *I. orientalis* strain yARA26 (Example 4C) was transformed with ApaI/SacI linearized pLUN127 (Example 4B). Transformants were selected on ScD-ura plates and screened by PCR across both integration junctions. Clones identified as having the TEF1:araB fragment inserted at the 1202 locus were named yARA30.

To loop out the URA3 marker gene from yARA29 and yARA30, both strains were grown on YPD overnight and plated on ScD-FOA media. Single colonies from yARA29 were lysed and screened in two separate PCR reactions. For yARA30 loopouts, genomic DNA was prepared and screened in two separate PCR reactions. Loopout colonies were screened by PCR to identify those that had lost the URA3 gene but retained the araB integration. These strains were replica plated on ScD-ura to verify lack of growth without uracil. The correct loopouts of yARA29 were named yARA33, and the correct loopouts of yARA30 were named yARA34.

To integrate the second copy of araB linked to the ENO1 promoter, strain yARA33 was transformed with ApaI/SacI linearized pLUN126 (Example 4B). Transformants were selected on ScD-ura and screened in separate PCR reactions to verify both junctions of the integration event. Clones identified as having the second copy of ENO1:araB correctly integrated were designated strain yARA36 (3936). These clones contained two copies each of the *B. thetaiotaomicron* araA, araB, and araD genes, with the araB genes under the control of the ENO1 promoter.

To integrate the second copy of araB linked to the TEF1 promoter, strain yARA34 was transformed with linearized integration fragment from ApaI/SacI digested pLUN128 (Example 4B). Genomic DNA of ura+ transformants was purified and screened in separate PCR reactions to verify both junctions of the integration event. Clones identified as having the second copy of TEF1:araB gene correctly integrated were designated strain yARA38 (3937). These clones contained two copies each of the *B. thetaiotaomicron* araA, araB, and araD genes, with the araB genes under the control of the TEF1 promoter.

Genetically modified *I. orientalis* strains generated in Examples 4C and 4D are summarized in Table 2.

TABLE 2

| Strain name | | araA | araB | araD |
|---|---|---|---|---|
| 3489 (ura+), 3514/yHJJ84 (ura−) (xylose fermenting parent strain) | Source | — | — | — |
| | # of copies | 0 | 0 | 0 |
| | Promoter | — | — | — |
| | Location | — | — | — |
| yARA21 (ura+), yARA22 (ura−) | Source | *B. thetaiotaomicron* | — | *B. thetaiotaomicron* |
| | # of copies | 1 | 0 | 1 |
| | Promoter | TDH3 | — | ENO1 |
| | Location | 9091 | — | 9091 |
| yARA25 (ura+), yARA26 (ura−) | Source | *B. thetaiotaomicron* | — | *B. thetaiotaomicron* |
| | # of copies | 2 | 0 | 2 |
| | Promoter | TDH3 | — | ENO1 |
| | Location | 9091 | — | 9091 |
| yARA29 (ura+), yARA33 (ura−) | Source | *B. thetaiotaomicron* | *B. thetaiotaomicron* | *B. thetaiotaomicron* |
| | # of copies | 2 | 1 | 2 |
| | Promoter | TDH3 | ENO1 | ENO1 |
| | Location | 9091 | 1202 | 9091 |
| yARA30 (ura+), yARA34 (ura−) | Source | *B. thetaiotaomicron* | *B. thetaiotaomicron* | *B. thetaiotaomicron* |
| | # of copies | 2 | 1 | 2 |
| | Promoter | TDH3 | TEF1 | ENO1 |
| | Location | 9091 | 1202 | 9091 |
| 3936/yARA36 | Source | *B. thetaiotaomicron* | *B. thetaiotaomicron* | *B. thetaiotaomicron* |
| | # of copies | 2 | 2 | 2 |
| | Promoter | TDH3 | ENO1 | ENO1 |
| | Location | 9091 | 1202 | 9091 |
| 3937/yARA38 (ura+), yLUN011 (ura−) | Source | *B. thetaiotaomicron* | *B. thetaiotaomicron* | *B. thetaiotaomicron* |
| | # of copies | 2 | 2 | 2 |
| | Promoter | TDH3 | TEF1 | ENO1 |
| | Location | 9091 | 1202 | 9091 |

Example 5

Characterization of Xylose-Utilizing *I. orientalis* Strains Engineered to Contain *B. thetaiotaomicron* Arabinose Pathway genes

*I. orientalis* dual pathway strains 3936 (Example 4D; two copies each of TDH3:araA, ENO1:araB, and ENO1:araD) and 3937 (Example 4D; two copies each of TDH3:araA, TEF1:araB, and ENO1:araD) were characterized using a shake flask experiment. Control strains for these experiments were the arabinose pathway strain 3408 (Example 1C) and xylose pathway strain yHJJ169 (3922). Strain 3922 contains the same genetic background as strain 3489 (xylose-utilizing strain from which strains 3936 and 3937 were derived), along with deletions at the 9091 and 1202 sites that served an integration sites for arabinose pathway genes in the dual pathway strains. Thus, the only genetic difference between strain 3922 and dual pathway strains 3936/3937 is the presence of the arabinose pathway genes in the latter.

All strains were grown aerobically overnight in YP with 20 g/L arabinose, and the amount of culture needed inoculate to an $OD_{600}=0.8$ was calculated. The calculated volume of culture was centrifuged at 4000 RPM for four minutes and the cell pellet was resuspended in 500 µL of YP+20 g/L arabinose. This was used to inoculate fermentative shake flasks to $OD_{600}=0.8$. Due to residual growth on YP, this protocol was sufficient to collect enough biomass to inoculate strain 3922.

Figure 3:
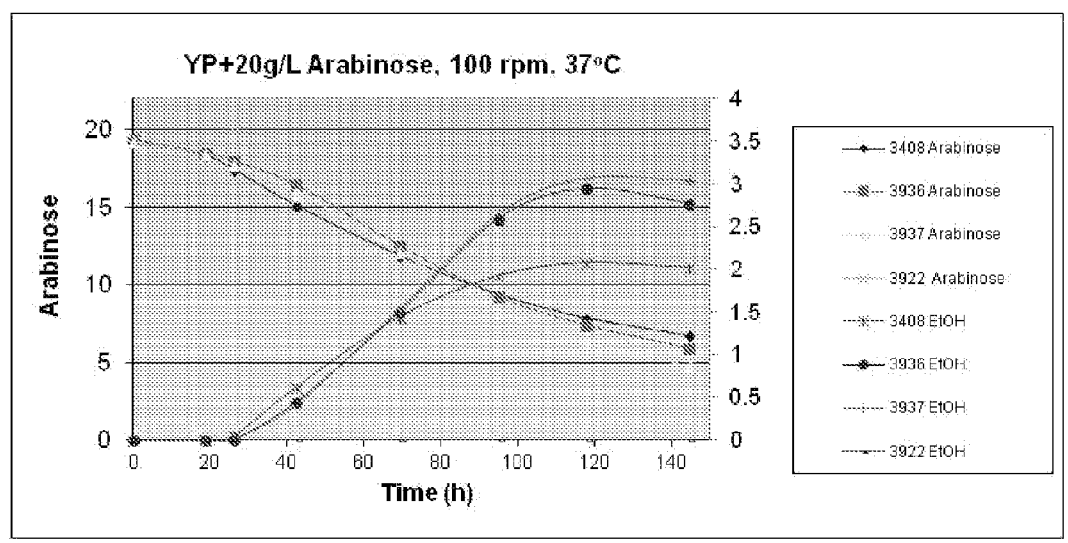
FIG. 3: Fermentation of arabinose to ethanol by strains 3922, 3936, 3937, and 3408 in YP media with 20 g/L arabinose.

Strains 3936 and 3937 behaved similar to or slightly better than strain 3408 with regard to arabinose consumption and ethanol production (FIG. 3), with each strain consuming approximately 12-14 g of arabinose in 145 hours and producing around 3-4 g/L of ethanol. As expected, strain 3922 did not consume arabinose or produce ethanol. These results confirmed that the exogenous arabinose pathways in strains 3936 and 3937 were complete and conferred these strains with the ability to ferment arabinose to ethanol.

Figure 4:
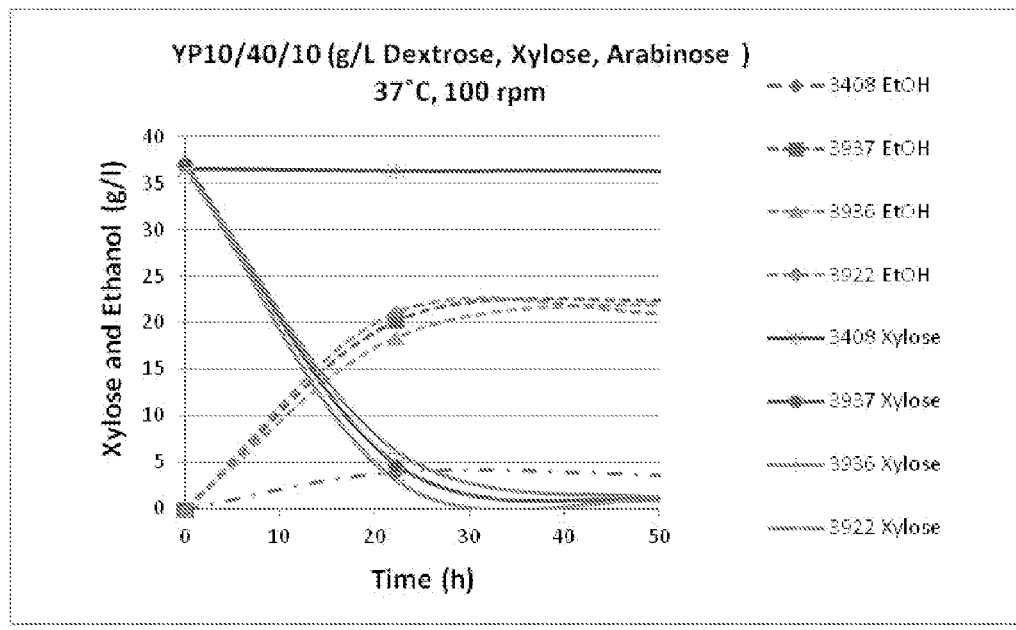
FIG. 4: Fermentation of xylose to ethanol by strains 3922, 3936, 3937, and 3408 in YP media with 10 g/L dextrose, 40 g/L xylose, and 10 g/L arabinose.
Figure 5:
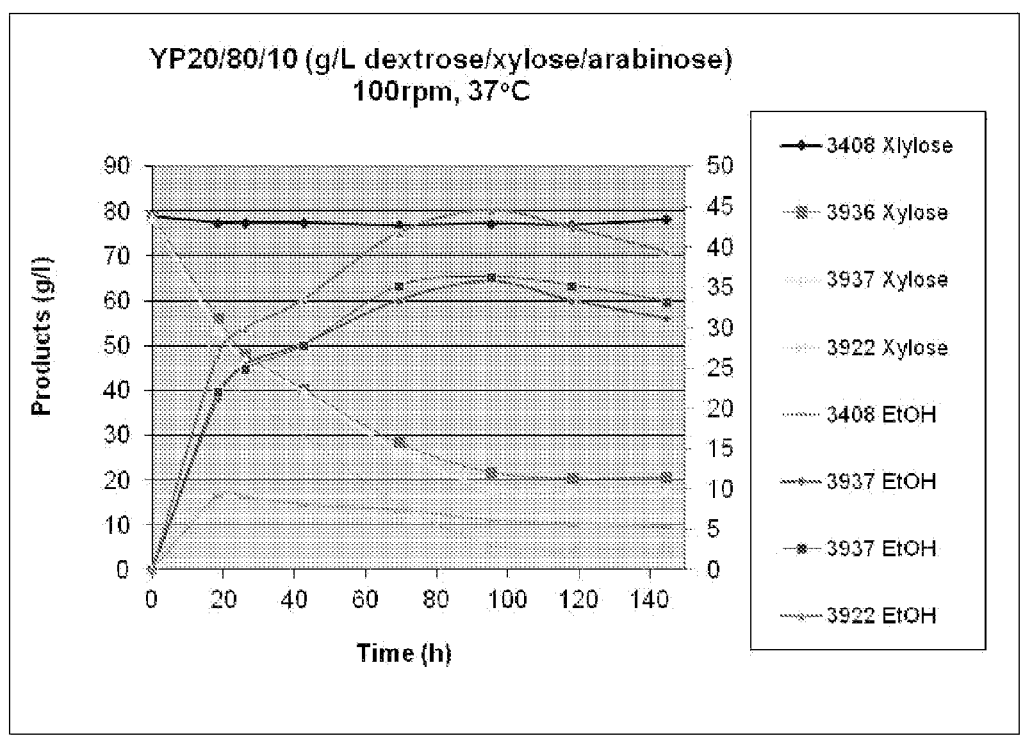
FIG. 5: Fermentation of xylose to ethanol by strains 3922, 3936, 3937, and 3408 in YP media with 20 g/L dextrose, 80 g/L xylose, and 10 g/L arabinose.

All four strains were next characterized in YP media containing either 20 g/L dextrose, 80 g/L xylose, and 10 g/L arabinose or 10 g/L dextrose, 40 g/L xylose, and 10 g/L arabinose. Strains 3936 and 3937 exhibited the ability to ferment xylose to ethanol and performed similarly to the control strain 3922 in the lower sugar media (FIG. 4). In the higher sugar media, however, xylose utilization was decreased in the dual pathway strains compared to xylose pathway strain 3922 (FIG. 5). This decrease in xylose utilization was observed even in media lacking arabinose, indicating that one of the arabinose pathway enzymes is responsible for decreased xylose utilization.

Figure 6:
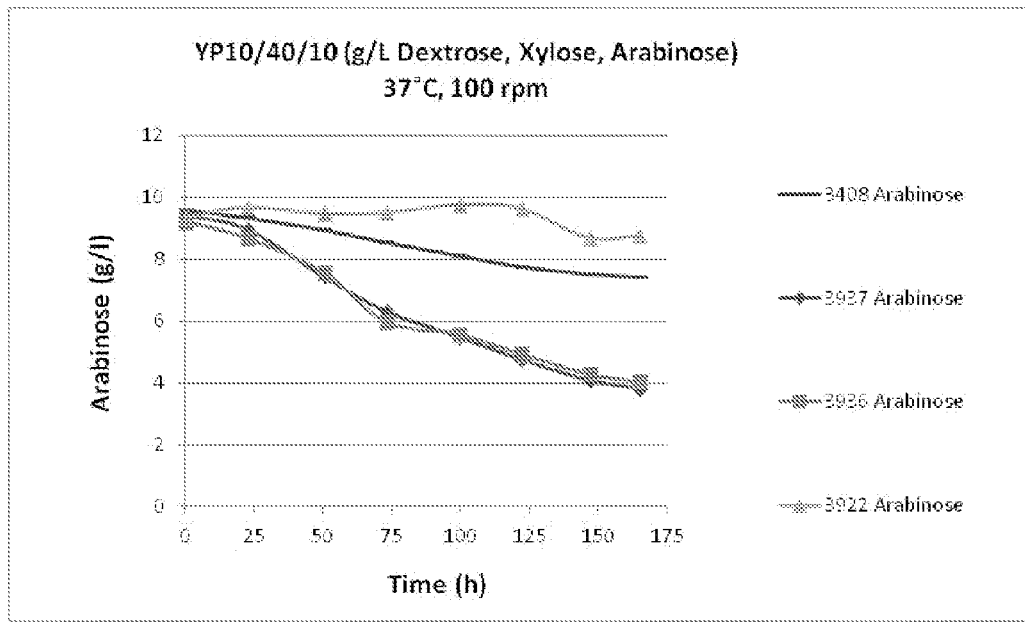
FIG. 6: Fermentation of arabinose by strains 3922, 3936, 3937, and 3408 in YP media with 10 g/L dextrose, 40 g/L xylose, and 10 g/L arabinose.

Arabinose consumption in the dual pathway strains appeared to begin only after dextrose and xylose were depleted. In the lower xylose media, the dual pathway strains used about 5 g/L arabinose, but this level of consumption required about 160 hours since arabinose was only consumed after xylose was depleted (FIG. 6). In the higher xylose media, the last 5 g of xylose was not consumed, and thus no arabinose was utilized.

Example 6

Figure 30:
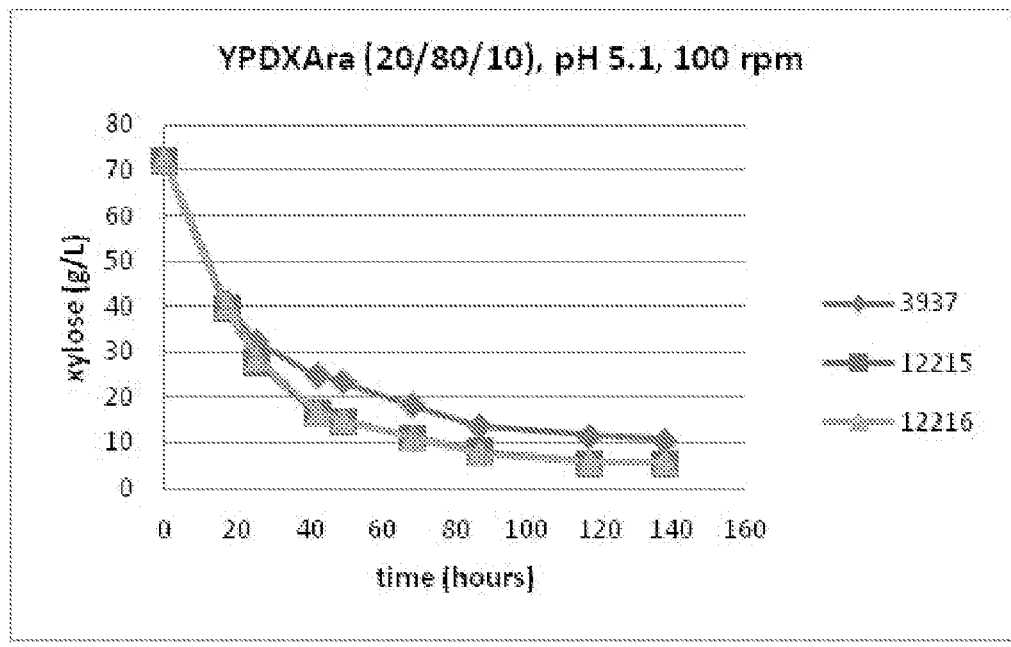
FIG. 30: Xylose consumption by strains 3937, 12215, and 12216 in YP media with 20 g/L dextrose, 80 g/L xylose, and 10 g/L arabinose.
Figure 31:
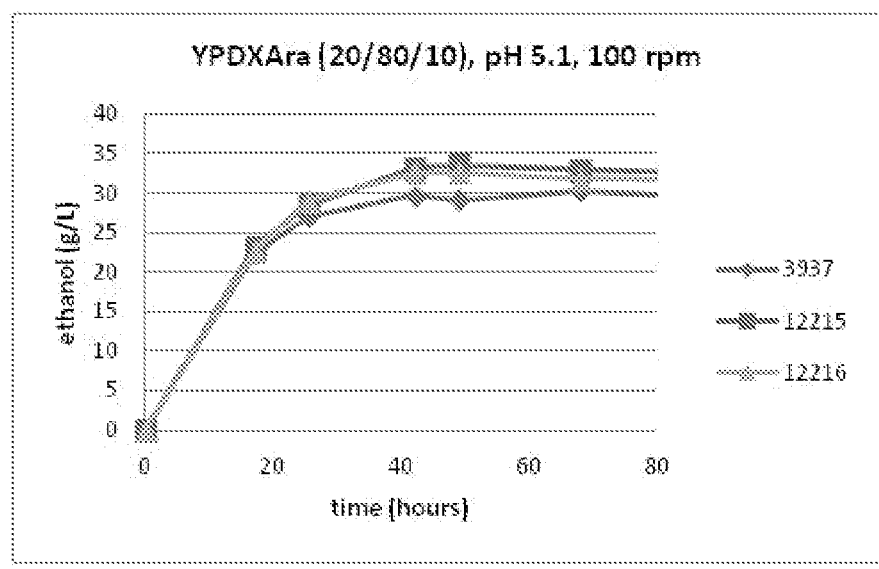
FIG. 31: Ethanol production by strains 3937, 12215, and 12216 in YP media with 20 g/L dextrose, 80 g/L xylose, and 10 g/L arabinose.
Figure 32:
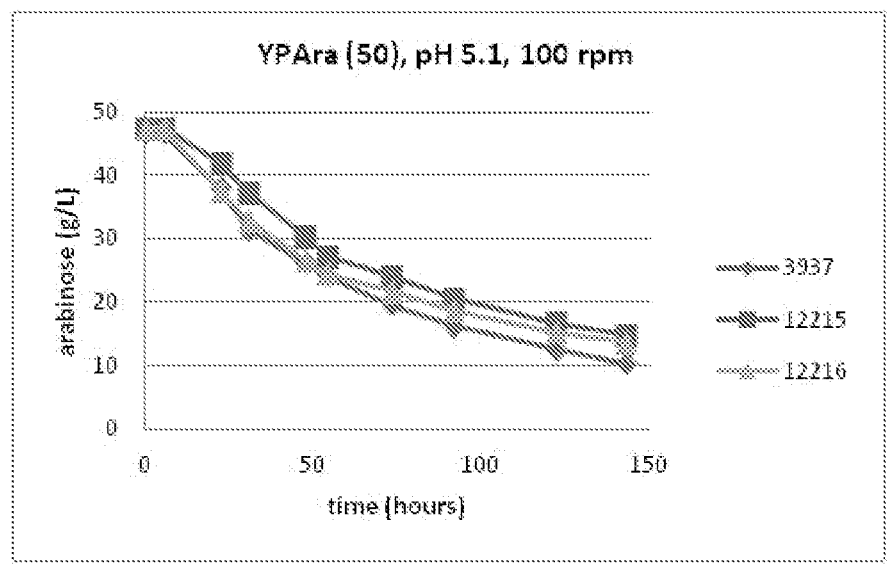
FIG. 32: Arabinose consumption by strains 3937, 12215, and 12216 in YP media with 50 g/L arabinose.

Utilization of *L. citreum* and Non-Codon Optimized *B. thetaiotaomicron* araB Gene Evaluation of strains having partial arabinose pathways showed that the inhibitory effect of the pathway on xylose utilization resulted primarily from action of the araB gene. Alternate araBs having lower activity than the codon optimized *B. thetaiotaomicron* araB were identified. A non-codon optimized *B. thetaiotaomicron* araB and an *L. citreum* araB had about $1/100^{th}$ and $1/33r^d$ the activity of codon optimized *B. thetaiotaomicron* araB respectively. Two copies of the non-codon optimized *B. thetaiotaomicron* or *L. citreum* araBs were integrated into strain yARA26 (Example 4C; contains two copies of *B. thetaiotaomicron* araA and araD), giving rise to strains 12216 and 12215, respectively. These strains were tested, along with control strain 3937, in YP media with mixed sugars (20 g/L dextrose, 80 g/L xylose, and 10 g/L arabinose) and in YP media with 50 g/L arabinose. In the mixed sugar media, strains 12215 and 12216 showed better xylose utilization and ethanol production than strain 3937 (FIGS. 30 and 31). In the arabinose-only media, strain 3937 had slightly faster arabinose use than strains 12215 or 12216 (FIG. 32).

Example 7

Identification of *K. marxianus* Xylose Transporter Genes

*I. orientalis* strains engineered for xylose utilization do not utilize xylose as a carbon source until the vast majority of glucose in the media has been utilized. This could be due to low xylose uptake into the cell relative to glucose uptake. If this is the case, it would be expected that modifications that increase xylose uptake in yeast cells would also increase xylose utilization.

The *K. marxianus* genome was screened for uncharacterized sugar transporters in order to evaluate the impact of these transporters on xylose consumption. Two of the putative transporter genes identified in this screen, KHT105 and RAG4, were selected for further study. The closest BLAST matches for both of these genes were hexose transporters. The nucleotide sequence of the coding region of the KHT105 gene is set forth in SEQ ID NO:1, and the amino acid sequence encoded by the gene is set forth in SEQ ID NO:2. The nucleotide sequence of the coding region of the RAG4 gene is set forth in SEQ ID NO:3, and the amino acid sequence encoded by the gene is set forth in SEQ ID NO:4.

Example 8

Characterization of *K. marxianus* Xylose Transporter Genes

BLAST analysis of the putative *K. marxianus* sugar transporter genes from Example 7 indicated that both genes shared their highest degree of homology with hexose transporters. To determine whether the sugar transporters encoded by these genes were also capable of transporting pentose sugars such as xylose, the genes were cloned and characterized by various xylose utilization assays.

Both genes were amplified from *K. marxianus* genomic DNA using primers that contained XbaI and PacI restriction sites, and the genes were TOPO cloned and sequenced. The transporter genes were digested from the TOPO vectors with XbaI and PacI and were ligated into similarly cut vector pHJJ16, generating the plasmids pJY20 (KHT105) and pJY21 (RAG4). Vector pHJJ16 contains an *I. orientalis* ARS sequence, which allows maintenance of the plasmid in the cytoplasm of the host, a PDC promoter upstream of the XbaI-PacI cloning site, and a URA3 selection marker.

Xylose fermenting *I. orientalis* strains yJY15 (3250) and yJLJ70 (3099) were transformed with plasmids pJY20, pJY21, and pHJJ16 (control). Prior to transformation, strain 3250 contained two copies each of an exogenous *B. thetaiotaomicron* XI gene, a native endogenous XK gene, and a native sequence exogenous XK gene. Strain 3099 had the same genetic changes as 3250, with two additional copies of the *B. thetaiotaomicron* XI gene. *I. orientalis* strains containing XI and XK genes had previously been shown to exhibit xylose utilization and ethanol production (see, e.g., WO04/099381). Transformed cells were plated with xylose as the sole carbon source, and growth was assessed. The transformants exhibited increased growth on xylose plates at 48 hours versus the control strain, indicating that both genes functioned in xylose transport and that xylose transport was a limiting factor in xylose utilization in *I. orientalis*.

Plasmid pJY27 was generated by ligating a XhoI/PacI fragment from an AXR1 integration vector containing the *I. orientalis* PDC terminator and URA3 selection cassette and an XhoI/PacI fragment containing the *I. orientalis* PDC promoter and *K. marxianus* KHT105 transporter gene. The resulting plasmid was digested with SacI and ApaI, and linearized integration fragments were transformed into *I. orientalis* strain 3099. Ura+ colonies were screened by colony PCR to identity cells with the desired integration using 5' and 3' AXR1 outside primers in combination with a primer homologous to the PDC promoter or URA3 cassette. One of the positive colonies was named yJY19.

Figure 7:
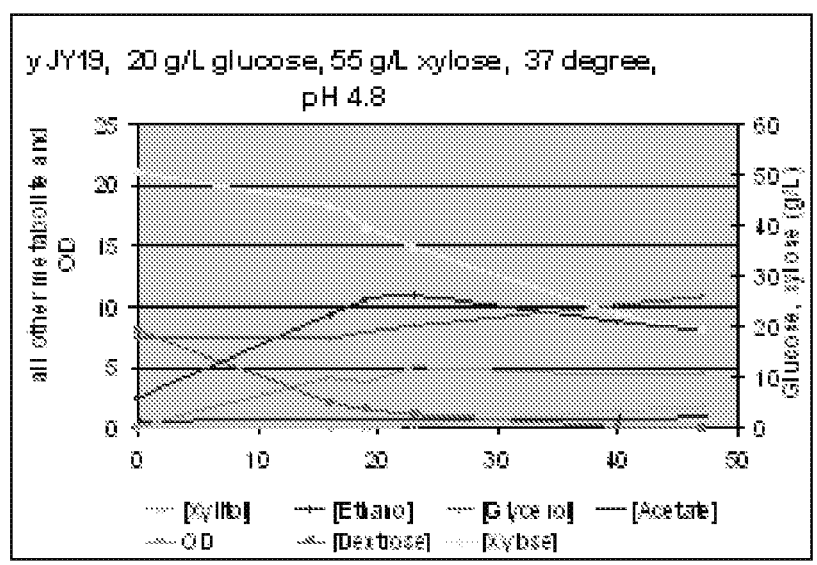
FIG. 7: Fermentation of xylose to ethanol by strain yJY19 in YP media with 20 g/L glucose and 55 g/L xylose.
Figure 8:
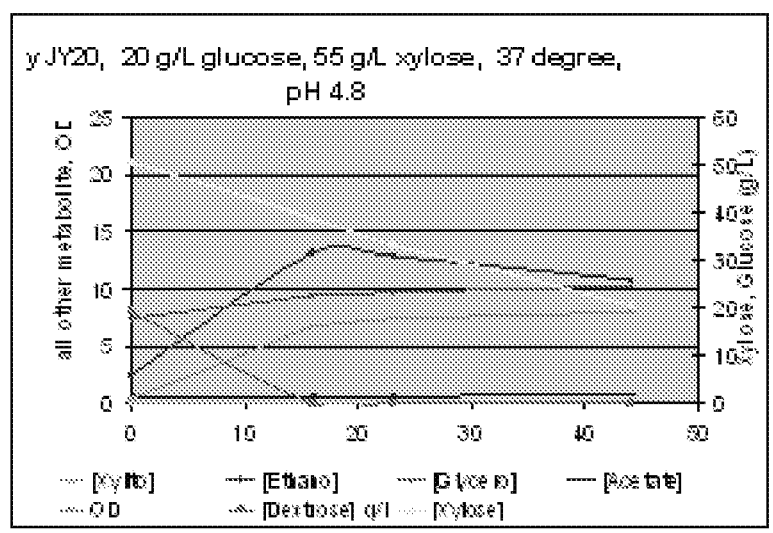
FIG. 8: Fermentation of xylose to ethanol by strain yJY20 in YP media with 20 g/L glucose and 55 g/L xylose.
Figure 9:
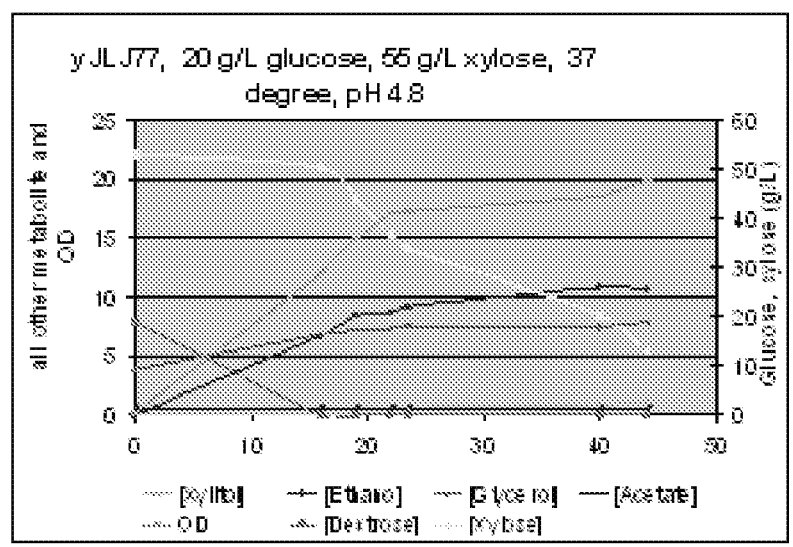
FIG. 9: Fermentation of xylose to ethanol by strain yJLJ77 in YP media with 20 g/L glucose and 55 g/L xylose.

Plasmid pJY28 was generated by ligating a XbaI/PacI fragment from an AXR1 integration vector containing the *I. orientalis* PDC promoter, terminator, URA3 selection cassette, and AXR1 targeting sequences and a XbaI/PacI fragment containing the *K. marxianus* RAG4 gene. The integration fragment was released by digestion of pJY28 with ApaI and KpnI, and linearized integration fragments were transformed into *I. orientalis* strain 3099. Ura+ colonies were screened by colony PCR to identity cells with the desired integration at the AXR1 locus; one such colony was named yJY20.

yJY19, yJY20, and *I. orientalis* strain 2973 (ura+ version of strain 3099) were cultured in a medium containing 20 g/L glucose and 55 g/L xylose at pH 4.8. Both transporter strains showed co-consumption of glucose and xylose, while strain 2973 only consumed xylose after glucose was depleted (FIGS. 7-9).

Based on these results, a second copy of each transporter gene was integrated into the genome. The URA3 marker in the yJY19 and yJY20 cells was looped out by plating these strains on ScD-FOA plates. Colonies were screened by colony PCR to identify colonies that retained the integration but lost the URA3 gene. One of the positive strains arising from yJY19 was named yJY25, and one of the positive strains arising from yJY20 was named yJY26.

A second copy of the KHT105 expression cassette from pJY27 was integrated, as described above, into strain yJY25.

Ura+ colonies were screened by colony PCR to identity cells with the desired integration at the AXR1 site, and one such clone was named strain yJY27 (3097). The URA3 marker in strain 3097 was looped out by plating on ScD-FOA plates after overnight growth. Colonies were screened by colony PCR to confirm retention of the KHT105 integration, and one of the resultant ura– strains was named yJY32. yJY32 was transformed with linearized DNA carrying the wild-type URA3 locus, and ura+ colonies were screened by colony PCR to identify colonies with the correct integration. One of these strains having URA3 at its original locus was named yJY34 (3081). Thus, there were three separate strains containing two copies of the KHT105 gene: 3097 (ura+), yJY32 (ura–), and 3081 (ura+).

A second copy of the RAG4 expression cassette from pJY28 was integrated, as described above, into strain yJY26. Ura+ colonies were screened by colony PCR to identity cells with the desired insertion at the AXR1 site, and one such clone was named strain yJY28.

Strains 3097 (two copies of KHT105), yJY28 (two copies of RAG4), and 2973 (parent) were grown overnight in YPD at 37° C. and 250 rpm. Overnight cultures were harvested and resuspended to a target $OD_{600}$ of 3.0 in YP+40 g/L glucose+ 40 g/L xylose medium (pH 4.8, 37° C., 100 rpm).

Figure 10:
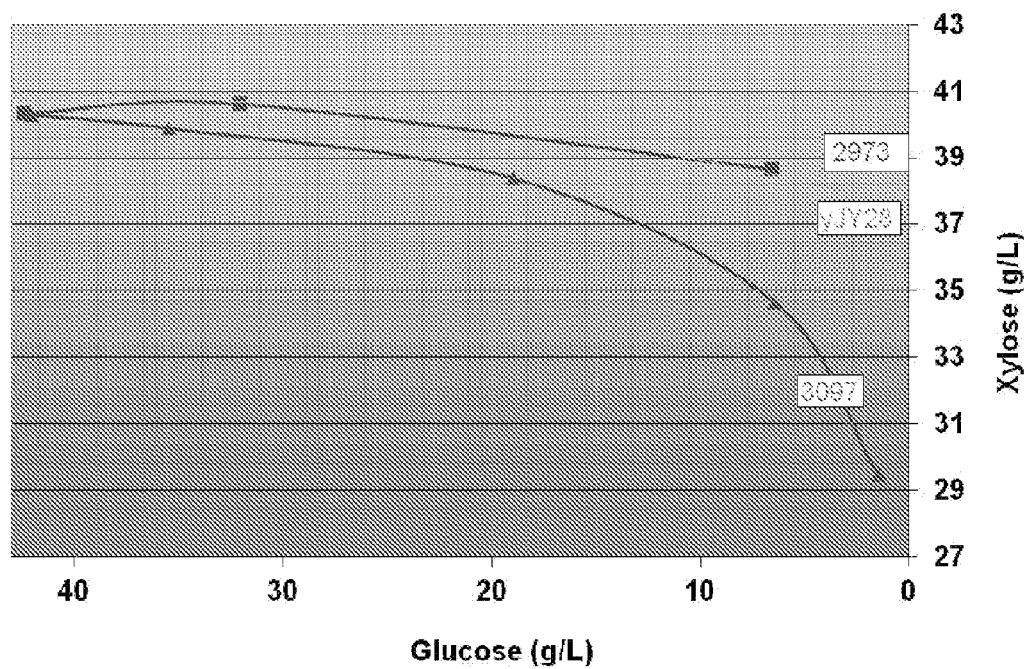
FIG. 10: Fermentation of xylose by strains 2973, 3097, and yJY28.
Figure 11:
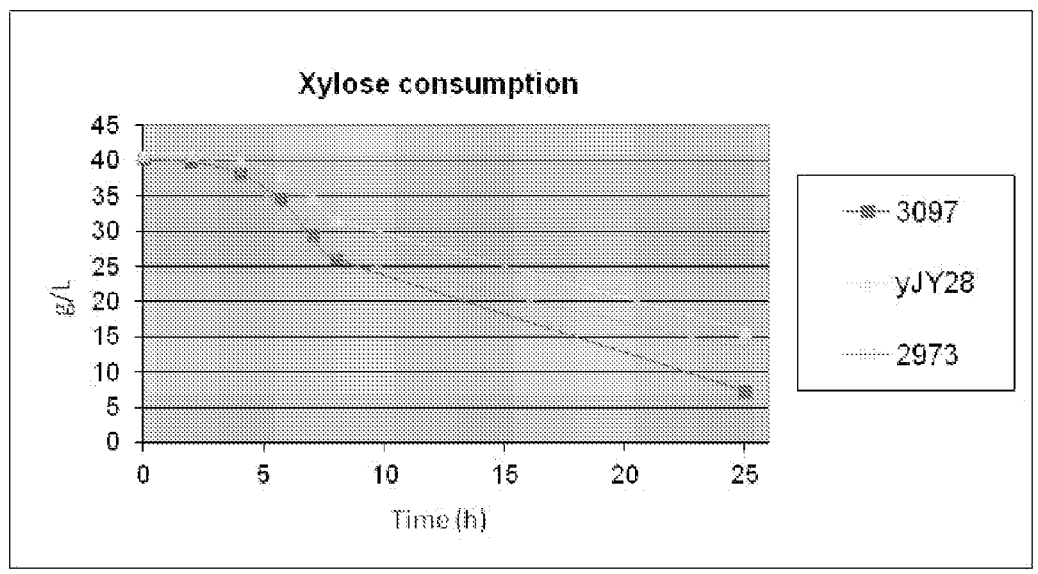
FIG. 11: Fermentation of xylose by strains 2973, 3097, and yJY28.
Figure 12:
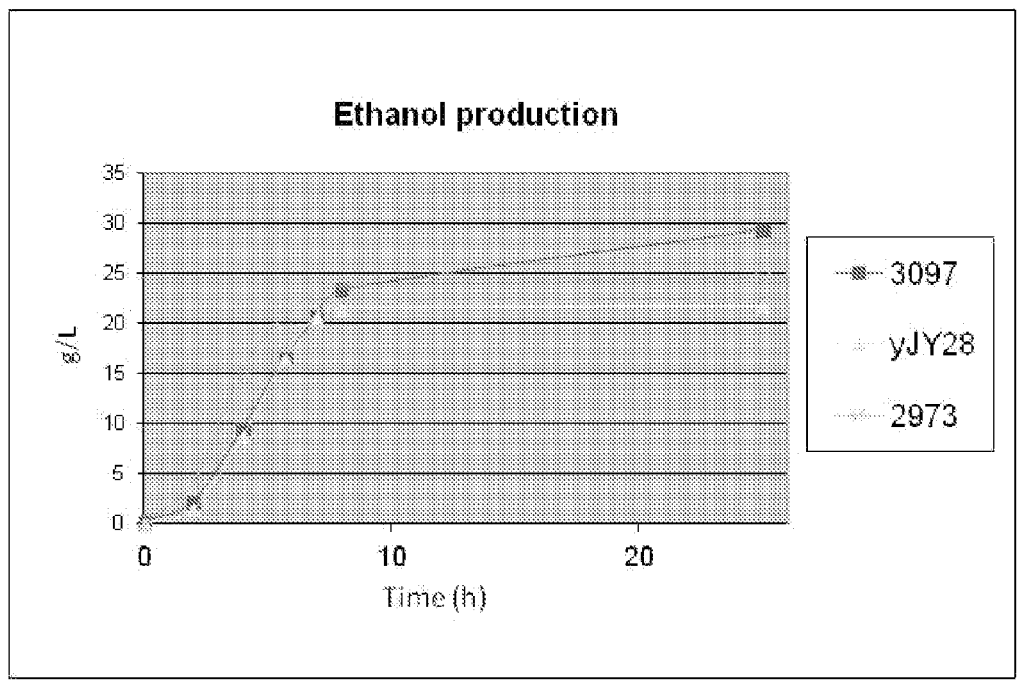
FIG. 12: Ethanol production by strains 2973, 3097, and yJY28.

Strain 3097 exhibited greater glucose/xylose co-consumption than control strain 2973 when the glucose concentration was below 20 g/L (FIG. 10). All glucose was consumed in about five hours by strain 2973, versus about eight hours for strains 3097 and yJY28. Xylose was utilized at a faster rate by strains 3097 and yJY28 versus the parent after all glucose was consumed (FIG. 11). The combination of greater co-consumption and faster xylose utilization rates led to higher ethanol production in strain 3097 (FIG. 12). Strain 3097 produced 29 g/L of ethanol in 25 hours with 7 g/L xylose left. Control strain 2973 produced 24 g/L of ethanol in 25 hours with 13 g/L of xylose left. Strain yJY28 produced 22 g/L of ethanol with 16 g/L of xylose left. These results showed that incorporation of the KHT105 transporter gene increased ethanol productivity from a glucose/xylose substrate mix.

*I. orientalis* strains containing *K. marxianus* transporter genes are summarized in Table 3.

TABLE 3

| Strain name | Parent strain | Transporter gene | # of copies | Insertion location |
|---|---|---|---|---|
| 2973 (ura+), 3099/yJLJ70 (ura–) (xylose fermenting parent strain) | — | — | 0 | — |
| yACN55 (ura–) (xylose fermenting parent strain with TAL, RKI, and RPE genes) | — | — | 0 | — |
| 3408/yHJJ47 (ura+), yJY39 (ura–) (parent strain with complete *B. thetaiotaomicron* arabinose pathway, deletion of XYL1, XYL2, and AXR1) | — | — | 0 | — |
| 3937/yARA38 (ura+), yLUN011 (ura–) (parent strain with complete *B. thetaiotaomicron* arabinose pathway, deletion of 9091 and 1202) | — | — | 0 | — |
| 12053/yGP44 (ura+), yLUN027 (ura–) (ethanol tolerant parent strain) | — | — | 0 | — |
| yJY19 (ura+), yJY25 (ura–) | 3099 | *K. marxianus* KHT105 | 1 | AXR1 (1) |
| yJY20 (ura+), yJY26 (ura–) | 3099 | *K. marxianus* RAG4 | 1 | AXR1 (1) |
| 3097/yJY27 (ura+), yJY32 (ura–), 3081/yJY34 (URA3 reintegrated at original locus) | yJY25 | *K. marxianus* KHT105 | 2 | AXR1 (2) |
| yJY28 | yJY26 | *K. marxianus* RAG4 | 2 | AXR1 (2) |
| yACN59 (ura+), yACN60 (ura+), yACN67 (ura–), yACN68 (ura–) | yACN55 | *K. marxianus* KHT105 | 1 | 9091 (1) |
| 3415/yACN71 (ura+), yACN72 (ura+), yACN74 (ura–), yACN75 (ura–), 4141 | yACN67 | *K. marxianus* KHT105 | 2 | 9091 (2) |
| 3849 (ura+), yHJJ172 (ura–) (2X ADH1) | 3415 | *K. marxianus* KHT105 | 2 | 9091 (2) |
| 4014 (ura+), yHJJ182 (ura–), 4084 | yHJJ172 | *K. marxianus* KHT105 | 3 | 9091 (2), S141G4546 (1) |
| 4083 (ura+), yLUN005 (ura–) | yHJJ172 | *K. marxianus* KHT105 | 3 | 9091 (2), ALD5680 (1) |
| 4085 | yHJJ182 | *K. marxianus* KHT105 | 4 | 9091 (2), S141G4546 (2) |
| 4086/yLUN007 (ura+), 4117 (ura–) | yLUN005 | *K. marxianus* KHT105 | 4 | 9091 (2), ALD5680 (2) |
| 12037/yLUN013 | 4117 | *K. marxianus* KHT105 | 6 | 9091 (2), ALD5680 (2), S141G4546 (2) |
| 3812/yARA19 | yJY39 | *K. marxianus* KHT105 | 1 | S141G4546 (1) |
| yLUN031 (ura+), yLUN033 (ura–) | yLUN027 | *K. marxianus* KHT105 | 1 | ALD5680 (1) |
| 12125/yLUN036 | yLUN033 | *K. marxianus* KHT105 | 2 | ALD5680 (2) |
| yLUN015 (ura+), yLUN016 (ura–) | yLUN011 | *K. marxianus* KHT105 | 1 | S141G4546 (1) |
| 12038/yLUN018 | yLUN016 | *K. marxianus* KHT105 | 2 | S141G4546 (2) |

Example 9

Integration of *K. marxianus* KHT105 Transporter Gene into a More Advanced *I. orientalis* Xylose Pathway Strain A modified *I. orientalis* strain containing the *K. marxianus* KHT105 transporter in combination with the XI/XK xylose utilization pathway, overexpression of the non-oxidative pentose phosphate genes, and knockout of the 9091 gene was analyzed for its ability to ferment xylose and glucose to ethanol relative to a comparable strain without the transporter.

A NotI fragment carrying the URA3 cassette was inserted into the NotI site of pHJJ22 (Example 4A) to create the 9091 deletion plasmids pHJJ27 (orientation 1) and pHJJ28 (orientation 2).

A NotI fragment from vector pJY27 (Example 8) carrying the *I. orientalis* PDC promoter, *K. marxianus* KHT105 transporter gene, *I. orientalis* PDC terminator, and URA3 selection cassette was cloned into pHJJ22 (Example 4A) to create the KHT105 expression vectors pHJJ23 (orientation 1) and pHJJ24 (orientation 2).

pHJJ23 was digested with ApaI and KpnI to release the integration fragment, and linearized DNA was transformed into yACN55 cells. yACN55 is a ura– strain that contains four copies of an exogenous *B. thetaiotaomicron* XI gene, two copies of a native sequence exogenous XK gene, and two copies each of native sequence exogenous pentose-phosphate pathway genes (TAL, RKI, RPE) in addition to endogenous copies of XK, TAL, TKL, RPE, and RKI genes. The ura+ parent of yACN55 is strain 3356/yACN53.

Transformants were selected and purified on ScD-ura plates. Ura+ colonies were screened by colony PCR for correct integration at the 9091 locus. Two isolates were named yACN59 and yACN60. Strain yACN59 was grown overnight in YPD and plated on ScD-FOA plates to loop out the URA3 gene. Colony PCR was used to confirm the retention of the integration, and two isolates were named yACN67 and yACN68.

pHJJ24 was digested with ApaI and KpnI to release the integration fragment, and linearized DNA was transformed into yACN67 cells. Transformants were selected and purified on ScD-ura plates. Ura+ colonies were screened by colony PCR for correct integration. Two isolates were named strains yACN71 (3415) and yACN72. Strain 3415 was grown overnight in YPD and plated on ScD-FOA plates to loop out the URA3 gene. Colony PCR was used to confirm the correct integration at the 9091 locus, and two such isolates were named yACN74 and yACN75.

pHJJ28 was digested with ApaI and SacI to release the integration fragment, and linearized DNA was transformed into yACN55 cells. Transformants were selected and purified on ScD-ura plates. Ura+ colonies were screened by colony PCR for the correct integration at the 9091 locus, and two such isolates were named yACN61 and yACN62. Strain yACN61 was grown overnight in YPD media and plated on ScD-FOA plates to loop out the URA3 gene. Colony PCR was used to confirm the retention of the integration; two such isolates were named yACN69 and yACN70.

pHJJ27 was digested with ApaI and SacI to release the integration fragment, and linearized DNA was transformed into yACN69 cells. Transformants were selected and purified on ScD-ura plates. Ura+ colonies were screened by colony PCR for the correct integration at the 9091 locus, and one such isolate was named strain yACN73 (3416).

Strains 3415 (2 copies of KHT105, both copies of 9091 deleted) and 3416 (both copies of 9091 deleted) were characterized in fermentors for performance on hydrolysate media. Loops of biomass from YPD plates were used to inoculate 250 mL baffled flasks containing 100 mL defined media (DMDX) having 20 g/L dextrose and 80 g/L xylose and pH adjusted to around 5.0. The defined media contained urea as a nitrogen source and 0.2M MES buffer. The cells were incubated at 250 rpm and 37° C. for 15-24 hours, and harvested in mid-late exponential growth phase. Cultures were mixed with 80% glycerol stock and separated into 1 mL aliquots. 50 to 400 µL from each aliquot was transferred to 100 mL of media in a 250 mL shake flask, incubated at 250 rpm and 37° C. for 15-24 hours, and harvested in mid-late exponential growth. 35 to 40 mL samples were harvested and inoculated into batch fermentation vessels containing various hydrolysate media. Samples were harvested at 4 to 8 hour intervals throughout the fermentation and tested for $OD_{600}$ using a spectrophotometer and for substrates and product levels using HPLC analyses.

Figure 13:
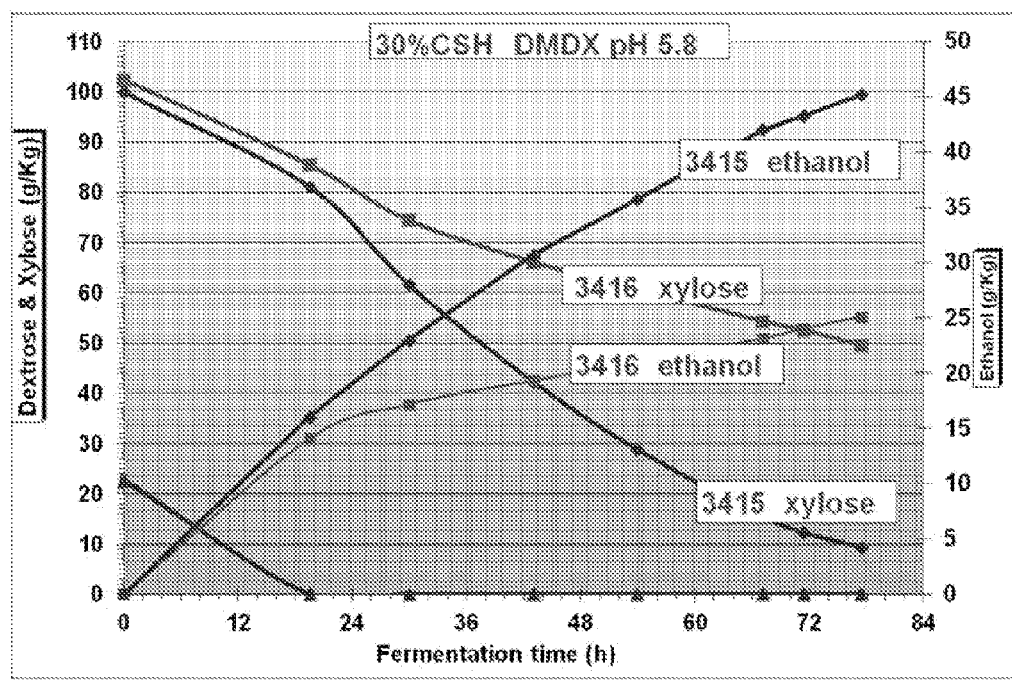
FIG. 13: Fermentation of xylose and dextrose to ethanol by strains 3415 and 3416 in 30% CSH DMDX media.

Strain 3415 exhibited an 80% increase in xylose consumption and ethanol production rate in a 30% corn stover hydrolysate (CSH) DMDX media at pH 5.8 (FIG. 13). These results confirm that KHT105 expression increases xylose consumption and ethanol titer in *I. orientalis* grown under fermentative conditions in hydrolysate media. Similarly a 75% increase in ethanol production rate was seen for 3415 over 3416 in a 15% hydrolysate medium (15% CSH 5 g/L acetic acid DMDX) at pH 4.9.

Example 10

Effect of *K. Marxianus* KHT105 on Arabinose Consumption in *I. orientalis* Strains Containing *B. thetaiotaomicron* araA, araB, and araD A single copy of the *K. marxianus* KHT105 gene was integrated into *I. orientalis* strain 3408 (Example 1C; contains two copies each of *B. thetaiotaomicron* araA, araB, and araD genes inserted at the XYL2, XYL1, and AXR1 loci, respectively) at the S141G4546 locus to evaluate the effect of the transporter on arabinose consumption. The S141G4546 locus has homology to sorbitol, butanediol, and glycerol dehydrogenases.

pSK1 is a vector that contains the upstream and downstream regions for the S141G4546 locus, separated by a NotI restriction site. NotI-digested pSKJ1 was ligated to the NotI fragment of pJY27 (Example 8) containing the *I. orientalis* PDC promoter, *K. marxianus* KHT105 gene, *I. orientalis* PDC terminator, and URA3 selection cassette. Plasmid DNA from colonies transformed with the ligation were screened by restriction digest. Plasmids with the desired insertion were named pLUN108 (orientation 1) and pLUN109 (orientation 2).

pLUN108 was digested with ApaI and SacI to release the integration fragment, and linearized DNA was transformed into yJY39 cells (ura– strain derived from strain 3408/yHJJ47. Transformants were selected and purified on ScD-ura plates. Genomic DNA isolated from the colonies was screened by PCR to identify colonies having KHT105 inserted into the S141G4546 locus, and one such strain was identified as yARA19 (3812).

Strain 3812 was tested for arabinose utilization in a shake flask experiment. Cells were grown overnight in 50 mL of YPD and inoculated into 50 mL of YP+40 g/L arabinose and 10 g/L dextrose. Duplicate shake flasks were inoculated to $OD_{600}=0.4$ and grown for at 37° C. and 100 rpm. The ura+ parent, strain 3408, was run as the control.

Figure 14:
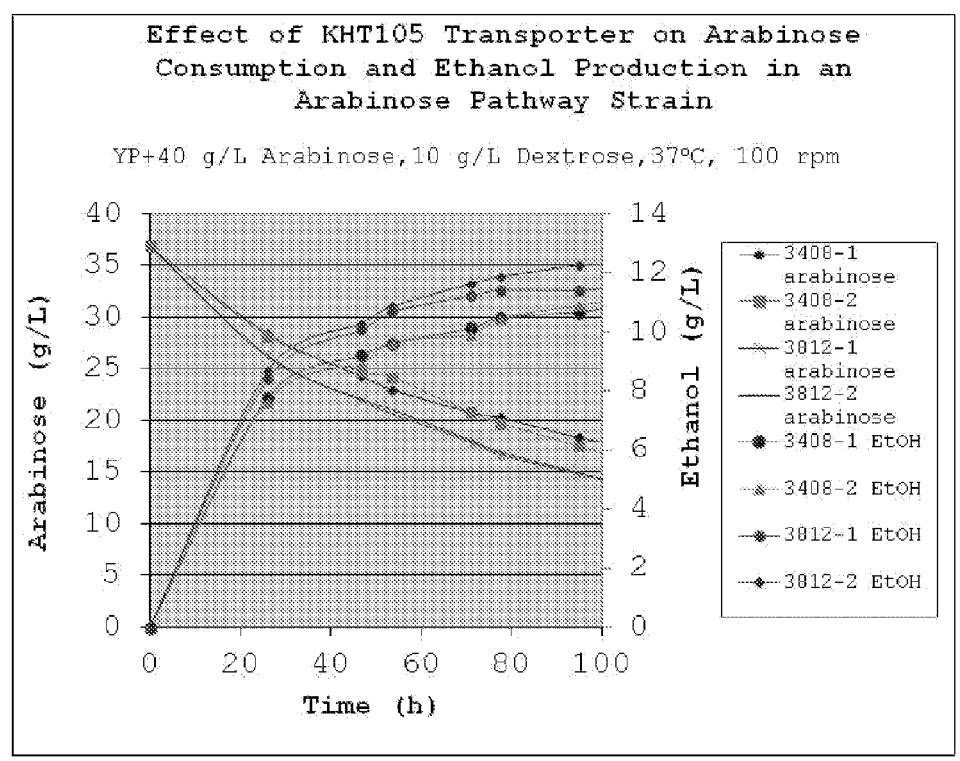
FIG. 14: Fermentation of arabinose to ethanol by strains 3408 and 3812 in YP media with 40 g/L arabinose and 10 g/L dextrose.

Dextrose was depleted by all strains before 25 hours. Addition of a single copy of the KHT105 gene resulted in a small increase in arabinose utilization (~5 g more than the parent strain) and a slightly higher ethanol yield after 100 hours (FIG. 14).

Example 11

Integration of the *K. marxianus* KHT105 Transporter Gene into the S141G4546 locus of an *I. orientalis* dual pathway strain The *K. marxianus* KHT105 transporter gene was integrated into the ura– derivative of *I. orientalis* strain 3937 (Example 4D; contains two copies each of *B. thetaiotaomicron* araA, araB, and araD genes inserted at the 9091, 1202, and 9091 loci, respectively), which had shown the ability to ferment both xylose and arabinose to ethanol (Example 5).

An integration cassette was constructed containing the *K. marxianus* KHT105 transporter gene between S141G4546 flanking regions. To construct the integration vector, a NotI fragment containing a PDC promoter, KHT105 gene, PDC terminator and URA3 selection cassette was ligated into NotI cut, dephosphorylated pSK1 (TOPO vector with S141G4546 upstream and downstream separated by NotI site). Colonies transformed with the ligation were screened by PCR for directionality, and vectors with the desired insertion were named pHJJ86 (orientation 1) and pHJJ87 (orientation 2).

pHJJ87 was digested with ApaI and SacI to release the integration fragment, and linearized DNA was transformed into yLUN011 (ura– version of strain 3937). Transformant colonies were selected and purified on ScD-ura plates and screened in two separate PCR reactions. Clones that exhibited PCR products indicating the correct integration of KHT105 at the S141G4546 locus were designated yLUN015.

yLUN015 was grown overnight in YPD and plated on ScD-FOA plates. Loop-out colonies were purified on YPD plates and screened in two separate PCR reactions. A clone was identified as having retained the integration but lost the URA3 gene. This strain (yLUN016) was replica plated onto SCD-ura to confirm the inability to grow without uracil.

pHJJ86 was digested with ApaI and SacI to release the integration fragment, and linearized DNA was transformed into yLUN016. Transformants were selected and purified on ScD-ura plates and screened by PCR across all four integration junctions. Clones identified as having both copies of the KHT105 gene integrated at the S141G4546 locus were designated strain yLUN018 (12038).

Example 12

Characterization of *I. orientalis* Dual Pathway Strain Containing Two Copies of the *K. marxianus* KHT105 Transporter Gene The ability of *I. orientalis* strain 12038 (Example 11) and its parental strain 3937 to ferment arabinose and xylose to ethanol was evaluated in shake flask experiments. Strains were grown at 37° C. and 100 rpm in either 1) YP+20 g/L dextrose, 80 g/L xylose and 10 g/L arabinose, pH 5.1 (YP20D/80X/10A) or 2) YP+10 g/L dextrose, 40 g/L xylose and 10 g/L arabinose, pH 5.1 (YP10D/40X/10A).

Figure 15:
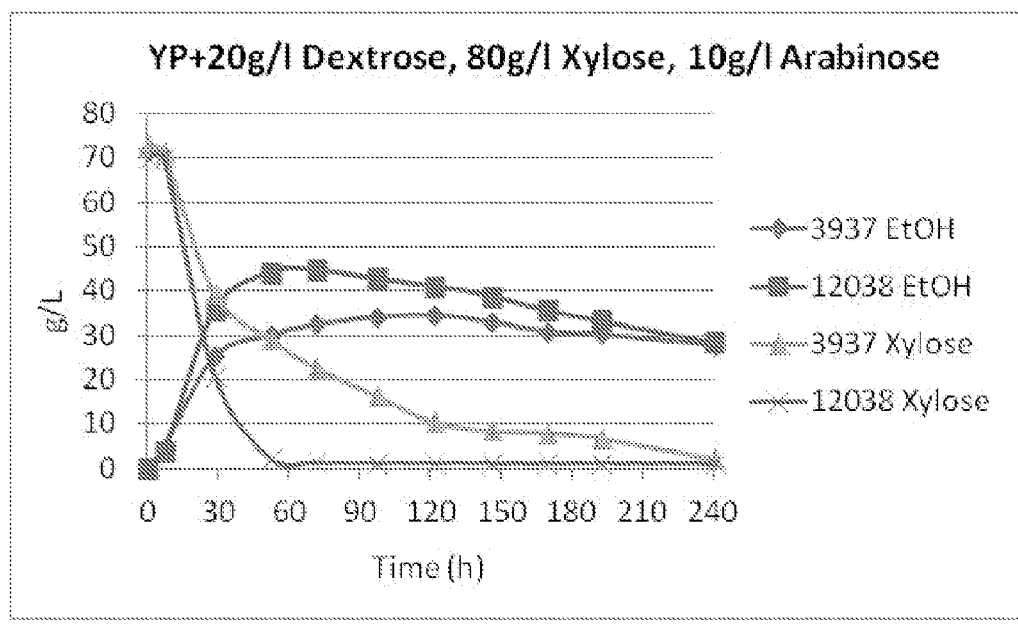
FIG. 15: Fermentation of xylose to ethanol by strains 3937 and 12038 in YP media with 20 g/L dextrose, 80 g/L xylose, and 10 g/L arabinose.
Figure 16:
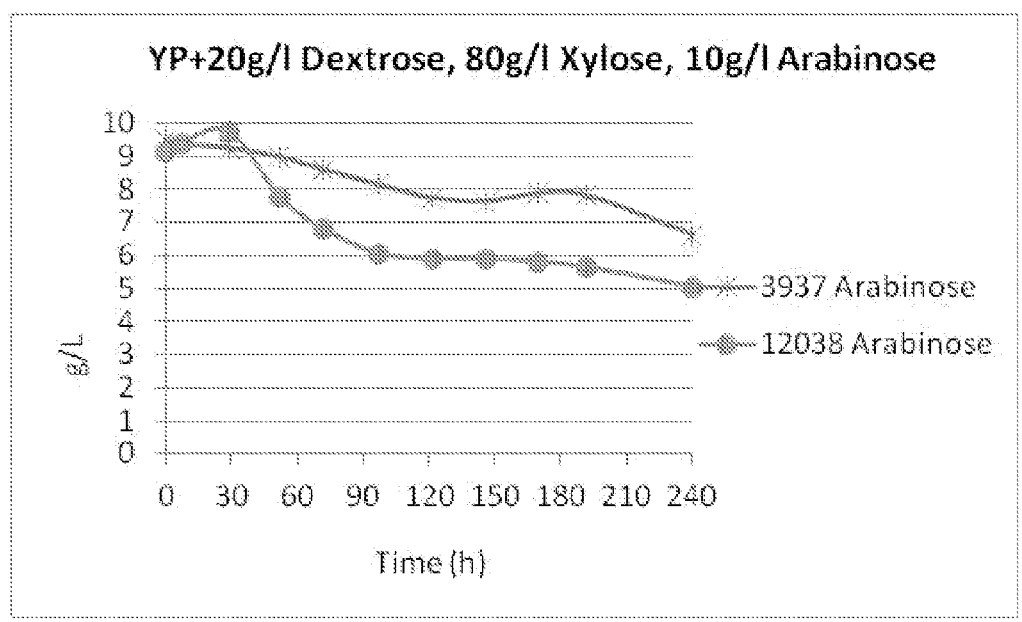
FIG. 16: Arabinose fermentation by strains 3937 and 12038 in YP media with 20 g/L dextrose, 80 g/L xylose, and 10 g/L arabinose.

In the YP20D/80X/10A media, strain 12038 exhibited a significant increase in xylose consumption versus parental strain 3937 (FIG. 15). This increase in xylose consumption corresponded to an increase in ethanol production (FIG. 15). Xylose consumption rates in strain 12038 in this media were similar to those seen in yeast strains without the bacterial arabinose pathway (e.g., strain 3922). Strain 12038 started arabinose consumption earlier in the fermentation, likely due to earlier xylose depletion, and used approximately 40% more arabinose compared to the parental strain 3937 (FIG. 16).

Figure 17:
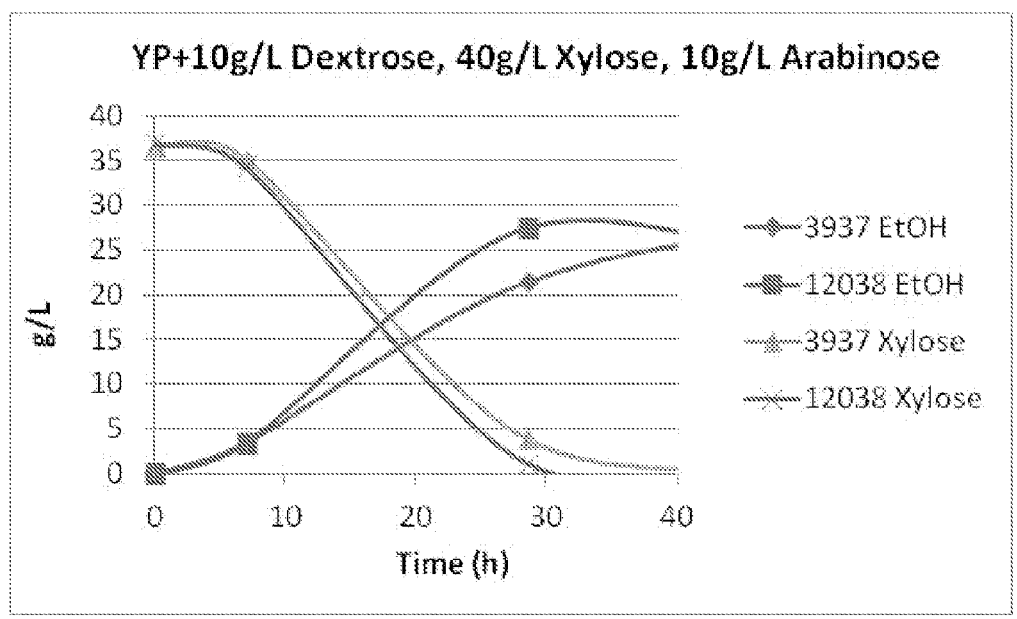
FIG. 17: Fermentation of xylose to ethanol by strains 3937 and 12038 in YP media with 10 g/L dextrose, 40 g/L xylose, and 10 g/L arabinose.
Figure 18:
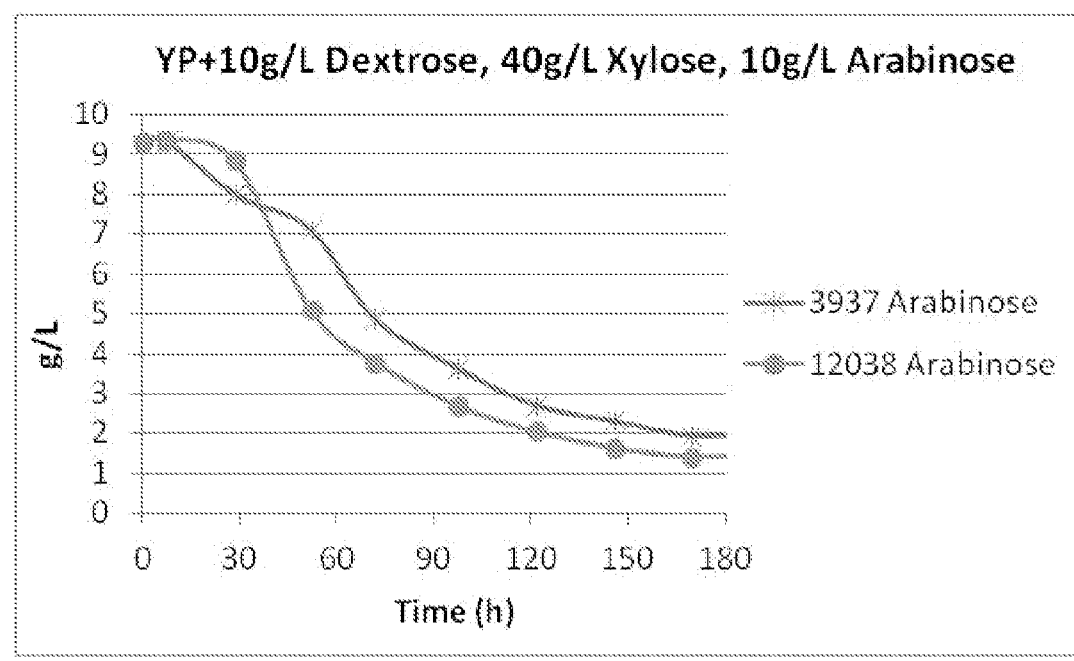
FIG. 18: Arabinose fermentation by strains 3937 and 12038 in YP media with 10 g/L dextrose, 40 g/L xylose, and 10 g/L arabinose.

The increase in xylose consumption rates for strain 12038 relative to its parent strain was not as great in the YP10D/40X/10A media as in the higher sugar media (FIG. 17). Strain 12038 again exhibited earlier arabinose consumption and an increase in total arabinose used, but with a smaller advantage than was seen in the higher sugar media (FIG. 18)

These results establish that yeast cells containing bacterial arabinose and xylose pathway genes and the KHT105 transporter gene are capable of fermenting both arabinose and xylose into ethanol in an efficient manner.

Example 13

Construction of *I. orientalis* ALD5680 Knockout Strain

Aldehyde dehydrogenase (ALD) unidirectionally converts acetaldehyde to acetate, and expression of ALD can divert carbon away from ethanol production. ALD activity is very important to the functioning of the PDH bypass in yeast; reducing ALD activity may cause yeast to utilize more acetate from media. In *S. cerevisiae*, the two main ALDs are encoded by the ALD4 and ALD6 genes. In *I. orientalis*, ALD homologs include S141G5680 ("ALD5680"), S141G9161 ("ALD9161"), and S141G6502 ("ALD6502"), with ALD9161 exhibiting the highest average expression. ALD6502 is more similar to *S. cerevisiae* ALD3, which may function in β-alanine metabolism, and appears to be cytoplasmic based on protein sequence. Both ALD5680 and ALD9161 encode proteins with a typical leader sequence, and expression of both was enhanced with growth on xylose and decreased by acetate addition. The nucleotide sequence of the coding region of ALD5680 is set forth in SEQ ID NO:72, and the polypeptide sequence of ALD5680 is set forth in SEQ ID NO:73. Attempts to knock out the ALD9161 locus in *I. orientalis* were unsuccessful, suggesting that this locus may be essential. However, both copies of the ALD5680 locus were knocked out in *I. orientalis* strain 3489 (previously engineered to ferment xylose to ethanol) to evaluate the effect on sugar and acetate utilization and ethanol production.

The upstream and downstream regions of ALD5680 were amplified from *I. orientalis* genomic DNA, and the resultant fragments were gel purified. The downstream fragment was digested with ApaI and NotI and the upstream fragment was digested with NotI and SacI. The digested fragments were ligated into ApaI/SacI cut TOPO vector in a three piece ligation. Colonies transformed with the ligation were screened by PCR for the correct insertion and the sequence of the insert was confirmed by DNA sequencing. This plasmid was named pHJJ75. A NotI fragment containing the URA3 selection cassette was ligated into NotI-cut pHJJ75. Colonies transformed with the ligation were screened for directionality of the insert. The vectors representing the two orientations were named pHJJ78 and pHJJ79.

pHJJ79 was cut with ApaI and SacI to release the integration fragment and linearized DNA was transformed into strain 3514, a ura– derivative of strain 3489. Transformants were streaked for purification and screened by PCR for correct integration at the ALD5680 locus. yHJJ114 was identified as having one copy of the ALD5680 knockout. yHJJ114 was grown overnight in YPD and plated on ScD-FOA media to select for URA3 gene loopouts. Two resultant ura– isolates were confirmed by PCR to have retained the ALD5680 knockout. These isolates were named yHJJ118 and yHJJ119.

pHJJ78 was cut with ApaI and SacI to release the integration fragment and linearized DNA was transformed into yHJJ118. Ura+ transformants were streaked for purification and single colonies were screened by PCR for the correct integration at the ALD5680 locus. Strains yHJJ123 and yHJJ124 (3861) were identified as having both copies of ALD5680 deleted.

Example 14

Characterization of *I. orientalis* ALD5680 Knockout Strain

The ALD5680 knockout strains from Example 13 were evaluated to determine the effect of the knockout. Sugar utilization and acetate production or utilization were examined using shake flask experiments in media without acetate at 100 and 135 rpm aeration and media with acetate at 135 rpm aeration. Strain 3861 (knockout of both copies of ALD5680) and parent strain 3489 were cultured in YP medium with 20 g/L dextrose and 80 g/L xylose, pH 4.8 at 37° C., or YP medium with 20 g/L dextrose, 80 g/L xylose, 4 g/L acetate, pH 5.1 at 37° C.

Figure 19:
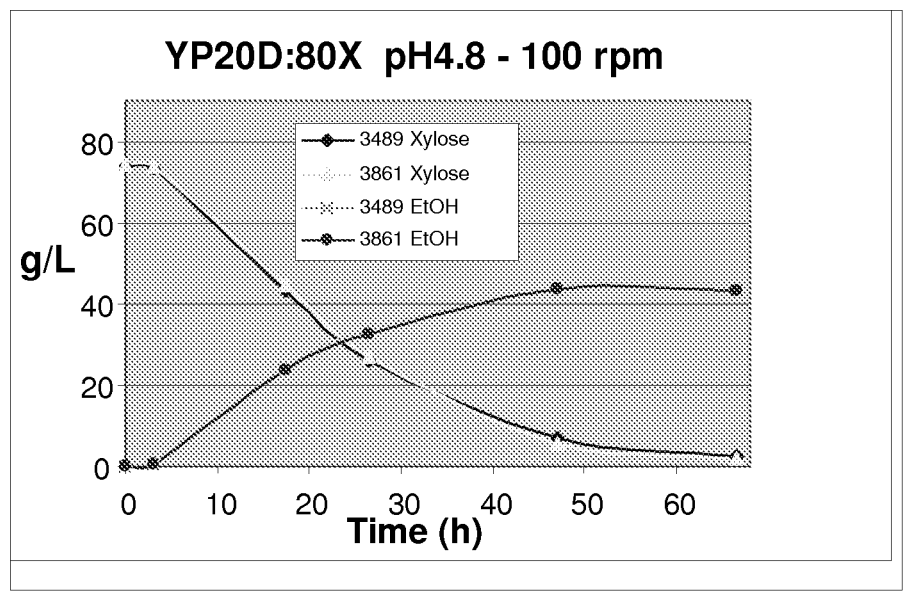
FIG. 19: Xylose fermentation to ethanol by strains 3489 and 3861 in YP media with 20 g/L dextrose and 80 g/L xylose.

The ALD5680 deletion strain exhibited lower acetate production in media without acetate at 100 rpm, although the parent strain only made 0.49 g/L acetate under these conditions (Table 4). The ALD5680 deletion strain did not show any significant benefit with regard to sugar utilization (FIG. 19).

TABLE 4

|  | Xylitol (g/L) | Arabitol (g/L) | Glycerol (g/L) | Acetate (g/L) |
|---|---|---|---|---|
| Strain 3489 | 1.42 | 0.61 | 2.43 | 0.49 |
| Strain 3861 | 1.29 | 0.81 | 2.38 | 0.06 |

Figure 20:
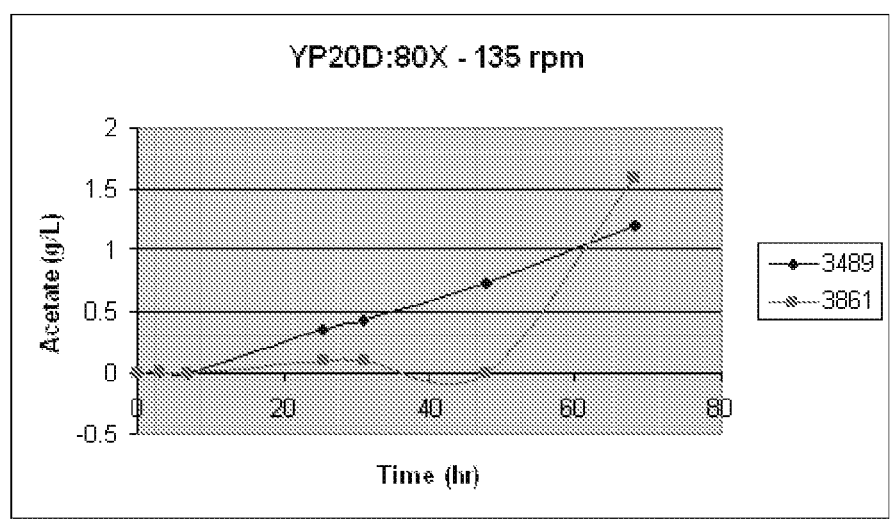
FIG. 20: Acetate production by strains 3489 and 3861 in YP media with 20 g/L dextrose and 80 g/L xylose.
Figure 21:
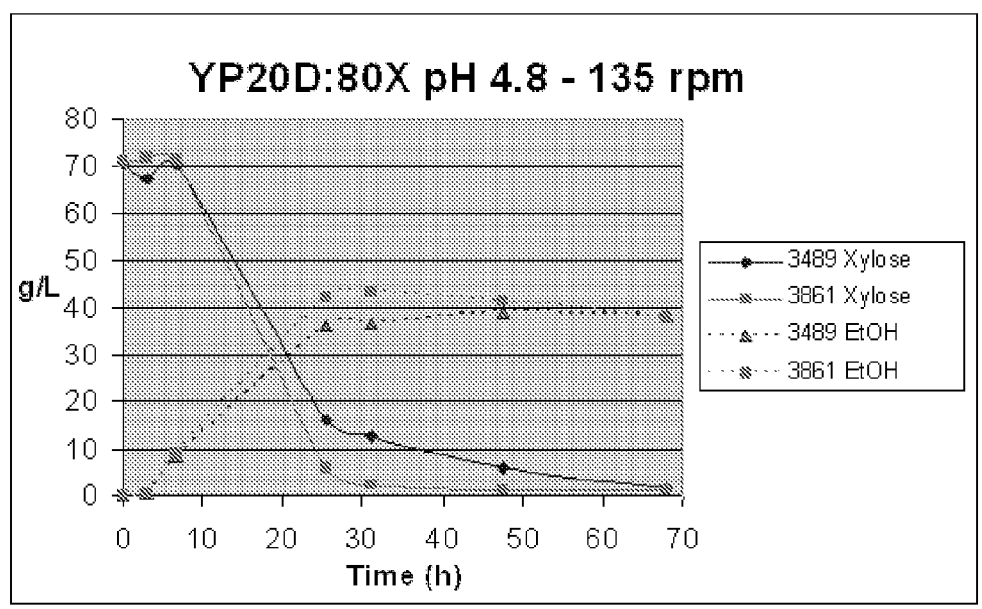
FIG. 21: Xylose fermentation to ethanol by strains 3489 and 3861 in YP media with 20 g/L dextrose and 80 g/L xylose.

The ALD5680 deletion strain also exhibited lower acetate production in media without acetate at 135 rpm (FIG. 20). The parent strain made over 1 g/L acetate linearly over time, whereas the deletion strain only made acetate after all xylose was gone. Under these conditions, the knockout strain exhibited higher xylose utilization and ethanol production than the parent strain, finishing the xylose approximately 30 hours earlier than the parent strain (FIG. 21). Byproducts produced by each strain are summarized in Table 5.

TABLE 5

|  | Xylitol (g/L) | Arabitol (g/L) | Glycerol (g/L) |
|---|---|---|---|
| Strain 3489 | 2.02 | 0.26 | 1.33 |
| Strain 3861 | 1.56 | 0.47 | 2.51 |

Figure 22:
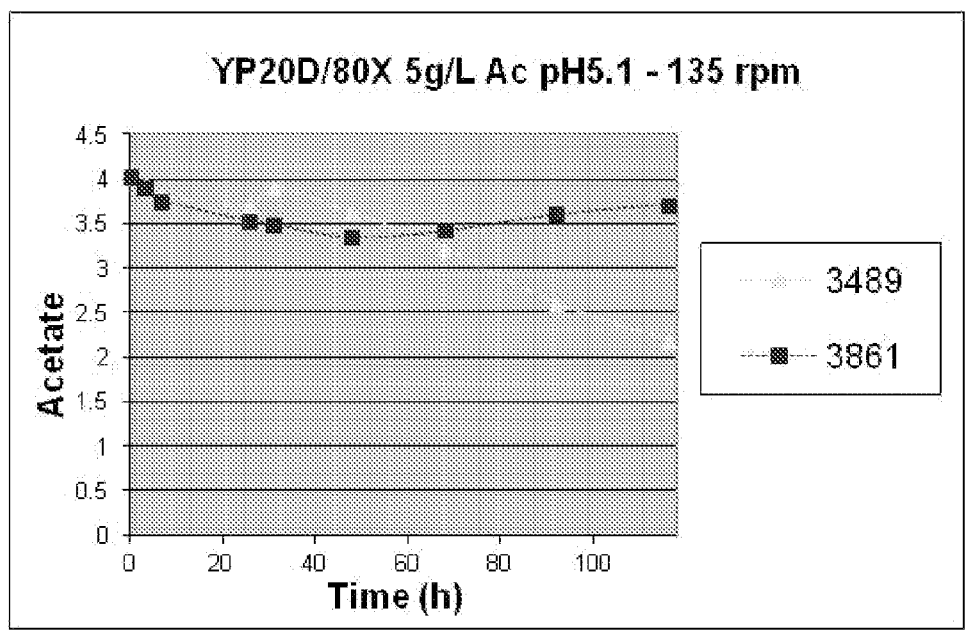
FIG. 22: Acetate production by strains 3489 and 3861 in YP media with 20 g/L dextrose and 80 g/L xylose.
Figure 23:
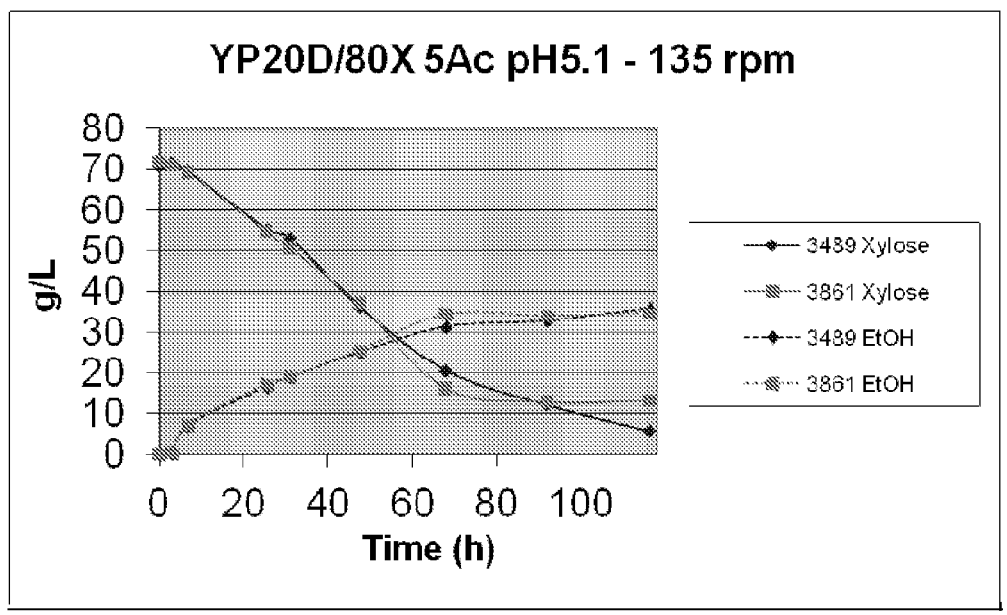
FIG. 23: Xylose fermentation to ethanol by strains 3489 and 3861 in YP media with 20 g/L dextrose and 80 g/L xylose.

In synthetic media with acetate, the deletion strain did not show a consistent advantage. It slowly used acetate for about the first 48 hours, but then started to produce acetate (FIG. 22, Table 6). Xylose utilization was relatively linear until 68 hours and then stopped (FIG. 23). In contrast, acetate utilization by the parent strain increased at about 48 hours and xylose utilization remained steady at the end of the fermentation (FIGS. 22-23).

TABLE 6

| Strain | Xylitol (g/L) | Arabitol (g/L) | Glycerol (g/L) | Acetate (g/L) |
|---|---|---|---|---|
| yHJJ82/3489 | 1.06 | 1.25 | 0.62 | 2.18 |
| Strain 3861 | 1.24 | 0.26 | 0.53 | 3.72 |

The ALD5680 deletion strain exhibited a significant advantage in hydrolysate-based media. 19 different strains having various genetic engineering modifications or mutations were tested in DM20D80×50% corn stover hydrolysate (CSH) medium at pH 6.2, 37° C., and 100 rpm. The two traits that conferred the largest benefit to ethanol production in this media were overexpression of KHT105 and deletion of ALD5680.

These results show that deletion of ALD5680 may confer an increased ability to ferment xylose to ethanol and reduce acetate production by the host, but that these advantages are potentially dependent on specific media and aeration conditions. These advantages are particularly significant during culture on hydrolysate-based media.

Example 15

Introduction of Additional Copies of the *K. Marxianus* KHT105 Transporter Gene into *I. orientalis* S141G9091, S141G4546, and S141G5680 Knockout Strains

*I. orientalis* strains were engineered to contain anywhere from two to six copies of the *K. marxianus* KHT105 gene. Strain 3849, which is equivalent to strain 3489 with the addition of two copies of the KHT105 gene integrated at the 9091 locus, was used as the parent strain.

Plasmid DNA from vector pHJJ86 (Example 11; contains PDC promoter, KHT105 gene, PDC terminator, and URA3 selection cassette between S141G4546 flanking regions) was linearized by restriction digest, and linearized DNA was transformed into strain yHJJ172 (ura− derivative of strain 3849) to produce strain 4014, which contained three copies of the KHT105 gene. The third copy of the gene was integrated into the S141G4546 site. Control strain 4141 was also constructed. Strain 4141 contained the URA3 marker rather than a third copy of KHT105 in the S141G4546 site. The vectors used to construct this strain were produced by ligating a NotI fragment containing the URA3 marker cassette into NotI-cut pSK1 (Example 10). *E. coli* colonies transformed with the ligation were screened by PCR, and vectors pHJJ88 (orientation 1) and pHJJ89 (orientation 2) were identified as containing the URA3 marker cassette in opposite orientations. Linearized pHJJ88 was transformed into yHJJ172 as previously described to obtain strain 4141.

Strain 4014 was grown overnight in YPD and plated on SCX-FOA plates. Loopout colonies were screened by PCR, and the correct loopout strain was named yHJJ182. A fourth copy of KHT105 was integrated into the S141G4546 locus of yHJJ182 by transformation with linearized pHJJ87 (Example 11; contains PDC promoter, KHT105 gene, PDC terminator, and URA3 selection cassette between S141G4546 flanking regions). Transformants were confirmed by PCR to have KHT105 integrated at both S141G4546 loci. These clones were named strain 4085. Control strain 4084, which contained the URA3 marker at S141G4546 rather than a third and fourth copy of KHT105, was produced by transforming a ura− derivative of strain 4141 (yHJJ180) with linearized pHJJ89 and selecting on ScD-ura plates. Transformants were screened by PCR at all four integration junctions to confirm that two copies of the URA3 marker were correctly integrated at the S141G4546 locus.

Plasmid pHJJ93, which contained a KHT105 expression cassette between ALD5680 flanking regions (orientation 1), was digested with ApaI and SacI to release the integration fragment, and linearized DNA was transformed into yHJJ172 cells. Colonies were selected and purified on ScD-ura plates and screened by PCR across both integration junctions to confirm integration of the KHT105 expression cassette at the ALD5680 locus. These clones were named strain 4083. The URA3 marker in strain 4083 was looped out by growing overnight in YPD and plating on ScX-FOA media. The resultant colonies were screened to confirm retention of the integration, and positive clones were replica plating on ScD-ura to confirm lack of growth on media without uracil. These loopouts were named yLUN005.

Plasmid pHJJ94, which contained a KHT105 expression cassette between ALD5680 flanking regions (orientation 2), was digested with ApaI and SacI to release the integration fragment and linearized DNA was transformed into yLUN005 cells. Colonies were selected and purified on ScD-ura plates and screened across both integration junctions to confirm integration at the ALD5680 locus. Clones confirmed by PCR to contain copies of KHT105 at both ALD5680 loci were designated strain yLUN007 (4086).

Figure 24:
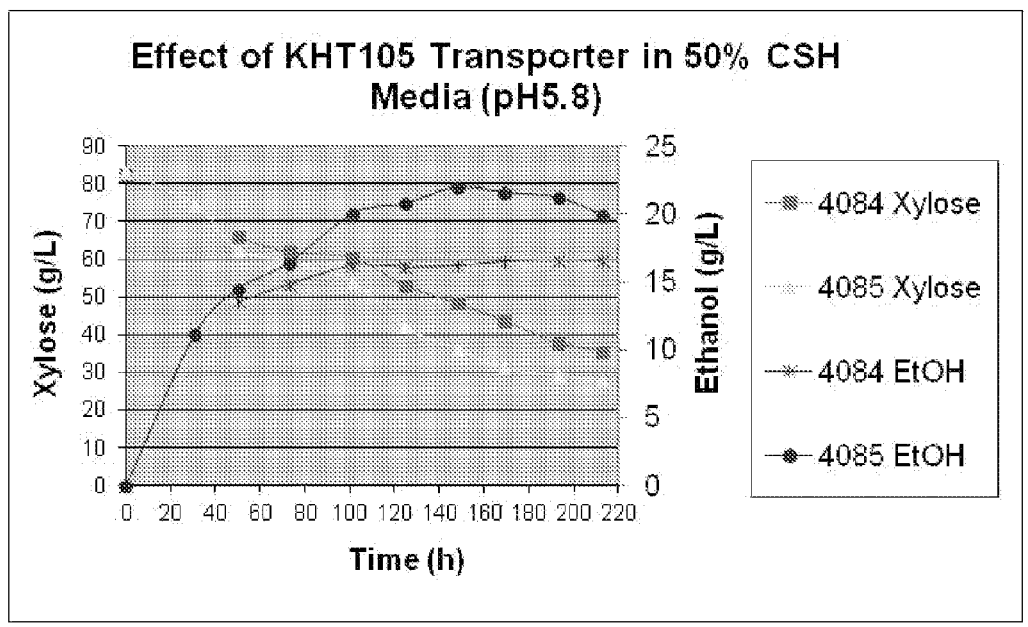
FIG. 24: Xylose fermentation to ethanol by strains 4084 and 4085 in 50% CSH media.

Shake flask experiments were performed to assess xylose fermentation in the various strains. In one experiment, strain 4084 (2×KHT105, 2× S141G4546 knockout), and 4085 (4×KHT105, 2× S141G4546 knockout) were grown at 37° C. and 100 rpm in DM20D80×50% CSH media, pH 6.2. Xylose consumption and ethanol production rates were increased by the additional copies of KHT105 (FIG. 24). Byproducts produced by each strain are summarized in Table 7.

TABLE 7

|  | Xylitol (g/L) | Arabitol (g/L) | Glycerol (g/L) | Acetate (g/L) |
| --- | --- | --- | --- | --- |
| Strain 4084 | 5.90 | BDL | 4.70 | 4.38 |
| Strain 4085 | 3.90 | 0.76 | 5.44 | 4.21 |

Figure 25:
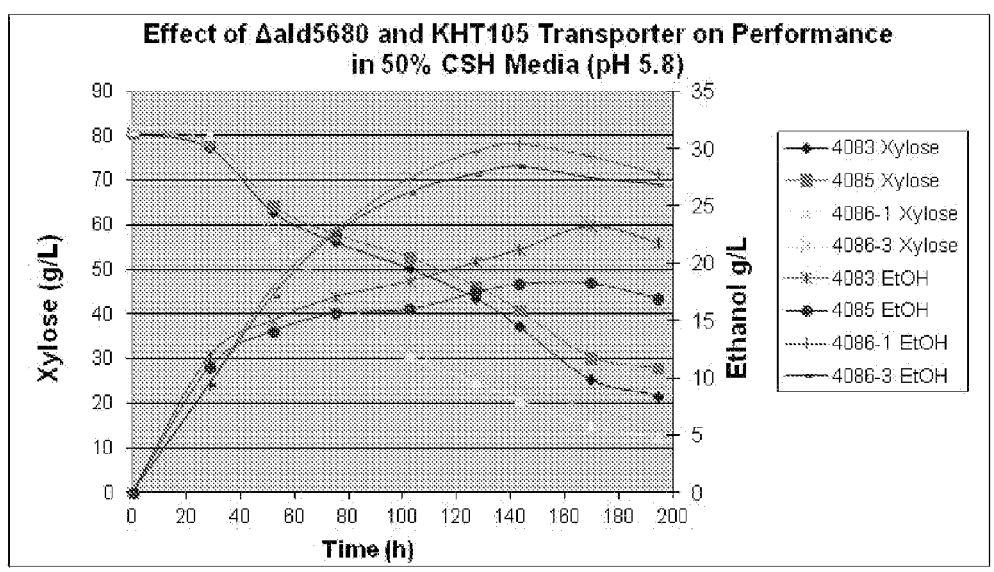
FIG. 25: Xylose fermentation to ethanol by strains 4083, 4085, and 4086 in 50% CSH media.

Strains 4083 (3×KHT105, 1× ALD5680 knockout), 4085 (4×KHT105, 2× S141G4546 knockout), and two clones of strain 4086 (4×KHT105, 2× ALD5680 knockout) were characterized using the same shake flask conditions. Results are summarized in Table 8 and FIG. 25. Addition of a fourth copy of KHT105 in combination with ALD5680 deletion substantially increased xylose consumption rates and ethanol titers over four copies of the KHT105 gene combined with the S141G4546 deletion (FIG. 25). The two clones of strain 4086 produced approximately 29 g/L ethanol at 140 hours, whereas strain 4085 and parent strain 3849 (data not shown) achieved their maximum titers of 17-18 g/L under the same conditions at this timepoint. The ALD5680 deletion also led to enhanced acetate consumption. Strain 4086 had increased glycerol and arabitol production, along with reduced xylitol production (Table 8).

TABLE 8

|  | Xylitol (g/L) | Arabitol (g/L) | Glycerol (g/L) | Acetate (g/L) |
| --- | --- | --- | --- | --- |
| Strain 4083 | 5.26 | BDL | 3.72 | 3.50 |
| Strain 4085 | 5.68 | BDL | 4.69 | 3.75 |
| Strain 4086 clone #1 | 2.53 | 1.28 | 7.27 | 2.09 |
| Strain 4086 clone #3 | 2.78 | 1.47 | 7.32 | 1.95 |

Example 16

Addition of KHT105 and/or Deletion of ALD5680 in an Ethanol Tolerant *I. orientalis* Strain

*I. orientalis* strain yGP44 (12053) is an ethanol tolerant mutant obtained by mutagenesis and selection of strain 3489, followed by engineering of the S141G1202 knockout. The URA3 selection marker was looped out by growing strain 12053 overnight in YPD and plating on ScD-FOA media. Colonies were screened by PCR and plated on ScD-ura media to confirm loss of the URA3 gene. Colonies positive for the loopout were named strain yLUN027.

To insert URA3 at the first locus of ALD5680, linearized integration fragments from plasmid pHJJ78 (Example 13) were transformed into yLUN027. Transformants were selected on ScD-ura plates and screened by PCR across both integration junctions to identify transformants positive for both junction PCR products. One such transformant was named yLUN030. The URA3 marker from yLUN030 was looped out by overnight growth on YPD and plating on ScD-FOA plates. Colonies were screened by PCR and for lack of growth on ScD-ura plates to identify those that had retained the ALD5680 deletion but lost the URA3 gene. Three such colonies were named strain yLUN032.

To knock out the second locus of ALD5680, plasmid DNA from pHJJ79 (Example 13) was digested with ApaI and SacI, and linearized integration fragments were transformed into yLUN032. Transformants were selected on ScD-ura plates and screened by PCR across both integration junctions for both loci. Two transformants were identified that were positive for all junction PCR products. These transformants were named strain yLUN035 (12124).

To insert the KHT105 transporter into the first ALD5680 locus, plasmid DNA from pHJJ93 (Example 15) was digested with ApaI and SacI, and linearized integration fragments were transformed into yLUN027. Transformants were selected on ScD-ura plates and screened by PCR across both integration junctions. Four transformants were identified that were positive for all junction PCR products. These transformants were named strain yLUN031.

The URA3 marker from yLUN031 was looped out by overnight growth on YPD and plating on ScD-FOA plates. Colonies were screened by PCR and for lack of growth on ScD-ura plates to identify those that had retained the KHT105 integration fragment at the ALD5680 site but lost the URA3 marker. One such colony was named strain yLUN033.

To add the second copy of KHT105 to yLUN033, plasmid DNA from pHJJ94 (Example 15) was digested with ApaI and SacI, and linearized integration fragments were transformed into yLUN033. Transformants were selected on ScD-ura plates and screened by PCR across both integration junctions for both loci. Four transformants were identified that were positive for all junction PCR products. These transformants were named strain yLUN036 (12125).

Strains 12124 (both ALD5680 loci knocked out), 12125 (2×KHT105, both ALD5680 loci knocked out), and 12053 (parent) were characterized by shake flask in DM+50% corn stover hydrolysate media with two different sugar concentrations. One set of shake flasks was run with 20 g/L dextrose and 80 g/L xylose, while the second contained 70 g/L dextrose and 40 g/L xylose. The pH of all media was 5.7. Shake flasks were inoculated to a starting $OD_{600}$=0.1 and grown at 100 rpm and 37° C.

Figure 26:
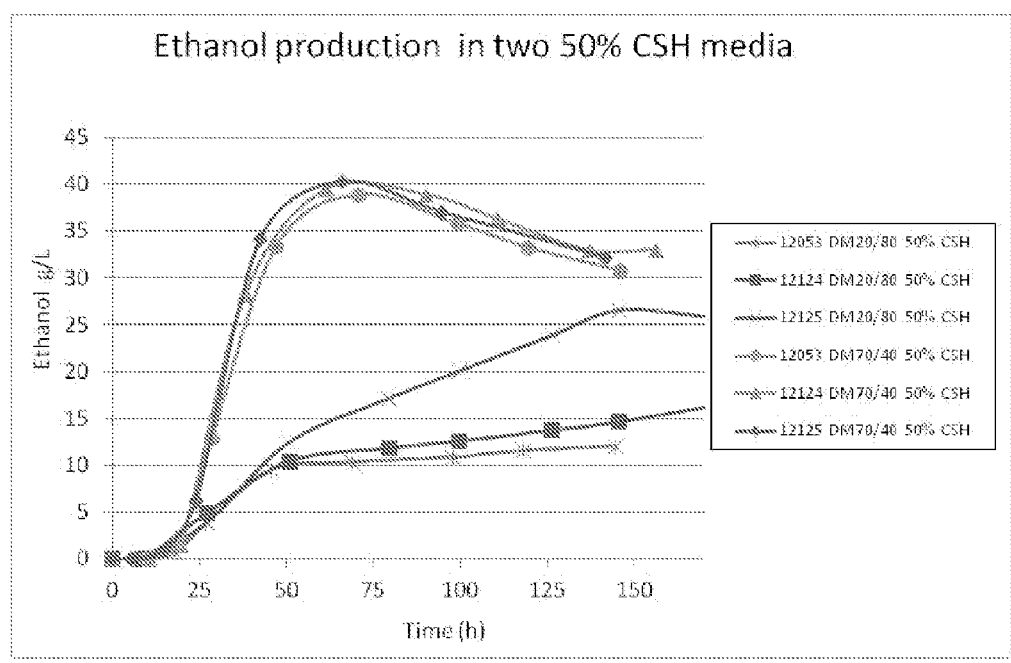
FIG. 26: Ethanol production by strains 12053, 12124, and 12125 in 50% CSH media with either 20 g/L dextrose and 80 g/L xylose or 70 g/L dextrose and 40 g/L xylose.
Figure 27:
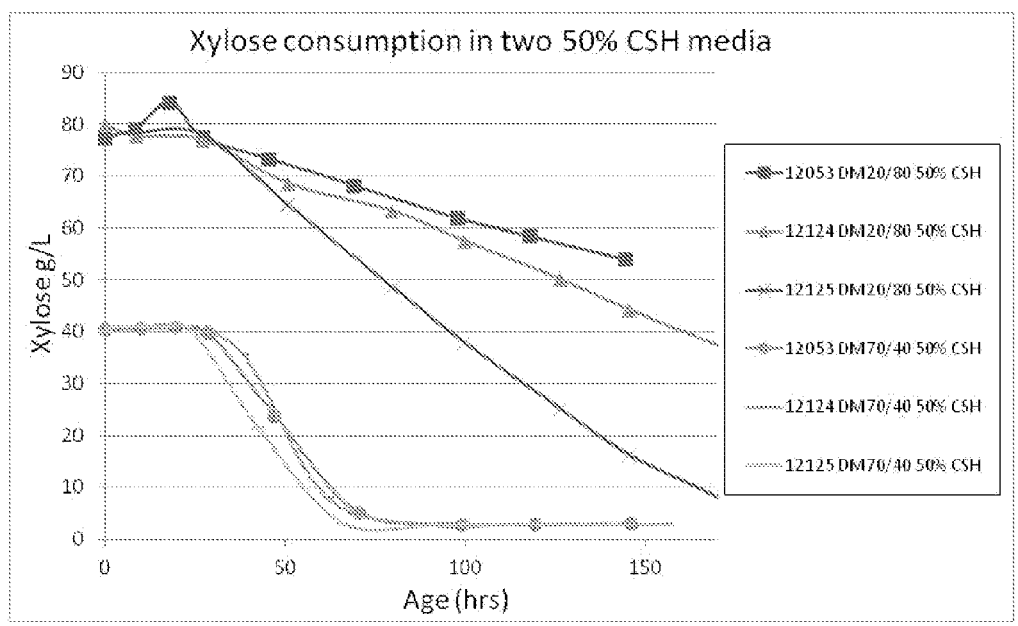
FIG. 27: Xylose fermentation by strains 12053, 12124, and 12125 in 50% CSH media with either 20 g/L dextrose and 80 g/L xylose or 70 g/L dextrose and 40 g/L xylose.

In the lower dextrose/higher xylose shake flasks, overexpression of KHT105 provided a significant advantage with regard to ethanol production (FIG. 26) and xylose consumption (FIG. 27). The ALD5680 deletion provided a 25% increase in ethanol titer, while the combination of this deletion with KHT105 overexpression gave an increase of approximately 125%. These advantages were much less pronounced in the higher dextrose/lower xylose defined media.

Example 17

Integration of B. animalis and L. lactis araD into I. orientalis and Characterization of Resultant Strains Due to relatively low activity of the previously tested REs, alternate araD genes were cloned and assayed for activity and performance in arabinose-containing media. These RE sequences were derived from B. animalis (SEQ ID NO:18) and L. lactis (SEQ ID NO:20) and codon optimized for expression in I. orientalis(SEQ ID NOs:17 and 19, respectively). The codon optimized B. animalis and L. lactis araD genes were integrated into the cyb2B site of strain 12038 (Table 3; Examples 11 and 12) using methods similar to those described above in Example 1. The cyb2b knockout had previously been shown to have no phenotypic effect under relevant test conditions. Strain 12038 was selected as the parent strain so that transport and araB activity were less likely to be limiting.

Figure 28:
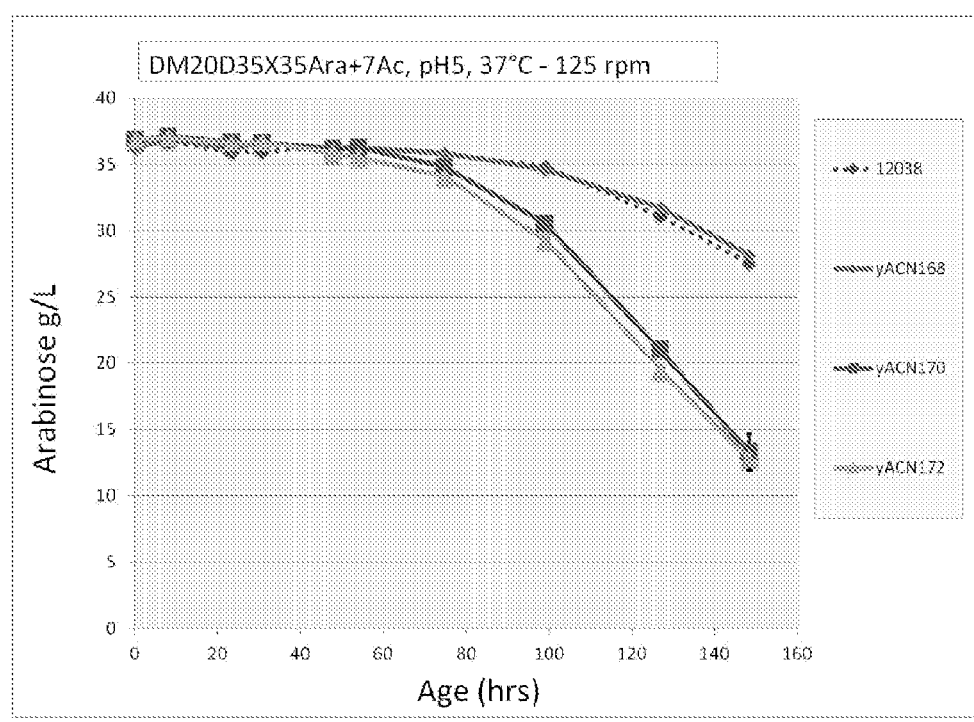
FIG. 28: Arabinose consumption by strains 12038, yACN168, yACN170, and yACN172 in DM media with 20 g/L dextrose, 35 g/L xylose, and 35 g/L arabinose.

Resultant strain yACN170 contained one copy of B. animalis araD and two copies of B. thetaiotaomicron araD, while strain yACN172 contained one copy of L. lactis araD and two copies of B. thetaiotaomicron araD. Strain yACN168 contained one copy of B. thetaiotaomicron araD integrated into the cyb2b site, for a total of three copies. All three strains were evaluated in shake flasks for arabinose fermentation relative to the parental strain. The testing media used was a defined media with 20 g/L dextrose, 35 g/L xylose, 35 g/L arabinose, 0.2M MES, and 7 g/L acetate, pH 5.0. Cells were grown at 37° C. and 125 rpm and sampled over time for substrates and products. Under these conditions, yACN170 and yACN172 had significantly increased arabinose consumption compared to the parent strain and yACN168 (FIG. 28).

Example 18

Integration of L. sakei araA and an Alternate B. Thetaiotaomicron araA into I. orientalis Cellulase enzymes used in cellulose hydrolysis have pH optimums of approximately 4-5.5 and temperature optimums of approximately 40-50° C. Pathway enzymes that demonstrate high activity under these conditions may provide a benefit to fermentative performance. Lactobacillus sakei AI/araA has recently been shown to have a pH optimum of 5-7, maintaining 80% of maximal activity at a pH of 3, and temperature stability up to 40° C. (Rhimi Bioresour Technol 101:9171 (2010)).

B. thetaiotaomicron has a second putative arabinose isomerase (araA2, SEQ ID NOs:7/8) that is only 17% homologous on an amino acid basis to the araA gene from this species that was used in previous examples. This homolog is shorter by 35 amino acids, located downstream of an L-arabinofuranosidase, and similar to L-arabinose isomerases of Pedobacter and Rhizobium.

Figure 29:
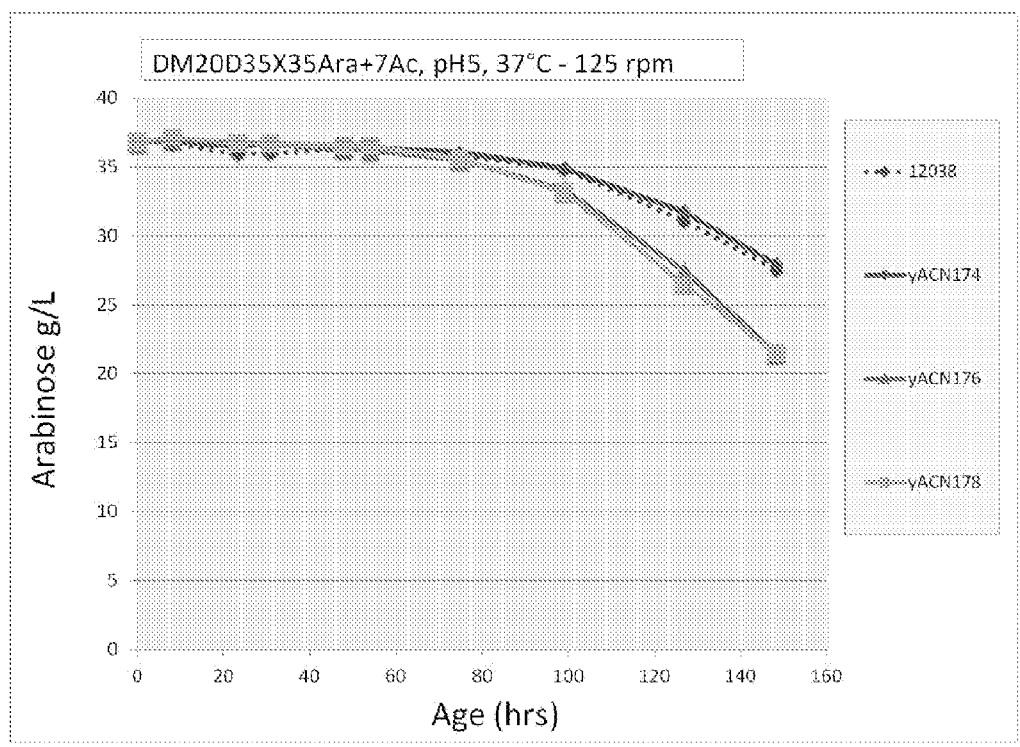
FIG. 29: Arabinose consumption by strains 12038, yACN174, yACN176, and yACN178 in DM media with 20 g/L dextrose, 35 g/L xylose, and 35 g/L arabinose.

L. sakei araA and B. thetaiotaomicron araA2 were integrated into the cyb2B site of strain 12038 using methods similar to those described above in Example 1. Resultant strain yACN176 contained one copy of L. sakei araA and two copies of B. thetaiotaomicron araA, while strain yACN178 contained one copy of B. thetaiotaomicron araA2 and two copies of B. thetaiotaomicron araA. Strain yACN174 contained one copy of B. thetaiotaomicron araD integrated into the cyb2b site, for a total of three copies. All three strains were evaluated in shake flasks for arabinose fermentation relative to the parental strain. The testing media used was a defined media with 20 g/L dextrose, 35 g/L xylose, 35 g/L arabinose, 0.2M MES, and 7 g/L acetate, pH 5.0. Cells were grown at 37° C. and 125 rpm and sampled over time for substrates and products. Under these conditions, yACN176 and yACN178 had significantly increased arabinose consumption compared to the parent strain and yACN174 (FIG. 29).

Example 19

Integration of Exogenous I. orientalis TAL genes into I. orientalis

Native sequence TAL genes from I. orientalis were incorporated into I. orientalis strain 3099 (Example 8) to determine whether over-expression of this enzyme increased xylose fermentation to ethanol.

To construct a TAL expression vector, the coding region of the I. orientalis TAL gene (SEQ ID NO:51) plus an additional 400 bp downstream of the gene were amplified from wild-type I. orientalis genomic DNA. The PCR product was cloned into pCR-Blunt II-TOPO to form plasmid pACN1 and sequence verified. An EcoRI/XbaI fragment of pACN1 carrying the TAL gene and terminator was ligated into a similarly cut vector fragment carrying the URA3 selection cassette and an I. orientalis PDC promoter to form plasmid pACN3. A NotI fragment of pACN3 carrying the promoter, TAL, terminator, and URA3 cassette was ligated with NotI-cut pHJJ4 (AXR1 targeting sequences, Example 1B) to form plasmids pACN5 (orientation 1) and pACN7 (orientation 2).

To construct a strain overexpressing TAL, strain 3099 was transformed with linearized DNA from pACN7 and plated on ScD-ura plates. Ura+ colonies were screened by colony PCR across both integration junctions; one isolate with the desired insertion was named yACN3. Strain yACN3 was plated on ScD-FOA plates to loop out the URA3 gene. Colony PCR was used to confirm retention of the desired integration; one such ura- isolate was named yACN7. Strain yACN7 was transformed with linearized DNA from pACN5 and plated on ScD-ura plates. Ura+ colonies were screened by colony PCR across all integration junctions; one isolate with the desired insertion at both AXR1 loci was named yACN11 (3082). A control strain, 3862, was generated by deleting both copies of the AXR1 locus in strain 3099 without overexpressing the TAL1 cassette. The deletion construct used to make this strain contained the URA3 selection cassette between the AXR1 targeting sequences.

Strains were characterized in shake flasks using YP media 20 g/L glucose and 80 g/L xylose at pH 4.8. Initial cultures (25 mL media in 125 mL flask) were grown during the day at 250 rpm. Overnight cultures (50 mL media in 250 mL flask) were inoculated to an OD of 0.00002 and grown at 230 rpm and 35° C. The next morning, all cultures had ODs of 3.8-5.3. Production flasks (50 mL media in 125 mL flasks) were inoculated to an OD of 0.1 and grown at 37° C. and 100 rpm. Samples were taken over time, centrifuged, and the supernatants were filtered and analyzed using HPLC.

Figure 33:
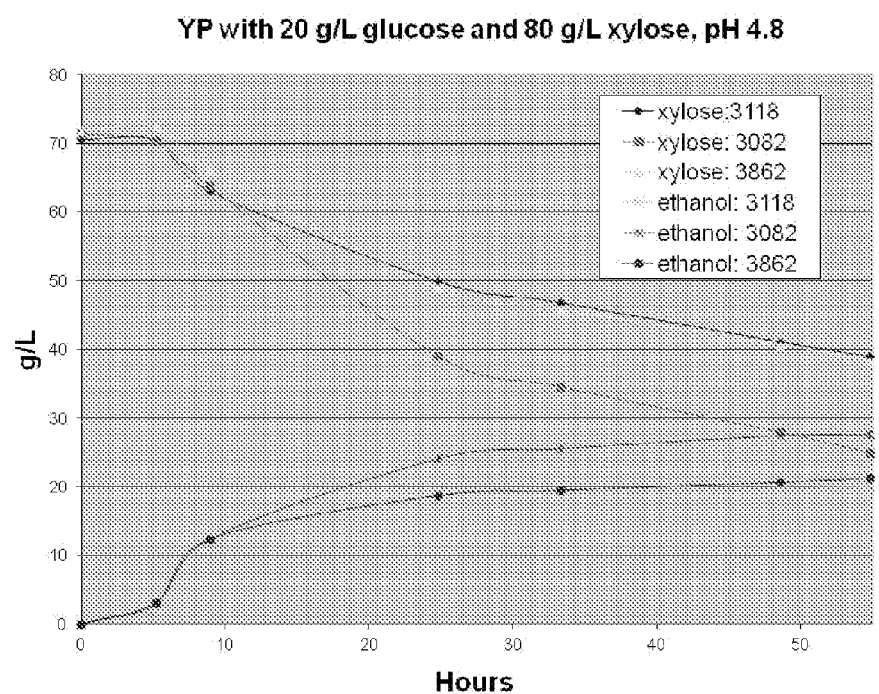
FIG. 33: Fermentation of glucose and xylose to ethanol by strains 3118, 3082, and 3862 in YP media with 20 g/L glucose and 80 g/L xylose.

The parent strain 3118 (ura+ version of 3099 prior to marker loopout) and the insertion site control strain 3862 produced 20-21 g/L ethanol in 55 hours, whereas strain 3082 produced 28 g/L in the same period (FIG. 33). In all three strains, glucose was depleted by nine hours. The additional ethanol formation in strain 3082 was correlated with an increased consumption of xylose. Strain 3082 produced less xylitol throughout the fermentation, and higher levels of glycerol and arabitol. Metabolite formation is summarized in Table 9.

TABLE 9

|  | Xylitol (g/L) | Glycerol (g/L) | Arabitol (g/L) |
|---|---|---|---|
| Strain 3118 | 2.2 | 0.9 | 0.4 |
| Strain 3082 | 1.2 | 2.0 | 1.3 |
| Strain 3862 | 2.0 | 1.0 | 0.5 |

Example 20

Integration of Exogenous *I. orientalis* RKI genes into *I. orientalis*

Native sequence RKI genes from *I. orientalis* were incorporated into *I. orientalis* strain yACN23 to determine whether over-expression of this enzyme increased xylose fermentation to ethanol.

To construct an integration vector targeting the GAL6 site, the 5' and 3' flanking regions of the GAL6 gene (SEQ ID NO:87) were amplified from wild-type *I. orientalis* genomic DNA. The PCR fragments were cloned into pCR-BluntII-TOPO to form plasmids pACN25 (upstream region) and pACN26 (downstream region) and were sequence verified. An ApaI/NotI fragment of pACN25, containing the upstream region, and a SacI/NotI fragment of pACN26, containing the downstream region, were ligated into ApaI/SacI-cut pCRII to form plasmid pACN29.

To construct an RKI expression vector, the coding region of the *I. orientalis* RKI gene (SEQ ID NO:39) plus an additional 400 bp downstream of the gene were amplified from wild-type *I. orientalis* genomic DNA. The PCR product was cloned into pCR-Blunt II-TOPO to form plasmids pACN27 and pACN28 and was sequence verified. The EcoRI/XbaI piece of pACN27 carrying the RKI gene and terminator was ligated into a similarly cut vector fragment carrying the URA3 selection cassette and an *I. orientalis* PDC promoter (EcoRI/XbaI fragment of pHJJ2, Example 1A) to form plasmid pACN31. The NotI fragment of pACN31 was ligated with NotI-cut pACN29 (GAL6 targeting sequences) to form plasmids pACN44 (orientation 1) and pACN45 (orientation 2).

Strain yACN23 is a derivative of strain 3082 (Example 19) that contains a deletion for the S141G4738 ("AXR4") locus. To construct a strain overexpressing RKI, strain yACN23 was transformed with linearized DNA from pACN44 and plated on ScD-ura plates. Ura+ colonies were screened by colony PCR across both integration junctions. One isolate with the desired insertion was named yACN25. Strain yACN25 was plated on ScD-FOA media to loop out the URA3 gene. Colony PCR across both integration junctions was used to confirm retention of the insert; one such ura– isolate was named yACN35. Strain yACN35 was transformed with linearized DNA from pACN43. Ura+ colonies were screened by colony PCR across all integration junctions; one isolate with the desired insert at both AXR4 loci was named yACN45 (3352).

Figure 34:
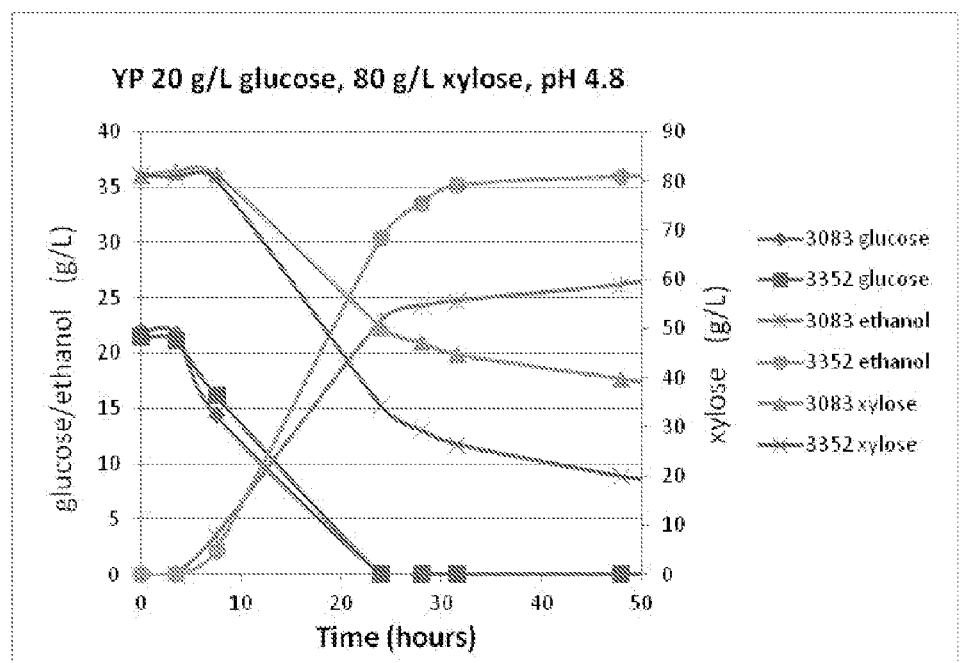
FIG. 34: Fermentation of glucose and xylose to ethanol by strains 3083 and 3352 in YP media with 20 g/L dextrose and 80 g/L xylose.

Characterization of strain 3352 and the ura+ parent strain 3083 (ura+ version of yACN23 with the URA3 at the AXR4 locus) was done in shake flasks as described in Example 19. Strain 3352 demonstrated an increased growth rate and maximum $OD_{600}$ compared to the parent strain. At 24 hours, strain 3083 was at its maximum $OD_{600}$ of 9.3, while strain 3352 had achieved an optical density of 13.5. Strain 3352 used 20 g/L more xylose in 52 hours than the parent strain (FIG. 34). The increase in xylose utilization resulted in higher ethanol levels, with strain 3352 producing 36.1 g/L ethanol at 52 hours versus 26.9 g/L for the parent (34% increase). Compared to strain 3083, strain 3352 showed decreased arabitol (0.3 versus 1.0 g/L) and glycerol (0.2 versus 1.5 g/L) levels.

Example 21

Integration of Exogenous *I. orientalis* TKL genes into *I. orientalis*

Native sequence TKL genes from *I. orientalis* were incorporated into *I. orientalis* strain yACN55 (Example 9) to determine whether over-expression of this enzyme increased xylose fermentation to ethanol.

To construction an AXR4 disruption cassette, the 5' and 3' flanking regions of S141G4738 were amplified from wild-type *I. orientalis* genomic DNA. The PCR fragments were cloned into a pCRII vector backbone with a NotI site between the upstream and downstream fragments and unique restriction sites on the 5' upstream and 3' downstream ends. The resulting plasmid was sequence verified and named pACN19.

To construct an *I. orientalis* TKL expression vector, the coding region of the *I. orientalis* TKL gene (SEQ ID NO:45) was amplified from *I. orientalis* genomic DNA and cloned into a vector containing the *I. orientalis* TDH3 promoter, TKL terminator, URA3 marker cassette and AXR4 targeting sequences such that the TKL gene was just downstream of the TDH3 promoter. The resulting vector was sequence verified and named pHJJ113. A second vector having the expression cassette in opposite orientation relative to the targeting sequences was obtained by ligating the pHJJ113 NotI fragment carrying the expression cassette with a NotI fragment carrying a vector backbone and the AXR4 targeting sequences. The desired orientation and insertion were confirmed by PCR on *E. coli* colonies transformed with this ligation. The resultant TKL expression vector was named pHJJ114.

To construct a strain over-expressing *I. orientalis* TKL, linearized DNA from pHJJ113 was transformed into yACN55 (ura– derivative of strain 3356). Single colonies were streaked for purification and single colonies from each streak were patched to ScD-ura. Colonies were screened for the desired integration by PCR across both integration junctions. One strain having the TKL over-expression cassette at the AXR4 site was named yHJJ221.

Clones of yHJJ221 were grown on YPD and plated on ScD-FOA media for marker loopout. Single colonies were streaked for purification and single colonies from each streak were patched to YPD. Marker loopout and retention of the TKL integration were confirmed by colony PCR across both integration junctions. One such ura– strain was named yHJJ226.

Linearized DNA from pHJJ114 was transformed into yHJJ226 and the transformation was plated on ScD-ura media. Single colonies were isolated and confirmed by PCR across all integration junctions. The final strain containing copies of *I. orientalis* TKL at both AXR4 loci was named strain yHJJ242 (12293).

A shake flask characterization was performed to compare parent strain 3356 and TKL over-expression strain 12293. The media used for this evaluation was YP media containing 20 g/l dextrose, 80 g/l xylose, and 10 g/l arabinose, at pH5.15. Cells from a fresh ScD-ura plate were used to inoculate a primary shake flask (50 mL media in a 250 mL flask). Flasks were grown at 250 rpm at 37° C. for about 7 hours. Cells from the primary seed were then used to inoculate a secondary seed flask (50 mL media in a 250 mL flask). The target inoculation $OD_{600}$ for these flasks was $5 \times 10^{-6}$. These flasks were grown overnight at 37° C. and 250 rpm. Cells from the secondary seed were used to inoculate the production flasks to a starting $OD_{600}$ of 0.2. The $OD_{600}$ of the secondary seeds ranged from 4.4 to 7.2 when the inoculums were taken. Production flasks were incubated at 37° C. and 100 rpm aeration, with samples taken one to two times per day. After using a portion of the sample to determine the OD, the remainders of the samples were spun down and the filtered supernatants were analyzed by HPLC.

Figure 35:
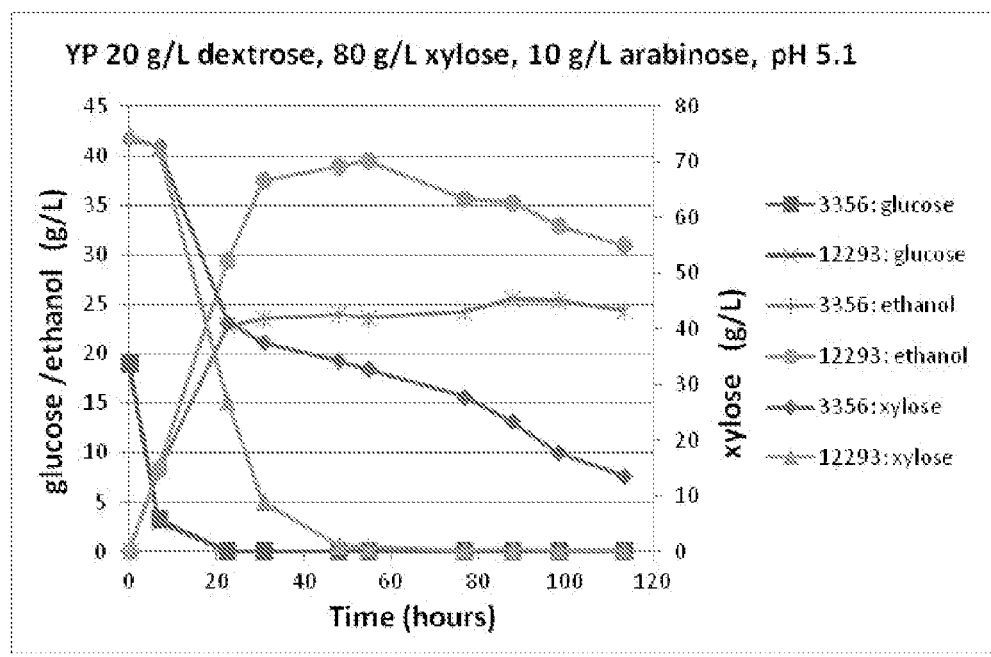
FIG. 35: Fermentation of glucose and xylose to ethanol by strains 3356 and 12293 in YP media with 20 g/L dextrose, 80 g/L xylose, and 10 g/L arabinose.

Strain 12293 showed a large improvement in xylose consumption and ethanol production rates versus the parent strain 3356 (FIG. 35). All xylose was consumed by strain 12293 during the first 50 hours of fermentation. For strain 3356, approximately 11 g of xylose remained in the media after 120 hours. In addition, several byproducts were reduced in strain 12293 relative to 3356: xylitol went from 2.8 g/L to 1.5 g/L, acetate from 2.8 to 1.1 g/L, and arabitol from 1.9 to 0 g/L.

As stated above, the foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein.

What is claimed is:

1. A genetically modified yeast cell that overexpresses a xylose transporter polypeptide comprising an amino acid sequence with at least 90% sequence identity to an amino acid sequence selected from the group consisting of SEQ ID NO:2 and SEQ ID NO:4.

2. The genetically modified yeast cell of claim 1 further comprising an active arabinose fermentation pathway, wherein said cell comprises one or more exogenous arabinose fermentation pathway genes selected from the group consisting of AI, RK, and RE genes.

3. The genetically modified yeast cell of claim 1 further comprising an active xylose fermentation pathway, wherein said cell comprises one or more exogenous xylose fermentation pathway genes selected from the group consisting of XI and XK genes.

4. The genetically modified yeast cell of claim 1 further comprising an active non-oxidative pentose phosphate pathway, wherein said cell comprises one or more exogenous non-oxidative pentose phosphate pathway genes selected from the group consisting of TKL and TAL genes.

5. The genetically modified yeast cell of claim 1, wherein said cell further comprises one or more exogenous non-oxidative pentose phosphate pathways genes selected from the group consisting of RPE and RKI genes.

6. The genetically modified yeast cell of claim 1, wherein said yeast cell further comprises a deletion or disruption of one or more genes selected from the group consisting of AR/XR, arabitol 4-dehydrogenase, xylulose reductase, and XDH genes.

7. The genetically modified yeast cell of claim 1, wherein said yeast cell further comprises a deletion or disruption of one or more genes selected from the group consisting of ALD and ADH genes.

8. The genetically modified yeast cell of claim 1, wherein said yeast cell belongs to the *I. orientalis/P. fermentans* clade.

9. The genetically modified yeast cell of claim 8, wherein said yeast cell is *I. orientalis*.

10. A fermentation process wherein a genetically modified yeast cell as recited in claim 1 is cultured in fermentation media comprising xylose.

11. The fermentation process of claim 10, wherein said fermentation media comprises at least 10 g/L xylose from a plant biomass hydrolysate.

12. The fermentation process of claim 11, wherein xylose is the most abundant sugar in said fermentation media.

13. A method of producing ethanol from a xylose-containing media comprising culturing a genetically modified yeast cell as recited in claim 1 in a xylose-containing media.

14. The method of claim 13, wherein said xylose-containing media comprises at least 10 g/L xylose from a plant biomass hydrolysate.

15. The method of claim 14, wherein xylose is the most abundant sugar in said media.

* * * * *

SEQUENCE LISTING

```
<160> NUMBER OF SEQ ID NOS: 88

<210> SEQ ID NO 1
<211> LENGTH: 1701
<212> TYPE: DNA
<213> ORGANISM: Kluyveromyces marxianus
<220> FEATURE:
<221> NAME/KEY: CDS
<222> LOCATION: (1)..(1701)

<400> SEQUENCE: 1 atg tcc gaa gct gct ggt tta caa acg ggc aca gct gct caa agc act        48
Met Ser Glu Ala Ala Gly Leu Gln Thr Gly Thr Ala Ala Gln Ser Thr
1               5                   10                  15 cct gta gac acc aag tct ttt gag agt tct caa gtt tcg act cca acc        96
Pro Val Asp Thr Lys Ser Phe Glu Ser Ser Gln Val Ser Thr Pro Thr
            20                  25                  30 aac gtt ggc tcg aag gat gag ttg aag gtc gat gag acc aac act gag       144
Asn Val Gly Ser Lys Asp Glu Leu Lys Val Asp Glu Thr Asn Thr Glu
        35                  40                  45 gtt gag ctt cca aag aaa cct gct tcc gct tac atc act gtc tcc att       192
Val Glu Leu Pro Lys Lys Pro Ala Ser Ala Tyr Ile Thr Val Ser Ile
    50                  55                  60 cta tgt tta atg gtt gcc ttt ggt ggt ttc gtt ttc ggt tgg gat acc       240
Leu Cys Leu Met Val Ala Phe Gly Gly Phe Val Phe Gly Trp Asp Thr
65                  70                  75                  80 ggt acc att tct ggt ttt gtt aac caa act gat ttc gtg aga aga ttc       288
Gly Thr Ile Ser Gly Phe Val Asn Gln Thr Asp Phe Val Arg Arg Phe
                85                  90                  95 ggt tct act cat gcc gat ggt act cac tat ttg tct aac gct aga act       336
Gly Ser Thr His Ala Asp Gly Thr His Tyr Leu Ser Asn Ala Arg Thr
            100                 105                 110 ggt atg att gtt tcc att ttc aac att ggt tgt gca ttt ggt ggt atc       384
Gly Met Ile Val Ser Ile Phe Asn Ile Gly Cys Ala Phe Gly Gly Ile
        115                 120                 125 ttt ttg tcc aag gtc ggt gac gtt tac ggt cgt cgt att ggt cta atg       432
Phe Leu Ser Lys Val Gly Asp Val Tyr Gly Arg Arg Ile Gly Leu Met
    130                 135                 140 gct gtt gtt cta gtt tac gtt gtt ggt att gtt atc caa atc gct tct       480
```

```
Ala Val Val Leu Val Tyr Val Val Gly Ile Val Ile Gln Ile Ala Ser
145                 150                 155                 160 tct gac aaa tgg tac caa tac ttc atc ggt aga att gtt tcc ggt ttg      528
Ser Asp Lys Trp Tyr Gln Tyr Phe Ile Gly Arg Ile Val Ser Gly Leu
            165                 170                 175 ggt gtc ggt ggt atc gct gtc ttg tcc cca atg ttg att tct gaa act      576
Gly Val Gly Gly Ile Ala Val Leu Ser Pro Met Leu Ile Ser Glu Thr
            180                 185                 190 gct cca aag caa ttg aga ggt act ttg gtg tct tgt tac caa ttg atg      624
Ala Pro Lys Gln Leu Arg Gly Thr Leu Val Ser Cys Tyr Gln Leu Met
    195                 200                 205 att acc ttc ggt atc ttc ttg ggt tac tgt acc aac tac ggt acc aag      672
Ile Thr Phe Gly Ile Phe Leu Gly Tyr Cys Thr Asn Tyr Gly Thr Lys
    210                 215                 220 act cac tcc gac tct gtc caa tgg aga gtc cca ttg ggt cta tgt ttc      720
Thr His Ser Asp Ser Val Gln Trp Arg Val Pro Leu Gly Leu Cys Phe
225                 230                 235                 240 ttg tgg gcc att ttc atg atc ggt ggt atg ttg ttc gtt cct gaa tcc      768
Leu Trp Ala Ile Phe Met Ile Gly Gly Met Leu Phe Val Pro Glu Ser
                245                 250                 255 cca aga tac ttg att gaa aag gac aga att gaa gaa gct aag gct tcc      816
Pro Arg Tyr Leu Ile Glu Lys Asp Arg Ile Glu Glu Ala Lys Ala Ser
            260                 265                 270 atc gcc aag tct aac aag gtt tcc atc gaa gac cca gct gtc caa gct      864
Ile Ala Lys Ser Asn Lys Val Ser Ile Glu Asp Pro Ala Val Gln Ala
            275                 280                 285 gaa act gat ttg ttg att gcc ggt gtt gaa gct gaa aga cta gct ggt      912
Glu Thr Asp Leu Leu Ile Ala Gly Val Glu Ala Glu Arg Leu Ala Gly
    290                 295                 300 tct gct tct ttc aag gag ttg ttc tcc acc aag acc aag gtt ttc caa      960
Ser Ala Ser Phe Lys Glu Leu Phe Ser Thr Lys Thr Lys Val Phe Gln
305                 310                 315                 320 cgt ttg gtc atg ggt att atg atc caa tct ttc caa caa ttg acc ggt     1008
Arg Leu Val Met Gly Ile Met Ile Gln Ser Phe Gln Gln Leu Thr Gly
                325                 330                 335 aac aac tac ttc ttc tac tac ggt act agt atc ttc aag tcc gtc ggt     1056
Asn Asn Tyr Phe Phe Tyr Tyr Gly Thr Ser Ile Phe Lys Ser Val Gly
            340                 345                 350 atg acc gat tct ttc gaa act tct att gtc ttg ggt att gtt aac ttc     1104
Met Thr Asp Ser Phe Glu Thr Ser Ile Val Leu Gly Ile Val Asn Phe
            355                 360                 365 gct tcc act ttc ttg ggt atc tac att gtt ggt aga ttt ggc cgt cgt     1152
Ala Ser Thr Phe Leu Gly Ile Tyr Ile Val Gly Arg Phe Gly Arg Arg
    370                 375                 380 caa tgt ttg cta tgg ggt gct gct cta atg acc tgt tgt atg gtt gtc     1200
Gln Cys Leu Leu Trp Gly Ala Ala Leu Met Thr Cys Cys Met Val Val
385                 390                 395                 400 ttt gca tcc gtc ggt gtt acc aag ttg tgg cca aag ggt cca aac ggt     1248
Phe Ala Ser Val Gly Val Thr Lys Leu Trp Pro Lys Gly Pro Asn Gly
                405                 410                 415 ggt gtt tct tct aag ggt gct ggt gac tgt atg att gtc ttc acc tgt     1296
Gly Val Ser Ser Lys Gly Ala Gly Asp Cys Met Ile Val Phe Thr Cys
            420                 425                 430 ttc tac att cta tgt ttc gct acc acc tgg gct cca att gct tac gtc     1344
Phe Tyr Ile Leu Cys Phe Ala Thr Thr Trp Ala Pro Ile Ala Tyr Val
            435                 440                 445 gtt gtt gct gaa tct tac cca ttg aga gtc aag tcc aag tgt atg ggt     1392
Val Val Ala Glu Ser Tyr Pro Leu Arg Val Lys Ser Lys Cys Met Gly
450                 455                 460
```

```
gtc gct acc gct tct aac tgg gtc tgg ggt ttc ttg att ggt ttc ttc    1440
Val Ala Thr Ala Ser Asn Trp Val Trp Gly Phe Leu Ile Gly Phe Phe
465             470                 475                 480 act cca ttc att act tct gac atc cac ttc tac tac ggt tac gtc ttc    1488
Thr Pro Phe Ile Thr Ser Asp Ile His Phe Tyr Tyr Gly Tyr Val Phe
                485                 490                 495 atg ggc tgt ttg gtt gcc atg ttc ttc tac gtc ttc ttc ttt gtc cca    1536
Met Gly Cys Leu Val Ala Met Phe Phe Tyr Val Phe Phe Phe Val Pro
                500                 505                 510 gaa acc aag ggt cta act ttg gaa gaa gtc gat gaa atg tgg tta gaa    1584
Glu Thr Lys Gly Leu Thr Leu Glu Glu Val Asp Glu Met Trp Leu Glu
                515                 520                 525 ggt gtc ttg cca tgg aag tcc gaa tca tgg gtc cca tct tcc aga aga    1632
Gly Val Leu Pro Trp Lys Ser Glu Ser Trp Val Pro Ser Ser Arg Arg
530                 535                 540 ggt gct gac tac aac gcc gat gac ttg caa cac gat gac aag cca tgg    1680
Gly Ala Asp Tyr Asn Ala Asp Asp Leu Gln His Asp Asp Lys Pro Trp
545                 550                 555                 560 tac aag gct atg atg aaa taa                                        1701
Tyr Lys Ala Met Met Lys
                565
```

```
<210> SEQ ID NO 2
<211> LENGTH: 566
<212> TYPE: PRT
<213> ORGANISM: Kluyveromyces marxianus

<400> SEQUENCE: 2

Met Ser Glu Ala Ala Gly Leu Gln Thr Gly Thr Ala Ala Gln Ser Thr
1               5                   10                  15

Pro Val Asp Thr Lys Ser Phe Glu Ser Ser Gln Val Ser Thr Pro Thr
                20                  25                  30

Asn Val Gly Ser Lys Asp Glu Leu Lys Val Asp Glu Thr Asn Thr Glu
            35                  40                  45

Val Glu Leu Pro Lys Lys Pro Ala Ser Ala Tyr Ile Thr Val Ser Ile
        50                  55                  60

Leu Cys Leu Met Val Ala Phe Gly Gly Phe Val Phe Gly Trp Asp Thr
65                  70                  75                  80

Gly Thr Ile Ser Gly Phe Val Asn Gln Thr Asp Phe Val Arg Arg Phe
                85                  90                  95

Gly Ser Thr His Ala Asp Gly Thr His Tyr Leu Ser Asn Ala Arg Thr
            100                 105                 110

Gly Met Ile Val Ser Ile Phe Asn Ile Gly Cys Ala Phe Gly Gly Ile
        115                 120                 125

Phe Leu Ser Lys Val Gly Asp Val Tyr Gly Arg Arg Ile Gly Leu Met
    130                 135                 140

Ala Val Val Leu Val Tyr Val Val Gly Ile Val Ile Gln Ile Ala Ser
145                 150                 155                 160

Ser Asp Lys Trp Tyr Gln Tyr Phe Ile Gly Arg Ile Val Ser Gly Leu
                165                 170                 175

Gly Val Gly Gly Ile Ala Val Leu Ser Pro Met Leu Ile Ser Glu Thr
            180                 185                 190

Ala Pro Lys Gln Leu Arg Gly Thr Leu Val Ser Cys Tyr Gln Leu Met
        195                 200                 205

Ile Thr Phe Gly Ile Phe Leu Gly Tyr Cys Thr Asn Tyr Gly Thr Lys
    210                 215                 220

Thr His Ser Asp Ser Val Gln Trp Arg Val Pro Leu Gly Leu Cys Phe
```

```
            225                 230                 235                 240
Leu Trp Ala Ile Phe Met Ile Gly Gly Met Leu Phe Val Pro Glu Ser
                245                 250                 255
Pro Arg Tyr Leu Ile Glu Lys Asp Arg Ile Glu Ala Lys Ala Ser
                260                 265                 270
Ile Ala Lys Ser Asn Lys Val Ser Ile Glu Asp Pro Ala Val Gln Ala
                275                 280                 285
Glu Thr Asp Leu Leu Ile Ala Gly Val Glu Ala Glu Arg Leu Ala Gly
                290                 295                 300
Ser Ala Ser Phe Lys Glu Leu Phe Ser Thr Lys Thr Lys Val Phe Gln
305                 310                 315                 320
Arg Leu Val Met Gly Ile Met Ile Gln Ser Phe Gln Gln Leu Thr Gly
                325                 330                 335
Asn Asn Tyr Phe Phe Tyr Tyr Gly Thr Ser Ile Phe Lys Ser Val Gly
                340                 345                 350
Met Thr Asp Ser Phe Glu Thr Ser Ile Val Leu Gly Ile Val Asn Phe
                355                 360                 365
Ala Ser Thr Phe Leu Gly Ile Tyr Ile Val Gly Arg Phe Gly Arg Arg
                370                 375                 380
Gln Cys Leu Leu Trp Gly Ala Ala Leu Met Thr Cys Cys Met Val Val
385                 390                 395                 400
Phe Ala Ser Val Gly Val Thr Lys Leu Trp Pro Lys Gly Pro Asn Gly
                405                 410                 415
Gly Val Ser Ser Lys Gly Ala Gly Asp Cys Met Ile Val Phe Thr Cys
                420                 425                 430
Phe Tyr Ile Leu Cys Phe Ala Thr Thr Trp Ala Pro Ile Ala Tyr Val
                435                 440                 445
Val Val Ala Glu Ser Tyr Pro Leu Arg Val Lys Ser Lys Cys Met Gly
                450                 455                 460
Val Ala Thr Ala Ser Asn Trp Val Trp Gly Phe Leu Ile Gly Phe Phe
465                 470                 475                 480
Thr Pro Phe Ile Thr Ser Asp Ile His Phe Tyr Tyr Gly Tyr Val Phe
                485                 490                 495
Met Gly Cys Leu Val Ala Met Phe Phe Tyr Val Phe Phe Val Pro
                500                 505                 510
Glu Thr Lys Gly Leu Thr Leu Glu Glu Val Asp Glu Met Trp Leu Glu
                515                 520                 525
Gly Val Leu Pro Trp Lys Ser Glu Ser Trp Val Pro Ser Ser Arg Arg
                530                 535                 540
Gly Ala Asp Tyr Asn Ala Asp Asp Leu Gln His Asp Asp Lys Pro Trp
545                 550                 555                 560
Tyr Lys Ala Met Met Lys
                565

<210> SEQ ID NO 3
<211> LENGTH: 2442
<212> TYPE: DNA
<213> ORGANISM: Kluyveromyces marxianus
<220> FEATURE:
<221> NAME/KEY: CDS
<222> LOCATION: (1)..(2442)

<400> SEQUENCE: 3 atg atc att aac tcc aat cat cga aag aac atc agt aaa gct gcg aga    48
Met Ile Ile Asn Ser Asn His Arg Lys Asn Ile Ser Lys Ala Ala Arg
1               5                   10                  15
```

| | | | | | | | | | | | | | | | | |
|---|---|---|---|---|---|---|---|---|---|---|---|---|---|---|---|---|
| ctc | gta | ttg | ctt | cga | cgg | agg | gca | aat | ggc | gac | aat | gag | gct | ggt | gta | 96 |
| Leu | Val | Leu | Leu | Arg | Arg | Arg | Ala | Asn | Gly | Asp | Asn | Glu | Ala | Gly | Val | |
| | | 20 | | | | | 25 | | | | | 30 | | | | |
| tct | gga | cta | cca | gct | gga | aat | aaa | tca | aac | aat | gga | cta | tca | gga | tcg | 144 |
| Ser | Gly | Leu | Pro | Ala | Gly | Asn | Lys | Ser | Asn | Asn | Gly | Leu | Ser | Gly | Ser | |
| | 35 | | | | | 40 | | | | | 45 | | | | | |
| gca | tcc | ccg | caa | gag | ctt | tac | caa | gaa | aat | ggc | gaa | gag | ttt | gaa | cta | 192 |
| Ala | Ser | Pro | Gln | Glu | Leu | Tyr | Gln | Glu | Asn | Gly | Glu | Glu | Phe | Glu | Leu | |
| 50 | | | | | 55 | | | | | 60 | | | | | | |
| agc | aat | ttt | gct | tcg | ctt | acc | gac | atg | gag | tcc | gag | atc | ttt | tta | caa | 240 |
| Ser | Asn | Phe | Ala | Ser | Leu | Thr | Asp | Met | Glu | Ser | Glu | Ile | Phe | Leu | Gln | |
| 65 | | | | | 70 | | | | | 75 | | | | | 80 | |
| cct | cca | gca | aaa | cag | tcg | aag | aaa | ata | tca | ata | ttc | gtt | ggt | tta | ttc | 288 |
| Pro | Pro | Ala | Lys | Gln | Ser | Lys | Lys | Ile | Ser | Ile | Phe | Val | Gly | Leu | Phe | |
| | | | | 85 | | | | | 90 | | | | | 95 | | |
| gtt | gca | gta | gga | gga | ttt | cta | ttt | ggc | tac | gat | acg | ggc | tta | atc | aat | 336 |
| Val | Ala | Val | Gly | Gly | Phe | Leu | Phe | Gly | Tyr | Asp | Thr | Gly | Leu | Ile | Asn | |
| | | | 100 | | | | | 105 | | | | | 110 | | | |
| aat | gtc | agt | caa | atg | cca | tat | gtt | ctt | aaa | aca | atc | gct | cca | aac | aaa | 384 |
| Asn | Val | Ser | Gln | Met | Pro | Tyr | Val | Leu | Lys | Thr | Ile | Ala | Pro | Asn | Lys | |
| | | 115 | | | | | 120 | | | | | 125 | | | | |
| cac | cag | ttc | act | act | tca | cag | ata | tca | att | cta | gta | tcc | ttt | ttg | tct | 432 |
| His | Gln | Phe | Thr | Thr | Ser | Gln | Ile | Ser | Ile | Leu | Val | Ser | Phe | Leu | Ser | |
| | 130 | | | | | 135 | | | | | 140 | | | | | |
| ctg | ggt | act | ttc | ttc | ggg | gca | tta | ttt | gca | cca | ttc | ata | tct | gac | cgt | 480 |
| Leu | Gly | Thr | Phe | Phe | Gly | Ala | Leu | Phe | Ala | Pro | Phe | Ile | Ser | Asp | Arg | |
| 145 | | | | | 150 | | | | | 155 | | | | | 160 | |
| tat | ggg | cgg | aaa | acc | acc | atg | ctc | ttt | agt | act | ttt | ttt | gtc | ttt | atg | 528 |
| Tyr | Gly | Arg | Lys | Thr | Thr | Met | Leu | Phe | Ser | Thr | Phe | Phe | Val | Phe | Met | |
| | | | | 165 | | | | | 170 | | | | | 175 | | |
| gtt | ggt | aac | tcc | tta | caa | gtg | gca | gcg | act | tct | atg | aca | tta | tta | gtc | 576 |
| Val | Gly | Asn | Ser | Leu | Gln | Val | Ala | Ala | Thr | Ser | Met | Thr | Leu | Leu | Val | |
| | | | 180 | | | | | 185 | | | | | 190 | | | |
| gta | gga | agg | gta | ctg | tct | gga | ctt | agt | gtt | gga | cta | ata | tcc | gct | gca | 624 |
| Val | Gly | Arg | Val | Leu | Ser | Gly | Leu | Ser | Val | Gly | Leu | Ile | Ser | Ala | Ala | |
| | | 195 | | | | | 200 | | | | | 205 | | | | |
| gtt | ccc | ttg | tat | cag | agt | gaa | gcc | gca | cag | aaa | tct | gtt | cgt | ggt | gct | 672 |
| Val | Pro | Leu | Tyr | Gln | Ser | Glu | Ala | Ala | Gln | Lys | Ser | Val | Arg | Gly | Ala | |
| 210 | | | | | 215 | | | | | 220 | | | | | | |
| att | att | tcc | acc | tat | cag | tgg | gct | ata | acc | tgg | ggt | tta | tta | gtt | gcc | 720 |
| Ile | Ile | Ser | Thr | Tyr | Gln | Trp | Ala | Ile | Thr | Trp | Gly | Leu | Leu | Val | Ala | |
| 225 | | | | | 230 | | | | | 235 | | | | | 240 | |
| agt | gca | gtt | tca | caa | gga | acc | tac | aaa | aga | atg | aat | gct | tca | agt | tat | 768 |
| Ser | Ala | Val | Ser | Gln | Gly | Thr | Tyr | Lys | Arg | Met | Asn | Ala | Ser | Ser | Tyr | |
| | | | | 245 | | | | | 250 | | | | | 255 | | |
| cga | att | cca | ata | agt | ttg | caa | tat | gtc | tgg | gct | ttt | act | ctt | ggt | gtt | 816 |
| Arg | Ile | Pro | Ile | Ser | Leu | Gln | Tyr | Val | Trp | Ala | Phe | Thr | Leu | Gly | Val | |
| | | | 260 | | | | | 265 | | | | | 270 | | | |
| ggt | gtc | tta | ttt | cta | cca | gag | agt | cca | cgt | tat | tat | gtt | ttc | aaa | gat | 864 |
| Gly | Val | Leu | Phe | Leu | Pro | Glu | Ser | Pro | Arg | Tyr | Tyr | Val | Phe | Lys | Asp | |
| | | 275 | | | | | 280 | | | | | 285 | | | | |
| agg | ctt | gat | cta | gct | gcc | aaa | tct | tta | tca | ttc | ttg | aga | gga | gtg | ccc | 912 |
| Arg | Leu | Asp | Leu | Ala | Ala | Lys | Ser | Leu | Ser | Phe | Leu | Arg | Gly | Val | Pro | |
| 290 | | | | | 295 | | | | | 300 | | | | | | |
| gaa | gat | gat | tcc | ggt | ttg | ctc | gag | gaa | tta | gta | gag | ata | aag | gca | acc | 960 |
| Glu | Asp | Asp | Ser | Gly | Leu | Leu | Glu | Glu | Leu | Val | Glu | Ile | Lys | Ala | Thr | |
| 305 | | | | | 310 | | | | | 315 | | | | | 320 | |
| tat | gat | tat | gaa | ctg | tct | ttc | ggt | aaa | aca | tca | ttt | ctt | gac | tgt | ttt | 1008 |
| Tyr | Asp | Tyr | Glu | Leu | Ser | Phe | Gly | Lys | Thr | Ser | Phe | Leu | Asp | Cys | Phe | |

-continued

```
                    325                 330                 335
agg tca acg aaa tca aga tcc aaa caa cgt ctt cgt atg atg acc ggt      1056
Arg Ser Thr Lys Ser Arg Ser Lys Gln Arg Leu Arg Met Met Thr Gly
            340                 345                 350 att gct ctt caa gca ttt caa caa gta agt ggt att aat ttc att ttt      1104
Ile Ala Leu Gln Ala Phe Gln Gln Val Ser Gly Ile Asn Phe Ile Phe
            355                 360                 365 tac tat ggt gtt aat ttc ttc aac aaa acg ggt atc aag aat agt tac      1152
Tyr Tyr Gly Val Asn Phe Phe Asn Lys Thr Gly Ile Lys Asn Ser Tyr
    370                 375                 380 ttg gtg tca ttc att act tac gct gta aat gtg gta ttt aat gtg cca      1200
Leu Val Ser Phe Ile Thr Tyr Ala Val Asn Val Val Phe Asn Val Pro
385                 390                 395                 400 ggt cta ttt tta gtc gaa tat att ggc cgg cgt aaa ctt tta ctt gga      1248
Gly Leu Phe Leu Val Glu Tyr Ile Gly Arg Arg Lys Leu Leu Leu Gly
                405                 410                 415 ggt ggc ata gtg atg aca tta gca aat ttt acc atc gcg gtt aca ggt      1296
Gly Gly Ile Val Met Thr Leu Ala Asn Phe Thr Ile Ala Val Thr Gly
            420                 425                 430 tta gtt gca gat tcc aag att gcc aac aaa gtg atg ata gcg ttt atc      1344
Leu Val Ala Asp Ser Lys Ile Ala Asn Lys Val Met Ile Ala Phe Ile
            435                 440                 445 tgt ttg ttt att gcc tca ttc tca gca acc tgg ggt ggt ggt gtt tgg      1392
Cys Leu Phe Ile Ala Ser Phe Ser Ala Thr Trp Gly Gly Gly Val Trp
    450                 455                 460 gtt ata tct gcc gaa ctt tat ccc tta ggt gtg cgt gct aag tgc act      1440
Val Ile Ser Ala Glu Leu Tyr Pro Leu Gly Val Arg Ala Lys Cys Thr
465                 470                 475                 480 tct ata tgc gca gct tcg aat tgg ctt ttc aat ttc atc tgt gcc cta      1488
Ser Ile Cys Ala Ala Ser Asn Trp Leu Phe Asn Phe Ile Cys Ala Leu
                485                 490                 495 ata acg ccg tac att gtt cgt atc gac aat ggt caa cat tct tca acc      1536
Ile Thr Pro Tyr Ile Val Arg Ile Asp Asn Gly Gln His Ser Ser Thr
            500                 505                 510 atg ggg agc aaa atc ttt ttt gtg tgg ggt tcg tta aac gct ata tcg      1584
Met Gly Ser Lys Ile Phe Phe Val Trp Gly Ser Leu Asn Ala Ile Ser
            515                 520                 525 gtg tta gtc ggg tac ttc acc att tac gag act agt gga ctc tca tta      1632
Val Leu Val Gly Tyr Phe Thr Ile Tyr Glu Thr Ser Gly Leu Ser Leu
    530                 535                 540 gaa gaa ata gac gaa ttg tac aag aat tcg tca tct ggt gtg gac tct      1680
Glu Glu Ile Asp Glu Leu Tyr Lys Asn Ser Ser Ser Gly Val Asp Ser
545                 550                 555                 560 atg aaa tgg aat aag aag ata agg tcc atg ccg gaa ctc ttc caa aga      1728
Met Lys Trp Asn Lys Lys Ile Arg Ser Met Pro Glu Leu Phe Gln Arg
                565                 570                 575 aac gca caa aat gat gat tca atc ggg gaa gag gta gta acg gga          1776
Asn Ala Gln Asn Asp Asp Ser Ile Gly Glu Glu Val Val Thr Gly
            580                 585                 590 aac aat gtt cac aac ttt ggg gcc gcg caa ggc tcg tct tcg aac gag      1824
Asn Asn Val His Asn Phe Gly Ala Ala Gln Gly Ser Ser Ser Asn Glu
            595                 600                 605 acc aac agc aac gag aac agc aac gag aag tac act tct cca ata gca      1872
Thr Asn Ser Asn Glu Asn Ser Asn Glu Lys Tyr Thr Ser Pro Ile Ala
    610                 615                 620 atg cct caa ttc ggt gca cgg agc atc gat cat cct tcc agc gct tct      1920
Met Pro Gln Phe Gly Ala Arg Ser Ile Asp His Pro Ser Ser Ala Ser
625                 630                 635                 640 gac atg ttc tca aag cgt ctg ccg tta gca gaa ctg aac ttt gtg gac      1968
```

```
                Asp Met Phe Ser Lys Arg Leu Pro Leu Ala Glu Leu Asn Phe Val Asp
                                645                 650                 655 ttg ggg aac gga ctt gga atc aca acc tac caa cgt ggc cca cct tcc         2016
Leu Gly Asn Gly Leu Gly Ile Thr Thr Tyr Gln Arg Gly Pro Pro Ser
        660                 665                 670 gtg ctt aca gat tcg agc gac gag gat gaa gaa gaa caa gac cta gca         2064
Val Leu Thr Asp Ser Ser Asp Glu Asp Glu Glu Glu Gln Asp Leu Ala
675                 680                 685 gat gca tac tct ttg gag cac gcc tcc cag gac aca gag gac ctg cat         2112
Asp Ala Tyr Ser Leu Glu His Ala Ser Gln Asp Thr Glu Asp Leu His
    690                 695                 700 cac ctg cat cac ctt acc tcc aac aga cgg aac act aat gga tca gaa         2160
His Leu His His Leu Thr Ser Asn Arg Arg Asn Thr Asn Gly Ser Glu
705                 710                 715                 720 cct ttg agc tct aag agc ggc agc agt gct gca gga acg gtg cgc acc         2208
Pro Leu Ser Ser Lys Ser Gly Ser Ser Ala Ala Gly Thr Val Arg Thr
                725                 730                 735 tct cca cct aaa cat aac aaa cac aga agg gaa gac ttt aac atg tac         2256
Ser Pro Pro Lys His Asn Lys His Arg Arg Glu Asp Phe Asn Met Tyr
            740                 745                 750 atg gct caa tta atc aac cgt ggg tct caa gag gct gta tct tgc tcc         2304
Met Ala Gln Leu Ile Asn Arg Gly Ser Gln Glu Ala Val Ser Cys Ser
        755                 760                 765 agc gag cct aaa aac cat cct ata ccc cac gac atc atg agc caa tgg         2352
Ser Glu Pro Lys Asn His Pro Ile Pro His Asp Ile Met Ser Gln Trp
770                 775                 780 aac tcg tct tcc aaa gaa gag tca aac aga cga aat tcc tca aca gac         2400
Asn Ser Ser Ser Lys Glu Glu Ser Asn Arg Arg Asn Ser Ser Thr Asp
785                 790                 795                 800 aat agc aac cca tct acg cca aaa aac aca cat cat aaa tag                 2442
Asn Ser Asn Pro Ser Thr Pro Lys Asn Thr His His Lys
                805                 810

<210> SEQ ID NO 4
<211> LENGTH: 813
<212> TYPE: PRT
<213> ORGANISM: Kluyveromyces marxianus

<400> SEQUENCE: 4

Met Ile Ile Asn Ser Asn His Arg Lys Asn Ile Ser Lys Ala Ala Arg
1               5                   10                  15

Leu Val Leu Leu Arg Arg Arg Ala Asn Gly Asp Asn Glu Ala Gly Val
            20                  25                  30

Ser Gly Leu Pro Ala Gly Asn Lys Ser Asn Asn Gly Leu Ser Gly Ser
        35                  40                  45

Ala Ser Pro Gln Glu Leu Tyr Gln Glu Asn Gly Glu Glu Phe Glu Leu
    50                  55                  60

Ser Asn Phe Ala Ser Leu Thr Asp Met Glu Ser Glu Ile Phe Leu Gln
65                  70                  75                  80

Pro Pro Ala Lys Gln Ser Lys Lys Ile Ser Ile Phe Val Gly Leu Phe
                85                  90                  95

Val Ala Val Gly Gly Phe Leu Phe Gly Tyr Asp Thr Gly Leu Ile Asn
            100                 105                 110

Asn Val Ser Gln Met Pro Tyr Val Leu Lys Thr Ile Ala Pro Asn Lys
        115                 120                 125

His Gln Phe Thr Thr Ser Gln Ile Ser Ile Leu Val Ser Phe Leu Ser
    130                 135                 140

Leu Gly Thr Phe Phe Gly Ala Leu Phe Ala Pro Phe Ile Ser Asp Arg
```

```
            145                 150                 155                 160
Tyr Gly Arg Lys Thr Thr Met Leu Phe Ser Thr Phe Val Phe Met
                165                 170                 175
Val Gly Asn Ser Leu Gln Val Ala Ala Thr Ser Met Thr Leu Leu Val
                180                 185                 190
Val Gly Arg Val Leu Ser Gly Leu Ser Val Gly Leu Ile Ser Ala Ala
                195                 200                 205
Val Pro Leu Tyr Gln Ser Glu Ala Ala Gln Lys Ser Val Arg Gly Ala
                210                 215                 220
Ile Ile Ser Thr Tyr Gln Trp Ala Ile Thr Trp Gly Leu Leu Val Ala
225                 230                 235                 240
Ser Ala Val Ser Gln Gly Thr Tyr Lys Arg Met Asn Ala Ser Ser Tyr
                245                 250                 255
Arg Ile Pro Ile Ser Leu Gln Tyr Val Trp Ala Phe Thr Leu Gly Val
                260                 265                 270
Gly Val Leu Phe Leu Pro Glu Ser Pro Arg Tyr Tyr Val Phe Lys Asp
                275                 280                 285
Arg Leu Asp Leu Ala Ala Lys Ser Leu Ser Phe Leu Arg Gly Val Pro
                290                 295                 300
Glu Asp Asp Ser Gly Leu Leu Glu Glu Leu Val Glu Ile Lys Ala Thr
305                 310                 315                 320
Tyr Asp Tyr Glu Leu Ser Phe Gly Lys Thr Ser Phe Leu Asp Cys Phe
                325                 330                 335
Arg Ser Thr Lys Ser Arg Ser Lys Gln Arg Leu Arg Met Met Thr Gly
                340                 345                 350
Ile Ala Leu Gln Ala Phe Gln Gln Val Ser Gly Ile Asn Phe Ile Phe
                355                 360                 365
Tyr Tyr Gly Val Asn Phe Phe Asn Lys Thr Gly Ile Lys Asn Ser Tyr
                370                 375                 380
Leu Val Ser Phe Ile Thr Tyr Ala Val Asn Val Val Phe Asn Val Pro
385                 390                 395                 400
Gly Leu Phe Leu Val Glu Tyr Ile Gly Arg Arg Lys Leu Leu Leu Gly
                405                 410                 415
Gly Gly Ile Val Met Thr Leu Ala Asn Phe Thr Ile Ala Val Thr Gly
                420                 425                 430
Leu Val Ala Asp Ser Lys Ile Ala Asn Lys Val Met Ile Ala Phe Ile
                435                 440                 445
Cys Leu Phe Ile Ala Ser Phe Ser Ala Thr Trp Gly Gly Gly Val Trp
                450                 455                 460
Val Ile Ser Ala Glu Leu Tyr Pro Leu Gly Val Arg Ala Lys Cys Thr
465                 470                 475                 480
Ser Ile Cys Ala Ala Ser Asn Trp Leu Phe Asn Phe Ile Cys Ala Leu
                485                 490                 495
Ile Thr Pro Tyr Ile Val Arg Ile Asp Asn Gly Gln His Ser Ser Thr
                500                 505                 510
Met Gly Ser Lys Ile Phe Phe Val Trp Gly Ser Leu Asn Ala Ile Ser
                515                 520                 525
Val Leu Val Gly Tyr Phe Thr Ile Tyr Glu Thr Ser Gly Leu Ser Leu
                530                 535                 540
Glu Glu Ile Asp Glu Leu Tyr Lys Asn Ser Ser Ser Gly Val Asp Ser
545                 550                 555                 560
Met Lys Trp Asn Lys Lys Ile Arg Ser Met Pro Glu Leu Phe Gln Arg
                565                 570                 575
```

```
Asn Ala Gln Asn Asp Asp Ser Ile Gly Glu Glu Val Val Thr Gly
            580                 585                 590

Asn Asn Val His Asn Phe Gly Ala Ala Gln Gly Ser Ser Ser Asn Glu
        595                 600                 605

Thr Asn Ser Asn Glu Asn Ser Asn Glu Lys Tyr Thr Ser Pro Ile Ala
    610                 615                 620

Met Pro Gln Phe Gly Ala Arg Ser Ile Asp His Pro Ser Ser Ala Ser
625                 630                 635                 640

Asp Met Phe Ser Lys Arg Leu Pro Leu Ala Glu Leu Asn Phe Val Asp
                645                 650                 655

Leu Gly Asn Gly Leu Gly Ile Thr Thr Tyr Gln Arg Gly Pro Pro Ser
            660                 665                 670

Val Leu Thr Asp Ser Ser Asp Glu Asp Glu Glu Gln Asp Leu Ala
        675                 680                 685

Asp Ala Tyr Ser Leu Glu His Ala Ser Gln Asp Thr Glu Asp Leu His
        690                 695                 700

His Leu His His Leu Thr Ser Asn Arg Arg Asn Thr Asn Gly Ser Glu
705                 710                 715                 720

Pro Leu Ser Ser Lys Ser Gly Ser Ser Ala Ala Gly Thr Val Arg Thr
                725                 730                 735

Ser Pro Pro Lys His Asn Lys His Arg Arg Glu Asp Phe Asn Met Tyr
            740                 745                 750

Met Ala Gln Leu Ile Asn Arg Gly Ser Gln Glu Ala Val Ser Cys Ser
        755                 760                 765

Ser Glu Pro Lys Asn His Pro Ile Pro His Asp Ile Met Ser Gln Trp
    770                 775                 780

Asn Ser Ser Ser Lys Glu Glu Ser Asn Arg Arg Asn Ser Ser Thr Asp
785                 790                 795                 800

Asn Ser Asn Pro Ser Thr Pro Lys Asn Thr His His Lys
                805                 810

<210> SEQ ID NO 5
<211> LENGTH: 1530
<212> TYPE: DNA
<213> ORGANISM: Artificial Sequence
<220> FEATURE:
<223> OTHER INFORMATION: Codon optimized B. thetaiotaomicron araA1
<220> FEATURE:
<221> NAME/KEY: CDS
<222> LOCATION: (1)..(1530)

<400> SEQUENCE: 5 atg aac aac gtt ttc gat caa tat gaa gtc tgg ttt gtt acc ggt gca    48
Met Asn Asn Val Phe Asp Gln Tyr Glu Val Trp Phe Val Thr Gly Ala
1               5                   10                  15 caa tta tta tat ggt ggt gac gct gtc att gca gtt gac gct cat tct    96
Gln Leu Leu Tyr Gly Gly Asp Ala Val Ile Ala Val Asp Ala His Ser
            20                  25                  30 aac gaa atg gtt aac ggt tta aac gaa tct ggt aag ttg cct gtt aag   144
Asn Glu Met Val Asn Gly Leu Asn Glu Ser Gly Lys Leu Pro Val Lys
        35                  40                  45 gtt gtc tat aag ggt act gct aac tct tct aag gag gtc gaa gct gtc   192
Val Val Tyr Lys Gly Thr Ala Asn Ser Ser Lys Glu Val Glu Ala Val
    50                  55                  60 ttc aag gca gca aac aac gat gac aag tgc gtc ggt gtt att acc tgg   240
Phe Lys Ala Ala Asn Asn Asp Asp Lys Cys Val Gly Val Ile Thr Trp
65                  70                  75                  80
```

| | | |
|---|---|---|
| atg cat acc ttc tcc cca gct aag atg tgg att cac ggt tta cag caa<br>Met His Thr Phe Ser Pro Ala Lys Met Trp Ile His Gly Leu Gln Gln<br>                    85                    90                95 | 288 |
| ttg aag aag cca tta ttg cac ttg cat acc caa ttc aac aag gaa att<br>Leu Lys Lys Pro Leu Leu His Leu His Thr Gln Phe Asn Lys Glu Ile<br>                100                105                110 | 336 |
| cca tgg gac aca atg gac atg gac ttc atg aat ctt aat caa tct gct<br>Pro Trp Asp Thr Met Asp Met Asp Phe Met Asn Leu Asn Gln Ser Ala<br>        115                  120                125 | 384 |
| cat ggt gat aga gaa ttc ggt cac att tgt acc aga atg aga att aga<br>His Gly Asp Arg Glu Phe Gly His Ile Cys Thr Arg Met Arg Ile Arg<br>130                    135                140 | 432 |
| aga aag gtc gtc gtc ggt tat tgg aaa gaa gaa gaa aca ttg cat aag<br>Arg Lys Val Val Val Gly Tyr Trp Lys Glu Glu Glu Thr Leu His Lys<br>145                    150                155                160 | 480 |
| atc gca gtc tgg atg aga gtc tgt gca ggt tgg gct gat tct caa gat<br>Ile Ala Val Trp Met Arg Val Cys Ala Gly Trp Ala Asp Ser Gln Asp<br>                165                170                175 | 528 |
| atg tta atc att aga ttt ggt gat caa atg aac aac gtt gct gtt act<br>Met Leu Ile Ile Arg Phe Gly Asp Gln Met Asn Asn Val Ala Val Thr<br>        180                  185                190 | 576 |
| gat ggt gat aag gtt gaa gct gaa caa aga atg ggt tac cac gtt gat<br>Asp Gly Asp Lys Val Glu Ala Glu Gln Arg Met Gly Tyr His Val Asp<br>                195                200                205 | 624 |
| tac tgt cca gct tcc gaa tta atg gaa tat cac aag gat att aag aac<br>Tyr Cys Pro Ala Ser Glu Leu Met Glu Tyr His Lys Asp Ile Lys Asn<br>210                    215                220 | 672 |
| gct gat gtt gat gca tta gtt gct acc tac ttt aat gat tac gat cat<br>Ala Asp Val Asp Ala Leu Val Ala Thr Tyr Phe Asn Asp Tyr Asp His<br>225                    230                235                240 | 720 |
| gat gca tct tta gaa gat aag tcc act gag gca tat caa aag gtt tgg<br>Asp Ala Ser Leu Glu Asp Lys Ser Thr Glu Ala Tyr Gln Lys Val Trp<br>                245                250                255 | 768 |
| aac gca gct aag gct gaa ttg gct tta aga gcc att ttg aag gct aag<br>Asn Ala Ala Lys Ala Glu Leu Ala Leu Arg Ala Ile Leu Lys Ala Lys<br>        260                  265                270 | 816 |
| ggt gca aag ggt ttt act act aac ttc gat gat ttg ggt caa acc gac<br>Gly Ala Lys Gly Phe Thr Thr Asn Phe Asp Asp Leu Gly Gln Thr Asp<br>275                    280                285 | 864 |
| ggt tct tat ttc gac caa att cca ggt tta gct tct caa aga tta atg<br>Gly Ser Tyr Phe Asp Gln Ile Pro Gly Leu Ala Ser Gln Arg Leu Met<br>        290                  295                300 | 912 |
| gcc gaa ggt tat ggt ttt ggt gct gaa ggt gat tgg aag tct gct gca<br>Ala Glu Gly Tyr Gly Phe Gly Ala Glu Gly Asp Trp Lys Ser Ala Ala<br>305                    310                315                320 | 960 |
| tta tac aga aca gtt tgg gtt atg aat caa ggt tta cct aag ggt tgt<br>Leu Tyr Arg Thr Val Trp Val Met Asn Gln Gly Leu Pro Lys Gly Cys<br>                325                330                335 | 1008 |
| tca ttc tta gaa gac tac acc tta aat ttc gat ggt gca aac tct tct<br>Ser Phe Leu Glu Asp Tyr Thr Leu Asn Phe Asp Gly Ala Asn Ser Ser<br>                340                345                350 | 1056 |
| att tta caa tct cac atg ttg gaa atc tgt cca ttg att gct gca aac<br>Ile Leu Gln Ser His Met Leu Glu Ile Cys Pro Leu Ile Ala Ala Asn<br>        355                  360                365 | 1104 |
| aag cca aga ttg gaa gtt cac ttc ttg ggt atc ggt att aga aag tct<br>Lys Pro Arg Leu Glu Val His Phe Leu Gly Ile Gly Ile Arg Lys Ser<br>370                    375                380 | 1152 |
| caa aca gct aga ttg gtt ttc act tcc aag acc ggt act ggt tgt act<br>Gln Thr Ala Arg Leu Val Phe Thr Ser Lys Thr Gly Thr Gly Cys Thr<br>385                    390                395                400 | 1200 |

```
gca acc gtc gtt gac atg ggt aac aga ttt aga ttg att gtc aat gac      1248
Ala Thr Val Val Asp Met Gly Asn Arg Phe Arg Leu Ile Val Asn Asp
            405                 410                 415 gtc gaa tgt att gaa cca aag cca tta cca aaa ttg cca gtt gct tca      1296
Val Glu Cys Ile Glu Pro Lys Pro Leu Pro Lys Leu Pro Val Ala Ser
        420                 425                 430 gct tta tgg att cca atg cca aac tta gag gtt ggt gca ggt gct tgg      1344
Ala Leu Trp Ile Pro Met Pro Asn Leu Glu Val Gly Ala Gly Ala Trp
    435                 440                 445 atc tta gct ggt ggt aca cac cac tct tgt ttc tct tat gat ttg acc      1392
Ile Leu Ala Gly Gly Thr His His Ser Cys Phe Ser Tyr Asp Leu Thr
450                 455                 460 gct gaa tac tgg gaa gac tac gct gaa atc gca ggt att gaa atg gtt      1440
Ala Glu Tyr Trp Glu Asp Tyr Ala Glu Ile Ala Gly Ile Glu Met Val
465                 470                 475                 480 cac att aac aag gat act act att tct tgc ttt aag aag gaa tta aga      1488
His Ile Asn Lys Asp Thr Thr Ile Ser Cys Phe Lys Lys Glu Leu Arg
            485                 490                 495 atg aac gaa gtc tat tat atg ttg aac aaa gct tta tgt taa              1530
Met Asn Glu Val Tyr Tyr Met Leu Asn Lys Ala Leu Cys
        500                 505

<210> SEQ ID NO 6
<211> LENGTH: 509
<212> TYPE: PRT
<213> ORGANISM: Artificial Sequence
<220> FEATURE:
<223> OTHER INFORMATION: Synthetic Construct

<400> SEQUENCE: 6

Met Asn Asn Val Phe Asp Gln Tyr Glu Val Trp Phe Val Thr Gly Ala
1               5                   10                  15

Gln Leu Leu Tyr Gly Gly Asp Ala Val Ile Ala Val Asp Ala His Ser
            20                  25                  30

Asn Glu Met Val Asn Gly Leu Asn Glu Ser Gly Lys Leu Pro Val Lys
        35                  40                  45

Val Val Tyr Lys Gly Thr Ala Asn Ser Ser Lys Glu Val Glu Ala Val
    50                  55                  60

Phe Lys Ala Ala Asn Asn Asp Asp Lys Cys Val Gly Val Ile Thr Trp
65                  70                  75                  80

Met His Thr Phe Ser Pro Ala Lys Met Trp Ile His Gly Leu Gln Gln
                85                  90                  95

Leu Lys Lys Pro Leu Leu His Leu His Thr Gln Phe Asn Lys Glu Ile
            100                 105                 110

Pro Trp Asp Thr Met Asp Met Asp Phe Met Asn Leu Asn Gln Ser Ala
        115                 120                 125

His Gly Asp Arg Glu Phe Gly His Ile Cys Thr Arg Met Arg Ile Arg
    130                 135                 140

Arg Lys Val Val Val Gly Tyr Trp Lys Glu Glu Thr Leu His Lys
145                 150                 155                 160

Ile Ala Val Trp Met Arg Val Cys Ala Gly Trp Ala Asp Ser Gln Asp
                165                 170                 175

Met Leu Ile Ile Arg Phe Gly Asp Gln Met Asn Asn Val Ala Val Thr
            180                 185                 190

Asp Gly Asp Lys Val Glu Ala Glu Gln Arg Met Gly Tyr His Val Asp
        195                 200                 205

Tyr Cys Pro Ala Ser Glu Leu Met Glu Tyr His Lys Asp Ile Lys Asn
```

```
                210                 215                 220
Ala Asp Val Asp Ala Leu Val Ala Thr Tyr Phe Asn Asp Tyr Asp His
225                 230                 235                 240

Asp Ala Ser Leu Glu Asp Lys Ser Thr Glu Ala Tyr Gln Lys Val Trp
                245                 250                 255

Asn Ala Ala Lys Ala Glu Leu Ala Leu Arg Ala Ile Leu Lys Ala Lys
            260                 265                 270

Gly Ala Lys Gly Phe Thr Thr Asn Phe Asp Asp Leu Gly Gln Thr Asp
        275                 280                 285

Gly Ser Tyr Phe Asp Gln Ile Pro Gly Leu Ala Ser Gln Arg Leu Met
290                 295                 300

Ala Glu Gly Tyr Gly Phe Gly Ala Glu Gly Asp Trp Lys Ser Ala Ala
305                 310                 315                 320

Leu Tyr Arg Thr Val Trp Val Met Asn Gln Gly Leu Pro Lys Gly Cys
                325                 330                 335

Ser Phe Leu Glu Asp Tyr Thr Leu Asn Phe Asp Gly Ala Asn Ser Ser
            340                 345                 350

Ile Leu Gln Ser His Met Leu Glu Ile Cys Pro Leu Ile Ala Ala Asn
        355                 360                 365

Lys Pro Arg Leu Glu Val His Phe Leu Gly Ile Gly Ile Arg Lys Ser
370                 375                 380

Gln Thr Ala Arg Leu Val Phe Thr Ser Lys Thr Gly Thr Gly Cys Thr
385                 390                 395                 400

Ala Thr Val Val Asp Met Gly Asn Arg Phe Arg Leu Ile Val Asn Asp
                405                 410                 415

Val Glu Cys Ile Glu Pro Lys Pro Leu Pro Lys Leu Pro Val Ala Ser
            420                 425                 430

Ala Leu Trp Ile Pro Met Pro Asn Leu Glu Val Gly Ala Gly Ala Trp
        435                 440                 445

Ile Leu Ala Gly Gly Thr His His Ser Cys Phe Ser Tyr Asp Leu Thr
450                 455                 460

Ala Glu Tyr Trp Glu Asp Tyr Ala Glu Ile Ala Gly Ile Glu Met Val
465                 470                 475                 480

His Ile Asn Lys Asp Thr Thr Ile Ser Cys Phe Lys Lys Glu Leu Arg
                485                 490                 495

Met Asn Glu Val Tyr Tyr Met Leu Asn Lys Ala Leu Cys
            500                 505

<210> SEQ ID NO 7
<211> LENGTH: 1425
<212> TYPE: DNA
<213> ORGANISM: Artificial Sequence
<220> FEATURE:
<223> OTHER INFORMATION: Codon optimized B. thetaiotaomicron araA2
<220> FEATURE:
<221> NAME/KEY: CDS
<222> LOCATION: (1)..(1425)

<400> SEQUENCE: 7 atg ata caa caa aaa gta aga gtg gga ctt tta gga gtc gga ttg gat    48
Met Ile Gln Gln Lys Val Arg Val Gly Leu Leu Gly Val Gly Leu Asp
1               5                   10                  15 act tat tgg gga caa ttt gaa ggg ctt ctt ccc cgt ctg tta act tat    96
Thr Tyr Trp Gly Gln Phe Glu Gly Leu Leu Pro Arg Leu Leu Thr Tyr
            20                  25                  30 cag gat gaa ata gct gcc aaa ata gag gca atg gac gta caa gtt atc   144
Gln Asp Glu Ile Ala Ala Lys Ile Glu Ala Met Asp Val Gln Val Ile
```

|  |  | 35 |  |  |  | 40 |  |  |  | 45 |  |  |  |  |
|---|---|---|---|---|---|---|---|---|---|---|---|---|---|---|
| aat | acg | ggg | atg | gtg | gat | tcg | cct | cta | aaa | gct | aat | gaa | tgt | gtc | cta | 192 |
| Asn | Thr | Gly | Met | Val | Asp | Ser | Pro | Leu | Lys | Ala | Asn | Glu | Cys | Val | Leu |  |
|  | 50 |  |  |  | 55 |  |  |  | 60 |  |  |  |  |  |  |  |

```
aat acg ggg atg gtg gat tcg cct cta aaa gct aat gaa tgt gtc cta    192
Asn Thr Gly Met Val Asp Ser Pro Leu Lys Ala Asn Glu Cys Val Leu
    50                  55                  60 caa tta aaa caa gct gat gta gaa ttg gtt ttt ctg ttt att tct act    240
Gln Leu Lys Gln Ala Asp Val Glu Leu Val Phe Leu Phe Ile Ser Thr
65                  70                  75                  80 tat gct ctt tct tct acg ata cta cct gta gct caa caa gta ggc aag    288
Tyr Ala Leu Ser Ser Thr Ile Leu Pro Val Ala Gln Gln Val Gly Lys
                85                  90                  95 cct att att ata tta aat ata cag cct gca tca gca ata gat tat caa    336
Pro Ile Ile Ile Leu Asn Ile Gln Pro Ala Ser Ala Ile Asp Tyr Gln
            100                 105                 110 aaa ctc aat tca atg ggg gat aga gga aga atg aca ggt gaa tgg ttg    384
Lys Leu Asn Ser Met Gly Asp Arg Gly Arg Met Thr Gly Glu Trp Leu
        115                 120                 125 gca cat tgt cag gca tgt tct gtt ccg gag ttt gcg agt gtt ttg aat    432
Ala His Cys Gln Ala Cys Ser Val Pro Glu Phe Ala Ser Val Leu Asn
    130                 135                 140 aga gcc ggt gtg cga tat gat att atc acc ggc tat tta tca gaa gat    480
Arg Ala Gly Val Arg Tyr Asp Ile Ile Thr Gly Tyr Leu Ser Glu Asp
145                 150                 155                 160 tat gtt tgg gag gaa ata gcc tct tgg gtt gac gct gta cgt gta atg    528
Tyr Val Trp Glu Glu Ile Ala Ser Trp Val Asp Ala Val Arg Val Met
                165                 170                 175 tat gga atg cgc aca agc cgt ttg gga gtt ttg ggg cat tac tat tgt    576
Tyr Gly Met Arg Thr Ser Arg Leu Gly Val Leu Gly His Tyr Tyr Cys
            180                 185                 190 ggt atg cta gat gta tat act gat ctt atg aag cag agc gca gtg ttt    624
Gly Met Leu Asp Val Tyr Thr Asp Leu Met Lys Gln Ser Ala Val Phe
        195                 200                 205 ggt act cat ata gag ttg ctg gag atg tgt gag cta aaa gct tat aga    672
Gly Thr His Ile Glu Leu Leu Glu Met Cys Glu Leu Lys Ala Tyr Arg
    210                 215                 220 gaa gaa gtt agc gat ggg gaa ctg aag cga aaa ctg gac gaa ttt tat    720
Glu Glu Val Ser Asp Gly Glu Leu Lys Arg Lys Leu Asp Glu Phe Tyr
225                 230                 235                 240 gat aag ttt aat gtg gaa gca tca tgt agt tcg gaa gag cta gtg agg    768
Asp Lys Phe Asn Val Glu Ala Ser Cys Ser Ser Glu Glu Leu Val Arg
                245                 250                 255 gct gca cgt act tct gtg gct ttg gat aaa tta gtg aat gtg cat caa    816
Ala Ala Arg Thr Ser Val Ala Leu Asp Lys Leu Val Asn Val His Gln
            260                 265                 270 ctg gga gcg atg gct tat tat tac gaa gga ttc tgt ggg aat gat tat    864
Leu Gly Ala Met Ala Tyr Tyr Tyr Glu Gly Phe Cys Gly Asn Asp Tyr
        275                 280                 285 gag aat att gta act tct gtt att gca ggt aat acg ttg ttg aca gga    912
Glu Asn Ile Val Thr Ser Val Ile Ala Gly Asn Thr Leu Leu Thr Gly
    290                 295                 300 tat gga ata ccc gtt gcc gga gaa tgt gaa gtg aaa aat gca cag gcg    960
Tyr Gly Ile Pro Val Ala Gly Glu Cys Glu Val Lys Asn Ala Gln Ala
305                 310                 315                 320 atg aaa att atg tca cta tta aaa gct ggt ggt tct ttc tct gaa ttt    1008
Met Lys Ile Met Ser Leu Leu Lys Ala Gly Gly Ser Phe Ser Glu Phe
                325                 330                 335 tat gca atg gat ttt aag gat gat att gta tta cta gga cat gat ggc    1056
Tyr Ala Met Asp Phe Lys Asp Asp Ile Val Leu Leu Gly His Asp Gly
            340                 345                 350 ccg gca cat ttt gca atc gcc gaa gag aaa gtg aaa cta gtg cct ctt    1104
```

```
                                      -continued

Pro Ala His Phe Ala Ile Ala Glu Glu Lys Val Lys Leu Val Pro Leu
            355                 360                 365 cca tta tat cac ggt aaa ccg ggt aaa ggt ctg tcc atc cag atg agt    1152
Pro Leu Tyr His Gly Lys Pro Gly Lys Gly Leu Ser Ile Gln Met Ser
370                 375                 380 gtt aaa cca ggt gat gtt aca ctt ttg tcg gta tgt gag gga aga gac    1200
Val Lys Pro Gly Asp Val Thr Leu Leu Ser Val Cys Glu Gly Arg Asp
385                 390                 395                 400 gga gtc ttt cta ctt gct gct gag gga gag gct gta caa gga gaa act    1248
Gly Val Phe Leu Leu Ala Ala Glu Gly Glu Ala Val Gln Gly Glu Thr
                405                 410                 415 cta cat att ggc aat aca aat agt cgt tat cgc ttt ccg tgt ggt gct    1296
Leu His Ile Gly Asn Thr Asn Ser Arg Tyr Arg Phe Pro Cys Gly Ala
            420                 425                 430 cgt cgg ttt atg gat caa tgg agt aaa gcg gga cct tca cat cat tgt    1344
Arg Arg Phe Met Asp Gln Trp Ser Lys Ala Gly Pro Ser His His Cys
            435                 440                 445 gcg att ggc att gga cat aaa gtc tct gaa ctg aag aaa ctg gca ttt    1392
Ala Ile Gly Ile Gly His Lys Val Ser Glu Leu Lys Lys Leu Ala Phe
450                 455                 460 ctt ctg gat att cca ata ata gta gtt gaa taa                        1425
Leu Leu Asp Ile Pro Ile Ile Val Val Glu
465                 470

<210> SEQ ID NO 8
<211> LENGTH: 474
<212> TYPE: PRT
<213> ORGANISM: Artificial Sequence
<220> FEATURE:
<223> OTHER INFORMATION: Synthetic Construct

<400> SEQUENCE: 8

Met Ile Gln Gln Lys Val Arg Val Gly Leu Gly Val Gly Leu Asp
1               5                   10                  15

Thr Tyr Trp Gly Gln Phe Glu Gly Leu Leu Pro Arg Leu Leu Thr Tyr
            20                  25                  30

Gln Asp Glu Ile Ala Ala Lys Ile Glu Ala Met Asp Val Gln Val Ile
        35                  40                  45

Asn Thr Gly Met Val Asp Ser Pro Leu Lys Ala Asn Glu Cys Val Leu
    50                  55                  60

Gln Leu Lys Gln Ala Asp Val Glu Leu Val Phe Leu Phe Ile Ser Thr
65                  70                  75                  80

Tyr Ala Leu Ser Ser Thr Ile Leu Pro Val Ala Gln Gln Val Gly Lys
                85                  90                  95

Pro Ile Ile Ile Leu Asn Ile Gln Pro Ala Ser Ala Ile Asp Tyr Gln
            100                 105                 110

Lys Leu Asn Ser Met Gly Asp Arg Gly Arg Met Thr Gly Glu Trp Leu
        115                 120                 125

Ala His Cys Gln Ala Cys Ser Val Pro Glu Phe Ala Ser Val Leu Asn
    130                 135                 140

Arg Ala Gly Val Arg Tyr Asp Ile Ile Thr Gly Tyr Leu Ser Glu Asp
145                 150                 155                 160

Tyr Val Trp Glu Glu Ile Ala Ser Trp Val Asp Ala Val Arg Val Met
                165                 170                 175

Tyr Gly Met Arg Thr Ser Arg Leu Gly Val Leu Gly His Tyr Tyr Cys
            180                 185                 190

Gly Met Leu Asp Val Tyr Thr Asp Leu Met Lys Gln Ser Ala Val Phe
        195                 200                 205
```

-continued

```
Gly Thr His Ile Glu Leu Leu Glu Met Cys Glu Leu Lys Ala Tyr Arg
    210                 215                 220
Glu Glu Val Ser Asp Gly Glu Leu Lys Arg Lys Leu Asp Glu Phe Tyr
225                 230                 235                 240
Asp Lys Phe Asn Val Glu Ala Ser Cys Ser Ser Glu Glu Leu Val Arg
                245                 250                 255
Ala Ala Arg Thr Ser Val Ala Leu Asp Lys Leu Val Asn Val His Gln
            260                 265                 270
Leu Gly Ala Met Ala Tyr Tyr Glu Gly Phe Cys Gly Asn Asp Tyr
        275                 280                 285
Glu Asn Ile Val Thr Ser Val Ile Ala Gly Asn Thr Leu Leu Thr Gly
290                 295                 300
Tyr Gly Ile Pro Val Ala Gly Glu Cys Glu Val Lys Asn Ala Gln Ala
305                 310                 315                 320
Met Lys Ile Met Ser Leu Leu Lys Ala Gly Gly Ser Phe Ser Glu Phe
                325                 330                 335
Tyr Ala Met Asp Phe Lys Asp Ile Val Leu Leu Gly His Asp Gly
            340                 345                 350
Pro Ala His Phe Ala Ile Ala Glu Glu Lys Val Lys Leu Val Pro Leu
        355                 360                 365
Pro Leu Tyr His Gly Lys Pro Gly Lys Gly Leu Ser Ile Gln Met Ser
    370                 375                 380
Val Lys Pro Gly Asp Val Thr Leu Leu Ser Val Cys Glu Gly Arg Asp
385                 390                 395                 400
Gly Val Phe Leu Leu Ala Ala Glu Gly Glu Ala Val Gln Gly Glu Thr
                405                 410                 415
Leu His Ile Gly Asn Thr Asn Ser Arg Tyr Arg Phe Pro Cys Gly Ala
            420                 425                 430
Arg Arg Phe Met Asp Gln Trp Ser Lys Ala Gly Pro Ser His His Cys
        435                 440                 445
Ala Ile Gly Ile Gly His Lys Val Ser Glu Leu Lys Lys Leu Ala Phe
    450                 455                 460
Leu Leu Asp Ile Pro Ile Ile Val Val Glu
465                 470
```

<210> SEQ ID NO 9
<211> LENGTH: 1425
<212> TYPE: DNA
<213> ORGANISM: Artificial Sequence
<220> FEATURE:
<223> OTHER INFORMATION: Codon optimized L. sakeii araA
<220> FEATURE:
<221> NAME/KEY: CDS
<222> LOCATION: (1)..(1425)

<400> SEQUENCE: 9

```
atg ttg aat acc gag aat tac gag ttt tgg ttc gtt act ggt tcc caa        48
Met Leu Asn Thr Glu Asn Tyr Glu Phe Trp Phe Val Thr Gly Ser Gln
1               5                   10                  15 tcc ttg tat ggt gag gaa acc tta aga tct gtc gaa aaa gat gca aag        96
Ser Leu Tyr Gly Glu Glu Thr Leu Arg Ser Val Glu Lys Asp Ala Lys
            20                  25                  30 gaa att gtt gag aaa ctt aat gcc tcc cat caa ttg cca tat cca att       144
Glu Ile Val Glu Lys Leu Asn Ala Ser His Gln Leu Pro Tyr Pro Ile
        35                  40                  45 gtt ttc aag tta gtt gcc act aca gca gat aac att acc aag gtt atg       192
Val Phe Lys Leu Val Ala Thr Thr Ala Asp Asn Ile Thr Lys Val Met
```

```
              50                  55                  60
aag gaa gca aac tac aat gat cat gtt gcc ggt gtt atc act tgg atg    240
Lys Glu Ala Asn Tyr Asn Asp His Val Ala Gly Val Ile Thr Trp Met
 65              70                  75                  80 cat acc ttt tct cct gcc aaa aac tgg atc aga ggt act aag tta ttg    288
His Thr Phe Ser Pro Ala Lys Asn Trp Ile Arg Gly Thr Lys Leu Leu
             85                  90                  95 caa aag cca tta ctt cac tta gca act cag ttc ctt aac aaa atc cca    336
Gln Lys Pro Leu Leu His Leu Ala Thr Gln Phe Leu Asn Lys Ile Pro
        100                 105                 110 tac gat act att gat ttc gac tac atg aac ttg aac caa tct gct cat    384
Tyr Asp Thr Ile Asp Phe Asp Tyr Met Asn Leu Asn Gln Ser Ala His
                115                 120                 125 ggt gac cgt gaa tac gca ttc atc aat gct aga ttg aga aag aat aac    432
Gly Asp Arg Glu Tyr Ala Phe Ile Asn Ala Arg Leu Arg Lys Asn Asn
    130                 135                 140 aag atc att tct ggt tat tgg ggt gat gaa gat gtc caa aag gct atg    480
Lys Ile Ile Ser Gly Tyr Trp Gly Asp Glu Asp Val Gln Lys Ala Met
145                 150                 155                 160 gca aaa tgg atg gat gtt gca gtc gct tac aac gaa tct ttc aag att    528
Ala Lys Trp Met Asp Val Ala Val Ala Tyr Asn Glu Ser Phe Lys Ile
                165                 170                 175 aag gtt gtc acc ttc gcc gat aag atg aga aat gtt gct gtc acc gac    576
Lys Val Val Thr Phe Ala Asp Lys Met Arg Asn Val Ala Val Thr Asp
            180                 185                 190 ggt gat aag gtc gag gca caa atc aag ttc ggc tgg aca gtt gat tac    624
Gly Asp Lys Val Glu Ala Gln Ile Lys Phe Gly Trp Thr Val Asp Tyr
        195                 200                 205 tgg ggt gtt ggc gat ctt gtt gct gaa gtt aat gcc gtt tct gaa gct    672
Trp Gly Val Gly Asp Leu Val Ala Glu Val Asn Ala Val Ser Glu Ala
210                 215                 220 gac att gat gca aag tat gct gac ttg caa aag gaa tac gat ttt gtc    720
Asp Ile Asp Ala Lys Tyr Ala Asp Leu Gln Lys Glu Tyr Asp Phe Val
225                 230                 235                 240 gaa ggt caa aac act cca gaa aag ttt gaa cac aac gtt aag tat cag    768
Glu Gly Gln Asn Thr Pro Glu Lys Phe Glu His Asn Val Lys Tyr Gln
                245                 250                 255 atc aga gaa tac ttt ggt ttg aaa aag ttt atg gat gat aga ggt tat    816
Ile Arg Glu Tyr Phe Gly Leu Lys Lys Phe Met Asp Asp Arg Gly Tyr
            260                 265                 270 act gca ttc acc acc aat ttc gag gac tta gtc ggt tta gaa cag tta    864
Thr Ala Phe Thr Thr Asn Phe Glu Asp Leu Val Gly Leu Glu Gln Leu
        275                 280                 285 cct ggt tta gct gct caa ttg ttg atg gct gag ggt tat ggt ttt gct    912
Pro Gly Leu Ala Ala Gln Leu Leu Met Ala Glu Gly Tyr Gly Phe Ala
    290                 295                 300 ggt gaa ggt gac tgg aaa aca gca gct tta gat aga ctt ttg aag att    960
Gly Glu Gly Asp Trp Lys Thr Ala Ala Leu Asp Arg Leu Leu Lys Ile
305                 310                 315                 320 atg gct cac aac gaa aag aca gtc ttt atg gaa gat tac acc tta gac   1008
Met Ala His Asn Glu Lys Thr Val Phe Met Glu Asp Tyr Thr Leu Asp
                325                 330                 335 ctt aga caa ggt cac gaa gca atc tta ggc tca cat atg tta gaa gtt   1056
Leu Arg Gln Gly His Glu Ala Ile Leu Gly Ser His Met Leu Glu Val
            340                 345                 350 gat cca tca att gct tct gac aaa cct cgt gtc gaa gtt cac cca tta   1104
Asp Pro Ser Ile Ala Ser Asp Lys Pro Arg Val Glu Val His Pro Leu
        355                 360                 365 gat att ggt gat aaa gac gat cca gct aga tta gtt ttc acc ggt atg   1152
```

```
Asp Ile Gly Asp Lys Asp Asp Pro Ala Arg Leu Val Phe Thr Gly Met
    370             375                 380 caa ggc gac gct gtt gat gtt aca atg gca gat tat ggt gac gag ttc      1200
Gln Gly Asp Ala Val Asp Val Thr Met Ala Asp Tyr Gly Asp Glu Phe
385                 390                 395                 400 aag ttg atg tct tac gat gtc aga ggt aac aaa cca gaa gca gat acc      1248
Lys Leu Met Ser Tyr Asp Val Arg Gly Asn Lys Pro Glu Ala Asp Thr
            405                 410                 415 cca cat ttg cca gtt gcc aaa cag ttg tgg act cca aag caa ggt tta      1296
Pro His Leu Pro Val Ala Lys Gln Leu Trp Thr Pro Lys Gln Gly Leu
        420                 425                 430 aga gaa ggt gca gtc ggt tgg ctt aca gtt ggc ggt ggt cat cac act      1344
Arg Glu Gly Ala Val Gly Trp Leu Thr Val Gly Gly Gly His His Thr
    435                 440                 445 gtt ttg tca ttt gct gtt gat tcc gaa caa ttg caa gac tta tcc cac      1392
Val Leu Ser Phe Ala Val Asp Ser Glu Gln Leu Gln Asp Leu Ser His
450                 455                 460 ttg ttc gac ttg act tat gtc aac att aag taa                          1425
Leu Phe Asp Leu Thr Tyr Val Asn Ile Lys
465                 470

<210> SEQ ID NO 10
<211> LENGTH: 474
<212> TYPE: PRT
<213> ORGANISM: Artificial Sequence
<220> FEATURE:
<223> OTHER INFORMATION: Synthetic Construct

<400> SEQUENCE: 10

Met Leu Asn Thr Glu Asn Tyr Glu Phe Trp Phe Val Thr Gly Ser Gln
1               5                   10                  15

Ser Leu Tyr Gly Glu Glu Thr Leu Arg Ser Val Glu Lys Asp Ala Lys
            20                  25                  30

Glu Ile Val Glu Lys Leu Asn Ala Ser His Gln Leu Pro Tyr Pro Ile
        35                  40                  45

Val Phe Lys Leu Val Ala Thr Thr Ala Asp Asn Ile Thr Lys Val Met
    50                  55                  60

Lys Glu Ala Asn Tyr Asn Asp His Val Ala Gly Val Ile Thr Trp Met
65                  70                  75                  80

His Thr Phe Ser Pro Ala Lys Asn Trp Ile Arg Gly Thr Lys Leu Leu
                85                  90                  95

Gln Lys Pro Leu Leu His Leu Ala Thr Gln Phe Leu Asn Lys Ile Pro
            100                 105                 110

Tyr Asp Thr Ile Asp Phe Asp Tyr Met Asn Leu Asn Gln Ser Ala His
        115                 120                 125

Gly Asp Arg Glu Tyr Ala Phe Ile Asn Ala Arg Leu Arg Lys Asn Asn
    130                 135                 140

Lys Ile Ile Ser Gly Tyr Trp Gly Asp Glu Asp Val Gln Lys Ala Met
145                 150                 155                 160

Ala Lys Trp Met Asp Val Ala Val Ala Tyr Asn Glu Ser Phe Lys Ile
                165                 170                 175

Lys Val Val Thr Phe Ala Asp Lys Met Arg Asn Val Ala Val Thr Asp
            180                 185                 190

Gly Asp Lys Val Glu Ala Gln Ile Lys Phe Gly Trp Thr Val Asp Tyr
        195                 200                 205

Trp Gly Val Gly Asp Leu Val Ala Glu Val Asn Ala Val Ser Glu Ala
    210                 215                 220
```

```
Asp Ile Asp Ala Lys Tyr Ala Asp Leu Gln Lys Glu Tyr Asp Phe Val
225                 230                 235                 240

Glu Gly Gln Asn Thr Pro Glu Lys Phe Glu His Asn Val Lys Tyr Gln
            245                 250                 255

Ile Arg Glu Tyr Phe Gly Leu Lys Lys Phe Met Asp Asp Arg Gly Tyr
        260                 265                 270

Thr Ala Phe Thr Thr Asn Phe Glu Asp Leu Val Gly Leu Glu Gln Leu
    275                 280                 285

Pro Gly Leu Ala Ala Gln Leu Leu Met Ala Glu Gly Tyr Gly Phe Ala
290                 295                 300

Gly Glu Gly Asp Trp Lys Thr Ala Ala Leu Asp Arg Leu Leu Lys Ile
305                 310                 315                 320

Met Ala His Asn Glu Lys Thr Val Phe Met Glu Asp Tyr Thr Leu Asp
                325                 330                 335

Leu Arg Gln Gly His Glu Ala Ile Leu Gly Ser His Met Leu Glu Val
            340                 345                 350

Asp Pro Ser Ile Ala Ser Asp Lys Pro Arg Val Glu Val His Pro Leu
        355                 360                 365

Asp Ile Gly Asp Lys Asp Pro Ala Arg Leu Val Phe Thr Gly Met
370                 375                 380

Gln Gly Asp Ala Val Asp Val Thr Met Ala Asp Tyr Gly Asp Glu Phe
385                 390                 395                 400

Lys Leu Met Ser Tyr Asp Val Arg Gly Asn Lys Pro Glu Ala Asp Thr
                405                 410                 415

Pro His Leu Pro Val Ala Lys Gln Leu Trp Thr Pro Lys Gln Gly Leu
            420                 425                 430

Arg Glu Gly Ala Val Gly Trp Leu Thr Val Gly Gly His His Thr
        435                 440                 445

Val Leu Ser Phe Ala Val Asp Ser Glu Gln Leu Gln Asp Leu Ser His
450                 455                 460

Leu Phe Asp Leu Thr Tyr Val Asn Ile Lys
465                 470

<210> SEQ ID NO 11
<211> LENGTH: 1596
<212> TYPE: DNA
<213> ORGANISM: Artificial Sequence
<220> FEATURE:
<223> OTHER INFORMATION: Codon optimized B. thetaiotaomicron araB
<220> FEATURE:
<221> NAME/KEY: CDS
<222> LOCATION: (1)..(1596)

<400> SEQUENCE: 11 atg aag tta gat gct aag tcc acc att gaa act ggt aag gct att tta      48
Met Lys Leu Asp Ala Lys Ser Thr Ile Glu Thr Gly Lys Ala Ile Leu
1               5                   10                  15 ggt atc gaa ttg ggt tct aca aga att aag gct gtt ttg att gat caa      96
Gly Ile Glu Leu Gly Ser Thr Arg Ile Lys Ala Val Leu Ile Asp Gln
                20                  25                  30 gaa aac aaa cca atc gct caa ggt tca cac acc tgg gaa aat caa tta     144
Glu Asn Lys Pro Ile Ala Gln Gly Ser His Thr Trp Glu Asn Gln Leu
            35                  40                  45 gtt aac ggt tta tgg act tac tcc atc gac gct att tgg tcc ggc ttg     192
Val Asn Gly Leu Trp Thr Tyr Ser Ile Asp Ala Ile Trp Ser Gly Leu
        50                  55                  60 caa gat tgt tat gct gac ttg aga tcc aat gtt aag aag ctt tac gat     240
Gln Asp Cys Tyr Ala Asp Leu Arg Ser Asn Val Lys Lys Leu Tyr Asp
```

```
            65                  70                   75                    80
act gaa att gaa acc tta gca gct att ggt gtc tct gca atg atg cac          288
Thr Glu Ile Glu Thr Leu Ala Ala Ile Gly Val Ser Ala Met Met His
                    85                    90                    95 ggt tat atg cca ttc aac gaa aag gaa gaa att ttg gtc cca ttc aga          336
Gly Tyr Met Pro Phe Asn Glu Lys Glu Glu Ile Leu Val Pro Phe Arg
                100                   105                   110 act tgg aga aat act aac act ggt aga gct gca gct gaa ttg tct gaa          384
Thr Trp Arg Asn Thr Asn Thr Gly Arg Ala Ala Ala Glu Leu Ser Glu
                115                   120                   125 ttg ttc gtc tac aat atc cca tta aga tgg tcc att tcc cat ctt tac          432
Leu Phe Val Tyr Asn Ile Pro Leu Arg Trp Ser Ile Ser His Leu Tyr
        130                   135                   140 caa gca atc ttg gat aat gaa gct cac gtc aag gac atc aag ttc ctt          480
Gln Ala Ile Leu Asp Asn Glu Ala His Val Lys Asp Ile Lys Phe Leu
145                   150                   155                   160 act act tta gct ggt tat gtc cac tgg caa atc act ggt gaa aag gtc          528
Thr Thr Leu Ala Gly Tyr Val His Trp Gln Ile Thr Gly Glu Lys Val
                165                   170                   175 tta ggt att ggt gat gct tcc ggt atg ttg cca atc gac cct act acc          576
Leu Gly Ile Gly Asp Ala Ser Gly Met Leu Pro Ile Asp Pro Thr Thr
                180                   185                   190 aac aat tac tct gct gaa atg gtt gct aag ttc aac aac ctt att gct          624
Asn Asn Tyr Ser Ala Glu Met Val Ala Lys Phe Asn Asn Leu Ile Ala
                195                   200                   205 tcc aaa gaa tac tct tgg aag ctt gaa gat att ttg cca aag gtc tta          672
Ser Lys Glu Tyr Ser Trp Lys Leu Glu Asp Ile Leu Pro Lys Val Leu
        210                   215                   220 tct gca ggt gaa aac gct ggt gtt ttg acc cca gaa ggt tgt aag aaa          720
Ser Ala Gly Glu Asn Ala Gly Val Leu Thr Pro Glu Gly Cys Lys Lys
225                   230                   235                   240 tta gat gct tcc ggt cat tta aag gca ggt atc cca gtt tgt cca cca          768
Leu Asp Ala Ser Gly His Leu Lys Ala Gly Ile Pro Val Cys Pro Pro
                245                   250                   255 gaa ggt gat gca ggt act ggc atg gtc gct acc aat gca gtc aag caa          816
Glu Gly Asp Ala Gly Thr Gly Met Val Ala Thr Asn Ala Val Lys Gln
                260                   265                   270 aga act ggt aac gtc tct gca ggt act tct tcc ttc tcc atg att gtc          864
Arg Thr Gly Asn Val Ser Ala Gly Thr Ser Ser Phe Ser Met Ile Val
                275                   280                   285 tta gag aag gaa tta tct aag cca tac gaa atg att gat atg gtt act          912
Leu Glu Lys Glu Leu Ser Lys Pro Tyr Glu Met Ile Asp Met Val Thr
        290                   295                   300 acc cca gat ggt tct tta gtt gcc atg gtt cac tgt aat aac tgt act          960
Thr Pro Asp Gly Ser Leu Val Ala Met Val His Cys Asn Asn Cys Thr
305                   310                   315                   320 tct gac tta aac gct tgg gtc aac tta ttc aag gaa tat caa gaa ttg         1008
Ser Asp Leu Asn Ala Trp Val Asn Leu Phe Lys Glu Tyr Gln Glu Leu
                325                   330                   335 tta ggt att cca gtc gat atg gac gaa tta tac ggt aag tta tac aat         1056
Leu Gly Ile Pro Val Asp Met Asp Glu Leu Tyr Gly Lys Leu Tyr Asn
                340                   345                   350 att gct tta act ggt gat act gat tgt ggc ggt ctt tta tct tat aat         1104
Ile Ala Leu Thr Gly Asp Thr Asp Cys Gly Gly Leu Leu Ser Tyr Asn
        355                   360                   365 tat att tcc ggt gaa cca gtc act ggt tta gca gaa ggt aga cca ttg         1152
Tyr Ile Ser Gly Glu Pro Val Thr Gly Leu Ala Glu Gly Arg Pro Leu
370                   375                   380 ttt gtc aga tcc gca aac gac aag ttt aat ttg gct aac ttt atg aga         1200
```

```
Phe Val Arg Ser Ala Asn Asp Lys Phe Asn Leu Ala Asn Phe Met Arg
385                 390                 395                 400 gca cac ttg tac gca tct gtc ggt gtt ctt aaa atc ggt aac gac atc    1248
Ala His Leu Tyr Ala Ser Val Gly Val Leu Lys Ile Gly Asn Asp Ile
                405                 410                 415 ttg ttc aac gaa gaa aag atc aag gtt gac aga att act ggt cat ggt    1296
Leu Phe Asn Glu Glu Lys Ile Lys Val Asp Arg Ile Thr Gly His Gly
            420                 425                 430 ggt tta ttc aga act aaa ggt gtt ggt caa aga gtt tta gca gct gct    1344
Gly Leu Phe Arg Thr Lys Gly Val Gly Gln Arg Val Leu Ala Ala Ala
            435                 440                 445 att aat tca cca att tcc gtt atg gaa act gca ggt gaa ggt ggt gct    1392
Ile Asn Ser Pro Ile Ser Val Met Glu Thr Ala Gly Glu Gly Gly Ala
        450                 455                 460 tgg ggt atc gca tta tta ggc tca tac tta gtc aat aac aag aaa ggt    1440
Trp Gly Ile Ala Leu Leu Gly Ser Tyr Leu Val Asn Asn Lys Lys Gly
465                 470                 475                 480 caa tcc tta gct gat ttc tta gac gaa tct gtt ttc gtt tct gac gca    1488
Gln Ser Leu Ala Asp Phe Leu Asp Glu Ser Val Phe Val Ser Asp Ala
                485                 490                 495 ggt gtt gaa gtt tct cca acc cca gaa gat gtt gct ggc ttc aat acc    1536
Gly Val Glu Val Ser Pro Thr Pro Glu Asp Val Ala Gly Phe Asn Thr
            500                 505                 510 tat atc gaa tcc tat aag gca ggt ttg cca att gag gaa gca gct gtt    1584
Tyr Ile Glu Ser Tyr Lys Ala Gly Leu Pro Ile Glu Glu Ala Ala Val
            515                 520                 525 aag ttc aag taa                                                     1596
Lys Phe Lys
    530

<210> SEQ ID NO 12
<211> LENGTH: 531
<212> TYPE: PRT
<213> ORGANISM: Artificial Sequence
<220> FEATURE:
<223> OTHER INFORMATION: Synthetic Construct

<400> SEQUENCE: 12

Met Lys Leu Asp Ala Lys Ser Thr Ile Glu Thr Gly Lys Ala Ile Leu
1               5                   10                  15

Gly Ile Glu Leu Gly Ser Thr Arg Ile Lys Ala Val Leu Ile Asp Gln
            20                  25                  30

Glu Asn Lys Pro Ile Ala Gln Gly Ser His Thr Trp Glu Asn Gln Leu
        35                  40                  45

Val Asn Gly Leu Trp Thr Tyr Ser Ile Asp Ala Ile Trp Ser Gly Leu
    50                  55                  60

Gln Asp Cys Tyr Ala Asp Leu Arg Ser Asn Val Lys Lys Leu Tyr Asp
65                  70                  75                  80

Thr Glu Ile Glu Thr Leu Ala Ala Ile Gly Val Ser Ala Met Met His
                85                  90                  95

Gly Tyr Met Pro Phe Asn Glu Lys Glu Ile Leu Val Pro Phe Arg
                100                 105                 110

Thr Trp Arg Asn Thr Asn Thr Gly Arg Ala Ala Glu Leu Ser Glu
            115                 120                 125

Leu Phe Val Tyr Asn Ile Pro Leu Arg Trp Ser Ile Ser His Leu Tyr
    130                 135                 140

Gln Ala Ile Leu Asp Asn Glu Ala His Val Lys Asp Ile Lys Phe Leu
145                 150                 155                 160
```

```
Thr Thr Leu Ala Gly Tyr Val His Trp Gln Ile Thr Gly Glu Lys Val
            165                 170                 175

Leu Gly Ile Gly Asp Ala Ser Gly Met Leu Pro Ile Asp Pro Thr Thr
        180                 185                 190

Asn Asn Tyr Ser Ala Glu Met Val Ala Lys Phe Asn Asn Leu Ile Ala
            195                 200                 205

Ser Lys Glu Tyr Ser Trp Lys Leu Glu Asp Ile Leu Pro Lys Val Leu
        210                 215                 220

Ser Ala Gly Glu Asn Ala Gly Val Leu Thr Pro Glu Gly Cys Lys Lys
225                 230                 235                 240

Leu Asp Ala Ser Gly His Leu Lys Ala Gly Ile Pro Val Cys Pro Pro
                245                 250                 255

Glu Gly Asp Ala Gly Thr Gly Met Val Ala Thr Asn Ala Val Lys Gln
            260                 265                 270

Arg Thr Gly Asn Val Ser Ala Gly Thr Ser Ser Phe Ser Met Ile Val
        275                 280                 285

Leu Glu Lys Glu Leu Ser Lys Pro Tyr Glu Met Ile Asp Met Val Thr
    290                 295                 300

Thr Pro Asp Gly Ser Leu Val Ala Met Val His Cys Asn Asn Cys Thr
305                 310                 315                 320

Ser Asp Leu Asn Ala Trp Val Asn Leu Phe Lys Glu Tyr Gln Glu Leu
                325                 330                 335

Leu Gly Ile Pro Val Asp Met Asp Glu Leu Tyr Gly Lys Leu Tyr Asn
            340                 345                 350

Ile Ala Leu Thr Gly Asp Thr Asp Cys Gly Gly Leu Leu Ser Tyr Asn
        355                 360                 365

Tyr Ile Ser Gly Glu Pro Val Thr Gly Leu Ala Glu Gly Arg Pro Leu
    370                 375                 380

Phe Val Arg Ser Ala Asn Asp Lys Phe Asn Leu Ala Asn Phe Met Arg
385                 390                 395                 400

Ala His Leu Tyr Ala Ser Val Gly Val Leu Lys Ile Gly Asn Asp Ile
                405                 410                 415

Leu Phe Asn Glu Glu Lys Ile Lys Val Asp Arg Ile Thr Gly His Gly
            420                 425                 430

Gly Leu Phe Arg Thr Lys Gly Val Gly Gln Arg Val Leu Ala Ala Ala
        435                 440                 445

Ile Asn Ser Pro Ile Ser Val Met Glu Thr Ala Gly Glu Gly Gly Ala
    450                 455                 460

Trp Gly Ile Ala Leu Leu Gly Ser Tyr Leu Val Asn Asn Lys Lys Gly
465                 470                 475                 480

Gln Ser Leu Ala Asp Phe Leu Asp Glu Ser Val Phe Val Ser Asp Ala
                485                 490                 495

Gly Val Glu Val Ser Pro Thr Pro Glu Asp Val Ala Gly Phe Asn Thr
            500                 505                 510

Tyr Ile Glu Ser Tyr Lys Ala Gly Leu Pro Ile Glu Glu Ala Ala Val
        515                 520                 525

Lys Phe Lys
    530

<210> SEQ ID NO 13
<211> LENGTH: 1623
<212> TYPE: DNA
<213> ORGANISM: Leuconostoc citreum
<220> FEATURE:
<221> NAME/KEY: CDS
```

<222> LOCATION: (1)..(1623)

<400> SEQUENCE: 13

```
atg aca gca caa caa ata caa gaa aaa gcc att gca acc gga cag gtg      48
Met Thr Ala Gln Gln Ile Gln Glu Lys Ala Ile Ala Thr Gly Gln Val
1               5                  10                  15 gca tta ggc gtg gaa ttt gga tcg aca aca att aaa gca gta ttg act      96
Ala Leu Gly Val Glu Phe Gly Ser Thr Thr Ile Lys Ala Val Leu Thr
            20                  25                  30 act aac agc gga tta acg att gct tca ggc agt tat gat tgg aca aac    144
Thr Asn Ser Gly Leu Thr Ile Ala Ser Gly Ser Tyr Asp Trp Thr Asn
        35                  40                  45 aat ttt caa aat ggt ctc tgg acg tat agc ctg gat gat gtt tgg cta    192
Asn Phe Gln Asn Gly Leu Trp Thr Tyr Ser Leu Asp Asp Val Trp Leu
    50                  55                  60 ggt tta cag agt gcc tat cga caa ctg aaa gca caa gtt gaa tca aaa    240
Gly Leu Gln Ser Ala Tyr Arg Gln Leu Lys Ala Gln Val Glu Ser Lys
65                  70                  75                  80 tat ggc ttg aaa ctt aaa aaa atc aaa aca atg ggt ttt tca gct atg    288
Tyr Gly Leu Lys Leu Lys Lys Ile Lys Thr Met Gly Phe Ser Ala Met
                85                  90                  95 atg cac ggc tac tta gca ttc gat aat caa gac aca cta cta gtt cca    336
Met His Gly Tyr Leu Ala Phe Asp Asn Gln Asp Thr Leu Leu Val Pro
            100                 105                 110 ttt cgt aca tgg cgc aat gcg aca act ggt cgg gca tca cgc gaa ttg    384
Phe Arg Thr Trp Arg Asn Ala Thr Thr Gly Arg Ala Ser Arg Glu Leu
        115                 120                 125 acc aag tta ttt ggc ttt aac gtg cca caa cga tgg agc att gca cat    432
Thr Lys Leu Phe Gly Phe Asn Val Pro Gln Arg Trp Ser Ile Ala His
    130                 135                 140 ttg tat caa gct atc tta gat cag gag acg cat gtt aaa aat att agt    480
Leu Tyr Gln Ala Ile Leu Asp Gln Glu Thr His Val Lys Asn Ile Ser
145                 150                 155                 160 tat ttc aca aca ctt gca gga tat gtt cat tgg caa tta acc ggt gaa    528
Tyr Phe Thr Thr Leu Ala Gly Tyr Val His Trp Gln Leu Thr Gly Glu
                165                 170                 175 aaa gtt tta ggt gtt ggc gat gcc tca ggg atg ttt cct atc gat gca    576
Lys Val Leu Gly Val Gly Asp Ala Ser Gly Met Phe Pro Ile Asp Ala
            180                 185                 190 gaa act ggt aat tat aat caa aat atg att gat caa ttt tct cat ttg    624
Glu Thr Gly Asn Tyr Asn Gln Asn Met Ile Asp Gln Phe Ser His Leu
        195                 200                 205 aaa gcg gtc caa caa tat cag tgg cag ata caa gat ata tta cca gaa    672
Lys Ala Val Gln Gln Tyr Gln Trp Gln Ile Gln Asp Ile Leu Pro Glu
    210                 215                 220 ccg cga cat gct ggt gat atg gcg ggt cat tta aca gca gct ggt gct    720
Pro Arg His Ala Gly Asp Met Ala Gly His Leu Thr Ala Ala Gly Ala
225                 230                 235                 240 aaa aag tta gac cca aca ggc gat tta atg gca ggt gtc atc gtg gca    768
Lys Lys Leu Asp Pro Thr Gly Asp Leu Met Ala Gly Val Ile Val Ala
                245                 250                 255 cca cca gaa ggc gac gct ggg acg ggt atg gta gcg acc aat agt acg    816
Pro Pro Glu Gly Asp Ala Gly Thr Gly Met Val Ala Thr Asn Ser Thr
            260                 265                 270 caa gta cga aca ggt aac att tca gtg gga aca tct att ttt tca atg    864
Gln Val Arg Thr Gly Asn Ile Ser Val Gly Thr Ser Ile Phe Ser Met
        275                 280                 285 att gtt tta gaa aaa agt tta aag cat gtt tat agt aat atc gat atc    912
Ile Val Leu Glu Lys Ser Leu Lys His Val Tyr Ser Asn Ile Asp Ile
    290                 295                 300
```

-continued

```
gtc act acg cca act ggc tta cct gtt gcc atg gtt cac gcc aat aat    960
Val Thr Thr Pro Thr Gly Leu Pro Val Ala Met Val His Ala Asn Asn
305                 310                 315                 320 tct gcc tct gat tta aat gct tgg tcc aaa ctg ttt gcg gaa ttt gca   1008
Ser Ala Ser Asp Leu Asn Ala Trp Ser Lys Leu Phe Ala Glu Phe Ala
                325                 330                 335 ggg atg att ggt cag aat tta tca aac gcg gcc ttg tat caa acc ctg   1056
Gly Met Ile Gly Gln Asn Leu Ser Asn Ala Ala Leu Tyr Gln Thr Leu
            340                 345                 350 ttc aat gct gct ttg aat gat gct gat gct gat gct ggt ggt tta act   1104
Phe Asn Ala Ala Leu Asn Asp Ala Asp Ala Asp Ala Gly Gly Leu Thr
        355                 360                 365 ggt tat ggc tac tat tcc ggt gaa aac att act gca gta ccg gaa gga   1152
Gly Tyr Gly Tyr Tyr Ser Gly Glu Asn Ile Thr Ala Val Pro Glu Gly
    370                 375                 380 cga cca tta tta gtc aga caa cca gac tca cat ttt acg att ggc aat   1200
Arg Pro Leu Leu Val Arg Gln Pro Asp Ser His Phe Thr Ile Gly Asn
385                 390                 395                 400 ctt atg cgt tta cat atc ttt agt gca ttc ggt gcg att aaa att ggc   1248
Leu Met Arg Leu His Ile Phe Ser Ala Phe Gly Ala Ile Lys Ile Gly
                405                 410                 415 atg cga att tta gca gat gaa aac gta cta acc gat aat att gtg gct   1296
Met Arg Ile Leu Ala Asp Glu Asn Val Leu Thr Asp Asn Ile Val Ala
            420                 425                 430 caa ggc ggt gtg ttt aaa aca cca att gtg gct caa aaa ttg tta gca   1344
Gln Gly Gly Val Phe Lys Thr Pro Ile Val Ala Gln Lys Leu Leu Ala
        435                 440                 445 gca gca ctc aac aca aac att act gtg atg gcc aat gct ggt gaa ggt   1392
Ala Ala Leu Asn Thr Asn Ile Thr Val Met Ala Asn Ala Gly Glu Gly
    450                 455                 460 ggg ccg tgg gga atg gct att ttg gca ctt tat gca gcc aat aaa tta   1440
Gly Pro Trp Gly Met Ala Ile Leu Ala Leu Tyr Ala Ala Asn Lys Leu
465                 470                 475                 480 ggc ggt cag aca cta gat gat tat tta gca aaa aac ata ttc gct gaa   1488
Gly Gly Gln Thr Leu Asp Asp Tyr Leu Ala Lys Asn Ile Phe Ala Glu
                485                 490                 495 act aaa gca caa aca ctc gcg cca gaa cca cgt gat gtt gca gga ttt   1536
Thr Lys Ala Gln Thr Leu Ala Pro Glu Pro Arg Asp Val Ala Gly Phe
            500                 505                 510 gaa gaa ttt atg aca cgt tat att gat ggc cta caa att gag tta acc   1584
Glu Glu Phe Met Thr Arg Tyr Ile Asp Gly Leu Gln Ile Glu Leu Thr
        515                 520                 525 gcc att aaa gca ttg cct agt aat caa ata aag gag taa               1623
Ala Ile Lys Ala Leu Pro Ser Asn Gln Ile Lys Glu
    530                 535                 540

<210> SEQ ID NO 14
<211> LENGTH: 540
<212> TYPE: PRT
<213> ORGANISM: Leuconostoc citreum

<400> SEQUENCE: 14

Met Thr Ala Gln Gln Ile Gln Glu Lys Ala Ile Ala Thr Gly Gln Val
1               5                   10                  15

Ala Leu Gly Val Glu Phe Gly Ser Thr Thr Ile Lys Ala Val Leu Thr
            20                  25                  30

Thr Asn Ser Gly Leu Thr Ile Ala Ser Gly Ser Tyr Asp Trp Thr Asn
        35                  40                  45

Asn Phe Gln Asn Gly Leu Trp Thr Tyr Ser Leu Asp Asp Val Trp Leu
```

-continued

```
                50                  55                  60
Gly Leu Gln Ser Ala Tyr Arg Gln Leu Lys Ala Gln Val Glu Ser Lys
 65                  70                  75                  80
Tyr Gly Leu Lys Leu Lys Lys Ile Lys Thr Met Gly Phe Ser Ala Met
                     85                  90                  95
Met His Gly Tyr Leu Ala Phe Asp Asn Gln Asp Thr Leu Leu Val Pro
                    100                 105                 110
Phe Arg Thr Trp Arg Asn Ala Thr Thr Gly Arg Ala Ser Arg Glu Leu
                    115                 120                 125
Thr Lys Leu Phe Gly Phe Asn Val Pro Gln Arg Trp Ser Ile Ala His
130                 135                 140
Leu Tyr Gln Ala Ile Leu Asp Gln Glu Thr His Val Lys Asn Ile Ser
145                 150                 155                 160
Tyr Phe Thr Thr Leu Ala Gly Tyr Val His Trp Gln Leu Thr Gly Glu
                    165                 170                 175
Lys Val Leu Gly Val Gly Asp Ala Ser Gly Met Phe Pro Ile Asp Ala
                    180                 185                 190
Glu Thr Gly Asn Tyr Asn Gln Asn Met Ile Asp Gln Phe Ser His Leu
                    195                 200                 205
Lys Ala Val Gln Gln Tyr Gln Trp Gln Ile Gln Asp Ile Leu Pro Glu
                    210                 215                 220
Pro Arg His Ala Gly Asp Met Ala Gly His Leu Thr Ala Ala Gly Ala
225                 230                 235                 240
Lys Lys Leu Asp Pro Thr Gly Asp Leu Met Ala Gly Val Ile Val Ala
                    245                 250                 255
Pro Pro Glu Gly Asp Ala Gly Thr Gly Met Val Ala Thr Asn Ser Thr
                    260                 265                 270
Gln Val Arg Thr Gly Asn Ile Ser Val Gly Thr Ser Ile Phe Ser Met
                    275                 280                 285
Ile Val Leu Glu Lys Ser Leu Lys His Val Tyr Ser Asn Ile Asp Ile
                    290                 295                 300
Val Thr Thr Pro Thr Gly Leu Pro Val Ala Met Val His Ala Asn Asn
305                 310                 315                 320
Ser Ala Ser Asp Leu Asn Ala Trp Ser Lys Leu Phe Ala Glu Phe Ala
                    325                 330                 335
Gly Met Ile Gly Gln Asn Leu Ser Asn Ala Ala Leu Tyr Gln Thr Leu
                    340                 345                 350
Phe Asn Ala Ala Leu Asn Asp Ala Asp Ala Asp Gly Gly Leu Thr
                    355                 360                 365
Gly Tyr Gly Tyr Tyr Ser Gly Glu Asn Ile Thr Ala Val Pro Glu Gly
370                 375                 380
Arg Pro Leu Leu Val Arg Gln Pro Asp Ser His Phe Thr Ile Gly Asn
385                 390                 395                 400
Leu Met Arg Leu His Ile Phe Ser Ala Phe Gly Ala Ile Lys Ile Gly
                    405                 410                 415
Met Arg Ile Leu Ala Asp Glu Asn Val Leu Thr Asp Asn Ile Val Ala
                    420                 425                 430
Gln Gly Gly Val Phe Lys Thr Pro Ile Val Ala Gln Lys Leu Leu Ala
                    435                 440                 445
Ala Ala Leu Asn Thr Asn Ile Thr Val Met Ala Asn Ala Gly Glu Gly
                    450                 455                 460
Gly Pro Trp Gly Met Ala Ile Leu Ala Leu Tyr Ala Ala Asn Lys Leu
465                 470                 475                 480
```

```
Gly Gly Gln Thr Leu Asp Asp Tyr Leu Ala Lys Asn Ile Phe Ala Glu
            485                 490                 495

Thr Lys Ala Gln Thr Leu Ala Pro Glu Pro Arg Asp Val Ala Gly Phe
            500                 505                 510

Glu Glu Phe Met Thr Arg Tyr Ile Asp Gly Leu Gln Ile Glu Leu Thr
            515                 520                 525

Ala Ile Lys Ala Leu Pro Ser Asn Gln Ile Lys Glu
            530                 535                 540

<210> SEQ ID NO 15
<211> LENGTH: 684
<212> TYPE: DNA
<213> ORGANISM: Artificial Sequence
<220> FEATURE:
<223> OTHER INFORMATION: Codon optimized B. thetaiotaomicron araD
<220> FEATURE:
<221> NAME/KEY: CDS
<222> LOCATION: (1)..(684)

<400> SEQUENCE: 15
```

| | | | | | | | | | | | | | | | | |
|---|---|---|---|---|---|---|---|---|---|---|---|---|---|---|---|---|
| atg | tta | gaa | gaa | tta | aag | gaa | aag | gtt | ttc | cac | gct | aat | ttg | gaa | tta | 48 |
| Met | Leu | Glu | Glu | Leu | Lys | Glu | Lys | Val | Phe | His | Ala | Asn | Leu | Glu | Leu | |
| 1 | | | | 5 | | | | | 10 | | | | | 15 | | |
| gtt | aag | cat | ggt | tta | gtt | att | ttc | acc | tgg | ggt | aac | gtt | tct | gct | att | 96 |
| Val | Lys | His | Gly | Leu | Val | Ile | Phe | Thr | Trp | Gly | Asn | Val | Ser | Ala | Ile | |
| | | | 20 | | | | | 25 | | | | | 30 | | | |
| gat | aga | gaa | acc | gaa | tta | gtt | gtt | att | aag | cca | tct | ggt | gtt | tct | tac | 144 |
| Asp | Arg | Glu | Thr | Glu | Leu | Val | Val | Ile | Lys | Pro | Ser | Gly | Val | Ser | Tyr | |
| | | 35 | | | | | 40 | | | | | 45 | | | | |
| gac | gat | atg | aag | gca | gaa | gat | atg | gtt | gtt | gtt | gat | tta | gat | ggt | aag | 192 |
| Asp | Asp | Met | Lys | Ala | Glu | Asp | Met | Val | Val | Val | Asp | Leu | Asp | Gly | Lys | |
| | 50 | | | | | 55 | | | | | 60 | | | | | |
| gtc | gtc | gaa | ggt | aga | tta | aag | cca | tct | tct | gac | acc | cca | acc | cac | gtt | 240 |
| Val | Val | Glu | Gly | Arg | Leu | Lys | Pro | Ser | Ser | Asp | Thr | Pro | Thr | His | Val | |
| 65 | | | | | 70 | | | | | 75 | | | | | 80 | |
| gtt | tta | tac | aag | gct | ttt | cca | gaa | att | ggt | ggt | gtt | gtt | cac | act | cac | 288 |
| Val | Leu | Tyr | Lys | Ala | Phe | Pro | Glu | Ile | Gly | Gly | Val | Val | His | Thr | His | |
| | | | | 85 | | | | | 90 | | | | | 95 | | |
| tct | acc | tac | gct | act | gca | tgg | gct | caa | gct | ggt | tgt | gat | atc | cca | aat | 336 |
| Ser | Thr | Tyr | Ala | Thr | Ala | Trp | Ala | Gln | Ala | Gly | Cys | Asp | Ile | Pro | Asn | |
| | | | 100 | | | | | 105 | | | | | 110 | | | |
| att | ggt | act | act | cac | gca | gat | tac | ttc | cac | gat | gca | att | cca | tgt | act | 384 |
| Ile | Gly | Thr | Thr | His | Ala | Asp | Tyr | Phe | His | Asp | Ala | Ile | Pro | Cys | Thr | |
| | | | 115 | | | | | 120 | | | | | 125 | | | |
| gca | gat | atg | act | gaa | gct | gaa | gtt | aag | ggt | gct | tat | gaa | tta | gaa | acc | 432 |
| Ala | Asp | Met | Thr | Glu | Ala | Glu | Val | Lys | Gly | Ala | Tyr | Glu | Leu | Glu | Thr | |
| | 130 | | | | | 135 | | | | | 140 | | | | | |
| ggt | aat | gtt | atc | gtc | aag | aga | ttt | gaa | ggt | ttg | aac | cca | gtc | cac | acc | 480 |
| Gly | Asn | Val | Ile | Val | Lys | Arg | Phe | Glu | Gly | Leu | Asn | Pro | Val | His | Thr | |
| 145 | | | | | 150 | | | | | 155 | | | | | 160 | |
| cca | ggt | gtc | tta | gtt | aag | aat | cat | ggt | cca | ttc | tcc | tgg | ggt | aag | gat | 528 |
| Pro | Gly | Val | Leu | Val | Lys | Asn | His | Gly | Pro | Phe | Ser | Trp | Gly | Lys | Asp | |
| | | | | 165 | | | | | 170 | | | | | 175 | | |
| gct | cac | gat | gca | gtt | cac | aac | gca | gtt | gtc | atg | gaa | caa | gtt | gca | aag | 576 |
| Ala | His | Asp | Ala | Val | His | Asn | Ala | Val | Val | Met | Glu | Gln | Val | Ala | Lys | |
| | | | 180 | | | | | 185 | | | | | 190 | | | |
| atg | gct | tct | att | gct | tac | gct | gtt | aat | cca | aac | tta | act | atg | aat | cca | 624 |
| Met | Ala | Ser | Ile | Ala | Tyr | Ala | Val | Asn | Pro | Asn | Leu | Thr | Met | Asn | Pro | |
| | | | 195 | | | | | 200 | | | | | 205 | | | |
| tta | tta | gtt | gaa | aag | cac | ttc | tcc | aga | aag | cac | ggt | cca | aac | gct | tat | 672 |

```
Leu Leu Val Glu Lys His Phe Ser Arg Lys His Gly Pro Asn Ala Tyr
        210                 215                 220 tac ggt caa taa                                                         684
Tyr Gly Gln
225

<210> SEQ ID NO 16
<211> LENGTH: 227
<212> TYPE: PRT
<213> ORGANISM: Artificial Sequence
<220> FEATURE:
<223> OTHER INFORMATION: Synthetic Construct

<400> SEQUENCE: 16

Met Leu Glu Glu Leu Lys Glu Lys Val Phe His Ala Asn Leu Glu Leu
1               5                   10                  15

Val Lys His Gly Leu Val Ile Phe Thr Trp Gly Asn Val Ser Ala Ile
            20                  25                  30

Asp Arg Glu Thr Glu Leu Val Val Ile Lys Pro Ser Gly Val Ser Tyr
        35                  40                  45

Asp Asp Met Lys Ala Glu Asp Met Val Val Asp Leu Asp Gly Lys
    50                  55                  60

Val Val Glu Gly Arg Leu Lys Pro Ser Ser Asp Thr Pro Thr His Val
65                  70                  75                  80

Val Leu Tyr Lys Ala Phe Pro Glu Ile Gly Gly Val Val His Thr His
                85                  90                  95

Ser Thr Tyr Ala Thr Ala Trp Ala Gln Ala Gly Cys Asp Ile Pro Asn
            100                 105                 110

Ile Gly Thr Thr His Ala Asp Tyr Phe His Asp Ala Ile Pro Cys Thr
        115                 120                 125

Ala Asp Met Thr Glu Ala Glu Val Lys Gly Ala Tyr Glu Leu Glu Thr
    130                 135                 140

Gly Asn Val Ile Val Lys Arg Phe Glu Gly Leu Asn Pro Val His Thr
145                 150                 155                 160

Pro Gly Val Leu Val Lys Asn His Gly Pro Phe Ser Trp Gly Lys Asp
                165                 170                 175

Ala His Asp Ala Val His Asn Ala Val Val Met Glu Gln Val Ala Lys
            180                 185                 190

Met Ala Ser Ile Ala Tyr Ala Val Asn Pro Asn Leu Thr Met Asn Pro
        195                 200                 205

Leu Leu Val Glu Lys His Phe Ser Arg Lys His Gly Pro Asn Ala Tyr
    210                 215                 220

Tyr Gly Gln
225

<210> SEQ ID NO 17
<211> LENGTH: 693
<212> TYPE: DNA
<213> ORGANISM: Artificial Sequence
<220> FEATURE:
<223> OTHER INFORMATION: Codon optimized B. animalis araD
<220> FEATURE:
<221> NAME/KEY: CDS
<222> LOCATION: (1)..(693)

<400> SEQUENCE: 17 atg gct aca ttg gca gac tat ggt cca gaa gtt aga gct gaa gtt aag       48
Met Ala Thr Leu Ala Asp Tyr Gly Pro Glu Val Arg Ala Glu Val Lys
1               5                   10                  15
```

| | | |
|---|---|---|
| cag gtc aga gaa gtt gtt gca gct tta cat gaa caa ttg att aag tgg<br>Gln Val Arg Glu Val Val Ala Ala Leu His Glu Gln Leu Ile Lys Trp<br>       20                      25               30 | | 96 |
| aac tta gtt gtt tgg acc gca ggc aat gtc tct caa aga ttg aga act<br>Asn Leu Val Val Trp Thr Ala Gly Asn Val Ser Gln Arg Leu Arg Thr<br>           35                   40               45 | | 144 |
| gca gac ctt atg gtt atc aag cct tca ggc ttg aga tac gaa tac tta<br>Ala Asp Leu Met Val Ile Lys Pro Ser Gly Leu Arg Tyr Glu Tyr Leu<br>50                     55               60 | | 192 |
| aca cca tcc tca atg gtt gtc tgt gac ttg gat ggt aac gtt gtt gat<br>Thr Pro Ser Ser Met Val Val Cys Asp Leu Asp Gly Asn Val Val Asp<br>65                     70               75               80 | | 240 |
| ggc gca gaa tcc cct tcc tcc gat act gca tct cat gca tac atc tat<br>Gly Ala Glu Ser Pro Ser Ser Asp Thr Ala Ser His Ala Tyr Ile Tyr<br>                  85               90               95 | | 288 |
| aga cat atg cca gaa gtt tac ggt gtt gtc cac act cat tct acc tat<br>Arg His Met Pro Glu Val Tyr Gly Val Val His Thr His Ser Thr Tyr<br>                100               105              110 | | 336 |
| gct act gct tgg gca gcc acc ggt cag aat atc cca tgt ggt tta acc<br>Ala Thr Ala Trp Ala Ala Thr Gly Gln Asn Ile Pro Cys Gly Leu Thr<br>             115                120               125 | | 384 |
| atg atg ggt gat gag ttc ggt ggt cca gtt cca gtc ggt cca ttt cgt<br>Met Met Gly Asp Glu Phe Gly Gly Pro Val Pro Val Gly Pro Phe Arg<br>130                    135               140 | | 432 |
| ttg att ggt tct gaa gct att ggt gaa ggt gtt gtc gag aca ttg aaa<br>Leu Ile Gly Ser Glu Ala Ile Gly Glu Gly Val Val Glu Thr Leu Lys<br>145                    150               155              160 | | 480 |
| gca tac cca aag tct cct gcc gtc tta atg caa aat cac ggt cca ttc<br>Ala Tyr Pro Lys Ser Pro Ala Val Leu Met Gln Asn His Gly Pro Phe<br>                  165               170              175 | | 528 |
| acc att ggt aaa gat gcc gaa gca gcc gtt aag gct gca gct atg act<br>Thr Ile Gly Lys Asp Ala Glu Ala Ala Val Lys Ala Ala Ala Met Thr<br>             180                185               190 | | 576 |
| gag gag gtc gct cac act atg tgg gct gcc aaa caa ttg ggt gat atc<br>Glu Glu Val Ala His Thr Met Trp Ala Ala Lys Gln Leu Gly Asp Ile<br>            195                200               205 | | 624 |
| att cca att cca caa gag gat att gac aag tta aac gat aga tat caa<br>Ile Pro Ile Pro Gln Glu Asp Ile Asp Lys Leu Asn Asp Arg Tyr Gln<br>210                    215               220 | | 672 |
| aac gtt tat ggt caa cac taa<br>Asn Val Tyr Gly Gln His<br>225                    230 | | 693 |

<210> SEQ ID NO 18
<211> LENGTH: 230
<212> TYPE: PRT
<213> ORGANISM: Artificial Sequence
<220> FEATURE:
<223> OTHER INFORMATION: Synthetic Construct

<400> SEQUENCE: 18

Met Ala Thr Leu Ala Asp Tyr Gly Pro Glu Val Arg Ala Glu Val Lys
1               5                   10                  15

Gln Val Arg Glu Val Val Ala Ala Leu His Glu Gln Leu Ile Lys Trp
            20                  25                  30

Asn Leu Val Val Trp Thr Ala Gly Asn Val Ser Gln Arg Leu Arg Thr
        35                  40                  45

Ala Asp Leu Met Val Ile Lys Pro Ser Gly Leu Arg Tyr Glu Tyr Leu
    50                  55                  60

Thr Pro Ser Ser Met Val Val Cys Asp Leu Asp Gly Asn Val Val Asp

```
                65                  70                  75                  80
Gly Ala Glu Ser Pro Ser Ser Asp Thr Ala Ser His Ala Tyr Ile Tyr
                        85                  90                  95

Arg His Met Pro Glu Val Tyr Gly Val Val His Thr His Ser Thr Tyr
                100                 105                 110

Ala Thr Ala Trp Ala Ala Thr Gly Gln Asn Ile Pro Cys Gly Leu Thr
                115                 120                 125

Met Met Gly Asp Glu Phe Gly Gly Pro Val Pro Val Gly Pro Phe Arg
        130                 135                 140

Leu Ile Gly Ser Glu Ala Ile Gly Glu Gly Val Val Glu Thr Leu Lys
145                 150                 155                 160

Ala Tyr Pro Lys Ser Pro Ala Val Leu Met Gln Asn His Gly Pro Phe
                165                 170                 175

Thr Ile Gly Lys Asp Ala Glu Ala Val Lys Ala Ala Ala Met Thr
                180                 185                 190

Glu Glu Val Ala His Thr Met Trp Ala Ala Lys Gln Leu Gly Asp Ile
            195                 200                 205

Ile Pro Ile Pro Gln Glu Asp Ile Asp Lys Leu Asn Asp Arg Tyr Gln
        210                 215                 220

Asn Val Tyr Gly Gln His
225                 230

<210> SEQ ID NO 19
<211> LENGTH: 702
<212> TYPE: DNA
<213> ORGANISM: Artificial Sequence
<220> FEATURE:
<223> OTHER INFORMATION: Codon optimized L. lactis araD
<220> FEATURE:
<221> NAME/KEY: CDS
<222> LOCATION: (1)..(702)

<400> SEQUENCE: 19 atg tta gag gat ttg aaa gag aag gtt ttg aag gca aat ctt gaa ttg     48
Met Leu Glu Asp Leu Lys Glu Lys Val Leu Lys Ala Asn Leu Glu Leu
1               5                   10                  15 cca gaa cat cac tta gtc gag ttc act tgg ggt aat gca tca gca ttt     96
Pro Glu His His Leu Val Glu Phe Thr Trp Gly Asn Ala Ser Ala Phe
                20                  25                  30 gat aag gaa acc ggt tac ttt gtc att aag cct tct ggt att gac tat    144
Asp Lys Glu Thr Gly Tyr Phe Val Ile Lys Pro Ser Gly Ile Asp Tyr
            35                  40                  45 ggt tcc tta aag gct tcc gat atg gtt gtc gtt gat ttg gaa ggt aaa    192
Gly Ser Leu Lys Ala Ser Asp Met Val Val Val Asp Leu Glu Gly Lys
        50                  55                  60 gtt att gaa ggc gag tta aac cca tcc tct gac act cca act cat gct    240
Val Ile Glu Gly Glu Leu Asn Pro Ser Ser Asp Thr Pro Thr His Ala
65                  70                  75                  80 gtt ttg tac aaa aag cat cca gaa ttg ggt ggt att gtt cac acc cac    288
Val Leu Tyr Lys Lys His Pro Glu Leu Gly Gly Ile Val His Thr His
                85                  90                  95 tcc aat tgg gca acc gcc tgg gca gaa tca ggt gtt gat gtt tct gcc    336
Ser Asn Trp Ala Thr Ala Trp Ala Glu Ser Gly Val Asp Val Ser Ala
                100                 105                 110 atg ggc acc act cat gca gac aca ttc tat ggt cca gtt cca tgt act    384
Met Gly Thr Thr His Ala Asp Thr Phe Tyr Gly Pro Val Pro Cys Thr
            115                 120                 125 cgt tac tta aca aag gaa gag att gat aag ggt tat gaa tat gaa aca    432
Arg Tyr Leu Thr Lys Glu Glu Ile Asp Lys Gly Tyr Glu Tyr Glu Thr
```

```
                130                 135                 140
ggc aag ctt atc att gaa acc ttc gag gaa aga ggt att gat atc tta       480
Gly Lys Leu Ile Ile Glu Thr Phe Glu Glu Arg Gly Ile Asp Ile Leu
145                 150                 155                 160 gac att cca gct gtc tta ttg aga ggt cac ggt cca ttc act tgg ggt       528
Asp Ile Pro Ala Val Leu Leu Arg Gly His Gly Pro Phe Thr Trp Gly
                165                 170                 175 gaa aat gtc gaa gct gcc gtc tac aac gct gtt gtt tta gaa aac gtt       576
Glu Asn Val Glu Ala Ala Val Tyr Asn Ala Val Val Leu Glu Asn Val
            180                 185                 190 tgt aag atg aac atc ttt gct aga caa atc aac tct tat gct gct gat       624
Cys Lys Met Asn Ile Phe Ala Arg Gln Ile Asn Ser Tyr Ala Ala Asp
        195                 200                 205 ttg cct cag aga atc ttg gat aag cac tat ctt aga aag cat ggt aaa       672
Leu Pro Gln Arg Ile Leu Asp Lys His Tyr Leu Arg Lys His Gly Lys
    210                 215                 220 gac gca tac tac ggt cag aaa aac aag taa                               702
Asp Ala Tyr Tyr Gly Gln Lys Asn Lys
225                 230

<210> SEQ ID NO 20
<211> LENGTH: 233
<212> TYPE: PRT
<213> ORGANISM: Artificial Sequence
<220> FEATURE:
<223> OTHER INFORMATION: Synthetic Construct

<400> SEQUENCE: 20

Met Leu Glu Asp Leu Lys Glu Lys Val Leu Lys Ala Asn Leu Glu Leu
1               5                   10                  15

Pro Glu His His Leu Val Glu Phe Thr Trp Gly Asn Ala Ser Ala Phe
            20                  25                  30

Asp Lys Glu Thr Gly Tyr Phe Val Ile Lys Pro Ser Gly Ile Asp Tyr
        35                  40                  45

Gly Ser Leu Lys Ala Ser Asp Met Val Val Asp Leu Glu Gly Lys
    50                  55                  60

Val Ile Glu Gly Glu Leu Asn Pro Ser Ser Asp Thr Pro Thr His Ala
65                  70                  75                  80

Val Leu Tyr Lys Lys His Pro Glu Leu Gly Gly Ile Val His Thr His
                85                  90                  95

Ser Asn Trp Ala Thr Ala Trp Ala Glu Ser Gly Val Asp Val Ser Ala
            100                 105                 110

Met Gly Thr Thr His Ala Asp Thr Phe Tyr Gly Pro Val Pro Cys Thr
        115                 120                 125

Arg Tyr Leu Thr Lys Glu Glu Ile Asp Lys Gly Tyr Glu Tyr Glu Thr
    130                 135                 140

Gly Lys Leu Ile Ile Glu Thr Phe Glu Glu Arg Gly Ile Asp Ile Leu
145                 150                 155                 160

Asp Ile Pro Ala Val Leu Leu Arg Gly His Gly Pro Phe Thr Trp Gly
                165                 170                 175

Glu Asn Val Glu Ala Ala Val Tyr Asn Ala Val Val Leu Glu Asn Val
            180                 185                 190

Cys Lys Met Asn Ile Phe Ala Arg Gln Ile Asn Ser Tyr Ala Ala Asp
        195                 200                 205

Leu Pro Gln Arg Ile Leu Asp Lys His Tyr Leu Arg Lys His Gly Lys
    210                 215                 220

Asp Ala Tyr Tyr Gly Gln Lys Asn Lys
```

<210> SEQ ID NO 21
<211> LENGTH: 1317
<212> TYPE: DNA
<213> ORGANISM: Artificial Sequence
<220> FEATURE:
<223> OTHER INFORMATION: Codon optimized B. thetaiotaomicron XI
<220> FEATURE:
<221> NAME/KEY: CDS
<222> LOCATION: (1)..(1317)

<400> SEQUENCE: 21

```
atg gct act aaa gaa ttt ttc cca ggt att gaa aag att aaa ttt gaa      48
Met Ala Thr Lys Glu Phe Phe Pro Gly Ile Glu Lys Ile Lys Phe Glu
1               5                   10                  15 ggt aaa gac tcc aaa aat cca atg gct ttt aga tat tac gac gca gaa      96
Gly Lys Asp Ser Lys Asn Pro Met Ala Phe Arg Tyr Tyr Asp Ala Glu
            20                  25                  30 aag gtt att aac ggt aaa aaa atg aag gac tgg ttg aga ttt gct atg     144
Lys Val Ile Asn Gly Lys Lys Met Lys Asp Trp Leu Arg Phe Ala Met
        35                  40                  45 gca tgg tgg cac acc cta tgt gct gaa ggt ggt gat caa ttc ggt ggt     192
Ala Trp Trp His Thr Leu Cys Ala Glu Gly Gly Asp Gln Phe Gly Gly
    50                  55                  60 ggt aca aaa caa ttt cct tgg aac ggt aac gct gac gct att caa gct     240
Gly Thr Lys Gln Phe Pro Trp Asn Gly Asn Ala Asp Ala Ile Gln Ala
65                  70                  75                  80 gca aag gac aag atg gac gcc ggt ttc gaa ttt atg caa aag atg ggt     288
Ala Lys Asp Lys Met Asp Ala Gly Phe Glu Phe Met Gln Lys Met Gly
                85                  90                  95 att gaa tac tac tgt ttt cac gat gtt gat ttg gtc tct gaa ggt gca     336
Ile Glu Tyr Tyr Cys Phe His Asp Val Asp Leu Val Ser Glu Gly Ala
            100                 105                 110 tct gtt gaa gaa tat gaa gct aac ttg aag gaa atc gtt gct tac gct     384
Ser Val Glu Glu Tyr Glu Ala Asn Leu Lys Glu Ile Val Ala Tyr Ala
        115                 120                 125 aag caa aag caa gct gag aca ggt att aaa ttg ttg tgg ggt aca gca     432
Lys Gln Lys Gln Ala Glu Thr Gly Ile Lys Leu Leu Trp Gly Thr Ala
    130                 135                 140 aac gtt ttc ggt cac gcc aga tat atg aat ggt gct gca act aac cca     480
Asn Val Phe Gly His Ala Arg Tyr Met Asn Gly Ala Ala Thr Asn Pro
145                 150                 155                 160 gat ttc gat gtt gtt gca aga gcc gca gtt caa atc aaa aac gct att     528
Asp Phe Asp Val Val Ala Arg Ala Ala Val Gln Ile Lys Asn Ala Ile
                165                 170                 175 gac gct aca atc gaa cta ggt ggt gaa aac tat gtt ttt tgg ggt ggt     576
Asp Ala Thr Ile Glu Leu Gly Gly Glu Asn Tyr Val Phe Trp Gly Gly
            180                 185                 190 aga gaa ggt tac atg tct ttg ttg aac act gac caa aaa aga gaa aag     624
Arg Glu Gly Tyr Met Ser Leu Leu Asn Thr Asp Gln Lys Arg Glu Lys
        195                 200                 205 gaa cac ttg gcc caa atg ttg act atc gct aga gat tac gct aga gct     672
Glu His Leu Ala Gln Met Leu Thr Ile Ala Arg Asp Tyr Ala Arg Ala
    210                 215                 220 aga ggt ttt aaa ggt act ttt ttg att gaa cca aaa cca atg gaa cca     720
Arg Gly Phe Lys Gly Thr Phe Leu Ile Glu Pro Lys Pro Met Glu Pro
225                 230                 235                 240 act aag cac caa tat gac gtt gat act gaa act gtt att ggt ttc ttg     768
Thr Lys His Gln Tyr Asp Val Asp Thr Glu Thr Val Ile Gly Phe Leu
                245                 250                 255
```

| | | |
|---|---|---|
| aag gca cac ggt ttg gat aag gat ttt aag gtg aat atc gaa gtt aac<br>Lys Ala His Gly Leu Asp Lys Asp Phe Lys Val Asn Ile Glu Val Asn<br>260                        265                    270 | | 816 |
| cac gct act ttg gcc ggt cat act ttc gaa cat gaa ttg gct gtt gct<br>His Ala Thr Leu Ala Gly His Thr Phe Glu His Glu Leu Ala Val Ala<br>        275                    280                    285 | | 864 |
| gtg gat aac ggt atg ttg ggt tct att gac gca aac aga ggt gac tat<br>Val Asp Asn Gly Met Leu Gly Ser Ile Asp Ala Asn Arg Gly Asp Tyr<br>290                        295                    300 | | 912 |
| caa aat ggt tgg gac act gat caa ttt cca att gac aac tat gaa ttg<br>Gln Asn Gly Trp Asp Thr Asp Gln Phe Pro Ile Asp Asn Tyr Glu Leu<br>305                        310                    315                    320 | | 960 |
| aca caa gca atg atg caa att att aga aac ggt ggt ttg ggt act ggt<br>Thr Gln Ala Met Met Gln Ile Ile Arg Asn Gly Gly Leu Gly Thr Gly<br>                    325                    330                    335 | | 1008 |
| ggt act aac ttc gac gct aag act aga aga aat tcc aca gat ttg gaa<br>Gly Thr Asn Phe Asp Ala Lys Thr Arg Arg Asn Ser Thr Asp Leu Glu<br>        340                    345                    350 | | 1056 |
| gac att ttt atc gct cac atc gct ggt atg gac gct atg gcc aga gct<br>Asp Ile Phe Ile Ala His Ile Ala Gly Met Asp Ala Met Ala Arg Ala<br>              355                    360                    365 | | 1104 |
| ttg gaa tcc gct gct gct ttg ttg gac gaa tcc cca tac aag aaa atg<br>Leu Glu Ser Ala Ala Ala Leu Leu Asp Glu Ser Pro Tyr Lys Lys Met<br>370                        375                    380 | | 1152 |
| ttg gcc gac aga tac gct tct ttc gac ggt ggt aag ggt aag gaa ttt<br>Leu Ala Asp Arg Tyr Ala Ser Phe Asp Gly Gly Lys Gly Lys Glu Phe<br>385                        390                    395                    400 | | 1200 |
| gag gac ggt aag ttg aca ttg gaa gat gtt gtt gct tac gct aag act<br>Glu Asp Gly Lys Leu Thr Leu Glu Asp Val Val Ala Tyr Ala Lys Thr<br>                    405                    410                    415 | | 1248 |
| aag ggt gaa cca aag caa aca tcc ggt aag caa gaa ttg tac gaa gct<br>Lys Gly Glu Pro Lys Gln Thr Ser Gly Lys Gln Glu Leu Tyr Glu Ala<br>                    420                    425                    430 | | 1296 |
| att cta aat atg tac tgt taa<br>Ile Leu Asn Met Tyr Cys<br>                  435 | | 1317 |

<210> SEQ ID NO 22
<211> LENGTH: 438
<212> TYPE: PRT
<213> ORGANISM: Artificial Sequence
<220> FEATURE:
<223> OTHER INFORMATION: Synthetic Construct

<400> SEQUENCE: 22

Met Ala Thr Lys Glu Phe Phe Pro Gly Ile Glu Lys Ile Lys Phe Glu
1                   5                    10                  15

Gly Lys Asp Ser Lys Asn Pro Met Ala Phe Arg Tyr Tyr Asp Ala Glu
                  20                    25                    30

Lys Val Ile Asn Gly Lys Lys Met Lys Asp Trp Leu Arg Phe Ala Met
            35                    40                    45

Ala Trp Trp His Thr Leu Cys Ala Glu Gly Gly Asp Gln Phe Gly Gly
    50                    55                    60

Gly Thr Lys Gln Phe Pro Trp Asn Gly Asn Ala Asp Ala Ile Gln Ala
65                  70                    75                    80

Ala Lys Asp Lys Met Asp Ala Gly Phe Glu Phe Met Gln Lys Met Gly
                  85                    90                    95

Ile Glu Tyr Tyr Cys Phe His Asp Val Asp Leu Val Ser Glu Gly Ala
            100                    105                    110

```
Ser Val Glu Glu Tyr Glu Ala Asn Leu Lys Glu Ile Val Ala Tyr Ala
        115                 120                 125
Lys Gln Lys Gln Ala Glu Thr Gly Ile Lys Leu Leu Trp Gly Thr Ala
130                 135                 140
Asn Val Phe Gly His Ala Arg Tyr Met Asn Gly Ala Ala Thr Asn Pro
145                 150                 155                 160
Asp Phe Asp Val Val Ala Arg Ala Val Gln Ile Lys Asn Ala Ile
                165                 170                 175
Asp Ala Thr Ile Glu Leu Gly Gly Glu Asn Tyr Val Phe Trp Gly Gly
            180                 185                 190
Arg Glu Gly Tyr Met Ser Leu Leu Asn Thr Asp Gln Lys Arg Glu Lys
        195                 200                 205
Glu His Leu Ala Gln Met Leu Thr Ile Ala Arg Asp Tyr Ala Arg Ala
    210                 215                 220
Arg Gly Phe Lys Gly Thr Phe Leu Ile Glu Pro Lys Pro Met Glu Pro
225                 230                 235                 240
Thr Lys His Gln Tyr Asp Val Asp Thr Glu Thr Val Ile Gly Phe Leu
                245                 250                 255
Lys Ala His Gly Leu Asp Lys Asp Phe Lys Val Asn Ile Glu Val Asn
            260                 265                 270
His Ala Thr Leu Ala Gly His Thr Phe Glu His Glu Leu Ala Val Ala
        275                 280                 285
Val Asp Asn Gly Met Leu Gly Ser Ile Asp Ala Asn Arg Gly Asp Tyr
    290                 295                 300
Gln Asn Gly Trp Asp Thr Asp Gln Phe Pro Ile Asp Asn Tyr Glu Leu
305                 310                 315                 320
Thr Gln Ala Met Met Gln Ile Ile Arg Asn Gly Gly Leu Gly Thr Gly
                325                 330                 335
Gly Thr Asn Phe Asp Ala Lys Thr Arg Arg Asn Ser Thr Asp Leu Glu
            340                 345                 350
Asp Ile Phe Ile Ala His Ile Ala Gly Met Asp Ala Met Ala Arg Ala
        355                 360                 365
Leu Glu Ser Ala Ala Ala Leu Leu Asp Glu Ser Pro Tyr Lys Lys Met
    370                 375                 380
Leu Ala Asp Arg Tyr Ala Ser Phe Asp Gly Gly Lys Gly Lys Glu Phe
385                 390                 395                 400
Glu Asp Gly Lys Leu Thr Leu Glu Asp Val Val Ala Tyr Ala Lys Thr
                405                 410                 415
Lys Gly Glu Pro Lys Gln Thr Ser Gly Lys Gln Glu Leu Tyr Glu Ala
            420                 425                 430
Ile Leu Asn Met Tyr Cys
        435

<210> SEQ ID NO 23
<211> LENGTH: 1782
<212> TYPE: DNA
<213> ORGANISM: Issatchenkia orientalis
<220> FEATURE:
<221> NAME/KEY: CDS
<222> LOCATION: (1)..(1782)

<400> SEQUENCE: 23 atg tct ttg gct cta ggt ttt gac ctc tca aca caa cag ctg aaa atc        48
Met Ser Leu Ala Leu Gly Phe Asp Leu Ser Thr Gln Gln Leu Lys Ile
1               5                   10                  15 gtc tcc tgt tat cag gat ctt agt ctt cat tca aaa tac tct att gat        96
```

```
Val Ser Cys Tyr Gln Asp Leu Ser Leu His Ser Lys Tyr Ser Ile Asp
         20                  25                  30 ttc gac gaa ttc aag gac att tac ggt atc cat aaa ggc gta ttg tcg    144
Phe Asp Glu Phe Lys Asp Ile Tyr Gly Ile His Lys Gly Val Leu Ser
         35                  40                  45 aat aga gat aca ggt gaa gtc gtt act cct gtc aag ttg ttt gta cat    192
Asn Arg Asp Thr Gly Glu Val Val Thr Pro Val Lys Leu Phe Val His
 50                  55                  60 gcc ctc cag acc ctc ctg gac cgc atg cac aat gat ggg ttc ccc ttt    240
Ala Leu Gln Thr Leu Leu Asp Arg Met His Asn Asp Gly Phe Pro Phe
 65                  70                  75                  80 gat tgc gtg aca tca att tca gga tcg tgc caa caa cat gga acg att    288
Asp Cys Val Thr Ser Ile Ser Gly Ser Cys Gln Gln His Gly Thr Ile
                 85                  90                  95 ttc tgt aca cgt caa ttc gat aca ctg ctc tcg aat ttg aat ccg gct    336
Phe Cys Thr Arg Gln Phe Asp Thr Leu Leu Ser Asn Leu Asn Pro Ala
                100                 105                 110 tct gat act tgg cac agc gat ttg tcc aat gcc ttc tcc tac gag aat    384
Ser Asp Thr Trp His Ser Asp Leu Ser Asn Ala Phe Ser Tyr Glu Asn
            115                 120                 125 gcc tcc aat tgg caa gac aga tca acg ggc gaa gaa ttg gcg gtg ttt    432
Ala Ser Asn Trp Gln Asp Arg Ser Thr Gly Glu Glu Leu Ala Val Phe
130                 135                 140 gaa aaa gca ttg gga tca gca gag aaa ctc tgt aaa atc act ggt tca    480
Glu Lys Ala Leu Gly Ser Ala Glu Lys Leu Cys Lys Ile Thr Gly Ser
145                 150                 155                 160 aag gcg cat ttc agg ttc tct ggt cct caa atg aga agg agg gcc aag    528
Lys Ala His Phe Arg Phe Ser Gly Pro Gln Met Arg Arg Arg Ala Lys
                165                 170                 175 gag ggt ggt gtc cat tgg gag gag acg gcc cac ata tcc ctc ata tcc    576
Glu Gly Gly Val His Trp Glu Glu Thr Ala His Ile Ser Leu Ile Ser
            180                 185                 190 aat ttt ctc gat tcc atc ttg tcc ggt aag gtt aga ggg gtg gaa att    624
Asn Phe Leu Asp Ser Ile Leu Ser Gly Lys Val Arg Gly Val Glu Ile
        195                 200                 205 gga gaa gct tgt ggt aca aac ctc ttt gat att gag cag aac gac tgg    672
Gly Glu Ala Cys Gly Thr Asn Leu Phe Asp Ile Glu Gln Asn Asp Trp
210                 215                 220 aac gat gag ttg ctt tcc ttg atc ttg atg aag aat tcc aat gtt gac    720
Asn Asp Glu Leu Leu Ser Leu Ile Leu Met Lys Asn Ser Asn Val Asp
225                 230                 235                 240 gga gtt cct ttg ggt gaa cag caa gag gct tct ttg aaa gcc cgt caa    768
Gly Val Pro Leu Gly Glu Gln Gln Glu Ala Ser Leu Lys Ala Arg Gln
                245                 250                 255 ctt cta aaa acc tta gtt gag cct gat gat tat tca aca att gcg cct    816
Leu Leu Lys Thr Leu Val Glu Pro Asp Asp Tyr Ser Thr Ile Ala Pro
            260                 265                 270 tac ttg gcc aaa agg tat ggc ttt aaa agg gac tgt aag gtc tgg ccc    864
Tyr Leu Ala Lys Arg Tyr Gly Phe Lys Arg Asp Cys Lys Val Trp Pro
        275                 280                 285 att act ggc gat aat ttg gca acc atc atg tcc ttg cca ttg aaa cat    912
Ile Thr Gly Asp Asn Leu Ala Thr Ile Met Ser Leu Pro Leu Lys His
    290                 295                 300 gac gat ttg ttg gtg tct atg ggg acc agt aca acg gtg ttg ttg ttg    960
Asp Asp Leu Leu Val Ser Met Gly Thr Ser Thr Thr Val Leu Leu Leu
305                 310                 315                 320 acg aaa aac tac ctt cca agt gtg aac tat cac ctc ttt aag cat cct    1008
Thr Lys Asn Tyr Leu Pro Ser Val Asn Tyr His Leu Phe Lys His Pro
                325                 330                 335
```

| | | |
|---|---|---|
| gtt gta agg gat atc tat atg ggt atg ttg tgc tat tca aat ggt gct<br>Val Val Arg Asp Ile Tyr Met Gly Met Leu Cys Tyr Ser Asn Gly Ala<br>340 345 350 | | 1056 |
| ctg gca cgt gag gaa att agg gat gaa att aac gac aag tat aaa acg<br>Leu Ala Arg Glu Glu Ile Arg Asp Glu Ile Asn Asp Lys Tyr Lys Thr<br>355 360 365 | | 1104 |
| gta aag tgg gat aaa ttc aac gag att tta gac act aga aag tct ccc<br>Val Lys Trp Asp Lys Phe Asn Glu Ile Leu Asp Thr Arg Lys Ser Pro<br>370 375 380 | | 1152 |
| gac aga gag gtt gga atc tat ttc ccc cta ggc gaa atc att ccc aac<br>Asp Arg Glu Val Gly Ile Tyr Phe Pro Leu Gly Glu Ile Ile Pro Asn<br>385 390 395 400 | | 1200 |
| gtc aag ccc tgt aag cgt atc ttc aag tat tcg gca gcg aag ggg ctt<br>Val Lys Pro Cys Lys Arg Ile Phe Lys Tyr Ser Ala Ala Lys Gly Leu<br>405 410 415 | | 1248 |
| gtg gaa gtg gac aga gaa gtc gag ctg gac gac caa gtg aag ctt atc<br>Val Glu Val Asp Arg Glu Val Glu Leu Asp Asp Gln Val Lys Leu Ile<br>420 425 430 | | 1296 |
| att gag tcg cag gcg tta tcc aat cga ctc cgt gta gca cca ctt cta<br>Ile Glu Ser Gln Ala Leu Ser Asn Arg Leu Arg Val Ala Pro Leu Leu<br>435 440 445 | | 1344 |
| acc gat gtt gaa acc gtg aag gag aag tcg gtg acc aga gac att gag<br>Thr Asp Val Glu Thr Val Lys Glu Lys Ser Val Thr Arg Asp Ile Glu<br>450 455 460 | | 1392 |
| agt gca agg aag att gtt ggt gac tcg gtt aca att gac cat gtc gct<br>Ser Ala Arg Lys Ile Val Gly Asp Ser Val Thr Ile Asp His Val Ala<br>465 470 475 480 | | 1440 |
| tac acg ttt gcc gat atc atc aag cgt ccc aat agt gta tac tat gct<br>Tyr Thr Phe Ala Asp Ile Ile Lys Arg Pro Asn Ser Val Tyr Tyr Ala<br>485 490 495 | | 1488 |
| gga ggt tct tca cag aat gca tcg att ctc aag att tac aat gac att<br>Gly Gly Ser Ser Gln Asn Ala Ser Ile Leu Lys Ile Tyr Asn Asp Ile<br>500 505 510 | | 1536 |
| cta gga cct aaa cat ggt ggc tac aag gtt gaa gtc ggt gat gcc tgt<br>Leu Gly Pro Lys His Gly Gly Tyr Lys Val Glu Val Gly Asp Ala Cys<br>515 520 525 | | 1584 |
| gcg cta ggc ggt tgt ttc cga gca atc tat gga tac aac gac agc ata<br>Ala Leu Gly Gly Cys Phe Arg Ala Ile Tyr Gly Tyr Asn Asp Ser Ile<br>530 535 540 | | 1632 |
| tca ttt cag gat tgg ttg gag agc aag ttt gat ttc cac aga cat acc<br>Ser Phe Gln Asp Trp Leu Glu Ser Lys Phe Asp Phe His Arg His Thr<br>545 550 555 560 | | 1680 |
| tct ccc att gag agg gac gaa acc cat gcc att tcc acg tgg gca agt<br>Ser Pro Ile Glu Arg Asp Glu Thr His Ala Ile Ser Thr Trp Ala Ser<br>565 570 575 | | 1728 |
| tat ctc gac aag gtt gcc ata ttg acc ttg gca gag cag caa tta gat<br>Tyr Leu Asp Lys Val Ala Ile Leu Thr Leu Ala Glu Gln Gln Leu Asp<br>580 585 590 | | 1776 |
| tgt tga<br>Cys | | 1782 |

<210> SEQ ID NO 24
<211> LENGTH: 593
<212> TYPE: PRT
<213> ORGANISM: Issatchenkia orientalis

<400> SEQUENCE: 24

Met Ser Leu Ala Leu Gly Phe Asp Leu Ser Thr Gln Gln Leu Lys Ile
1               5                   10                  15

Val Ser Cys Tyr Gln Asp Leu Ser Leu His Ser Lys Tyr Ser Ile Asp

-continued

```
                20                  25                  30
Phe Asp Glu Phe Lys Asp Ile Tyr Gly Ile His Lys Gly Val Leu Ser
            35                  40                  45
Asn Arg Asp Thr Gly Glu Val Val Thr Pro Val Lys Leu Phe Val His
 50                  55                  60
Ala Leu Gln Thr Leu Leu Asp Arg Met His Asn Asp Gly Phe Pro Phe
 65                  70                  75                  80
Asp Cys Val Thr Ser Ile Ser Gly Ser Cys Gln Gln His Gly Thr Ile
                85                  90                  95
Phe Cys Thr Arg Gln Phe Asp Thr Leu Leu Ser Asn Leu Asn Pro Ala
                100                 105                 110
Ser Asp Thr Trp His Ser Asp Leu Ser Asn Ala Phe Ser Tyr Glu Asn
            115                 120                 125
Ala Ser Asn Trp Gln Asp Arg Ser Thr Gly Glu Glu Leu Ala Val Phe
            130                 135                 140
Glu Lys Ala Leu Gly Ser Ala Glu Lys Leu Cys Lys Ile Thr Gly Ser
145                 150                 155                 160
Lys Ala His Phe Arg Phe Ser Gly Pro Gln Met Arg Arg Arg Ala Lys
                165                 170                 175
Glu Gly Gly Val His Trp Glu Gly Thr Ala His Ile Ser Leu Ile Ser
                180                 185                 190
Asn Phe Leu Asp Ser Ile Leu Ser Gly Lys Val Arg Gly Val Glu Ile
            195                 200                 205
Gly Glu Ala Cys Gly Thr Asn Leu Phe Asp Ile Glu Gln Asn Asp Trp
            210                 215                 220
Asn Asp Glu Leu Leu Ser Leu Ile Leu Met Lys Asn Ser Asn Val Asp
225                 230                 235                 240
Gly Val Pro Leu Gly Glu Gln Gln Glu Ala Ser Leu Lys Ala Arg Gln
                245                 250                 255
Leu Leu Lys Thr Leu Val Glu Pro Asp Asp Tyr Ser Thr Ile Ala Pro
                260                 265                 270
Tyr Leu Ala Lys Arg Tyr Gly Phe Lys Arg Asp Cys Lys Val Trp Pro
            275                 280                 285
Ile Thr Gly Asp Asn Leu Ala Thr Ile Met Ser Leu Pro Leu Lys His
            290                 295                 300
Asp Asp Leu Leu Val Ser Met Gly Thr Ser Thr Thr Val Leu Leu Leu
305                 310                 315                 320
Thr Lys Asn Tyr Leu Pro Ser Val Asn Tyr His Leu Phe Lys His Pro
                325                 330                 335
Val Val Arg Asp Ile Tyr Met Gly Met Leu Cys Tyr Ser Asn Gly Ala
                340                 345                 350
Leu Ala Arg Glu Glu Ile Arg Asp Glu Ile Asn Asp Lys Tyr Lys Thr
            355                 360                 365
Val Lys Trp Asp Lys Phe Asn Glu Ile Leu Asp Thr Arg Lys Ser Pro
            370                 375                 380
Asp Arg Glu Val Gly Ile Tyr Phe Pro Leu Gly Glu Ile Ile Pro Asn
385                 390                 395                 400
Val Lys Pro Cys Lys Arg Ile Phe Lys Tyr Ser Ala Ala Lys Gly Leu
                405                 410                 415
Val Glu Val Asp Arg Glu Val Glu Leu Asp Asp Gln Val Lys Leu Ile
                420                 425                 430
Ile Glu Ser Gln Ala Leu Ser Asn Arg Leu Arg Val Ala Pro Leu Leu
            435                 440                 445
```

```
Thr Asp Val Glu Thr Val Lys Glu Lys Ser Val Thr Arg Asp Ile Glu
    450                 455                 460

Ser Ala Arg Lys Ile Val Gly Asp Ser Val Thr Ile Asp His Val Ala
465                 470                 475                 480

Tyr Thr Phe Ala Asp Ile Ile Lys Arg Pro Asn Ser Val Tyr Tyr Ala
                485                 490                 495

Gly Gly Ser Ser Gln Asn Ala Ser Ile Leu Lys Ile Tyr Asn Asp Ile
                500                 505                 510

Leu Gly Pro Lys His Gly Gly Tyr Lys Val Glu Val Gly Asp Ala Cys
        515                 520                 525

Ala Leu Gly Gly Cys Phe Arg Ala Ile Tyr Gly Tyr Asn Asp Ser Ile
        530                 535                 540

Ser Phe Gln Asp Trp Leu Glu Ser Lys Phe Asp Phe His Arg His Thr
545                 550                 555                 560

Ser Pro Ile Glu Arg Asp Glu Thr His Ala Ile Ser Thr Trp Ala Ser
                565                 570                 575

Tyr Leu Asp Lys Val Ala Ile Leu Thr Leu Ala Glu Gln Gln Leu Asp
                580                 585                 590

Cys

<210> SEQ ID NO 25
<211> LENGTH: 1803
<212> TYPE: DNA
<213> ORGANISM: Saccharomyces cerevisiae
<220> FEATURE:
<221> NAME/KEY: CDS
<222> LOCATION: (1)..(1803)

<400> SEQUENCE: 25 atg ttg tgt tca gta att cag aga cag aca aga gag gtt tcc aac aca      48
Met Leu Cys Ser Val Ile Gln Arg Gln Thr Arg Glu Val Ser Asn Thr
1               5                   10                  15 atg tct tta gac tca tac tat ctt ggg ttt gat ctt tcg acc caa caa      96
Met Ser Leu Asp Ser Tyr Tyr Leu Gly Phe Asp Leu Ser Thr Gln Gln
            20                  25                  30 ctg aaa tgt ctc gcc att aac cag gac cta aaa att gtc cat tca gaa     144
Leu Lys Cys Leu Ala Ile Asn Gln Asp Leu Lys Ile Val His Ser Glu
        35                  40                  45 aca gtg gaa ttt gaa aag gat ctt ccg cat tat cac aca aag aag ggt     192
Thr Val Glu Phe Glu Lys Asp Leu Pro His Tyr His Thr Lys Lys Gly
    50                  55                  60 gtc tat ata cac ggc gac act atc gaa tgt ccc gta gcc atg tgg tta     240
Val Tyr Ile His Gly Asp Thr Ile Glu Cys Pro Val Ala Met Trp Leu
65                  70                  75                  80 gag gct cta gat ctg gtt ctc tcg aaa tat cgc gag gct aaa ttt cca     288
Glu Ala Leu Asp Leu Val Leu Ser Lys Tyr Arg Glu Ala Lys Phe Pro
                85                  90                  95 ttg aac aaa gtt atg gcc gtc tca ggg tcc tgc cag cag cac ggg tct     336
Leu Asn Lys Val Met Ala Val Ser Gly Ser Cys Gln Gln His Gly Ser
            100                 105                 110 gtc tac tgg tcc tcc caa gcc gaa tct ctg tta gag caa ttg aat aag     384
Val Tyr Trp Ser Ser Gln Ala Glu Ser Leu Leu Glu Gln Leu Asn Lys
        115                 120                 125 aaa ccg gaa aaa gat tta ttg cac tac gtg agc tct gta gca ttt gca     432
Lys Pro Glu Lys Asp Leu Leu His Tyr Val Ser Ser Val Ala Phe Ala
    130                 135                 140 agg caa acc gcc ccc aat tgg caa gac cac agt act gca aag caa tgt     480
Arg Gln Thr Ala Pro Asn Trp Gln Asp His Ser Thr Ala Lys Gln Cys
```

```
                 145                 150                 155                 160
       caa gag ttt gaa gag tgc ata ggt ggg cct gaa aaa atg gct caa tta        528
       Gln Glu Phe Glu Glu Cys Ile Gly Gly Pro Glu Lys Met Ala Gln Leu
                           165                 170                 175 aca ggg tcc aga gcc cat ttt aga ttt act ggt cct caa att ctg aaa        576
       Thr Gly Ser Arg Ala His Phe Arg Phe Thr Gly Pro Gln Ile Leu Lys
                       180                 185                 190 att gca caa tta gaa cca gaa gct tac gaa aaa aca aag acc att tct        624
       Ile Ala Gln Leu Glu Pro Glu Ala Tyr Glu Lys Thr Lys Thr Ile Ser
                   195                 200                 205 tta gtg tct aat ttt ttg act tct atc tta gtg ggc cat ctt gtt gaa        672
       Leu Val Ser Asn Phe Leu Thr Ser Ile Leu Val Gly His Leu Val Glu
               210                 215                 220 ttg gag gag gca gat gcc tgt ggt atg aac ctt tat gat ata cgt gaa        720
       Leu Glu Glu Ala Asp Ala Cys Gly Met Asn Leu Tyr Asp Ile Arg Glu
       225                 230                 235                 240 aga aaa ttc agt gat gag cta cta cat cta att gat agt tct tct aag        768
       Arg Lys Phe Ser Asp Glu Leu Leu His Leu Ile Asp Ser Ser Ser Lys
                           245                 250                 255 gat aaa act atc aga caa aaa tta atg aga gca ccc atg aaa aat ttg        816
       Asp Lys Thr Ile Arg Gln Lys Leu Met Arg Ala Pro Met Lys Asn Leu
                       260                 265                 270 ata gcg ggt acc atc tgt aaa tat ttt att gag aag tac ggt ttc aat        864
       Ile Ala Gly Thr Ile Cys Lys Tyr Phe Ile Glu Lys Tyr Gly Phe Asn
                   275                 280                 285 aca aac tgc aag gtc tct ccc atg act ggg gat aat tta gcc act ata        912
       Thr Asn Cys Lys Val Ser Pro Met Thr Gly Asp Asn Leu Ala Thr Ile
               290                 295                 300 tgt tct tta ccc ctg cgg aag aat gac gtt ctc gtt tcc cta gga aca        960
       Cys Ser Leu Pro Leu Arg Lys Asn Asp Val Leu Val Ser Leu Gly Thr
       305                 310                 315                 320 agt act aca gtt ctt ctg gtc acc gat aag tat cac ccc tct ccg aac       1008
       Ser Thr Thr Val Leu Leu Val Thr Asp Lys Tyr His Pro Ser Pro Asn
                           325                 330                 335 tat cat ctt ttc att cat cca act ctg cca aac cat tat atg ggt atg       1056
       Tyr His Leu Phe Ile His Pro Thr Leu Pro Asn His Tyr Met Gly Met
                       340                 345                 350 att tgt tat tgt aat ggt tct ttg gca agg gag agg ata aga gac gag       1104
       Ile Cys Tyr Cys Asn Gly Ser Leu Ala Arg Glu Arg Ile Arg Asp Glu
                   355                 360                 365 tta aac aaa gaa cgg gaa aat aat tat gag aag act aac gat tgg act       1152
       Leu Asn Lys Glu Arg Glu Asn Asn Tyr Glu Lys Thr Asn Asp Trp Thr
               370                 375                 380 ctt ttt aat caa gct gtg cta gat gac tca gaa agt agt gaa aat gaa       1200
       Leu Phe Asn Gln Ala Val Leu Asp Asp Ser Glu Ser Ser Glu Asn Glu
       385                 390                 395                 400 tta ggt gta tat ttt cct ctg ggg gag atc gtt cct agc gta aaa gcc       1248
       Leu Gly Val Tyr Phe Pro Leu Gly Glu Ile Val Pro Ser Val Lys Ala
                           405                 410                 415 ata aac aaa agg gtt atc ttc aat cca aaa acg ggt atg att gaa aga       1296
       Ile Asn Lys Arg Val Ile Phe Asn Pro Lys Thr Gly Met Ile Glu Arg
                       420                 425                 430 gag gtg gcc aag ttc aaa gac aag agg cac gat gcc aaa aat att gta       1344
       Glu Val Ala Lys Phe Lys Asp Lys Arg His Asp Ala Lys Asn Ile Val
                   435                 440                 445 gaa tca cag gct tta agt tgc agg gta aga ata tct ccc ctg ctt tcg       1392
       Glu Ser Gln Ala Leu Ser Cys Arg Val Arg Ile Ser Pro Leu Leu Ser
               450                 455                 460 gat tca aac gca agc tca caa cag aga ctg aac gaa gat aca atc gtg       1440
```

```
Asp Ser Asn Ala Ser Ser Gln Gln Arg Leu Asn Glu Asp Thr Ile Val
465                 470                 475                 480 aag ttt gat tac gat gaa tct ccg ctg cgg gac tac cta aat aaa agg      1488
Lys Phe Asp Tyr Asp Glu Ser Pro Leu Arg Asp Tyr Leu Asn Lys Arg
                485                 490                 495 cca gaa agg act ttt ttt gta ggt ggg gct tct aaa aac gat gct att      1536
Pro Glu Arg Thr Phe Phe Val Gly Gly Ala Ser Lys Asn Asp Ala Ile
            500                 505                 510 gtg aag aag ttt gct caa gtc att ggt gct aca aag ggt aat ttt agg      1584
Val Lys Lys Phe Ala Gln Val Ile Gly Ala Thr Lys Gly Asn Phe Arg
        515                 520                 525 cta gaa aca cca aac tca tgt gcc ctt ggt ggt tgt tat aag gcc atg      1632
Leu Glu Thr Pro Asn Ser Cys Ala Leu Gly Gly Cys Tyr Lys Ala Met
    530                 535                 540 tgg tca ttg tta tat gac tct aat aaa att gca gtt cct ttt gat aaa      1680
Trp Ser Leu Leu Tyr Asp Ser Asn Lys Ile Ala Val Pro Phe Asp Lys
545                 550                 555                 560 ttt ctg aat gac aat ttt cca tgg cat gta atg gaa agc ata tcc gat      1728
Phe Leu Asn Asp Asn Phe Pro Trp His Val Met Glu Ser Ile Ser Asp
                565                 570                 575 gtg gat aat gaa aat tgg gat cgc tat aat tcc aag att gtc ccc tta      1776
Val Asp Asn Glu Asn Trp Asp Arg Tyr Asn Ser Lys Ile Val Pro Leu
            580                 585                 590 agc gaa ctg gaa aag act ctc atc taa                                  1803
Ser Glu Leu Glu Lys Thr Leu Ile
        595                 600

<210> SEQ ID NO 26
<211> LENGTH: 600
<212> TYPE: PRT
<213> ORGANISM: Saccharomyces cerevisiae

<400> SEQUENCE: 26

Met Leu Cys Ser Val Ile Gln Arg Gln Thr Arg Glu Val Ser Asn Thr
1               5                   10                  15

Met Ser Leu Asp Ser Tyr Tyr Leu Gly Phe Asp Leu Ser Thr Gln Gln
            20                  25                  30

Leu Lys Cys Leu Ala Ile Asn Gln Asp Leu Lys Ile Val His Ser Glu
        35                  40                  45

Thr Val Glu Phe Glu Lys Asp Leu Pro His Tyr His Thr Lys Lys Gly
    50                  55                  60

Val Tyr Ile His Gly Asp Thr Ile Glu Cys Pro Val Ala Met Trp Leu
65                  70                  75                  80

Glu Ala Leu Asp Leu Val Leu Ser Lys Tyr Arg Glu Ala Lys Phe Pro
                85                  90                  95

Leu Asn Lys Val Met Ala Val Ser Gly Ser Cys Gln Gln His Gly Ser
            100                 105                 110

Val Tyr Trp Ser Ser Gln Ala Glu Ser Leu Leu Glu Gln Leu Asn Lys
        115                 120                 125

Lys Pro Glu Lys Asp Leu Leu His Tyr Val Ser Ser Val Ala Phe Ala
    130                 135                 140

Arg Gln Thr Ala Pro Asn Trp Gln Asp His Ser Thr Ala Lys Gln Cys
145                 150                 155                 160

Gln Glu Phe Glu Glu Cys Ile Gly Gly Pro Glu Lys Met Ala Gln Leu
                165                 170                 175

Thr Gly Ser Arg Ala His Phe Arg Phe Thr Gly Pro Gln Ile Leu Lys
            180                 185                 190
```

-continued

Ile Ala Gln Leu Glu Pro Glu Ala Tyr Glu Lys Thr Lys Thr Ile Ser
            195                 200                 205
Leu Val Ser Asn Phe Leu Thr Ser Ile Leu Val Gly His Leu Val Glu
        210                 215                 220
Leu Glu Glu Ala Asp Ala Cys Gly Met Asn Leu Tyr Asp Ile Arg Glu
225                 230                 235                 240
Arg Lys Phe Ser Asp Glu Leu Leu His Leu Ile Asp Ser Ser Ser Lys
                245                 250                 255
Asp Lys Thr Ile Arg Gln Lys Leu Met Arg Ala Pro Met Lys Asn Leu
            260                 265                 270
Ile Ala Gly Thr Ile Cys Lys Tyr Phe Ile Glu Lys Tyr Gly Phe Asn
        275                 280                 285
Thr Asn Cys Lys Val Ser Pro Met Thr Gly Asp Asn Leu Ala Thr Ile
    290                 295                 300
Cys Ser Leu Pro Leu Arg Lys Asn Asp Val Leu Val Ser Leu Gly Thr
305                 310                 315                 320
Ser Thr Thr Val Leu Leu Val Thr Asp Lys Tyr His Pro Ser Pro Asn
                325                 330                 335
Tyr His Leu Phe Ile His Pro Thr Leu Pro Asn His Tyr Met Gly Met
            340                 345                 350
Ile Cys Tyr Cys Asn Gly Ser Leu Ala Arg Glu Arg Ile Arg Asp Glu
        355                 360                 365
Leu Asn Lys Glu Arg Glu Asn Tyr Glu Lys Thr Asn Asp Trp Thr
    370                 375                 380
Leu Phe Asn Gln Ala Val Leu Asp Asp Ser Glu Ser Ser Glu Asn Glu
385                 390                 395                 400
Leu Gly Val Tyr Phe Pro Leu Gly Glu Ile Val Pro Ser Val Lys Ala
                405                 410                 415
Ile Asn Lys Arg Val Ile Phe Asn Pro Lys Thr Gly Met Ile Glu Arg
            420                 425                 430
Glu Val Ala Lys Phe Lys Asp Lys Arg His Asp Ala Lys Asn Ile Val
        435                 440                 445
Glu Ser Gln Ala Leu Ser Cys Arg Val Arg Ile Ser Pro Leu Leu Ser
    450                 455                 460
Asp Ser Asn Ala Ser Ser Gln Gln Arg Leu Asn Glu Asp Thr Ile Val
465                 470                 475                 480
Lys Phe Asp Tyr Asp Glu Ser Pro Leu Arg Asp Tyr Leu Asn Lys Arg
                485                 490                 495
Pro Glu Arg Thr Phe Val Gly Gly Ala Ser Lys Asn Asp Ala Ile
            500                 505                 510
Val Lys Lys Phe Ala Gln Val Ile Gly Ala Thr Lys Gly Asn Phe Arg
        515                 520                 525
Leu Glu Thr Pro Asn Ser Cys Ala Leu Gly Gly Cys Tyr Lys Ala Met
    530                 535                 540
Trp Ser Leu Leu Tyr Asp Ser Asn Lys Ile Ala Val Pro Phe Asp Lys
545                 550                 555                 560
Phe Leu Asn Asp Asn Phe Pro Trp His Val Met Glu Ser Ile Ser Asp
                565                 570                 575
Val Asp Asn Glu Asn Trp Asp Arg Tyr Asn Ser Lys Ile Val Pro Leu
            580                 585                 590
Ser Glu Leu Glu Lys Thr Leu Ile
        595                 600

<210> SEQ ID NO 27
<211> LENGTH: 1809
<212> TYPE: DNA
<213> ORGANISM: Kluyveromyces marxianus
<220> FEATURE:
<221> NAME/KEY: CDS
<222> LOCATION: (1)..(1809)

<400> SEQUENCE: 27

| | | | | | | | | | | | | | | | | |
|---|---|---|---|---|---|---|---|---|---|---|---|---|---|---|---|---|
| atg | tct | acc | cca | tac | tat | tta | ggt | ttc | gat | ctt | tct | acg | cag | caa | ttg | 48 |
| Met | Ser | Thr | Pro | Tyr | Tyr | Leu | Gly | Phe | Asp | Leu | Ser | Thr | Gln | Gln | Leu | |
| 1 | | | | 5 | | | | | 10 | | | | | 15 | | |
| aaa | tgt | ctc | gct | atc | gat | gac | caa | ttg | aac | atc | gtc | acc | agt | gtt | tcc | 96 |
| Lys | Cys | Leu | Ala | Ile | Asp | Asp | Gln | Leu | Asn | Ile | Val | Thr | Ser | Val | Ser | |
| | | | 20 | | | | | 25 | | | | | 30 | | | |
| atc | gag | ttc | gac | agg | gac | ttc | ccg | gct | tac | aac | acc | aag | aag | ggt | gtg | 144 |
| Ile | Glu | Phe | Asp | Arg | Asp | Phe | Pro | Ala | Tyr | Asn | Thr | Lys | Lys | Gly | Val | |
| | | | | 35 | | | | | 40 | | | | | 45 | | |
| tac | atc | aag | aat | ggc | ggt | gtt | att | gat | gct | cca | gtg | gcc | atg | tgg | cta | 192 |
| Tyr | Ile | Lys | Asn | Gly | Gly | Val | Ile | Asp | Ala | Pro | Val | Ala | Met | Trp | Leu | |
| | 50 | | | | | 55 | | | | | 60 | | | | | |
| gaa | gct | gtg | gac | ttg | tgt | ttc | tca | cag | cta | gcg | gaa | cga | atc | gat | ttg | 240 |
| Glu | Ala | Val | Asp | Leu | Cys | Phe | Ser | Gln | Leu | Ala | Glu | Arg | Ile | Asp | Leu | |
| 65 | | | | | 70 | | | | | 75 | | | | | 80 | |
| aaa | cga | gtc | cag | tcg | atg | tct | ggc | tcg | tgc | caa | caa | cac | gga | acc | gtg | 288 |
| Lys | Arg | Val | Gln | Ser | Met | Ser | Gly | Ser | Cys | Gln | Gln | His | Gly | Thr | Val | |
| | | | | 85 | | | | | 90 | | | | | 95 | | |
| tac | tgg | aat | tgc | gaa | cac | ttg | ccc | tca | aac | ctg | gac | ccg | gca | tcc | acg | 336 |
| Tyr | Trp | Asn | Cys | Glu | His | Leu | Pro | Ser | Asn | Leu | Asp | Pro | Ala | Ser | Thr | |
| | | | 100 | | | | | 105 | | | | | 110 | | | |
| ctt | cgc | gaa | caa | ttg | caa | ggg | tcg | ctc | agc | aga | ccg | gtg | gcc | ccc | aat | 384 |
| Leu | Arg | Glu | Gln | Leu | Gln | Gly | Ser | Leu | Ser | Arg | Pro | Val | Ala | Pro | Asn | |
| | | 115 | | | | | 120 | | | | | 125 | | | | |
| tgg | caa | gac | cac | agc | aca | aag | aaa | cag | tgc | gat | gag | ttg | gca | gaa | agc | 432 |
| Trp | Gln | Asp | His | Ser | Thr | Lys | Lys | Gln | Cys | Asp | Glu | Leu | Ala | Glu | Ser | |
| | 130 | | | | | 135 | | | | | 140 | | | | | |
| gtt | gga | ggt | cca | gaa | gaa | ttg | gca | cga | atc | act | ggt | tct | ggt | gcc | cat | 480 |
| Val | Gly | Gly | Pro | Glu | Glu | Leu | Ala | Arg | Ile | Thr | Gly | Ser | Gly | Ala | His | |
| 145 | | | | | 150 | | | | | 155 | | | | | 160 | |
| tac | agg | ttt | tcc | ggc | tcg | caa | ata | gcc | aag | atc | cac | gag | acc | gag | ccc | 528 |
| Tyr | Arg | Phe | Ser | Gly | Ser | Gln | Ile | Ala | Lys | Ile | His | Glu | Thr | Glu | Pro | |
| | | | | 165 | | | | | 170 | | | | | 175 | | |
| gag | gtt | tac | gaa | gct | acc | aag | agg | atc | tcg | ctt | gtg | tcg | tct | ttc | cta | 576 |
| Glu | Val | Tyr | Glu | Ala | Thr | Lys | Arg | Ile | Ser | Leu | Val | Ser | Ser | Phe | Leu | |
| | | | 180 | | | | | 185 | | | | | 190 | | | |
| gcc | tct | gtg | ctt | gtt | ggg | gac | att | gtc | cca | ttg | gaa | gaa | gcg | gat | gcg | 624 |
| Ala | Ser | Val | Leu | Val | Gly | Asp | Ile | Val | Pro | Leu | Glu | Glu | Ala | Asp | Ala | |
| | | 195 | | | | | 200 | | | | | 205 | | | | |
| tgc | ggc | atg | aac | ttg | tac | gac | ttg | agc | aag | cac | gat | ttc | gac | gag | act | 672 |
| Cys | Gly | Met | Asn | Leu | Tyr | Asp | Leu | Ser | Lys | His | Asp | Phe | Asp | Glu | Thr | |
| | 210 | | | | | 215 | | | | | 220 | | | | | |
| tta | ctg | gca | gtt | gta | gac | cac | gac | acg | gct | cgt | ctc | agg | aga | aag | ttg | 720 |
| Leu | Leu | Ala | Val | Val | Asp | His | Asp | Thr | Ala | Arg | Leu | Arg | Arg | Lys | Leu | |
| 225 | | | | | 230 | | | | | 235 | | | | | 240 | |
| agc | gat | cca | ccg | gtg | gga | gct | ccg | act | cga | gag | tcc | cct | ttg | acc | agt | 768 |
| Ser | Asp | Pro | Pro | Val | Gly | Ala | Pro | Thr | Arg | Glu | Ser | Pro | Leu | Thr | Ser | |
| | | | | 245 | | | | | 250 | | | | | 255 | | |
| ttg | ggt | aaa | gtg | tcc | aag | tac | ttc | cag | gac | aag | tac | ggc | gtg | aac | tgc | 816 |
| Leu | Gly | Lys | Val | Ser | Lys | Tyr | Phe | Gln | Asp | Lys | Tyr | Gly | Val | Asn | Cys | |
| | | | 260 | | | | | 265 | | | | | 270 | | | |
| gag | tgc | gag | atc | ttc | ccc | ttc | act | gga | gac | aac | cta | gcc | acc | ata | tgc | 864 |

| | |
|---|---|
| Glu Cys Glu Ile Phe Pro Phe Thr Gly Asp Asn Leu Ala Thr Ile Cys<br>275                     280                     285 | |
| tcg ctt ccc ttg cag aag aac gac gtg ttg atc tcg ttg ggc acc tcg<br>Ser Leu Pro Leu Gln Lys Asn Asp Val Leu Ile Ser Leu Gly Thr Ser<br>290                     295                     300 | 912 |
| acc acg att ctc ttg gtc acg gac cag tac cac tcg tcg ccc aat tac<br>Thr Thr Ile Leu Leu Val Thr Asp Gln Tyr His Ser Ser Pro Asn Tyr<br>305                     310                     315                     320 | 960 |
| cac ttg ttc atc cat cca acg gtg ccc gga tac tac atg ggc atg att<br>His Leu Phe Ile His Pro Thr Val Pro Gly Tyr Tyr Met Gly Met Ile<br>                     325                     330                     335 | 1008 |
| tgc tac tgc aac ggg tct ttg gcg cgc gag cgt gtt cgc gac gac ttg<br>Cys Tyr Cys Asn Gly Ser Leu Ala Arg Glu Arg Val Arg Asp Asp Leu<br>                  340                     345                     350 | 1056 |
| gcg gga cca cag gcc tcg cag gcc ccc gga gaa cag gtg ccc tgg acc<br>Ala Gly Pro Gln Ala Ser Gln Ala Pro Gly Glu Gln Val Pro Trp Thr<br>             355                     360                     365 | 1104 |
| caa ttc aac gac gct ttg ctc gac gac agt tta tcc aac gac aac gaa<br>Gln Phe Asn Asp Ala Leu Leu Asp Asp Ser Leu Ser Asn Asp Asn Glu<br>370                     375                     380 | 1152 |
| atc ggg ttg tac ttc cca ttg ggc gag atc gtg ccc aac gtc gac gcc<br>Ile Gly Leu Tyr Phe Pro Leu Gly Glu Ile Val Pro Asn Val Asp Ala<br>385                     390                     395                     400 | 1200 |
| gtg acc aag cgc tgg acg ttc gag cgc aag gaa aac cat ccc aac aaa<br>Val Thr Lys Arg Trp Thr Phe Glu Arg Lys Glu Asn His Pro Asn Lys<br>                          405                     410                     415 | 1248 |
| acc att gtg cta cac gag ctc gac caa ttc acc cca aaa cgc aag gac<br>Thr Ile Val Leu His Glu Leu Asp Gln Phe Thr Pro Lys Arg Lys Asp<br>                  420                     425                     430 | 1296 |
| gcc aag aat atc gtc gag tcg caa gcc tta agc tgc agg gtc cgc att<br>Ala Lys Asn Ile Val Glu Ser Gln Ala Leu Ser Cys Arg Val Arg Ile<br>             435                     440                     445 | 1344 |
| tct cca cta ttg tcc gac gaa acg gac gcc ctg agc gag acc cag gtg<br>Ser Pro Leu Leu Ser Asp Glu Thr Asp Ala Leu Ser Glu Thr Gln Val<br>450                     455                     460 | 1392 |
| cta tcc aag aaa gaa aac acc caa gtg aca ttc gac tac gac gca ttc<br>Leu Ser Lys Lys Glu Asn Thr Gln Val Thr Phe Asp Tyr Asp Ala Phe<br>465                     470                     475                     480 | 1440 |
| cca ctc tgg act tac gca aag aga ccc aac cgt gcc ttc ttc gtt ggt<br>Pro Leu Trp Thr Tyr Ala Lys Arg Pro Asn Arg Ala Phe Phe Val Gly<br>                          485                     490                     495 | 1488 |
| ggt gcc tcc aag aac gat gcc att gtc cgg aca atg gcc aac gtc att<br>Gly Ala Ser Lys Asn Asp Ala Ile Val Arg Thr Met Ala Asn Val Ile<br>                  500                     505                     510 | 1536 |
| ggc gcc aga aac ggc aac tac aga cta gaa acg ccc aat tcg tgc gca<br>Gly Ala Arg Asn Gly Asn Tyr Arg Leu Glu Thr Pro Asn Ser Cys Ala<br>             515                     520                     525 | 1584 |
| ttg ggc ggc tgc tac aag gcg atg tgg tcc tgg ttg aag gtc cac gag<br>Leu Gly Gly Cys Tyr Lys Ala Met Trp Ser Trp Leu Lys Val His Glu<br>530                     535                     540 | 1632 |
| ccc acg acc acc cca tcc ttc gac gtt tgg ctg aat gcc agt ttc aac<br>Pro Thr Thr Thr Pro Ser Phe Asp Val Trp Leu Asn Ala Ser Phe Asn<br>545                     550                     555                     560 | 1680 |
| tgg caa aga gac tgc gaa ttt gtg tgt caa tct gac gct gcc aaa tgg<br>Trp Gln Arg Asp Cys Glu Phe Val Cys Gln Ser Asp Ala Ala Lys Trp<br>                          565                     570                     575 | 1728 |
| gag caa tgc aac ggc aag ata cag gca ttg agc gaa gca gag gcg tac<br>Glu Gln Cys Asn Gly Lys Ile Gln Ala Leu Ser Glu Ala Glu Ala Tyr<br>                  580                     585                     590 | 1776 |

```
gtc aag gcc ctg gcc cac gac caa ggc cag tga                    1809
Val Lys Ala Leu Ala His Asp Gln Gly Gln
        595                 600
```

<210> SEQ ID NO 28
<211> LENGTH: 602
<212> TYPE: PRT
<213> ORGANISM: Kluyveromyces marxianus

<400> SEQUENCE: 28

```
Met Ser Thr Pro Tyr Tyr Leu Gly Phe Asp Leu Ser Thr Gln Gln Leu
1               5                   10                  15

Lys Cys Leu Ala Ile Asp Asp Gln Leu Asn Ile Val Thr Ser Val Ser
            20                  25                  30

Ile Glu Phe Asp Arg Asp Phe Pro Ala Tyr Asn Thr Lys Lys Gly Val
        35                  40                  45

Tyr Ile Lys Asn Gly Gly Val Ile Asp Ala Pro Val Ala Met Trp Leu
    50                  55                  60

Glu Ala Val Asp Leu Cys Phe Ser Gln Leu Ala Glu Arg Ile Asp Leu
65                  70                  75                  80

Lys Arg Val Gln Ser Met Ser Gly Ser Cys Gln Gln His Gly Thr Val
                85                  90                  95

Tyr Trp Asn Cys Glu His Leu Pro Ser Asn Leu Asp Pro Ala Ser Thr
            100                 105                 110

Leu Arg Glu Gln Leu Gln Gly Ser Leu Ser Arg Pro Val Ala Pro Asn
        115                 120                 125

Trp Gln Asp His Ser Thr Lys Lys Gln Cys Asp Glu Leu Ala Glu Ser
    130                 135                 140

Val Gly Gly Pro Glu Glu Leu Ala Arg Ile Thr Gly Ser Gly Ala His
145                 150                 155                 160

Tyr Arg Phe Ser Gly Ser Gln Ile Ala Lys Ile His Glu Thr Glu Pro
                165                 170                 175

Glu Val Tyr Glu Ala Thr Lys Arg Ile Ser Leu Val Ser Ser Phe Leu
            180                 185                 190

Ala Ser Val Leu Val Gly Asp Ile Val Pro Leu Glu Glu Ala Asp Ala
        195                 200                 205

Cys Gly Met Asn Leu Tyr Asp Leu Ser Lys His Asp Phe Asp Glu Thr
    210                 215                 220

Leu Leu Ala Val Val Asp His Asp Thr Ala Arg Leu Arg Arg Lys Leu
225                 230                 235                 240

Ser Asp Pro Pro Val Gly Ala Pro Thr Arg Glu Ser Pro Leu Thr Ser
                245                 250                 255

Leu Gly Lys Val Ser Lys Tyr Phe Gln Asp Lys Tyr Gly Val Asn Cys
            260                 265                 270

Glu Cys Glu Ile Phe Pro Phe Thr Gly Asp Asn Leu Ala Thr Ile Cys
        275                 280                 285

Ser Leu Pro Leu Gln Lys Asn Asp Val Leu Ile Ser Leu Gly Thr Ser
    290                 295                 300

Thr Thr Ile Leu Leu Val Thr Asp Gln Tyr His Ser Ser Pro Asn Tyr
305                 310                 315                 320

His Leu Phe Ile His Pro Thr Val Pro Gly Tyr Tyr Met Gly Met Ile
                325                 330                 335

Cys Tyr Cys Asn Gly Ser Leu Ala Arg Glu Arg Val Arg Asp Asp Leu
            340                 345                 350

Ala Gly Pro Gln Ala Ser Gln Ala Pro Gly Glu Gln Val Pro Trp Thr
```

```
                355                 360                 365
Gln Phe Asn Asp Ala Leu Leu Asp Asp Ser Leu Ser Asn Asp Asn Glu
    370                 375                 380

Ile Gly Leu Tyr Phe Pro Leu Gly Glu Ile Val Pro Asn Val Asp Ala
385                 390                 395                 400

Val Thr Lys Arg Trp Thr Phe Glu Arg Lys Glu Asn His Pro Asn Lys
                405                 410                 415

Thr Ile Val Leu His Glu Leu Asp Gln Phe Thr Pro Lys Arg Lys Asp
            420                 425                 430

Ala Lys Asn Ile Val Glu Ser Gln Ala Leu Ser Cys Arg Val Arg Ile
        435                 440                 445

Ser Pro Leu Leu Ser Asp Glu Thr Asp Ala Leu Ser Glu Thr Gln Val
    450                 455                 460

Leu Ser Lys Lys Glu Asn Thr Gln Val Thr Phe Asp Tyr Asp Ala Phe
465                 470                 475                 480

Pro Leu Trp Thr Tyr Ala Lys Arg Pro Asn Arg Ala Phe Phe Val Gly
                485                 490                 495

Gly Ala Ser Lys Asn Asp Ala Ile Val Arg Thr Met Ala Asn Val Ile
            500                 505                 510

Gly Ala Arg Asn Gly Asn Tyr Arg Leu Glu Thr Pro Asn Ser Cys Ala
        515                 520                 525

Leu Gly Gly Cys Tyr Lys Ala Met Trp Ser Trp Leu Lys Val His Glu
    530                 535                 540

Pro Thr Thr Thr Pro Ser Phe Asp Val Trp Leu Asn Ala Ser Phe Asn
545                 550                 555                 560

Trp Gln Arg Asp Cys Glu Phe Val Cys Gln Ser Asp Ala Ala Lys Trp
                565                 570                 575

Glu Gln Cys Asn Gly Lys Ile Gln Ala Leu Ser Glu Ala Glu Ala Tyr
            580                 585                 590

Val Lys Ala Leu Ala His Asp Gln Gly Gln
        595                 600

<210> SEQ ID NO 29
<211> LENGTH: 957
<212> TYPE: DNA
<213> ORGANISM: Pichia stipitis
<220> FEATURE:
<221> NAME/KEY: CDS
<222> LOCATION: (1)..(957)

<400> SEQUENCE: 29 atg cct tct att aag ttg aac tct ggt tac gac atg cca gcc gtc ggt      48
Met Pro Ser Ile Lys Leu Asn Ser Gly Tyr Asp Met Pro Ala Val Gly
1               5                   10                  15 ttc ggc tgt tgg aaa gtc gac gtc gac acc tgt tct gaa cag atc tac      96
Phe Gly Cys Trp Lys Val Asp Val Asp Thr Cys Ser Glu Gln Ile Tyr
            20                  25                  30 cgt gct atc aag acc ggt tac aga ttg ttc gac ggt gcc gaa gat tac     144
Arg Ala Ile Lys Thr Gly Tyr Arg Leu Phe Asp Gly Ala Glu Asp Tyr
        35                  40                  45 gcc aac gaa aag tta gtt ggt gcc ggt gtc aag aag gcc att gac gaa     192
Ala Asn Glu Lys Leu Val Gly Ala Gly Val Lys Lys Ala Ile Asp Glu
    50                  55                  60 ggt atc gtc aag cgt gaa gac ttg ttc ctt acc tcc aag ttg tgg aac     240
Gly Ile Val Lys Arg Glu Asp Leu Phe Leu Thr Ser Lys Leu Trp Asn
65                  70                  75                  80 aac tac cac cac cca gac aac gtc gaa aag gcc ttg aac aga acc ctt     288
```

```
                                                            Asn Tyr His His Pro Asp Asn Val Glu Lys Ala Leu Asn Arg Thr Leu
                                                                        85                  90                  95 tct gac ttg caa gtt gac tac gtt gac ttg ttc ttg atc cac ttc cca         336
Ser Asp Leu Gln Val Asp Tyr Val Asp Leu Phe Leu Ile His Phe Pro
            100                 105                 110 gtc acc ttc aag ttc gtt cca tta gaa gaa aag tac cca cca gga ttc         384
Val Thr Phe Lys Phe Val Pro Leu Glu Glu Lys Tyr Pro Pro Gly Phe
            115                 120                 125 tac tgt ggt aag ggt gac aac ttc gac tac gaa gat gtt cca att tta         432
Tyr Cys Gly Lys Gly Asp Asn Phe Asp Tyr Glu Asp Val Pro Ile Leu
            130                 135                 140 gag acc tgg aag gct ctt gaa aag ttg gtc aag gcc ggt aag atc aga         480
Glu Thr Trp Lys Ala Leu Glu Lys Leu Val Lys Ala Gly Lys Ile Arg
145                 150                 155                 160 tct atc ggt gtt tct aac ttc cca ggt gct ttg ctc ttg gac ttg ttg         528
Ser Ile Gly Val Ser Asn Phe Pro Gly Ala Leu Leu Leu Asp Leu Leu
                165                 170                 175 aga ggt gct acc atc aag cca tct gtc ttg caa gtt gaa cac cac cca         576
Arg Gly Ala Thr Ile Lys Pro Ser Val Leu Gln Val Glu His His Pro
            180                 185                 190 tac ttg caa caa cca aga ttg atc gaa ttc gct caa tcc cgt ggt att         624
Tyr Leu Gln Gln Pro Arg Leu Ile Glu Phe Ala Gln Ser Arg Gly Ile
            195                 200                 205 gct gtc acc gct tac tct tcg ttc ggt cct caa tct ttc gtt gaa ttg         672
Ala Val Thr Ala Tyr Ser Ser Phe Gly Pro Gln Ser Phe Val Glu Leu
            210                 215                 220 aac caa ggt aga gct ttg aac act tct cca ttg ttc gag aac gaa act         720
Asn Gln Gly Arg Ala Leu Asn Thr Ser Pro Leu Phe Glu Asn Glu Thr
225                 230                 235                 240 atc aag gct atc gct gct aag cac ggt aag tct cca gct caa gtc ttg         768
Ile Lys Ala Ile Ala Ala Lys His Gly Lys Ser Pro Ala Gln Val Leu
                245                 250                 255 ttg aga tgg tct tcc caa aga ggc att gcc atc att cca aag tcc aac         816
Leu Arg Trp Ser Ser Gln Arg Gly Ile Ala Ile Ile Pro Lys Ser Asn
            260                 265                 270 act gtc cca aga ttg ttg gaa aac aag gac gtc aac agc ttc gac ttg         864
Thr Val Pro Arg Leu Leu Glu Asn Lys Asp Val Asn Ser Phe Asp Leu
            275                 280                 285 gac gaa caa gat ttc gct gac att gcc aag ttg gac atc aac ttg aga         912
Asp Glu Gln Asp Phe Ala Asp Ile Ala Lys Leu Asp Ile Asn Leu Arg
            290                 295                 300 ttc aac gac cca tgg gac tgg gac aag att cct atc ttc gtc taa             957
Phe Asn Asp Pro Trp Asp Trp Asp Lys Ile Pro Ile Phe Val
305                 310                 315

<210> SEQ ID NO 30
<211> LENGTH: 318
<212> TYPE: PRT
<213> ORGANISM: Pichia stipitis

<400> SEQUENCE: 30

Met Pro Ser Ile Lys Leu Asn Ser Gly Tyr Asp Met Pro Ala Val Gly
1               5                   10                  15

Phe Gly Cys Trp Lys Val Asp Val Asp Thr Cys Ser Glu Gln Ile Tyr
            20                  25                  30

Arg Ala Ile Lys Thr Gly Tyr Arg Leu Phe Asp Gly Ala Glu Asp Tyr
        35                  40                  45

Ala Asn Glu Lys Leu Val Gly Ala Gly Val Lys Lys Ala Ile Asp Glu
    50                  55                  60
```

```
Gly Ile Val Lys Arg Glu Asp Leu Phe Leu Thr Ser Lys Leu Trp Asn
 65                  70                  75                  80

Asn Tyr His His Pro Asp Asn Val Glu Lys Ala Leu Asn Arg Thr Leu
                 85                  90                  95

Ser Asp Leu Gln Val Asp Tyr Val Asp Leu Phe Leu Ile His Phe Pro
            100                 105                 110

Val Thr Phe Lys Phe Val Pro Leu Glu Glu Lys Tyr Pro Pro Gly Phe
        115                 120                 125

Tyr Cys Gly Lys Gly Asp Asn Phe Asp Tyr Glu Asp Val Pro Ile Leu
    130                 135                 140

Glu Thr Trp Lys Ala Leu Glu Lys Leu Val Lys Ala Gly Lys Ile Arg
145                 150                 155                 160

Ser Ile Gly Val Ser Asn Phe Pro Gly Ala Leu Leu Leu Asp Leu Leu
                165                 170                 175

Arg Gly Ala Thr Ile Lys Pro Ser Val Leu Gln Val Glu His His Pro
            180                 185                 190

Tyr Leu Gln Gln Pro Arg Leu Ile Glu Phe Ala Gln Ser Arg Gly Ile
        195                 200                 205

Ala Val Thr Ala Tyr Ser Ser Phe Gly Pro Gln Ser Phe Val Glu Leu
    210                 215                 220

Asn Gln Gly Arg Ala Leu Asn Thr Ser Pro Leu Phe Glu Asn Glu Thr
225                 230                 235                 240

Ile Lys Ala Ile Ala Ala Lys His Gly Lys Ser Pro Ala Gln Val Leu
                245                 250                 255

Leu Arg Trp Ser Ser Gln Arg Gly Ile Ala Ile Ile Pro Lys Ser Asn
            260                 265                 270

Thr Val Pro Arg Leu Leu Glu Asn Lys Asp Val Asn Ser Phe Asp Leu
        275                 280                 285

Asp Glu Gln Asp Phe Ala Asp Ile Ala Lys Leu Asp Ile Asn Leu Arg
    290                 295                 300

Phe Asn Asp Pro Trp Asp Trp Asp Lys Ile Pro Ile Phe Val
305                 310                 315

<210> SEQ ID NO 31
<211> LENGTH: 1092
<212> TYPE: DNA
<213> ORGANISM: Pichia stipitis
<220> FEATURE:
<221> NAME/KEY: CDS
<222> LOCATION: (1)..(1092)

<400> SEQUENCE: 31 atg act gct aac cct tcc ttg gtg ttg aac aag atc gac gac att tcg      48
Met Thr Ala Asn Pro Ser Leu Val Leu Asn Lys Ile Asp Asp Ile Ser
 1               5                  10                  15 ttc gaa act tac gat gcc cca gaa atc tct gaa cct acc gat gtc ctc      96
Phe Glu Thr Tyr Asp Ala Pro Glu Ile Ser Glu Pro Thr Asp Val Leu
            20                  25                  30 gtc cag gtc aag aaa acc ggt atc tgt ggt tcc gac atc cac ttc tac     144
Val Gln Val Lys Lys Thr Gly Ile Cys Gly Ser Asp Ile His Phe Tyr
        35                  40                  45 gcc cat ggt aga atc ggt aac ttc gtt ttg acc aag cca atg gtc ttg     192
Ala His Gly Arg Ile Gly Asn Phe Val Leu Thr Lys Pro Met Val Leu
    50                  55                  60 ggt cac gaa tcc gcc ggt act gtt gtc cag gtt ggt aag ggt gtc acc     240
Gly His Glu Ser Ala Gly Thr Val Val Gln Val Gly Lys Gly Val Thr
65                  70                  75                  80
```

```
tct ctt aag gtt ggt gac aac gtc gct atc gaa cca ggt att cca tcc      288
Ser Leu Lys Val Gly Asp Asn Val Ala Ile Glu Pro Gly Ile Pro Ser
            85                  90                  95 aga ttc tcc gac gaa tac aag agc ggt cac tac aac ttg tgt cct cac      336
Arg Phe Ser Asp Glu Tyr Lys Ser Gly His Tyr Asn Leu Cys Pro His
        100                 105                 110 atg gcc ttc gcc gct act cct aac tcc aag gaa ggt gaa cca aac cca      384
Met Ala Phe Ala Ala Thr Pro Asn Ser Lys Glu Gly Glu Pro Asn Pro
    115                 120                 125 cca ggt acc tta tgt aag tac ttc aag tcg cca gaa gac ttc ttg gtc      432
Pro Gly Thr Leu Cys Lys Tyr Phe Lys Ser Pro Glu Asp Phe Leu Val
130                 135                 140 aag ttg cca gac cac gtc agc ttg gaa ctc ggt gct ctt gtt gag cca      480
Lys Leu Pro Asp His Val Ser Leu Glu Leu Gly Ala Leu Val Glu Pro
145                 150                 155                 160 ttg tct gtt ggt gtc cac gcc tct aag ttg ggt tcc gtt gct ttc ggc      528
Leu Ser Val Gly Val His Ala Ser Lys Leu Gly Ser Val Ala Phe Gly
                165                 170                 175 gac tac gtt gcc gtc ttt ggt gct ggt cct gtt ggt ctt ttg gct gct      576
Asp Tyr Val Ala Val Phe Gly Ala Gly Pro Val Gly Leu Leu Ala Ala
            180                 185                 190 gct gtc gcc aag acc ttc ggt gct aag ggt gtc atc gtc gtt gac att      624
Ala Val Ala Lys Thr Phe Gly Ala Lys Gly Val Ile Val Val Asp Ile
        195                 200                 205 ttc gac aac aag ttg aag atg gcc aag gac att ggt gct gct act cac      672
Phe Asp Asn Lys Leu Lys Met Ala Lys Asp Ile Gly Ala Ala Thr His
    210                 215                 220 acc ttc aac tcc aag acc ggt ggt tct gaa gaa ttg atc aag gct ttc      720
Thr Phe Asn Ser Lys Thr Gly Gly Ser Glu Glu Leu Ile Lys Ala Phe
225                 230                 235                 240 ggt ggt aac gtg cca aac gtc gtt ttg gaa tgt act ggt gct gaa cct      768
Gly Gly Asn Val Pro Asn Val Val Leu Glu Cys Thr Gly Ala Glu Pro
                245                 250                 255 tgt atc aag ttg ggt gtt gac gcc att gcc cca ggt ggt cgt ttc gtt      816
Cys Ile Lys Leu Gly Val Asp Ala Ile Ala Pro Gly Gly Arg Phe Val
            260                 265                 270 caa gtc ggt aac gct gct ggt cca gtc agc ttc cca atc acc gtt ttc      864
Gln Val Gly Asn Ala Ala Gly Pro Val Ser Phe Pro Ile Thr Val Phe
        275                 280                 285 gcc atg aag gaa ttg act ttg ttc ggt tct ttc aga tac gga ttc aac      912
Ala Met Lys Glu Leu Thr Leu Phe Gly Ser Phe Arg Tyr Gly Phe Asn
    290                 295                 300 gac tac aag act gct gtt gga atc ttt gac act aac tac caa aac ggt      960
Asp Tyr Lys Thr Ala Val Gly Ile Phe Asp Thr Asn Tyr Gln Asn Gly
305                 310                 315                 320 aga gaa aat gct cca att gac ttt gaa caa ttg atc acc cac aga tac     1008
Arg Glu Asn Ala Pro Ile Asp Phe Glu Gln Leu Ile Thr His Arg Tyr
                325                 330                 335 aag ttc aag gac gct att gaa gcc tac gac ttg gtc aga gcc ggt aag     1056
Lys Phe Lys Asp Ala Ile Glu Ala Tyr Asp Leu Val Arg Ala Gly Lys
            340                 345                 350 ggt gct gtc aag tgt ctc att gac ggc cct gag taa                     1092
Gly Ala Val Lys Cys Leu Ile Asp Gly Pro Glu
        355                 360
```

<210> SEQ ID NO 32
<211> LENGTH: 363
<212> TYPE: PRT
<213> ORGANISM: Pichia stipitis

<400> SEQUENCE: 32

```
Met Thr Ala Asn Pro Ser Leu Val Leu Asn Lys Ile Asp Asp Ile Ser
1               5                   10                  15

Phe Glu Thr Tyr Asp Ala Pro Glu Ile Ser Glu Pro Thr Asp Val Leu
            20                  25                  30

Val Gln Val Lys Lys Thr Gly Ile Cys Gly Ser Asp Ile His Phe Tyr
        35                  40                  45

Ala His Gly Arg Ile Gly Asn Phe Val Leu Thr Lys Pro Met Val Leu
    50                  55                  60

Gly His Glu Ser Ala Gly Thr Val Val Gln Val Gly Lys Gly Val Thr
65                  70                  75                  80

Ser Leu Lys Val Gly Asp Asn Val Ala Ile Glu Pro Gly Ile Pro Ser
                85                  90                  95

Arg Phe Ser Asp Glu Tyr Lys Ser Gly His Tyr Asn Leu Cys Pro His
            100                 105                 110

Met Ala Phe Ala Ala Thr Pro Asn Ser Lys Glu Gly Glu Pro Asn Pro
        115                 120                 125

Pro Gly Thr Leu Cys Lys Tyr Phe Lys Ser Pro Glu Asp Phe Leu Val
    130                 135                 140

Lys Leu Pro Asp His Val Ser Leu Glu Leu Gly Ala Leu Val Glu Pro
145                 150                 155                 160

Leu Ser Val Gly Val His Ala Ser Lys Leu Gly Ser Val Ala Phe Gly
                165                 170                 175

Asp Tyr Val Ala Val Phe Gly Ala Gly Pro Val Gly Leu Leu Ala Ala
            180                 185                 190

Ala Val Ala Lys Thr Phe Gly Ala Lys Gly Val Ile Val Val Asp Ile
        195                 200                 205

Phe Asp Asn Lys Leu Lys Met Ala Lys Asp Ile Gly Ala Ala Thr His
210                 215                 220

Thr Phe Asn Ser Lys Thr Gly Gly Ser Glu Glu Leu Ile Lys Ala Phe
225                 230                 235                 240

Gly Gly Asn Val Pro Asn Val Val Leu Glu Cys Thr Gly Ala Glu Pro
                245                 250                 255

Cys Ile Lys Leu Gly Val Asp Ala Ile Ala Pro Gly Gly Arg Phe Val
            260                 265                 270

Gln Val Gly Asn Ala Ala Gly Pro Val Ser Phe Pro Ile Thr Val Phe
        275                 280                 285

Ala Met Lys Glu Leu Thr Leu Phe Gly Ser Phe Arg Tyr Gly Phe Asn
290                 295                 300

Asp Tyr Lys Thr Ala Val Gly Ile Phe Asp Thr Asn Tyr Gln Asn Gly
305                 310                 315                 320

Arg Glu Asn Ala Pro Ile Asp Phe Glu Gln Leu Ile Thr His Arg Tyr
                325                 330                 335

Lys Phe Lys Asp Ala Ile Glu Ala Tyr Asp Leu Val Arg Ala Gly Lys
            340                 345                 350

Gly Ala Val Lys Cys Leu Ile Asp Gly Pro Glu
        355                 360
```

<210> SEQ ID NO 33
<211> LENGTH: 690
<212> TYPE: DNA
<213> ORGANISM: Issatchenkia orientalis
<220> FEATURE:
<221> NAME/KEY: CDS
<222> LOCATION: (1)..(690)

```
<400> SEQUENCE: 33 atg gtg aaa tca att att gcg cca tct ttg cta gcc ggt gac ttt gca      48
Met Val Lys Ser Ile Ile Ala Pro Ser Leu Leu Ala Gly Asp Phe Ala
1               5                   10                  15 cac ctt gga tgc gac tgt caa cgt atg ttt gat aat ggc tct gac tgg      96
His Leu Gly Cys Asp Cys Gln Arg Met Phe Asp Asn Gly Ser Asp Trp
                20                  25                  30 gtc cat tta gac gtc atg gat gga cat ttt gtg cca aac att aca atg     144
Val His Leu Asp Val Met Asp Gly His Phe Val Pro Asn Ile Thr Met
            35                  40                  45 ggg cca ccg gtt ata tca tgt ttg aga aaa gca gtg cca aga aag gag     192
Gly Pro Pro Val Ile Ser Cys Leu Arg Lys Ala Val Pro Arg Lys Glu
        50                  55                  60 gat cag cct ggt aag aac ttc ttt gat tgc cat atg atg gtc tcc aat     240
Asp Gln Pro Gly Lys Asn Phe Phe Asp Cys His Met Met Val Ser Asn
65                  70                  75                  80 cct gaa cag tgg gta ccg gag att gcc aaa gct gga ggt gat caa tac     288
Pro Glu Gln Trp Val Pro Glu Ile Ala Lys Ala Gly Gly Asp Gln Tyr
                85                  90                  95 acc ttc cat tac gaa tcc acc aag gat cct gtt gga ttg gtc aag tcc     336
Thr Phe His Tyr Glu Ser Thr Lys Asp Pro Val Gly Leu Val Lys Ser
                100                 105                 110 ata aag gcg cac ggt atg aag gcg gca tgc gcc gtt aaa ccg ggc act     384
Ile Lys Ala His Gly Met Lys Ala Ala Cys Ala Val Lys Pro Gly Thr
            115                 120                 125 gat gtc tct gtc ttg tat gag ctg gcg cca atg cta gat atg gct ttg     432
Asp Val Ser Val Leu Tyr Glu Leu Ala Pro Met Leu Asp Met Ala Leu
        130                 135                 140 gtt atg act gtc gag cca ggt ttt ggt gga caa agt ttc atg cca gat     480
Val Met Thr Val Glu Pro Gly Phe Gly Gly Gln Ser Phe Met Pro Asp
145                 150                 155                 160 atg atg cag aag gtt agg gac cta agg gcc aag ttt cca gat ctc aac     528
Met Met Gln Lys Val Arg Asp Leu Arg Ala Lys Phe Pro Asp Leu Asn
                165                 170                 175 atc caa gtc gac gga ggg ttg ggt aaa ggt act gtt gaa gtt gca gcc     576
Ile Gln Val Asp Gly Gly Leu Gly Lys Gly Thr Val Glu Val Ala Ala
                180                 185                 190 gag gca ggg gcc aat gtt att gtt gct gga aca tcg gtg ttc aag gct     624
Glu Ala Gly Ala Asn Val Ile Val Ala Gly Thr Ser Val Phe Lys Ala
            195                 200                 205 gaa gat cct agt gca atg att tct tat ttg aga gaa gaa gtt gaa aag     672
Glu Asp Pro Ser Ala Met Ile Ser Tyr Leu Arg Glu Glu Val Glu Lys
        210                 215                 220 aat ctg aag aaa gat tag                                              690
Asn Leu Lys Lys Asp
225

<210> SEQ ID NO 34
<211> LENGTH: 229
<212> TYPE: PRT
<213> ORGANISM: Issatchenkia orientalis

<400> SEQUENCE: 34

Met Val Lys Ser Ile Ile Ala Pro Ser Leu Leu Ala Gly Asp Phe Ala
1               5                   10                  15

His Leu Gly Cys Asp Cys Gln Arg Met Phe Asp Asn Gly Ser Asp Trp
                20                  25                  30

Val His Leu Asp Val Met Asp Gly His Phe Val Pro Asn Ile Thr Met
            35                  40                  45
```

```
Gly Pro Pro Val Ile Ser Cys Leu Arg Lys Ala Val Pro Arg Lys Glu
    50                  55                  60

Asp Gln Pro Gly Lys Asn Phe Phe Asp Cys His Met Met Val Ser Asn
 65                  70                  75                  80

Pro Glu Gln Trp Val Pro Glu Ile Ala Lys Ala Gly Gly Asp Gln Tyr
                 85                  90                  95

Thr Phe His Tyr Glu Ser Thr Lys Asp Pro Val Gly Leu Val Lys Ser
                100                 105                 110

Ile Lys Ala His Gly Met Lys Ala Cys Ala Val Lys Pro Gly Thr
                115                 120                 125

Asp Val Ser Val Leu Tyr Glu Leu Ala Pro Met Leu Asp Met Ala Leu
130                 135                 140

Val Met Thr Val Glu Pro Gly Phe Gly Gly Gln Ser Phe Met Pro Asp
145                 150                 155                 160

Met Met Gln Lys Val Arg Asp Leu Arg Ala Lys Phe Pro Asp Leu Asn
                165                 170                 175

Ile Gln Val Asp Gly Gly Leu Gly Lys Gly Thr Val Glu Val Ala Ala
                180                 185                 190

Glu Ala Gly Ala Asn Val Ile Val Ala Gly Thr Ser Val Phe Lys Ala
                195                 200                 205

Glu Asp Pro Ser Ala Met Ile Ser Tyr Leu Arg Glu Glu Val Glu Lys
210                 215                 220

Asn Leu Lys Lys Asp
225

<210> SEQ ID NO 35
<211> LENGTH: 717
<212> TYPE: DNA
<213> ORGANISM: Saccharomyces cerevisiae
<220> FEATURE:
<221> NAME/KEY: CDS
<222> LOCATION: (1)..(717)

<400> SEQUENCE: 35 atg gtc aaa cca att ata gct ccc agt atc ctt gct tct gac ttc gcc    48
Met Val Lys Pro Ile Ile Ala Pro Ser Ile Leu Ala Ser Asp Phe Ala
 1               5                  10                  15 aac ttg ggt tgc gaa tgt cat aag gtc atc aac gcc ggc gca gat tgg    96
Asn Leu Gly Cys Glu Cys His Lys Val Ile Asn Ala Gly Ala Asp Trp
            20                  25                  30 tta cat atc gat gtc atg gac ggc cat ttt gtt cca aac att act ctg   144
Leu His Ile Asp Val Met Asp Gly His Phe Val Pro Asn Ile Thr Leu
        35                  40                  45 ggc caa cca att gtt acc tcc cta cgt cgt tct gtg cca cgc cct ggc   192
Gly Gln Pro Ile Val Thr Ser Leu Arg Arg Ser Val Pro Arg Pro Gly
    50                  55                  60 gat gct agc aac aca gaa aag aag ccc act gcg ttc ttc gat tgt cac   240
Asp Ala Ser Asn Thr Glu Lys Lys Pro Thr Ala Phe Phe Asp Cys His
 65                  70                  75                  80 atg atg gtt gaa aat cct gaa aaa tgg gtc gac gat ttt gct aaa tgt   288
Met Met Val Glu Asn Pro Glu Lys Trp Val Asp Asp Phe Ala Lys Cys
                 85                  90                  95 ggt gct gac caa ttt acg ttc cac tac gag gcc aca caa gac cct ttg   336
Gly Ala Asp Gln Phe Thr Phe His Tyr Glu Ala Thr Gln Asp Pro Leu
                100                 105                 110 cat tta gtt aag ttg att aag tct aag ggc atc aaa gct gca tgc gcc   384
His Leu Val Lys Leu Ile Lys Ser Lys Gly Ile Lys Ala Ala Cys Ala
            115                 120                 125
```

```
atc aaa cct ggt act tct gtt gac gtt tta ttt gaa cta gct cct cat    432
Ile Lys Pro Gly Thr Ser Val Asp Val Leu Phe Glu Leu Ala Pro His
130                 135                 140 ttg gat atg gct ctt gtt atg act gtg gaa cct ggg ttt gga ggc caa    480
Leu Asp Met Ala Leu Val Met Thr Val Glu Pro Gly Phe Gly Gly Gln
145                 150                 155                 160 aaa ttc atg gaa gac atg atg cca aaa gtg gaa act ttg aga gcc aag    528
Lys Phe Met Glu Asp Met Met Pro Lys Val Glu Thr Leu Arg Ala Lys
                165                 170                 175 ttc ccc cat ttg aat atc caa gtc gat ggt ggt ttg ggc aag gag acc    576
Phe Pro His Leu Asn Ile Gln Val Asp Gly Gly Leu Gly Lys Glu Thr
            180                 185                 190 atc ccg aaa gcc gcc aaa gcc ggt gcc aac gtt att gtc gct ggt acc    624
Ile Pro Lys Ala Ala Lys Ala Gly Ala Asn Val Ile Val Ala Gly Thr
        195                 200                 205 agt gtt ttc act gca gct gac ccg cac gat gtt atc tcc ttc atg aaa    672
Ser Val Phe Thr Ala Ala Asp Pro His Asp Val Ile Ser Phe Met Lys
210                 215                 220 gaa gaa gtc tcg aag gaa ttg cgt tct aga gat ttg cta gat tag        717
Glu Glu Val Ser Lys Glu Leu Arg Ser Arg Asp Leu Leu Asp
225                 230                 235
```

<210> SEQ ID NO 36
<211> LENGTH: 238
<212> TYPE: PRT
<213> ORGANISM: Saccharomyces cerevisiae

<400> SEQUENCE: 36

```
Met Val Lys Pro Ile Ala Pro Ser Ile Leu Ala Ser Asp Phe Ala
1               5                   10                  15

Asn Leu Gly Cys Glu Cys His Lys Val Ile Asn Ala Gly Ala Asp Trp
                20                  25                  30

Leu His Ile Asp Val Met Asp Gly His Phe Val Pro Asn Ile Thr Leu
            35                  40                  45

Gly Gln Pro Ile Val Thr Ser Leu Arg Arg Ser Val Pro Arg Pro Gly
50                  55                  60

Asp Ala Ser Asn Thr Glu Lys Lys Pro Thr Ala Phe Phe Asp Cys His
65                  70                  75                  80

Met Met Val Glu Asn Pro Glu Lys Trp Val Asp Asp Phe Ala Lys Cys
                85                  90                  95

Gly Ala Asp Gln Phe Thr Phe His Tyr Glu Ala Thr Gln Asp Pro Leu
                100                 105                 110

His Leu Val Lys Leu Ile Lys Ser Lys Gly Ile Lys Ala Ala Cys Ala
            115                 120                 125

Ile Lys Pro Gly Thr Ser Val Asp Val Leu Phe Glu Leu Ala Pro His
130                 135                 140

Leu Asp Met Ala Leu Val Met Thr Val Glu Pro Gly Phe Gly Gly Gln
145                 150                 155                 160

Lys Phe Met Glu Asp Met Met Pro Lys Val Glu Thr Leu Arg Ala Lys
                165                 170                 175

Phe Pro His Leu Asn Ile Gln Val Asp Gly Gly Leu Gly Lys Glu Thr
            180                 185                 190

Ile Pro Lys Ala Ala Lys Ala Gly Ala Asn Val Ile Val Ala Gly Thr
        195                 200                 205

Ser Val Phe Thr Ala Ala Asp Pro His Asp Val Ile Ser Phe Met Lys
210                 215                 220

Glu Glu Val Ser Lys Glu Leu Arg Ser Arg Asp Leu Leu Asp
```

<210> SEQ ID NO 37
<211> LENGTH: 711
<212> TYPE: DNA
<213> ORGANISM: Kluyveromyces marxianus
<220> FEATURE:
<221> NAME/KEY: CDS
<222> LOCATION: (1)..(711)

<400> SEQUENCE: 37

```
atg gtc caa cct atc att gct cct tct atc tta gcc agt gat ttt tgt      48
Met Val Gln Pro Ile Ile Ala Pro Ser Ile Leu Ala Ser Asp Phe Cys
1               5                   10                  15 aat ctt ggg tgc gag tgc cac aag gtg atc aac tcc ggt gcc gaa tgg      96
Asn Leu Gly Cys Glu Cys His Lys Val Ile Asn Ser Gly Ala Glu Trp
            20                  25                  30 ttg cac att gac att atg gac ggc cat ttc gtt cca aat atg tct ttg     144
Leu His Ile Asp Ile Met Asp Gly His Phe Val Pro Asn Met Ser Leu
        35                  40                  45 ggg cag cca gtt gtc gag tcg ttg cgt aag gtg att ggg aag tac aac     192
Gly Gln Pro Val Val Glu Ser Leu Arg Lys Val Ile Gly Lys Tyr Asn
50                  55                  60 gat cca gat acc aag ttg ccc aag gcg ttt ttc gac tgc cac atg atg     240
Asp Pro Asp Thr Lys Leu Pro Lys Ala Phe Phe Asp Cys His Met Met
65                  70                  75                  80 gtg agc gag cct gag aaa tgg gta gag gac ttt gcg agg att ggg tgc     288
Val Ser Glu Pro Glu Lys Trp Val Glu Asp Phe Ala Arg Ile Gly Cys
                85                  90                  95 gac caa ttc acg ttc cat tac gag gcc acg aag gat cca aag ggg ttg     336
Asp Gln Phe Thr Phe His Tyr Glu Ala Thr Lys Asp Pro Lys Gly Leu
            100                 105                 110 gtg gag ttg atc aag aag aac ggg atg aag gcc gcg tgt gct gtg aaa     384
Val Glu Leu Ile Lys Lys Asn Gly Met Lys Ala Ala Cys Ala Val Lys
        115                 120                 125 ccg ggc acc ccg gtt gat gtg cta tac gag ttg gca cct gag ttg gat     432
Pro Gly Thr Pro Val Asp Val Leu Tyr Glu Leu Ala Pro Glu Leu Asp
130                 135                 140 atg gcg ctt gtg atg acg gtg gag ccc ggt ttt ggt ggc cag aag ttc     480
Met Ala Leu Val Met Thr Val Glu Pro Gly Phe Gly Gly Gln Lys Phe
145                 150                 155                 160 atg agc gat atg atg agc aag gtg aag gat ttg aga gag agg ttc cca     528
Met Ser Asp Met Met Ser Lys Val Lys Asp Leu Arg Glu Arg Phe Pro
                165                 170                 175 acg ttg aac atc cag gtc gac ggt ggg ttg ggt aag caa aac gtc gaa     576
Thr Leu Asn Ile Gln Val Asp Gly Gly Leu Gly Lys Gln Asn Val Glu
            180                 185                 190 cag gcc tcg gaa gcg ggt gcg aat gtg att gtc gcg ggt acg tcc gtg     624
Gln Ala Ser Glu Ala Gly Ala Asn Val Ile Val Ala Gly Thr Ser Val
        195                 200                 205 ttc cga tcg gac gac ccg gcg gac gtt atc ggc ttc atg aaa agt aag     672
Phe Arg Ser Asp Asp Pro Ala Asp Val Ile Gly Phe Met Lys Ser Lys
    210                 215                 220 gtc aag gat gcg ttg gtg gcc aaa gac ctc ttg aca tag                 711
Val Lys Asp Ala Leu Val Ala Lys Asp Leu Leu Thr
225                 230                 235
```

<210> SEQ ID NO 38
<211> LENGTH: 236
<212> TYPE: PRT
<213> ORGANISM: Kluyveromyces marxianus

<400> SEQUENCE: 38

| | | | | | | | | | | | | | | | |
|---|---|---|---|---|---|---|---|---|---|---|---|---|---|---|---|
| Met | Val | Gln | Pro | Ile | Ile | Ala | Pro | Ser | Ile | Leu | Ala | Ser | Asp | Phe | Cys |
| 1 | | | | 5 | | | | | 10 | | | | | 15 | |
| Asn | Leu | Gly | Cys | Glu | Cys | His | Lys | Val | Ile | Asn | Ser | Gly | Ala | Glu | Trp |
| | | | 20 | | | | | 25 | | | | | 30 | | |
| Leu | His | Ile | Asp | Ile | Met | Asp | Gly | His | Phe | Val | Pro | Asn | Met | Ser | Leu |
| | | 35 | | | | | 40 | | | | | 45 | | | |
| Gly | Gln | Pro | Val | Val | Glu | Ser | Leu | Arg | Lys | Val | Ile | Gly | Lys | Tyr | Asn |
| | 50 | | | | | 55 | | | | | 60 | | | | |
| Asp | Pro | Asp | Thr | Lys | Leu | Pro | Lys | Ala | Phe | Phe | Asp | Cys | His | Met | Met |
| 65 | | | | | 70 | | | | | 75 | | | | | 80 |
| Val | Ser | Glu | Pro | Glu | Lys | Trp | Val | Glu | Asp | Phe | Ala | Arg | Ile | Gly | Cys |
| | | | | 85 | | | | | 90 | | | | | 95 | |
| Asp | Gln | Phe | Thr | Phe | His | Tyr | Glu | Ala | Thr | Lys | Asp | Pro | Lys | Gly | Leu |
| | | | 100 | | | | | 105 | | | | | 110 | | |
| Val | Glu | Leu | Ile | Lys | Lys | Asn | Gly | Met | Lys | Ala | Ala | Cys | Ala | Val | Lys |
| | | | 115 | | | | | 120 | | | | | 125 | | |
| Pro | Gly | Thr | Pro | Val | Asp | Val | Leu | Tyr | Glu | Leu | Ala | Pro | Glu | Leu | Asp |
| | 130 | | | | | 135 | | | | | 140 | | | | |
| Met | Ala | Leu | Val | Met | Thr | Val | Glu | Pro | Gly | Phe | Gly | Gly | Gln | Lys | Phe |
| 145 | | | | | 150 | | | | | 155 | | | | | 160 |
| Met | Ser | Asp | Met | Met | Ser | Lys | Val | Lys | Asp | Leu | Arg | Glu | Arg | Phe | Pro |
| | | | | 165 | | | | | 170 | | | | | 175 | |
| Thr | Leu | Asn | Ile | Gln | Val | Asp | Gly | Gly | Leu | Gly | Lys | Gln | Asn | Val | Glu |
| | | | 180 | | | | | 185 | | | | | 190 | | |
| Gln | Ala | Ser | Glu | Ala | Gly | Ala | Asn | Val | Ile | Val | Ala | Gly | Thr | Ser | Val |
| | | 195 | | | | | 200 | | | | | 205 | | | |
| Phe | Arg | Ser | Asp | Asp | Pro | Ala | Ser | Val | Ile | Gly | Phe | Met | Lys | Ser | Lys |
| | 210 | | | | | 215 | | | | | 220 | | | | |
| Val | Lys | Asp | Ala | Leu | Val | Ala | Lys | Asp | Leu | Leu | Thr | | | | |
| 225 | | | | 230 | | | | | 235 | | | | | | |

<210> SEQ ID NO 39
<211> LENGTH: 780
<212> TYPE: DNA
<213> ORGANISM: Issatchenkia orientalis
<220> FEATURE:
<221> NAME/KEY: CDS
<222> LOCATION: (1)..(780)

<400> SEQUENCE: 39

| atg | ttt | gga | cga | tat | tcc | cgt | cat | att | tct | cgt | cta | aaa | cca | acc | ttc | 48 |
|---|---|---|---|---|---|---|---|---|---|---|---|---|---|---|---|---|
| Met | Phe | Gly | Arg | Tyr | Ser | Arg | His | Ile | Ser | Arg | Leu | Lys | Pro | Thr | Phe | |
| 1 | | | | 5 | | | | | 10 | | | | | 15 | | |

| tct | cac | cta | cta | tcg | aaa | ggg | atg | tct | gac | ttg | gtc | gaa | aaa | tct | aag | 96 |
|---|---|---|---|---|---|---|---|---|---|---|---|---|---|---|---|---|
| Ser | His | Leu | Leu | Ser | Lys | Gly | Met | Ser | Asp | Leu | Val | Glu | Lys | Ser | Lys | |
| | | | 20 | | | | | 25 | | | | | 30 | | | |

| aaa | ctt | tgc | gct | tat | act | gcg | gtt | gac | aag | aat | tta | aag | cca | agc | cat | 144 |
|---|---|---|---|---|---|---|---|---|---|---|---|---|---|---|---|---|
| Lys | Leu | Cys | Ala | Tyr | Thr | Ala | Val | Asp | Lys | Asn | Leu | Lys | Pro | Ser | His | |
| | | 35 | | | | | 40 | | | | | 45 | | | | |

| aaa | gtt | att | ggt | atc | ggt | tct | ggc | tct | aca | gta | gtt | tat | gtt | gct | gag | 192 |
|---|---|---|---|---|---|---|---|---|---|---|---|---|---|---|---|---|
| Lys | Val | Ile | Gly | Ile | Gly | Ser | Gly | Ser | Thr | Val | Val | Tyr | Val | Ala | Glu | |
| | 50 | | | | | 55 | | | | | 60 | | | | | |

| cgt | atc | ggt | cag | cta | gaa | aac | aaa | aac | cac | tat | gtt | tgc | att | ccc | act | 240 |
|---|---|---|---|---|---|---|---|---|---|---|---|---|---|---|---|---|
| Arg | Ile | Gly | Gln | Leu | Glu | Asn | Lys | Asn | His | Tyr | Val | Cys | Ile | Pro | Thr | |
| 65 | | | | | 70 | | | | | 75 | | | | | 80 | |

| ggt | ttc | caa | tct | aaa | cag | cta | atc | att | gaa | aat | ggt | ttg | agg | ttg | ggt | 288 |
|---|---|---|---|---|---|---|---|---|---|---|---|---|---|---|---|---|

```
                Gly Phe Gln Ser Lys Gln Leu Ile Ile Glu Asn Gly Leu Arg Leu Gly
                                85                  90                  95 ggt ttg gaa gaa tat cca act atc gat att gca ttt gat ggt gct gat      336
Gly Leu Glu Glu Tyr Pro Thr Ile Asp Ile Ala Phe Asp Gly Ala Asp
            100                 105                 110 gag atc gat acc ggc ttg aac tgt atc aaa ggt ggt ggt gct tgt caa      384
Glu Ile Asp Thr Gly Leu Asn Cys Ile Lys Gly Gly Gly Ala Cys Gln
        115                 120                 125 tta cag gaa aag ttg gtt gct gac tca gca act gag ttt att att gtt      432
Leu Gln Glu Lys Leu Val Ala Asp Ser Ala Thr Glu Phe Ile Ile Val
    130                 135                 140 gca gat gat cgt aaa aat acc ggt gtg ttg ggt aaa ggt tgg aag aaa      480
Ala Asp Asp Arg Lys Asn Thr Gly Val Leu Gly Lys Gly Trp Lys Lys
145                 150                 155                 160 ggg att cca att gaa gtc atc cca aat gca tat gct aag atc agt aaa      528
Gly Ile Pro Ile Glu Val Ile Pro Asn Ala Tyr Ala Lys Ile Ser Lys
                165                 170                 175 gag cta aga gaa cta ggt ggc aat cca gta gta agg tct ggt gct ccg      576
Glu Leu Arg Glu Leu Gly Gly Asn Pro Val Val Arg Ser Gly Ala Pro
            180                 185                 190 tca aaa gca ggt cct gca atc act gat aat ggc aac ttt gtc atc gat      624
Ser Lys Ala Gly Pro Ala Ile Thr Asp Asn Gly Asn Phe Val Ile Asp
        195                 200                 205 tgt gat ttt gga gaa atc gaa gtc tct aaa gta gaa gcg ctc aac agt      672
Cys Asp Phe Gly Glu Ile Glu Val Ser Lys Val Glu Ala Leu Asn Ser
    210                 215                 220 aaa atc aaa gct atg att ggt gtt gtg gaa aca ggt tta ttt gtt aat      720
Lys Ile Lys Ala Met Ile Gly Val Val Glu Thr Gly Leu Phe Val Asn
225                 230                 235                 240 atg gcc aag aag gct tat att ggt aat gca gac ggt agt gtt act aca      768
Met Ala Lys Lys Ala Tyr Ile Gly Asn Ala Asp Gly Ser Val Thr Thr
                245                 250                 255 tta tct gtt taa                                                      780
Leu Ser Val <210> SEQ ID NO 40
<211> LENGTH: 259
<212> TYPE: PRT
<213> ORGANISM: Issatchenkia orientalis

<400> SEQUENCE: 40

Met Phe Gly Arg Tyr Ser Arg His Ile Ser Arg Leu Lys Pro Thr Phe
1               5                   10                  15

Ser His Leu Leu Ser Lys Gly Met Ser Asp Leu Val Glu Lys Ser Lys
                20                  25                  30

Lys Leu Cys Ala Tyr Thr Ala Val Asp Lys Asn Leu Lys Pro Ser His
            35                  40                  45

Lys Val Ile Gly Ile Gly Ser Gly Ser Thr Val Val Tyr Val Ala Glu
        50                  55                  60

Arg Ile Gly Gln Leu Glu Asn Lys Asn His Tyr Val Cys Ile Pro Thr
65                  70                  75                  80

Gly Phe Gln Ser Lys Gln Leu Ile Ile Glu Asn Gly Leu Arg Leu Gly
                85                  90                  95

Gly Leu Glu Glu Tyr Pro Thr Ile Asp Ile Ala Phe Asp Gly Ala Asp
            100                 105                 110

Glu Ile Asp Thr Gly Leu Asn Cys Ile Lys Gly Gly Gly Ala Cys Gln
        115                 120                 125

Leu Gln Glu Lys Leu Val Ala Asp Ser Ala Thr Glu Phe Ile Ile Val
```

```
                130                 135                 140
Ala Asp Asp Arg Lys Asn Thr Gly Val Leu Gly Lys Gly Trp Lys Lys
145                 150                 155                 160

Gly Ile Pro Ile Glu Val Ile Pro Asn Ala Tyr Ala Lys Ile Ser Lys
                165                 170                 175

Glu Leu Arg Glu Leu Gly Gly Asn Pro Val Val Arg Ser Gly Ala Pro
            180                 185                 190

Ser Lys Ala Gly Pro Ala Ile Thr Asp Asn Gly Asn Phe Val Ile Asp
            195                 200                 205

Cys Asp Phe Gly Glu Ile Glu Val Ser Lys Val Glu Ala Leu Asn Ser
            210                 215                 220

Lys Ile Lys Ala Met Ile Gly Val Val Glu Thr Gly Leu Phe Val Asn
225                 230                 235                 240

Met Ala Lys Lys Ala Tyr Ile Gly Asn Ala Asp Gly Ser Val Thr Thr
                245                 250                 255

Leu Ser Val

<210> SEQ ID NO 41
<211> LENGTH: 777
<212> TYPE: DNA
<213> ORGANISM: Saccharomyces cerevisiae
<220> FEATURE:
<221> NAME/KEY: CDS
<222> LOCATION: (1)..(777)

<400> SEQUENCE: 41 atg gct gcc ggt gtc cca aaa att gat gcg tta gaa tct ttg ggc aat    48
Met Ala Ala Gly Val Pro Lys Ile Asp Ala Leu Glu Ser Leu Gly Asn
1               5                  10                  15 cct ttg gag gat gcc aag aga gct gca gca tac aga gca gtt gat gaa    96
Pro Leu Glu Asp Ala Lys Arg Ala Ala Ala Tyr Arg Ala Val Asp Glu
                20                  25                  30 aat tta aaa ttt gat gat cac aaa att att gga att ggt agt ggt agc   144
Asn Leu Lys Phe Asp Asp His Lys Ile Ile Gly Ile Gly Ser Gly Ser
            35                  40                  45 aca gtg gtt tat gtt gcc gaa aga att gga caa tat ttg cat gac cct   192
Thr Val Val Tyr Val Ala Glu Arg Ile Gly Gln Tyr Leu His Asp Pro
        50                  55                  60 aaa ttt tat gaa gta gcg tct aaa ttc att tgc att cca aca gga ttc   240
Lys Phe Tyr Glu Val Ala Ser Lys Phe Ile Cys Ile Pro Thr Gly Phe
65                  70                  75                  80 caa tca aga aac ttg att ttg gat aac aag ttg caa tta ggc tcc att   288
Gln Ser Arg Asn Leu Ile Leu Asp Asn Lys Leu Gln Leu Gly Ser Ile
                85                  90                  95 gaa cag tat cct cgc att gat ata gcg ttt gac ggt gct gat gaa gtg   336
Glu Gln Tyr Pro Arg Ile Asp Ile Ala Phe Asp Gly Ala Asp Glu Val
            100                 105                 110 gat gag aat tta caa tta att aaa ggt ggt ggt gct tgt cta ttt caa   384
Asp Glu Asn Leu Gln Leu Ile Lys Gly Gly Gly Ala Cys Leu Phe Gln
        115                 120                 125 gaa aaa ttg gtt agt act agt gct aaa acc ttc att gtc gtt gct gat   432
Glu Lys Leu Val Ser Thr Ser Ala Lys Thr Phe Ile Val Val Ala Asp
130                 135                 140 tca aga aaa aag tca cca aaa cat tta ggt aag aac tgg agg caa ggt   480
Ser Arg Lys Lys Ser Pro Lys His Leu Gly Lys Asn Trp Arg Gln Gly
145                 150                 155                 160 gtt ccc att gaa att gta cct tcc tca tac gtg agg gtc aag aat gat   528
Val Pro Ile Glu Ile Val Pro Ser Ser Tyr Val Arg Val Lys Asn Asp
                165                 170                 175
```

```
cta tta gaa caa ttg cat gct gaa aaa gtt gac atc aga caa gga ggt    576
Leu Leu Glu Gln Leu His Ala Glu Lys Val Asp Ile Arg Gln Gly Gly
            180                 185                 190 tct gct aaa gca ggt cct gtt gta act gac aat aat aac ttc att atc    624
Ser Ala Lys Ala Gly Pro Val Val Thr Asp Asn Asn Asn Phe Ile Ile
        195                 200                 205 gat gcg gat ttc ggt gaa att tcc gat cca aga aaa ttg cat aga gaa    672
Asp Ala Asp Phe Gly Glu Ile Ser Asp Pro Arg Lys Leu His Arg Glu
    210                 215                 220 atc aaa ctg tta gtg ggc gtg gtg gaa aca ggt tta ttc atc gac aac    720
Ile Lys Leu Leu Val Gly Val Val Glu Thr Gly Leu Phe Ile Asp Asn
225                 230                 235                 240 gct tca aaa gcc tac ttc ggt aat tct gac ggt agt gtt gaa gtt acc    768
Ala Ser Lys Ala Tyr Phe Gly Asn Ser Asp Gly Ser Val Glu Val Thr
                245                 250                 255 gaa aag tga                                                        777
Glu Lys

<210> SEQ ID NO 42
<211> LENGTH: 258
<212> TYPE: PRT
<213> ORGANISM: Saccharomyces cerevisiae

<400> SEQUENCE: 42

Met Ala Ala Gly Val Pro Lys Ile Asp Ala Leu Glu Ser Leu Gly Asn
1               5                   10                  15

Pro Leu Glu Asp Ala Lys Arg Ala Ala Ala Tyr Arg Ala Val Asp Glu
            20                  25                  30

Asn Leu Lys Phe Asp Asp His Lys Ile Ile Gly Ile Gly Ser Gly Ser
        35                  40                  45

Thr Val Val Tyr Val Ala Glu Arg Ile Gly Gln Tyr Leu His Asp Pro
    50                  55                  60

Lys Phe Tyr Glu Val Ala Ser Lys Phe Ile Cys Ile Pro Thr Gly Phe
65                  70                  75                  80

Gln Ser Arg Asn Leu Ile Leu Asp Asn Lys Leu Gln Leu Gly Ser Ile
                85                  90                  95

Glu Gln Tyr Pro Arg Ile Asp Ile Ala Phe Asp Gly Ala Asp Glu Val
            100                 105                 110

Asp Glu Asn Leu Gln Leu Ile Lys Gly Gly Gly Ala Cys Leu Phe Gln
        115                 120                 125

Glu Lys Leu Val Ser Thr Ser Ala Lys Thr Phe Ile Val Val Ala Asp
    130                 135                 140

Ser Arg Lys Lys Ser Pro Lys His Leu Gly Lys Asn Trp Arg Gln Gly
145                 150                 155                 160

Val Pro Ile Glu Ile Val Pro Ser Ser Tyr Val Arg Val Lys Asn Asp
                165                 170                 175

Leu Leu Glu Gln Leu His Ala Glu Lys Val Asp Ile Arg Gln Gly Gly
            180                 185                 190

Ser Ala Lys Ala Gly Pro Val Val Thr Asp Asn Asn Asn Phe Ile Ile
        195                 200                 205

Asp Ala Asp Phe Gly Glu Ile Ser Asp Pro Arg Lys Leu His Arg Glu
    210                 215                 220

Ile Lys Leu Leu Val Gly Val Val Glu Thr Gly Leu Phe Ile Asp Asn
225                 230                 235                 240

Ala Ser Lys Ala Tyr Phe Gly Asn Ser Asp Gly Ser Val Glu Val Thr
                245                 250                 255
```

Glu Lys

<210> SEQ ID NO 43
<211> LENGTH: 819
<212> TYPE: DNA
<213> ORGANISM: Kluyveromyces marxianus
<220> FEATURE:
<221> NAME/KEY: CDS
<222> LOCATION: (1)..(819)

<400> SEQUENCE: 43

| | | | | | | | | | | | | | | | | |
|---|---|---|---|---|---|---|---|---|---|---|---|---|---|---|---|---|
| atg | tac | tgt | gct | gta | agc | agg | cgt | gtt | cat | aga | ctc | ata | tta | cca | agc | 48 |
| Met | Tyr | Cys | Ala | Val | Ser | Arg | Arg | Val | His | Arg | Leu | Ile | Leu | Pro | Ser | |
| 1 | | | | 5 | | | | | 10 | | | | | 15 | | |

| ttt | cca | cac | gtt | ttc | aag | atg | cca | tta | agc | gat | ctc | tcg | aaa | ctg | cca | 96 |
| Phe | Pro | His | Val | Phe | Lys | Met | Pro | Leu | Ser | Asp | Leu | Ser | Lys | Leu | Pro | |
| | | | 20 | | | | | 25 | | | | | 30 | | | |

| cct | ctt | tcg | gac | caa | ttg | gag | cag | gct | aaa | cgt | act | gct | gca | tac | cgt | 144 |
| Pro | Leu | Ser | Asp | Gln | Leu | Glu | Gln | Ala | Lys | Arg | Thr | Ala | Ala | Tyr | Arg | |
| | | | | 35 | | | | | 40 | | | | | 45 | | |

| gcg | gtt | gat | gag | aat | ttt | gat | gcc | aag | att | cat | aaa | gta | gtg | ggt | gtt | 192 |
| Ala | Val | Asp | Glu | Asn | Phe | Asp | Ala | Lys | Ile | His | Lys | Val | Val | Gly | Val | |
| | 50 | | | | | 55 | | | | | 60 | | | | | |

| ggt | agt | ggt | act | act | gta | gtt | tat | gtt | gcc | gaa | agg | ctt | gga | gag | tat | 240 |
| Gly | Ser | Gly | Thr | Thr | Val | Val | Tyr | Val | Ala | Glu | Arg | Leu | Gly | Glu | Tyr | |
| 65 | | | | | 70 | | | | | 75 | | | | | 80 | |

| gtg | aac | gat | agc | agc | aac | ttt | gtg | tgt | ata | cct | act | gga | ttc | cag | tcc | 288 |
| Val | Asn | Asp | Ser | Ser | Asn | Phe | Val | Cys | Ile | Pro | Thr | Gly | Phe | Gln | Ser | |
| | | | | 85 | | | | | 90 | | | | | 95 | | |

| aaa | cag | ttg | att | cta | tcg | aac | agg | ttg | cag | tta | ggg | agc | att | gag | cag | 336 |
| Lys | Gln | Leu | Ile | Leu | Ser | Asn | Arg | Leu | Gln | Leu | Gly | Ser | Ile | Glu | Gln | |
| | | | | 100 | | | | | 105 | | | | | 110 | | |

| tat | cct | gag | atc | gat | att | gcg | ttc | gat | ggt | gca | gat | gag | gtc | gat | gag | 384 |
| Tyr | Pro | Glu | Ile | Asp | Ile | Ala | Phe | Asp | Gly | Ala | Asp | Glu | Val | Asp | Glu | |
| | | | 115 | | | | | 120 | | | | | 125 | | | |

| aat | tta | cag | ttg | att | aaa | ggt | ggt | gga | gcg | tgc | ttg | ttt | cag | gaa | aag | 432 |
| Asn | Leu | Gln | Leu | Ile | Lys | Gly | Gly | Gly | Ala | Cys | Leu | Phe | Gln | Glu | Lys | |
| | 130 | | | | | 135 | | | | | 140 | | | | | |

| ttg | gtg | agc | act | agt | gcg | aag | aag | ttt | att | gtt | gtt | gca | gac | tcg | aga | 480 |
| Leu | Val | Ser | Thr | Ser | Ala | Lys | Lys | Phe | Ile | Val | Val | Ala | Asp | Ser | Arg | |
| 145 | | | | | 150 | | | | | 155 | | | | | 160 | |

| aaa | cgg | tcg | cca | aag | cac | ttg | ggg | acc | aac | tgg | aaa | cgc | ggt | gtg | ccg | 528 |
| Lys | Arg | Ser | Pro | Lys | His | Leu | Gly | Thr | Asn | Trp | Lys | Arg | Gly | Val | Pro | |
| | | | | 165 | | | | | 170 | | | | | 175 | | |

| att | gaa | gtg | gtg | ccc | agt | tcc | tat | gtg | cat | gtg | ctt | act | gcg | ttg | aaa | 576 |
| Ile | Glu | Val | Val | Pro | Ser | Ser | Tyr | Val | His | Val | Leu | Thr | Ala | Leu | Lys | |
| | | | 180 | | | | | 185 | | | | | 190 | | | |

| gat | aga | cta | cat | tgc | aag | agc | gct | att | gtg | aga | cag | ggc | ggt | agc | gcg | 624 |
| Asp | Arg | Leu | His | Cys | Lys | Ser | Ala | Ile | Val | Arg | Gln | Gly | Gly | Ser | Ala | |
| | 195 | | | | | 200 | | | | | 205 | | | | | |

| aaa | gcg | ggg | ccc | gtg | gtt | acg | gat | aac | tgc | aac | ttc | atc | att | gac | gct | 672 |
| Lys | Ala | Gly | Pro | Val | Val | Thr | Asp | Asn | Cys | Asn | Phe | Ile | Ile | Asp | Ala | |
| | 210 | | | | | 215 | | | | | 220 | | | | | |

| gac | ttt | ggc | gag | atc | gcg | gac | cct | aga | aag | cta | cat | caa | gac | atc | aag | 720 |
| Asp | Phe | Gly | Glu | Ile | Ala | Asp | Pro | Arg | Lys | Leu | His | Gln | Asp | Ile | Lys | |
| 225 | | | | | 230 | | | | | 235 | | | | | 240 | |

| atg | ttg | gtt | ggg | gtt | gtt | gag | acc | gga | tta | ttc | att | gac | aat | gcg | gaa | 768 |
| Met | Leu | Val | Gly | Val | Val | Glu | Thr | Gly | Leu | Phe | Ile | Asp | Asn | Ala | Glu | |
| | | | | 245 | | | | | 250 | | | | | 255 | | |

| aag | gcg | tac | ttc | ggt | tcg | cca | gat | ggg | tcc | gtc | gag | ctg | cag | gtg | ttg | 816 |

-continued

```
Lys Ala Tyr Phe Gly Ser Pro Asp Gly Ser Val Glu Leu Gln Val Leu
            260                 265                 270
tag                                                                 819

<210> SEQ ID NO 44
<211> LENGTH: 272
<212> TYPE: PRT
<213> ORGANISM: Kluyveromyces marxianus

<400> SEQUENCE: 44

Met Tyr Cys Ala Val Ser Arg Arg Val His Arg Leu Ile Leu Pro Ser
1               5                   10                  15

Phe Pro His Val Phe Lys Met Pro Leu Ser Asp Leu Ser Lys Leu Pro
            20                  25                  30

Pro Leu Ser Asp Gln Leu Glu Gln Ala Lys Arg Thr Ala Ala Tyr Arg
        35                  40                  45

Ala Val Asp Glu Asn Phe Asp Ala Lys Ile His Lys Val Val Gly Val
    50                  55                  60

Gly Ser Gly Thr Thr Val Val Tyr Val Ala Glu Arg Leu Gly Glu Tyr
65                  70                  75                  80

Val Asn Asp Ser Ser Asn Phe Val Cys Ile Pro Thr Gly Phe Gln Ser
                85                  90                  95

Lys Gln Leu Ile Leu Ser Asn Arg Leu Gln Leu Gly Ser Ile Glu Gln
            100                 105                 110

Tyr Pro Glu Ile Asp Ile Ala Phe Asp Gly Ala Asp Glu Val Asp Glu
        115                 120                 125

Asn Leu Gln Leu Ile Lys Gly Gly Gly Ala Cys Leu Phe Gln Glu Lys
    130                 135                 140

Leu Val Ser Thr Ser Ala Lys Lys Phe Ile Val Val Ala Asp Ser Arg
145                 150                 155                 160

Lys Arg Ser Pro Lys His Leu Gly Thr Asn Trp Lys Arg Gly Val Pro
                165                 170                 175

Ile Glu Val Val Pro Ser Ser Tyr Val His Val Leu Thr Ala Leu Lys
            180                 185                 190

Asp Arg Leu His Cys Lys Ser Ala Ile Val Arg Gln Gly Gly Ser Ala
        195                 200                 205

Lys Ala Gly Pro Val Val Thr Asp Asn Cys Asn Phe Ile Ile Asp Ala
    210                 215                 220

Asp Phe Gly Glu Ile Ala Asp Pro Arg Lys Leu His Gln Asp Ile Lys
225                 230                 235                 240

Met Leu Val Gly Val Val Glu Thr Gly Leu Phe Ile Asp Asn Ala Glu
                245                 250                 255

Lys Ala Tyr Phe Gly Ser Pro Asp Gly Ser Val Glu Leu Gln Val Leu
            260                 265                 270

<210> SEQ ID NO 45
<211> LENGTH: 2031
<212> TYPE: DNA
<213> ORGANISM: Issatchenkia orientalis
<220> FEATURE:
<221> NAME/KEY: CDS
<222> LOCATION: (1)..(2031)

<400> SEQUENCE: 45 atg tcg gac atc acc acc aag gca gtc aac acg atc cgt gtg tta gcg    48
Met Ser Asp Ile Thr Thr Lys Ala Val Asn Thr Ile Arg Val Leu Ala
1               5                   10                  15
```

-continued

| | | |
|---|---|---|
| gca gac gtt gtt gca aag gcg aat tcc ggg cat cca ggt gcc cca atg<br>Ala Asp Val Val Ala Lys Ala Asn Ser Gly His Pro Gly Ala Pro Met<br>20              25              30 | | 96 |
| gga atg gct cca gca gcc cat gtt tta ttt tcc cag tta aag act aat<br>Gly Met Ala Pro Ala Ala His Val Leu Phe Ser Gln Leu Lys Thr Asn<br>    35              40              45 | | 144 |
| cca aag aat cca gaa tgg atc aac aga gac cgg ttt gtg ctc tcc aat<br>Pro Lys Asn Pro Glu Trp Ile Asn Arg Asp Arg Phe Val Leu Ser Asn<br>50              55              60 | | 192 |
| ggc cat gcg gtt gca tta ttg tac gtc atg ctg cat ctc tcc ggg tac<br>Gly His Ala Val Ala Leu Leu Tyr Val Met Leu His Leu Ser Gly Tyr<br>65              70              75              80 | | 240 |
| cct att tct atg gag gat ttg aaa cag ttt aga cag ttg gat tca aag<br>Pro Ile Ser Met Glu Asp Leu Lys Gln Phe Arg Gln Leu Asp Ser Lys<br>            85              90              95 | | 288 |
| act cct ggc cat cca gag agt gag act gtt ggt gtt gac gtc act aca<br>Thr Pro Gly His Pro Glu Ser Glu Thr Val Gly Val Asp Val Thr Thr<br>       100             105             110 | | 336 |
| ggt cca tta ggt caa ggt atc tcc aat gcc gtt ggt ctg gcc att gcg<br>Gly Pro Leu Gly Gln Gly Ile Ser Asn Ala Val Gly Leu Ala Ile Ala<br>    115             120             125 | | 384 |
| cag gcg aat ttc ggc gca acc tac aac aaa ccg ggc tac acc atc tca<br>Gln Ala Asn Phe Gly Ala Thr Tyr Asn Lys Pro Gly Tyr Thr Ile Ser<br>130             135             140 | | 432 |
| aat aac tac aca tac acg ttt ttc ggt gac ggt tgt atg atg gaa ggt<br>Asn Asn Tyr Thr Tyr Thr Phe Phe Gly Asp Gly Cys Met Met Glu Gly<br>145             150             155             160 | | 480 |
| gtt gcc tct gag gca gca tct ctt gct ggc cat tta cag ttg ggc aac<br>Val Ala Ser Glu Ala Ala Ser Leu Ala Gly His Leu Gln Leu Gly Asn<br>            165             170             175 | | 528 |
| ttg att gcc ttt tat gat gat aac aag atc tca att gat ggt tcc acc<br>Leu Ile Ala Phe Tyr Asp Asp Asn Lys Ile Ser Ile Asp Gly Ser Thr<br>       180             185             190 | | 576 |
| aat atg gcc ttc acc gag gat gtt tcc aag agg tta gaa tct tac ggt<br>Asn Met Ala Phe Thr Glu Asp Val Ser Lys Arg Leu Glu Ser Tyr Gly<br>    195             200             205 | | 624 |
| tgg gaa gtt att gaa gtt aag gat gca gac act gat ttt gat gcc ctg<br>Trp Glu Val Ile Glu Val Lys Asp Ala Asp Thr Asp Phe Asp Ala Leu<br>210             215             220 | | 672 |
| gct ctt gcc att gaa aag gca aag tcc aac aag aac caa cca tct tgt<br>Ala Leu Ala Ile Glu Lys Ala Lys Ser Asn Lys Asn Gln Pro Ser Cys<br>225             230             235             240 | | 720 |
| att aga atg tcc act acc att ggt tat ggt tcc ttg aaa cag gga act<br>Ile Arg Met Ser Thr Thr Ile Gly Tyr Gly Ser Leu Lys Gln Gly Thr<br>            245             250             255 | | 768 |
| gcc ggt gtc cat ggt tct cca tta aag gca gac gac att gcc caa ttg<br>Ala Gly Val His Gly Ser Pro Leu Lys Ala Asp Asp Ile Ala Gln Leu<br>       260             265             270 | | 816 |
| aag gag aaa tgg ggg ttt gat cct gca aag tca ttt aat gtc gaa gat<br>Lys Glu Lys Trp Gly Phe Asp Pro Ala Lys Ser Phe Asn Val Glu Asp<br>    275             280             285 | | 864 |
| gat gtc tat gat tat tgg aag tct gtt gct gct agg ggg gaa gag gaa<br>Asp Val Tyr Asp Tyr Trp Lys Ser Val Ala Ala Arg Gly Glu Glu Glu<br>290             295             300 | | 912 |
| aat aga aaa tgg gat tct ctc ttt gaa gct tat tca aag gag tac cct<br>Asn Arg Lys Trp Asp Ser Leu Phe Glu Ala Tyr Ser Lys Glu Tyr Pro<br>305             310             315             320 | | 960 |
| aag gaa gcc gaa gaa atc aag agg aga gtc tct tat aag tta cca caa<br>Lys Glu Ala Glu Glu Ile Lys Arg Arg Val Ser Tyr Lys Leu Pro Gln<br>            325             330             335 | | 1008 |

```
ggt tgg gag aag gtc tta cca act tac acc aag gat gat aaa cct ctt    1056
Gly Trp Glu Lys Val Leu Pro Thr Tyr Thr Lys Asp Asp Lys Pro Leu
        340                 345                 350 gca tca aga aaa tta tca gaa att gtc ctg ggt aaa atc gaa gaa tct    1104
Ala Ser Arg Lys Leu Ser Glu Ile Val Leu Gly Lys Ile Glu Glu Ser
    355                 360                 365 tta cct gaa cta att ggt ggt tca gcg gat ttg act cct tcc aac ttg    1152
Leu Pro Glu Leu Ile Gly Gly Ser Ala Asp Leu Thr Pro Ser Asn Leu
370                 375                 380 acc aga tgg ggt ggt gca gtt gat ttc caa cct cct caa acc gga ttg    1200
Thr Arg Trp Gly Gly Ala Val Asp Phe Gln Pro Pro Gln Thr Gly Leu
385                 390                 395                 400 gga gat tat gcc ggc aga tac atc aga ttt ggt gtt aga gaa cac ggt    1248
Gly Asp Tyr Ala Gly Arg Tyr Ile Arg Phe Gly Val Arg Glu His Gly
                405                 410                 415 atg ggt gca atc atg aat ggt att gca gca tac ggt gct aac tac aag    1296
Met Gly Ala Ile Met Asn Gly Ile Ala Ala Tyr Gly Ala Asn Tyr Lys
            420                 425                 430 cct tat ggt ggt acc ttt ttg aac ttt gtc tct tat gct gcc ggt gca    1344
Pro Tyr Gly Gly Thr Phe Leu Asn Phe Val Ser Tyr Ala Ala Gly Ala
        435                 440                 445 gtt aga tta tct gca ttg tcg ggc cac cct gtc att tgg gtt gct act    1392
Val Arg Leu Ser Ala Leu Ser Gly His Pro Val Ile Trp Val Ala Thr
    450                 455                 460 cat gac tct att ggt ttg ggt gaa gac ggt cca acc cat caa cca att    1440
His Asp Ser Ile Gly Leu Gly Glu Asp Gly Pro Thr His Gln Pro Ile
465                 470                 475                 480 gaa acc ttg gct cac ttt aga gct act cca aac ttg atg gtc tgg aga    1488
Glu Thr Leu Ala His Phe Arg Ala Thr Pro Asn Leu Met Val Trp Arg
                485                 490                 495 cca gca gat ggt aat gaa gtt tct gca gct tat aag gtt gcc ctg gaa    1536
Pro Ala Asp Gly Asn Glu Val Ser Ala Ala Tyr Lys Val Ala Leu Glu
            500                 505                 510 tct ctt gca act cct tcc atc att gca ttg acc aga caa aac ttg cca    1584
Ser Leu Ala Thr Pro Ser Ile Ile Ala Leu Thr Arg Gln Asn Leu Pro
        515                 520                 525 caa ttg gaa aac tcc tct att gaa aag gca act aaa ggt ggt tac atc    1632
Gln Leu Glu Asn Ser Ser Ile Glu Lys Ala Thr Lys Gly Gly Tyr Ile
    530                 535                 540 tta aac gac att gat aat gcc aag ttg att att gcc gca aca ggt tcc    1680
Leu Asn Asp Ile Asp Asn Ala Lys Leu Ile Ile Ala Ala Thr Gly Ser
545                 550                 555                 560 gaa gtt tcc ctt gca gtt gaa gct gct gac aaa tta acc agt gag ggc    1728
Glu Val Ser Leu Ala Val Glu Ala Ala Asp Lys Leu Thr Ser Glu Gly
                565                 570                 575 att cca acc aag gtt gtc tct gtt cca gac ttc tac acc ttt gac aag    1776
Ile Pro Thr Lys Val Val Ser Val Pro Asp Phe Tyr Thr Phe Asp Lys
            580                 585                 590 caa tcc cac gag tac aag atg tct gtc ttc ccg cac ggc att cca gtt    1824
Gln Ser His Glu Tyr Lys Met Ser Val Phe Pro His Gly Ile Pro Val
        595                 600                 605 gtt tct ctc gaa gtt atg tca tcc ttt ggt tgg tcc aaa tat gct cat    1872
Val Ser Leu Glu Val Met Ser Ser Phe Gly Trp Ser Lys Tyr Ala His
    610                 615                 620 gca cat att tca tta gac aga ttt ggt gca tct gct cca gct gat aaa    1920
Ala His Ile Ser Leu Asp Arg Phe Gly Ala Ser Ala Pro Ala Asp Lys
625                 630                 635                 640 ttg ttt gaa aag ttt ggt ttc acc aag gac gtt gtt gct gac aag gca    1968
Leu Phe Glu Lys Phe Gly Phe Thr Lys Asp Val Val Ala Asp Lys Ala
```

-continued

```
                        645                 650                 655
aag aag gtg gtc tcg tat tac gcg ggc aag gag gtc ttg tcc caa ttg    2016
Lys Lys Val Val Ser Tyr Tyr Ala Gly Lys Glu Val Leu Ser Gln Leu
        660                 665                 670 gaa act cct ttt taa                                                2031
Glu Thr Pro Phe
        675

<210> SEQ ID NO 46
<211> LENGTH: 676
<212> TYPE: PRT
<213> ORGANISM: Issatchenkia orientalis

<400> SEQUENCE: 46

Met Ser Asp Ile Thr Thr Lys Ala Val Asn Thr Ile Arg Val Leu Ala
1               5                   10                  15

Ala Asp Val Val Ala Lys Ala Asn Ser Gly His Pro Gly Ala Pro Met
            20                  25                  30

Gly Met Ala Pro Ala Ala His Val Leu Phe Ser Gln Leu Lys Thr Asn
        35                  40                  45

Pro Lys Asn Pro Glu Trp Ile Asn Arg Asp Arg Phe Val Leu Ser Asn
    50                  55                  60

Gly His Ala Val Ala Leu Leu Tyr Val Met Leu His Leu Ser Gly Tyr
65                  70                  75                  80

Pro Ile Ser Met Glu Asp Leu Lys Gln Phe Arg Gln Leu Asp Ser Lys
                85                  90                  95

Thr Pro Gly His Pro Glu Ser Glu Thr Val Gly Val Asp Val Thr Thr
            100                 105                 110

Gly Pro Leu Gly Gln Gly Ile Ser Asn Ala Val Gly Leu Ala Ile Ala
        115                 120                 125

Gln Ala Asn Phe Gly Ala Thr Tyr Asn Lys Pro Gly Tyr Thr Ile Ser
    130                 135                 140

Asn Asn Tyr Thr Tyr Thr Phe Phe Gly Asp Gly Cys Met Met Glu Gly
145                 150                 155                 160

Val Ala Ser Glu Ala Ala Ser Leu Ala Gly His Leu Gln Leu Gly Asn
                165                 170                 175

Leu Ile Ala Phe Tyr Asp Asp Asn Lys Ile Ser Ile Asp Gly Ser Thr
            180                 185                 190

Asn Met Ala Phe Thr Glu Asp Val Ser Lys Arg Leu Glu Ser Tyr Gly
        195                 200                 205

Trp Glu Val Ile Glu Val Lys Asp Ala Asp Thr Asp Phe Asp Ala Leu
    210                 215                 220

Ala Leu Ala Ile Glu Lys Ala Lys Ser Asn Lys Asn Gln Pro Ser Cys
225                 230                 235                 240

Ile Arg Met Ser Thr Thr Ile Gly Tyr Gly Ser Leu Lys Gln Gly Thr
                245                 250                 255

Ala Gly Val His Gly Ser Pro Leu Lys Ala Asp Asp Ile Ala Gln Leu
            260                 265                 270

Lys Glu Lys Trp Gly Phe Asp Pro Ala Lys Ser Phe Asn Val Glu Asp
        275                 280                 285

Asp Val Tyr Asp Tyr Trp Lys Ser Val Ala Ala Arg Gly Glu Glu Glu
    290                 295                 300

Asn Arg Lys Trp Asp Ser Leu Phe Glu Ala Tyr Ser Lys Glu Tyr Pro
305                 310                 315                 320

Lys Glu Ala Glu Glu Ile Lys Arg Arg Val Ser Tyr Lys Leu Pro Gln
```

|       |       |       | 325   |       |       |       | 330   |       |       |       | 335   |       |       |
|-------|-------|-------|-------|-------|-------|-------|-------|-------|-------|-------|-------|-------|-------|

Gly Trp Glu Lys Val Leu Pro Thr Tyr Thr Lys Asp Asp Lys Pro Leu
            340                 345                 350

Ala Ser Arg Lys Leu Ser Glu Ile Val Leu Gly Lys Ile Glu Glu Ser
        355                 360                 365

Leu Pro Glu Leu Ile Gly Gly Ser Ala Asp Leu Thr Pro Ser Asn Leu
    370                 375                 380

Thr Arg Trp Gly Gly Ala Val Asp Phe Gln Pro Gln Thr Gly Leu
385                 390                 395                 400

Gly Asp Tyr Ala Gly Arg Tyr Ile Arg Phe Gly Val Arg Glu His Gly
                405                 410                 415

Met Gly Ala Ile Met Asn Gly Ile Ala Ala Tyr Gly Ala Asn Tyr Lys
            420                 425                 430

Pro Tyr Gly Gly Thr Phe Leu Asn Phe Val Ser Tyr Ala Ala Gly Ala
        435                 440                 445

Val Arg Leu Ser Ala Leu Ser Gly His Pro Val Ile Trp Val Ala Thr
    450                 455                 460

His Asp Ser Ile Gly Leu Gly Glu Asp Gly Pro Thr His Gln Pro Ile
465                 470                 475                 480

Glu Thr Leu Ala His Phe Arg Ala Thr Pro Asn Leu Met Val Trp Arg
                485                 490                 495

Pro Ala Asp Gly Asn Glu Val Ser Ala Ala Tyr Lys Val Ala Leu Glu
            500                 505                 510

Ser Leu Ala Thr Pro Ser Ile Ile Ala Leu Thr Arg Gln Asn Leu Pro
        515                 520                 525

Gln Leu Glu Asn Ser Ser Ile Glu Lys Ala Thr Lys Gly Gly Tyr Ile
    530                 535                 540

Leu Asn Asp Ile Asp Asn Ala Lys Leu Ile Ile Ala Ala Thr Gly Ser
545                 550                 555                 560

Glu Val Ser Leu Ala Val Glu Ala Ala Asp Lys Leu Thr Ser Glu Gly
                565                 570                 575

Ile Pro Thr Lys Val Val Ser Val Pro Asp Phe Tyr Thr Phe Asp Lys
            580                 585                 590

Gln Ser His Glu Tyr Lys Met Ser Val Phe Pro His Gly Ile Pro Val
        595                 600                 605

Val Ser Leu Glu Val Met Ser Ser Phe Gly Trp Ser Lys Tyr Ala His
    610                 615                 620

Ala His Ile Ser Leu Asp Arg Phe Gly Ala Ser Ala Pro Ala Asp Lys
625                 630                 635                 640

Leu Phe Glu Lys Phe Gly Phe Thr Lys Asp Val Val Ala Asp Lys Ala
                645                 650                 655

Lys Lys Val Val Ser Tyr Tyr Ala Gly Lys Glu Val Leu Ser Gln Leu
            660                 665                 670

Glu Thr Pro Phe
        675

<210> SEQ ID NO 47
<211> LENGTH: 2043
<212> TYPE: DNA
<213> ORGANISM: Saccharomyces cerevisiae
<220> FEATURE:
<221> NAME/KEY: CDS
<222> LOCATION: (1)..(2043)

<400> SEQUENCE: 47

```
-continued atg act caa ttc act gac att gat aag cta gcc gtc tcc acc ata aga      48
Met Thr Gln Phe Thr Asp Ile Asp Lys Leu Ala Val Ser Thr Ile Arg
1               5                   10                  15 att ttg gct gtg gac acc gta tcc aag gcc aac tca ggt cac cca ggt      96
Ile Leu Ala Val Asp Thr Val Ser Lys Ala Asn Ser Gly His Pro Gly
            20                  25                  30 gct cca ttg ggt atg gca cca gct gca cac gtt cta tgg agt caa atg    144
Ala Pro Leu Gly Met Ala Pro Ala Ala His Val Leu Trp Ser Gln Met
        35                  40                  45 cgc atg aac cca acc aac cca gac tgg atc aac aga gat aga ttt gtc    192
Arg Met Asn Pro Thr Asn Pro Asp Trp Ile Asn Arg Asp Arg Phe Val
    50                  55                  60 ttg tct aac ggt cac gcg gtc gct ttg ttg tat tct atg cta cat ttg    240
Leu Ser Asn Gly His Ala Val Ala Leu Leu Tyr Ser Met Leu His Leu
65                  70                  75                  80 act ggt tac gat ctg tct att gaa gac ttg aaa cag ttc aga cag ttg    288
Thr Gly Tyr Asp Leu Ser Ile Glu Asp Leu Lys Gln Phe Arg Gln Leu
                85                  90                  95 ggt tcc aga aca cca ggt cat cct gaa ttt gag ttg cca ggt gtt gaa    336
Gly Ser Arg Thr Pro Gly His Pro Glu Phe Glu Leu Pro Gly Val Glu
            100                 105                 110 gtt act acc ggt cca tta ggt caa ggt atc tcc aac gct gtt ggt atg    384
Val Thr Thr Gly Pro Leu Gly Gln Gly Ile Ser Asn Ala Val Gly Met
        115                 120                 125 gcc atg gct caa gct aac ctg gct gcc act tac aac aag ccg ggc ttt    432
Ala Met Ala Gln Ala Asn Leu Ala Ala Thr Tyr Asn Lys Pro Gly Phe
    130                 135                 140 acc ttg tct gac aac tac acc tat gtt ttc ttg ggt gac ggt tgt ttg    480
Thr Leu Ser Asp Asn Tyr Thr Tyr Val Phe Leu Gly Asp Gly Cys Leu
145                 150                 155                 160 caa gaa ggt att tct tca gaa gct tcc tcc ttg gct ggt cat ttg aaa    528
Gln Glu Gly Ile Ser Ser Glu Ala Ser Ser Leu Ala Gly His Leu Lys
                165                 170                 175 ttg ggt aac ttg att gcc atc tac gat gac aac aag atc act atc gat    576
Leu Gly Asn Leu Ile Ala Ile Tyr Asp Asp Asn Lys Ile Thr Ile Asp
            180                 185                 190 ggt gct acc agt atc tca ttc gat gaa gat gtt gct aag aga tac gaa    624
Gly Ala Thr Ser Ile Ser Phe Asp Glu Asp Val Ala Lys Arg Tyr Glu
        195                 200                 205 gcc tac ggt tgg gaa gtt ttg tac gta gaa aat ggt aac gaa gat cta    672
Ala Tyr Gly Trp Glu Val Leu Tyr Val Glu Asn Gly Asn Glu Asp Leu
    210                 215                 220 gcc ggt att gcc aag gct att gct caa gct aag tta tcc aag gac aaa    720
Ala Gly Ile Ala Lys Ala Ile Ala Gln Ala Lys Leu Ser Lys Asp Lys
225                 230                 235                 240 cca act ttg atc aaa atg acc aca acc att ggt tac ggt tcc ttg cat    768
Pro Thr Leu Ile Lys Met Thr Thr Thr Ile Gly Tyr Gly Ser Leu His
                245                 250                 255 gcc ggc tct cac tct gtg cac ggt gcc cca ttg aaa gca gat gat gtt    816
Ala Gly Ser His Ser Val His Gly Ala Pro Leu Lys Ala Asp Asp Val
            260                 265                 270 aaa caa cta aag agc aaa ttc ggt ttc aac cca gac aag tcc ttt gtt    864
Lys Gln Leu Lys Ser Lys Phe Gly Phe Asn Pro Asp Lys Ser Phe Val
        275                 280                 285 gtt cca caa gaa gtt tac gac cac tac caa aag aca att tta aag cca    912
Val Pro Gln Glu Val Tyr Asp His Tyr Gln Lys Thr Ile Leu Lys Pro
    290                 295                 300 ggt gtc gaa gcc aac aac aag tgg aac aag ttg ttc agc gaa tac caa    960
Gly Val Glu Ala Asn Asn Lys Trp Asn Lys Leu Phe Ser Glu Tyr Gln
305                 310                 315                 320
```

```
aag aaa ttc cca gaa tta ggt gct gaa ttg gct aga aga ttg agc ggc      1008
Lys Lys Phe Pro Glu Leu Gly Ala Glu Leu Ala Arg Arg Leu Ser Gly
                325                 330                 335 caa cta ccc gca aat tgg gaa tct aag ttg cca act tac acc gcc aag      1056
Gln Leu Pro Ala Asn Trp Glu Ser Lys Leu Pro Thr Tyr Thr Ala Lys
            340                 345                 350 gac tct gcc gtg gcc act aga aaa tta tca gaa act gtt ctt gag gat      1104
Asp Ser Ala Val Ala Thr Arg Lys Leu Ser Glu Thr Val Leu Glu Asp
        355                 360                 365 gtt tac aat caa ttg cca gag ttg att ggt ggt tct gcc gat tta aca      1152
Val Tyr Asn Gln Leu Pro Glu Leu Ile Gly Gly Ser Ala Asp Leu Thr
    370                 375                 380 cct tct aac ttg acc aga tgg aag gaa gcc ctt gac ttc caa cct cct      1200
Pro Ser Asn Leu Thr Arg Trp Lys Glu Ala Leu Asp Phe Gln Pro Pro
385                 390                 395                 400 tct tcc ggt tca ggt aac tac tct ggt aga tac att agg tac ggt att      1248
Ser Ser Gly Ser Gly Asn Tyr Ser Gly Arg Tyr Ile Arg Tyr Gly Ile
                405                 410                 415 aga gaa cac gct atg ggt gcc ata atg aac ggt att tca gct ttc ggt      1296
Arg Glu His Ala Met Gly Ala Ile Met Asn Gly Ile Ser Ala Phe Gly
            420                 425                 430 gcc aac tac aaa cca tac ggt ggt act ttc ttg aac ttc gtt tct tat      1344
Ala Asn Tyr Lys Pro Tyr Gly Gly Thr Phe Leu Asn Phe Val Ser Tyr
        435                 440                 445 gct gct ggt gcc gtt aga ttg tcc gct ttg tct ggc cac cca gtt att      1392
Ala Ala Gly Ala Val Arg Leu Ser Ala Leu Ser Gly His Pro Val Ile
    450                 455                 460 tgg gtt gct aca cat gac tct atc ggt gtc ggt gaa gat ggt cca aca      1440
Trp Val Ala Thr His Asp Ser Ile Gly Val Gly Glu Asp Gly Pro Thr
465                 470                 475                 480 cat caa cct att gaa act tta gca cac ttc aga tcc cta cca aac att      1488
His Gln Pro Ile Glu Thr Leu Ala His Phe Arg Ser Leu Pro Asn Ile
                485                 490                 495 caa gtt tgg aga cca gct gat ggt aac gaa gtt tct gcc gcc tac aag      1536
Gln Val Trp Arg Pro Ala Asp Gly Asn Glu Val Ser Ala Ala Tyr Lys
            500                 505                 510 aac tct tta gaa tcc aag cat act cca agt atc att gct ttg tcc aga      1584
Asn Ser Leu Glu Ser Lys His Thr Pro Ser Ile Ile Ala Leu Ser Arg
        515                 520                 525 caa aac ttg cca caa ttg gaa ggt agc tct att gaa agc gct tct aag      1632
Gln Asn Leu Pro Gln Leu Glu Gly Ser Ser Ile Glu Ser Ala Ser Lys
    530                 535                 540 ggt ggt tac gta cta caa gat gtt gct aac cca gat att att tta gtg      1680
Gly Gly Tyr Val Leu Gln Asp Val Ala Asn Pro Asp Ile Ile Leu Val
545                 550                 555                 560 gct act ggt tcc gaa gtg tct ttg agt gtt gaa gct gct aag act ttg      1728
Ala Thr Gly Ser Glu Val Ser Leu Ser Val Glu Ala Ala Lys Thr Leu
                565                 570                 575 gcc gca aag aac atc aag gct cgt gtt gtt tct cta cca gat ttc ttc      1776
Ala Ala Lys Asn Ile Lys Ala Arg Val Val Ser Leu Pro Asp Phe Phe
            580                 585                 590 act ttt gac aaa caa ccc cta gaa tac aga cta tca gtc tta cca gac      1824
Thr Phe Asp Lys Gln Pro Leu Glu Tyr Arg Leu Ser Val Leu Pro Asp
        595                 600                 605 aac gtt cca atc atg tct gtt gaa gtt ttg gct acc aca tgt tgg ggc      1872
Asn Val Pro Ile Met Ser Val Glu Val Leu Ala Thr Thr Cys Trp Gly
    610                 615                 620 aaa tac gct cat caa tcc ttc ggt att gac aga ttt ggt gcc tcc ggt      1920
Lys Tyr Ala His Gln Ser Phe Gly Ile Asp Arg Phe Gly Ala Ser Gly
```

-continued

```
                 625                 630                 635                 640
aag gca cca gaa gtc ttc aag ttc ttc ggt ttc acc cca gaa ggt gtt         1968
Lys Ala Pro Glu Val Phe Lys Phe Phe Gly Phe Thr Pro Glu Gly Val
                     645                 650                 655 gct gaa aga gct caa aag acc att gca ttc tat aag ggt gac aag cta         2016
Ala Glu Arg Ala Gln Lys Thr Ile Ala Phe Tyr Lys Gly Asp Lys Leu
                     660                 665                 670 att tct cct ttg aaa aaa gct ttc taa                                      2043
Ile Ser Pro Leu Lys Lys Ala Phe
                     675                 680

<210> SEQ ID NO 48
<211> LENGTH: 680
<212> TYPE: PRT
<213> ORGANISM: Saccharomyces cerevisiae

<400> SEQUENCE: 48

Met Thr Gln Phe Thr Asp Ile Asp Lys Leu Ala Val Ser Thr Ile Arg
1               5                   10                  15

Ile Leu Ala Val Asp Thr Val Ser Lys Ala Asn Ser Gly His Pro Gly
                20                  25                  30

Ala Pro Leu Gly Met Ala Pro Ala Ala His Val Leu Trp Ser Gln Met
            35                  40                  45

Arg Met Asn Pro Thr Asn Pro Asp Trp Ile Asn Arg Asp Arg Phe Val
        50                  55                  60

Leu Ser Asn Gly His Ala Val Ala Leu Leu Tyr Ser Met Leu His Leu
65                  70                  75                  80

Thr Gly Tyr Asp Leu Ser Ile Glu Asp Leu Lys Gln Phe Arg Gln Leu
                85                  90                  95

Gly Ser Arg Thr Pro Gly His Pro Glu Phe Glu Leu Pro Gly Val Glu
            100                 105                 110

Val Thr Thr Gly Pro Leu Gly Gln Gly Ile Ser Asn Ala Val Gly Met
        115                 120                 125

Ala Met Ala Gln Ala Asn Leu Ala Ala Thr Tyr Asn Lys Pro Gly Phe
    130                 135                 140

Thr Leu Ser Asp Asn Tyr Thr Tyr Val Phe Leu Gly Asp Gly Cys Leu
145                 150                 155                 160

Gln Glu Gly Ile Ser Ser Glu Ala Ser Ser Leu Ala Gly His Leu Lys
                165                 170                 175

Leu Gly Asn Leu Ile Ala Ile Tyr Asp Asp Asn Lys Ile Thr Ile Asp
            180                 185                 190

Gly Ala Thr Ser Ile Ser Phe Asp Glu Asp Val Ala Lys Arg Tyr Glu
        195                 200                 205

Ala Tyr Gly Trp Glu Val Leu Tyr Val Glu Asn Gly Asn Glu Asp Leu
    210                 215                 220

Ala Gly Ile Ala Lys Ala Ile Ala Gln Ala Lys Leu Ser Lys Asp Lys
225                 230                 235                 240

Pro Thr Leu Ile Lys Met Thr Thr Thr Ile Gly Tyr Gly Ser Leu His
                245                 250                 255

Ala Gly Ser His Ser Val His Gly Ala Pro Leu Lys Ala Asp Asp Val
            260                 265                 270

Lys Gln Leu Lys Ser Lys Phe Gly Phe Asn Pro Asp Lys Ser Phe Val
        275                 280                 285

Val Pro Gln Glu Val Tyr Asp His Tyr Gln Lys Thr Ile Leu Lys Pro
    290                 295                 300
```

```
Gly Val Glu Ala Asn Asn Lys Trp Asn Lys Leu Phe Ser Glu Tyr Gln
305                 310                 315                 320

Lys Lys Phe Pro Glu Leu Gly Ala Glu Leu Ala Arg Arg Leu Ser Gly
            325                 330                 335

Gln Leu Pro Ala Asn Trp Glu Ser Lys Leu Pro Thr Tyr Thr Ala Lys
            340                 345                 350

Asp Ser Ala Val Ala Thr Arg Lys Leu Ser Glu Thr Val Leu Glu Asp
            355                 360                 365

Val Tyr Asn Gln Leu Pro Glu Leu Ile Gly Gly Ser Ala Asp Leu Thr
370                 375                 380

Pro Ser Asn Leu Thr Arg Trp Lys Glu Ala Leu Asp Phe Gln Pro Pro
385                 390                 395                 400

Ser Ser Gly Ser Gly Asn Tyr Ser Gly Arg Tyr Ile Arg Tyr Gly Ile
                405                 410                 415

Arg Glu His Ala Met Gly Ala Ile Met Asn Gly Ile Ser Ala Phe Gly
            420                 425                 430

Ala Asn Tyr Lys Pro Tyr Gly Gly Thr Phe Leu Asn Phe Val Ser Tyr
            435                 440                 445

Ala Ala Gly Ala Val Arg Leu Ser Ala Leu Ser Gly His Pro Val Ile
450                 455                 460

Trp Val Ala Thr His Asp Ser Ile Gly Val Gly Glu Asp Gly Pro Thr
465                 470                 475                 480

His Gln Pro Ile Glu Thr Leu Ala His Phe Arg Ser Leu Pro Asn Ile
                485                 490                 495

Gln Val Trp Arg Pro Ala Asp Gly Asn Glu Val Ser Ala Ala Tyr Lys
            500                 505                 510

Asn Ser Leu Glu Ser Lys His Thr Pro Ser Ile Ile Ala Leu Ser Arg
515                 520                 525

Gln Asn Leu Pro Gln Leu Glu Gly Ser Ser Ile Glu Ser Ala Ser Lys
            530                 535                 540

Gly Gly Tyr Val Leu Gln Asp Val Ala Asn Pro Asp Ile Ile Leu Val
545                 550                 555                 560

Ala Thr Gly Ser Glu Val Ser Leu Ser Val Glu Ala Ala Lys Thr Leu
                565                 570                 575

Ala Ala Lys Asn Ile Lys Ala Arg Val Val Ser Leu Pro Asp Phe Phe
            580                 585                 590

Thr Phe Asp Lys Gln Pro Leu Glu Tyr Arg Leu Ser Val Leu Pro Asp
            595                 600                 605

Asn Val Pro Ile Met Ser Val Glu Val Leu Ala Thr Thr Cys Trp Gly
610                 615                 620

Lys Tyr Ala His Gln Ser Phe Gly Ile Asp Arg Phe Gly Ala Ser Gly
625                 630                 635                 640

Lys Ala Pro Glu Val Phe Lys Phe Phe Gly Phe Thr Pro Glu Gly Val
                645                 650                 655

Ala Glu Arg Ala Gln Lys Thr Ile Ala Phe Tyr Lys Gly Asp Lys Leu
            660                 665                 670

Ile Ser Pro Leu Lys Lys Ala Phe
            675                 680

<210> SEQ ID NO 49
<211> LENGTH: 2040
<212> TYPE: DNA
<213> ORGANISM: Kluyveromyces marxianus
<220> FEATURE:
<221> NAME/KEY: CDS
```

<222> LOCATION: (1)..(2040)

<400> SEQUENCE: 49

| | | | | | | | | | | | | | | | | |
|---|---|---|---|---|---|---|---|---|---|---|---|---|---|---|---|---|
| atg | tct | caa | tat | tcc | gat | atc | gat | cgt | cta | gct | atc | aac | act | atc | aga | 48 |
| Met | Ser | Gln | Tyr | Ser | Asp | Ile | Asp | Arg | Leu | Ala | Ile | Asn | Thr | Ile | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttg | ttg | tct | gtt | gac | caa | gtt | gca | tca | gcc | aac | tct | ggt | cac | cca | ggt | 96 |
| Leu | Leu | Ser | Val | Asp | Gln | Val | Ala | Ser | Ala | Asn | Ser | Gly | His | Pro | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| gct | cca | ttg | ggt | cta | gct | cca | gca | gcc | cat | gtt | gtc | tgg | aag | caa | atg | 144 |
| Ala | Pro | Leu | Gly | Leu | Ala | Pro | Ala | Ala | His | Val | Val | Trp | Lys | Gln | Met | |
| | | 35 | | | | | 40 | | | | | 45 | | | | |

| | | | | | | | | | | | | | | | | |
|---|---|---|---|---|---|---|---|---|---|---|---|---|---|---|---|---|
| aga | ttg | aac | cca | aag | aac | cca | gaa | tgg | atc | aac | cgt | gac | aga | ttt | gtt | 192 |
| Arg | Leu | Asn | Pro | Lys | Asn | Pro | Glu | Trp | Ile | Asn | Arg | Asp | Arg | Phe | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| ttg | tct | aac | ggt | cac | gca | tgt | gct | ttg | tac | tcc | ttg | ttg | cat | ctg | | 240 |
| Leu | Ser | Asn | Gly | His | Ala | Cys | Ala | Leu | Leu | Tyr | Ser | Leu | Leu | His | Leu | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ttt | gga | tac | gac | ttc | tcc | att | gag | gat | ttg | aag | caa | ttc | aga | cac | ttg | 288 |
| Phe | Gly | Tyr | Asp | Phe | Ser | Ile | Glu | Asp | Leu | Lys | Gln | Phe | Arg | His | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| ggc | tcc | aag | act | cca | ggt | cac | cca | gaa | ttc | gaa | ttg | cca | ggt | gtc | gaa | 336 |
| Gly | Ser | Lys | Thr | Pro | Gly | His | Pro | Glu | Phe | Glu | Leu | Pro | Gly | Val | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| gtg | act | act | ggt | cca | ttg | ggt | caa | ggt | atc | tct | aac | gct | gtt | ggt | ttg | 384 |
| Val | Thr | Thr | Gly | Pro | Leu | Gly | Gln | Gly | Ile | Ser | Asn | Ala | Val | Gly | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| gct | att | gct | cag | gcc | aac | ttt | gct | gcc | act | tac | aac | aag | cca | gac | ttt | 432 |
| Ala | Ile | Ala | Gln | Ala | Asn | Phe | Ala | Ala | Thr | Tyr | Asn | Lys | Pro | Asp | Phe | |
| | 130 | | | | | 135 | | | | | 140 | | | | | |

| | | | | | | | | | | | | | | | | |
|---|---|---|---|---|---|---|---|---|---|---|---|---|---|---|---|---|
| gaa | ttg | tct | gac | tca | ttc | aca | tac | gtg | ttt | ttg | ggt | gac | ggt | tgt | ttg | 480 |
| Glu | Leu | Ser | Asp | Ser | Phe | Thr | Tyr | Val | Phe | Leu | Gly | Asp | Gly | Cys | Leu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| caa | gaa | ggt | gtt | tca | tct | gaa | gct | tgt | tct | ttg | gct | ggc | cat | ttg | aaa | 528 |
| Gln | Glu | Gly | Val | Ser | Ser | Glu | Ala | Cys | Ser | Leu | Ala | Gly | His | Leu | Lys | |
| | | | | 165 | | | | | 170 | | | | | 175 | | |

| | | | | | | | | | | | | | | | | |
|---|---|---|---|---|---|---|---|---|---|---|---|---|---|---|---|---|
| ttg | aag | aac | ttg | att | gcc | ttt | tac | gac | gac | aac | aag | atc | acc | atc | gat | 576 |
| Leu | Lys | Asn | Leu | Ile | Ala | Phe | Tyr | Asp | Asp | Asn | Lys | Ile | Thr | Ile | Asp | |
| | | | 180 | | | | | 185 | | | | | 190 | | | |

| | | | | | | | | | | | | | | | | |
|---|---|---|---|---|---|---|---|---|---|---|---|---|---|---|---|---|
| ggt | aac | acc | aac | gtg | tct | ttc | gac | gaa | gat | gtt | ggc | aag | aga | tac | gag | 624 |
| Gly | Asn | Thr | Asn | Val | Ser | Phe | Asp | Glu | Asp | Val | Gly | Lys | Arg | Tyr | Glu | |
| | | 195 | | | | | 200 | | | | | 205 | | | | |

| | | | | | | | | | | | | | | | | |
|---|---|---|---|---|---|---|---|---|---|---|---|---|---|---|---|---|
| gcc | tac | ggc | tgg | gaa | gtg | ttg | agc | gtc | gaa | aac | ggt | aac | gac | gat | ctg | 672 |
| Ala | Tyr | Gly | Trp | Glu | Val | Leu | Ser | Val | Glu | Asn | Gly | Asn | Asp | Asp | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| gac | tcc | atc | agc | aag | gcc | ttg | gag | caa | gcc | aag | cgc | tcc | gac | aag | cca | 720 |
| Asp | Ser | Ile | Ser | Lys | Ala | Leu | Glu | Gln | Ala | Lys | Arg | Ser | Asp | Lys | Pro | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| act | ttg | atc | aag | ttg | gtc | acc | acc | atc | ggt | ttc | ggt | tcc | cta | caa | gcc | 768 |
| Thr | Leu | Ile | Lys | Leu | Val | Thr | Thr | Ile | Gly | Phe | Gly | Ser | Leu | Gln | Ala | |
| | | | 245 | | | | | 250 | | | | | 255 | | | |

| | | | | | | | | | | | | | | | | |
|---|---|---|---|---|---|---|---|---|---|---|---|---|---|---|---|---|
| ggt | acc | cac | gcc | gtc | cac | ggt | gcc | cca | ttg | aag | gcc | gac | gat | atc | aag | 816 |
| Gly | Thr | His | Ala | Val | His | Gly | Ala | Pro | Leu | Lys | Ala | Asp | Asp | Ile | Lys | |
| | | 260 | | | | | 265 | | | | | 270 | | | | |

| | | | | | | | | | | | | | | | | |
|---|---|---|---|---|---|---|---|---|---|---|---|---|---|---|---|---|
| caa | ttg | aag | acc | aag | ttc | ggc | ttc | aac | cca | gaa | gaa | tcc | ttc | gtc | gtc | 864 |
| Gln | Leu | Lys | Thr | Lys | Phe | Gly | Phe | Asn | Pro | Glu | Glu | Ser | Phe | Val | Val | |
| | 275 | | | | | 280 | | | | | 285 | | | | | |

| | | | | | | | | | | | | | | | | |
|---|---|---|---|---|---|---|---|---|---|---|---|---|---|---|---|---|
| cca | caa | gaa | gtc | tac | gac | cta | tac | aac | aag | tcc | acc | atc | gaa | cct | ggt | 912 |
| Pro | Gln | Glu | Val | Tyr | Asp | Leu | Tyr | Asn | Lys | Ser | Thr | Ile | Glu | Pro | Gly | |
| 290 | | | | | 295 | | | | | 300 | | | | | | |

```
atc gaa gcc aac aac aag tgg aac gct cta ttc gag gcc tac tcc gcc      960
Ile Glu Ala Asn Asn Lys Trp Asn Ala Leu Phe Glu Ala Tyr Ser Ala
305                 310                 315                 320 aag ttc cca gaa ttg ggt gcc gaa atc aag aga aga ctt gca ggt gaa     1008
Lys Phe Pro Glu Leu Gly Ala Glu Ile Lys Arg Arg Leu Ala Gly Glu
                325                 330                 335 ttg cca act ggt tgg gaa aac aag ttg cca act tac act cca aag gac     1056
Leu Pro Thr Gly Trp Glu Asn Lys Leu Pro Thr Tyr Thr Pro Lys Asp
            340                 345                 350 tcc gcc gtc gct tcc aga aag ttg tcc gag atc cta ttg caa aac atc     1104
Ser Ala Val Ala Ser Arg Lys Leu Ser Glu Ile Leu Leu Gln Asn Ile
        355                 360                 365 ttc gaa gac att cca gaa ttg att ggt ggt tcc gcc gat ttg acc cca     1152
Phe Glu Asp Ile Pro Glu Leu Ile Gly Gly Ser Ala Asp Leu Thr Pro
    370                 375                 380 tct aac ttg act aga acc aag gaa gtt gtc gac ttc caa gct cct tcc     1200
Ser Asn Leu Thr Arg Thr Lys Glu Val Val Asp Phe Gln Ala Pro Ser
385                 390                 395                 400 tcc ggt cta ggt gac tac acc ggt aga tac atc aga tac ggt gtc cgt     1248
Ser Gly Leu Gly Asp Tyr Thr Gly Arg Tyr Ile Arg Tyr Gly Val Arg
                405                 410                 415 gaa cac ggt atg ggt gcc atc atg aac ggt atc tcc gct ttc ggt gct     1296
Glu His Gly Met Gly Ala Ile Met Asn Gly Ile Ser Ala Phe Gly Ala
            420                 425                 430 aac tac aag cca tac ggt ggt act ttc ttg aac ttc gtc tct tac gcc     1344
Asn Tyr Lys Pro Tyr Gly Gly Thr Phe Leu Asn Phe Val Ser Tyr Ala
        435                 440                 445 gct ggt gcc ttg aga ttg tcc gct ttg tcc ggt cac cca gtc atc tgg     1392
Ala Gly Ala Leu Arg Leu Ser Ala Leu Ser Gly His Pro Val Ile Trp
    450                 455                 460 gtc gcc act cac gac tcc atc ggt cta ggt gaa gat ggt cca acc cat     1440
Val Ala Thr His Asp Ser Ile Gly Leu Gly Glu Asp Gly Pro Thr His
465                 470                 475                 480 caa cct atc gaa act ttg gcc cac ttc aga gct ctt cca aac ttg caa     1488
Gln Pro Ile Glu Thr Leu Ala His Phe Arg Ala Leu Pro Asn Leu Gln
                485                 490                 495 gtt tgg aga cca gct gac ggt aac gaa gtt tcc gct gct tac aag gtc     1536
Val Trp Arg Pro Ala Asp Gly Asn Glu Val Ser Ala Ala Tyr Lys Val
            500                 505                 510 gcc ttg aag agc aag cac act cca gcc gtc att gct cta tct aga caa     1584
Ala Leu Lys Ser Lys His Thr Pro Ala Val Ile Ala Leu Ser Arg Gln
        515                 520                 525 aac ttg cct caa ttg gaa ggc tct tcc atc gaa aag gcc gcc aag ggt     1632
Asn Leu Pro Gln Leu Glu Gly Ser Ser Ile Glu Lys Ala Ala Lys Gly
    530                 535                 540 ggt tac gtc ttg caa gac gtc gaa caa cca gac atc gcc atc gtc tcc     1680
Gly Tyr Val Leu Gln Asp Val Glu Gln Pro Asp Ile Ala Ile Val Ser
545                 550                 555                 560 act ggt tcc gaa gtt ggt att gcc gtc gaa gct gct aag gtt ttg gct     1728
Thr Gly Ser Glu Val Gly Ile Ala Val Glu Ala Ala Lys Val Leu Ala
                565                 570                 575 gaa aag aac atc aag gcc cgt atc gtc tct cta cca gac ttc cac acc     1776
Glu Lys Asn Ile Lys Ala Arg Ile Val Ser Leu Pro Asp Phe His Thr
            580                 585                 590 ttt gac caa caa cca aag gaa tac caa ttg tcc gtt cta cca gat ggt     1824
Phe Asp Gln Gln Pro Lys Glu Tyr Gln Leu Ser Val Leu Pro Asp Gly
        595                 600                 605 gtc cca atc ttg tcc gtc gaa gtc ttg tcc act tcc ggt tgg gct aag     1872
Val Pro Ile Leu Ser Val Glu Val Leu Ser Thr Ser Gly Trp Ala Lys
```

```
                 610                 615                 620
tac tct cac caa caa ttc ggt ttg aac aga ttc ggt gcc tcc ggt aag       1920
Tyr Ser His Gln Gln Phe Gly Leu Asn Arg Phe Gly Ala Ser Gly Lys
625                 630                 635                 640 ggt cca gcc gtc tac gag aag ttc gat ttc act cca caa ggt att gct       1968
Gly Pro Ala Val Tyr Glu Lys Phe Asp Phe Thr Pro Gln Gly Ile Ala
                645                 650                 655 tcc aga gct gaa aag act gtt gaa ttc tac aag ggt aag caa gtc tat       2016
Ser Arg Ala Glu Lys Thr Val Glu Phe Tyr Lys Gly Lys Gln Val Tyr
            660                 665                 670 tct cct ttg aac act gct ttc taa                                       2040
Ser Pro Leu Asn Thr Ala Phe
        675
```

<210> SEQ ID NO 50
<211> LENGTH: 679
<212> TYPE: PRT
<213> ORGANISM: Kluyveromyces marxianus

<400> SEQUENCE: 50

```
Met Ser Gln Tyr Ser Asp Ile Asp Arg Leu Ala Ile Asn Thr Ile Arg
1               5                   10                  15

Leu Leu Ser Val Asp Gln Val Ala Ser Ala Asn Ser Gly His Pro Gly
            20                  25                  30

Ala Pro Leu Gly Leu Ala Pro Ala Ala His Val Val Trp Lys Gln Met
        35                  40                  45

Arg Leu Asn Pro Lys Asn Pro Glu Trp Ile Asn Arg Asp Arg Phe Val
    50                  55                  60

Leu Ser Asn Gly His Ala Cys Ala Leu Leu Tyr Ser Leu Leu His Leu
65                  70                  75                  80

Phe Gly Tyr Asp Phe Ser Ile Glu Asp Leu Lys Gln Phe Arg His Leu
                85                  90                  95

Gly Ser Lys Thr Pro Gly His Pro Glu Phe Glu Leu Pro Gly Val Glu
            100                 105                 110

Val Thr Thr Gly Pro Leu Gly Gln Gly Ile Ser Asn Ala Val Gly Leu
        115                 120                 125

Ala Ile Ala Gln Ala Asn Phe Ala Ala Thr Tyr Asn Lys Pro Asp Phe
    130                 135                 140

Glu Leu Ser Asp Ser Phe Thr Tyr Val Phe Leu Gly Asp Gly Cys Leu
145                 150                 155                 160

Gln Glu Gly Val Ser Ser Glu Ala Cys Ser Leu Ala Gly His Leu Lys
                165                 170                 175

Leu Lys Asn Leu Ile Ala Phe Tyr Asp Asp Asn Lys Ile Thr Ile Asp
            180                 185                 190

Gly Asn Thr Asn Val Ser Phe Asp Glu Asp Val Gly Lys Arg Tyr Glu
        195                 200                 205

Ala Tyr Gly Trp Glu Val Leu Ser Val Glu Asn Gly Asn Asp Asp Leu
    210                 215                 220

Asp Ser Ile Ser Lys Ala Leu Glu Gln Ala Lys Arg Ser Asp Lys Pro
225                 230                 235                 240

Thr Leu Ile Lys Leu Val Thr Thr Ile Gly Phe Gly Ser Leu Gln Ala
                245                 250                 255

Gly Thr His Ala Val His Gly Ala Pro Leu Lys Ala Asp Asp Ile Lys
            260                 265                 270

Gln Leu Lys Thr Lys Phe Gly Phe Asn Pro Glu Glu Ser Phe Val Val
        275                 280                 285
```

Pro Gln Glu Val Tyr Asp Leu Tyr Asn Lys Ser Thr Ile Glu Pro Gly
    290                 295                 300

Ile Glu Ala Asn Asn Lys Trp Asn Ala Leu Phe Glu Ala Tyr Ser Ala
305                 310                 315                 320

Lys Phe Pro Glu Leu Gly Ala Glu Ile Lys Arg Arg Leu Ala Gly Glu
                325                 330                 335

Leu Pro Thr Gly Trp Glu Asn Lys Leu Pro Thr Tyr Thr Pro Lys Asp
            340                 345                 350

Ser Ala Val Ala Ser Arg Lys Leu Ser Glu Ile Leu Leu Gln Asn Ile
        355                 360                 365

Phe Glu Asp Ile Pro Glu Leu Ile Gly Gly Ser Ala Asp Leu Thr Pro
370                 375                 380

Ser Asn Leu Thr Arg Thr Lys Glu Val Val Asp Phe Gln Ala Pro Ser
385                 390                 395                 400

Ser Gly Leu Gly Asp Tyr Thr Gly Arg Tyr Ile Arg Tyr Gly Val Arg
                405                 410                 415

Glu His Gly Met Gly Ala Ile Met Asn Gly Ile Ser Ala Phe Gly Ala
            420                 425                 430

Asn Tyr Lys Pro Tyr Gly Gly Thr Phe Leu Asn Phe Val Ser Tyr Ala
        435                 440                 445

Ala Gly Ala Leu Arg Leu Ser Ala Leu Ser Gly His Pro Val Ile Trp
    450                 455                 460

Val Ala Thr His Asp Ser Ile Gly Leu Gly Glu Asp Gly Pro Thr His
465                 470                 475                 480

Gln Pro Ile Glu Thr Leu Ala His Phe Arg Ala Leu Pro Asn Leu Gln
                485                 490                 495

Val Trp Arg Pro Ala Asp Gly Asn Glu Val Ser Ala Ala Tyr Lys Val
            500                 505                 510

Ala Leu Lys Ser Lys His Thr Pro Ala Val Ile Ala Leu Ser Arg Gln
        515                 520                 525

Asn Leu Pro Gln Leu Glu Gly Ser Ser Ile Glu Lys Ala Ala Lys Gly
    530                 535                 540

Gly Tyr Val Leu Gln Asp Val Glu Gln Pro Asp Ile Ala Ile Val Ser
545                 550                 555                 560

Thr Gly Ser Glu Val Gly Ile Ala Val Glu Ala Ala Lys Val Leu Ala
                565                 570                 575

Glu Lys Asn Ile Lys Ala Arg Ile Val Ser Leu Pro Asp Phe His Thr
            580                 585                 590

Phe Asp Gln Gln Pro Lys Glu Tyr Gln Leu Ser Val Leu Pro Asp Gly
        595                 600                 605

Val Pro Ile Leu Ser Val Glu Val Leu Ser Thr Ser Gly Trp Ala Lys
    610                 615                 620

Tyr Ser His Gln Gln Phe Gly Leu Asn Arg Phe Gly Ala Ser Gly Lys
625                 630                 635                 640

Gly Pro Ala Val Tyr Glu Lys Phe Asp Phe Thr Pro Gln Gly Ile Ala
                645                 650                 655

Ser Arg Ala Glu Lys Thr Val Glu Phe Tyr Lys Gly Lys Gln Val Tyr
            660                 665                 670

Ser Pro Leu Asn Thr Ala Phe
        675

<210> SEQ ID NO 51
<211> LENGTH: 972

```
<212> TYPE: DNA
<213> ORGANISM: Issatchenkia orientalis
<220> FEATURE:
<221> NAME/KEY: CDS
<222> LOCATION: (1)..(972)

<400> SEQUENCE: 51 atg tct caa tta gaa caa ctt aag aag tca ggt acc act gtt gtt gca        48
Met Ser Gln Leu Glu Gln Leu Lys Lys Ser Gly Thr Thr Val Val Ala
1               5                   10                  15 gat act ggt gat ttt gaa tct att gca aag ttc act cca caa gat gca        96
Asp Thr Gly Asp Phe Glu Ser Ile Ala Lys Phe Thr Pro Gln Asp Ala
                20                  25                  30 act acg aat cca tcg ttg att ttg gca gct act aag caa cca caa tac       144
Thr Thr Asn Pro Ser Leu Ile Leu Ala Ala Thr Lys Gln Pro Gln Tyr
            35                  40                  45 gcc aag tta att gac att gct att gac tat gcc aag agc aag ggt tcc       192
Ala Lys Leu Ile Asp Ile Ala Ile Asp Tyr Ala Lys Ser Lys Gly Ser
        50                  55                  60 acc aag gag gaa cag gct agt cta gca ctt gac aga ttg ttg gtt gaa       240
Thr Lys Glu Glu Gln Ala Ser Leu Ala Leu Asp Arg Leu Leu Val Glu
65                  70                  75                  80 ttt ggt gct gag att ctc aag att gtg cca ggt cgg gtg tcc acc gag       288
Phe Gly Ala Glu Ile Leu Lys Ile Val Pro Gly Arg Val Ser Thr Glu
                85                  90                  95 gtt gat gca agg tta tcc ttc aac agg gac gcc aca att aag aag gcc       336
Val Asp Ala Arg Leu Ser Phe Asn Arg Asp Ala Thr Ile Lys Lys Ala
                100                 105                 110 att gag att att gaa tta tac aag gca cag gga atc gac aag gag aga       384
Ile Glu Ile Ile Glu Leu Tyr Lys Ala Gln Gly Ile Asp Lys Glu Arg
            115                 120                 125 gta ttg atc aag att gcc tcc act tgg gaa ggt atc caa gct gca agg       432
Val Leu Ile Lys Ile Ala Ser Thr Trp Glu Gly Ile Gln Ala Ala Arg
        130                 135                 140 gag ttg gaa tcc aag cat ggt atc cac tgt aat ttg acg ctt ttg ttc       480
Glu Leu Glu Ser Lys His Gly Ile His Cys Asn Leu Thr Leu Leu Phe
145                 150                 155                 160 tcc ttt gtt cag gct gtt gca tgt gca gaa gct aat gtc aca ctt att       528
Ser Phe Val Gln Ala Val Ala Cys Ala Glu Ala Asn Val Thr Leu Ile
                165                 170                 175 tct cca ttt gtc ggt aga att ttg gac tgg tac aag gct tcc act ggt       576
Ser Pro Phe Val Gly Arg Ile Leu Asp Trp Tyr Lys Ala Ser Thr Gly
                180                 185                 190 aag gaa tac acc tct gaa acc gat cct ggt gtt ttg tcc gtt aga aac       624
Lys Glu Tyr Thr Ser Glu Thr Asp Pro Gly Val Leu Ser Val Arg Asn
            195                 200                 205 atc ttc aac tac tac aag aag ttt ggc tac aag aca att gtc atg ggt       672
Ile Phe Asn Tyr Tyr Lys Lys Phe Gly Tyr Lys Thr Ile Val Met Gly
        210                 215                 220 gcc tcc ttc aga aac act ggt gaa att gca gct ttg gca ggt tgt gac       720
Ala Ser Phe Arg Asn Thr Gly Glu Ile Ala Ala Leu Ala Gly Cys Asp
225                 230                 235                 240 tac ttg acc att tct cca agt ttg ttg gat aaa ctg gct aat tcc aat       768
Tyr Leu Thr Ile Ser Pro Ser Leu Leu Asp Lys Leu Ala Asn Ser Asn
                245                 250                 255 gac cca ctt cca aag gtt tta gac gct tct aag gca aag gaa ttg gat       816
Asp Pro Leu Pro Lys Val Leu Asp Ala Ser Lys Ala Lys Glu Leu Asp
                260                 265                 270 ctt gaa aaa gtc tcc tat gtt gac gat gag cca gat ttt aga ttc ctc       864
Leu Glu Lys Val Ser Tyr Val Asp Asp Glu Pro Asp Phe Arg Phe Leu
            275                 280                 285
```

```
ttg aat gag gat gca atg gca act gaa aaa ttg tct gaa ggt atc aga      912
Leu Asn Glu Asp Ala Met Ala Thr Glu Lys Leu Ser Glu Gly Ile Arg
    290                 295                 300 aag ttc tct gct gat tgt gag gct ctt tac aat gaa tta tta aag aga      960
Lys Phe Ser Ala Asp Cys Glu Ala Leu Tyr Asn Glu Leu Leu Lys Arg
305                 310                 315                 320 gtt tct gct tga                                                      972
Val Ser Ala
```

<210> SEQ ID NO 52
<211> LENGTH: 323
<212> TYPE: PRT
<213> ORGANISM: Issatchenkia orientalis

<400> SEQUENCE: 52

```
Met Ser Gln Leu Glu Gln Leu Lys Lys Ser Gly Thr Thr Val Val Ala
1               5                   10                  15

Asp Thr Gly Asp Phe Glu Ser Ile Ala Lys Phe Thr Pro Gln Asp Ala
            20                  25                  30

Thr Thr Asn Pro Ser Leu Ile Leu Ala Ala Thr Lys Gln Pro Gln Tyr
        35                  40                  45

Ala Lys Leu Ile Asp Ile Ala Ile Asp Tyr Ala Lys Ser Lys Gly Ser
    50                  55                  60

Thr Lys Glu Glu Gln Ala Ser Leu Ala Leu Asp Arg Leu Leu Val Glu
65                  70                  75                  80

Phe Gly Ala Glu Ile Leu Lys Ile Val Pro Gly Arg Val Ser Thr Glu
                85                  90                  95

Val Asp Ala Arg Leu Ser Phe Asn Arg Asp Ala Thr Ile Lys Lys Ala
            100                 105                 110

Ile Glu Ile Ile Glu Leu Tyr Lys Ala Gln Gly Ile Asp Lys Glu Arg
        115                 120                 125

Val Leu Ile Lys Ile Ala Ser Thr Trp Glu Gly Ile Gln Ala Ala Arg
    130                 135                 140

Glu Leu Glu Ser Lys His Gly Ile His Cys Asn Leu Thr Leu Leu Phe
145                 150                 155                 160

Ser Phe Val Gln Ala Val Ala Cys Ala Glu Ala Asn Val Thr Leu Ile
                165                 170                 175

Ser Pro Phe Val Gly Arg Ile Leu Asp Trp Tyr Lys Ala Ser Thr Gly
            180                 185                 190

Lys Glu Tyr Thr Ser Glu Thr Asp Pro Gly Val Leu Ser Val Arg Asn
        195                 200                 205

Ile Phe Asn Tyr Tyr Lys Lys Phe Gly Tyr Lys Thr Ile Val Met Gly
    210                 215                 220

Ala Ser Phe Arg Asn Thr Gly Glu Ile Ala Ala Leu Ala Gly Cys Asp
225                 230                 235                 240

Tyr Leu Thr Ile Ser Pro Ser Leu Leu Asp Lys Leu Ala Asn Ser Asn
                245                 250                 255

Asp Pro Leu Pro Lys Val Leu Asp Ala Ser Lys Ala Lys Glu Leu Asp
            260                 265                 270

Leu Glu Lys Val Ser Tyr Val Asp Asp Glu Pro Asp Phe Arg Phe Leu
        275                 280                 285

Leu Asn Glu Asp Ala Met Ala Thr Glu Lys Leu Ser Glu Gly Ile Arg
    290                 295                 300

Lys Phe Ser Ala Asp Cys Glu Ala Leu Tyr Asn Glu Leu Leu Lys Arg
305                 310                 315                 320
```

Val Ser Ala

<210> SEQ ID NO 53
<211> LENGTH: 1008
<212> TYPE: DNA
<213> ORGANISM: Saccharomyces cerevisiae
<220> FEATURE:
<221> NAME/KEY: CDS
<222> LOCATION: (1)..(1008)

<400> SEQUENCE: 53

| | | | | | | | | | | | | | | | | |
|---|---|---|---|---|---|---|---|---|---|---|---|---|---|---|---|---|
| atg | tct | gaa | cca | gct | caa | aag | aaa | caa | aag | gtt | gct | aac | aac | tct | cta | 48 |
| Met | Ser | Glu | Pro | Ala | Gln | Lys | Lys | Gln | Lys | Val | Ala | Asn | Asn | Ser | Leu | |
| 1 | | | | 5 | | | | | 10 | | | | | 15 | | |
| gaa | caa | ttg | aaa | gcc | tcc | ggc | act | gtc | gtt | gtt | gcc | gac | act | ggt | gat | 96 |
| Glu | Gln | Leu | Lys | Ala | Ser | Gly | Thr | Val | Val | Val | Ala | Asp | Thr | Gly | Asp | |
| | | | 20 | | | | | 25 | | | | | 30 | | | |
| ttc | ggc | tct | att | gcc | aag | ttt | caa | cct | caa | gac | tcc | aca | act | aac | cca | 144 |
| Phe | Gly | Ser | Ile | Ala | Lys | Phe | Gln | Pro | Gln | Asp | Ser | Thr | Thr | Asn | Pro | |
| | | | 35 | | | | | 40 | | | | | 45 | | | |
| tca | ttg | atc | ttg | gct | gct | gcc | aag | caa | cca | act | tac | gcc | aag | ttg | atc | 192 |
| Ser | Leu | Ile | Leu | Ala | Ala | Ala | Lys | Gln | Pro | Thr | Tyr | Ala | Lys | Leu | Ile | |
| | 50 | | | | | 55 | | | | | 60 | | | | | |
| gat | gtt | gcc | gtg | gaa | tac | ggt | aag | aag | cat | ggt | aag | acc | acc | gaa | gaa | 240 |
| Asp | Val | Ala | Val | Glu | Tyr | Gly | Lys | Lys | His | Gly | Lys | Thr | Thr | Glu | Glu | |
| 65 | | | | | 70 | | | | | 75 | | | | | 80 | |
| caa | gtc | gaa | aat | gct | gtg | gac | aga | ttg | tta | gtc | gaa | ttc | ggt | aag | gag | 288 |
| Gln | Val | Glu | Asn | Ala | Val | Asp | Arg | Leu | Leu | Val | Glu | Phe | Gly | Lys | Glu | |
| | | | | 85 | | | | | 90 | | | | | 95 | | |
| atc | tta | aag | att | gtt | cca | ggc | aga | gtc | tcc | acc | gaa | gtt | gat | gct | aga | 336 |
| Ile | Leu | Lys | Ile | Val | Pro | Gly | Arg | Val | Ser | Thr | Glu | Val | Asp | Ala | Arg | |
| | | | 100 | | | | | 105 | | | | | 110 | | | |
| ttg | tct | ttt | gac | act | caa | gct | acc | att | gaa | aag | gct | aga | cat | atc | att | 384 |
| Leu | Ser | Phe | Asp | Thr | Gln | Ala | Thr | Ile | Glu | Lys | Ala | Arg | His | Ile | Ile | |
| | | | 115 | | | | | 120 | | | | | 125 | | | |
| aaa | ttg | ttt | gaa | caa | gaa | ggt | gtc | tcc | aag | gaa | aga | gtc | ctt | att | aaa | 432 |
| Lys | Leu | Phe | Glu | Gln | Glu | Gly | Val | Ser | Lys | Glu | Arg | Val | Leu | Ile | Lys | |
| | 130 | | | | | 135 | | | | | 140 | | | | | |
| att | gct | tcc | act | tgg | gaa | ggt | att | caa | gct | gcc | aaa | gaa | ttg | gaa | gaa | 480 |
| Ile | Ala | Ser | Thr | Trp | Glu | Gly | Ile | Gln | Ala | Ala | Lys | Glu | Leu | Glu | Glu | |
| 145 | | | | | 150 | | | | | 155 | | | | | 160 | |
| aag | gac | ggt | atc | cac | tgt | aat | ttg | act | cta | tta | ttc | tcc | ttc | gtt | caa | 528 |
| Lys | Asp | Gly | Ile | His | Cys | Asn | Leu | Thr | Leu | Leu | Phe | Ser | Phe | Val | Gln | |
| | | | | 165 | | | | | 170 | | | | | 175 | | |
| gca | gtt | gcc | tgt | gcc | gag | gcc | caa | gtt | act | ttg | att | tcc | cca | ttt | gtt | 576 |
| Ala | Val | Ala | Cys | Ala | Glu | Ala | Gln | Val | Thr | Leu | Ile | Ser | Pro | Phe | Val | |
| | | | 180 | | | | | 185 | | | | | 190 | | | |
| ggt | aga | att | cta | gac | tgg | tac | aaa | tcc | agc | act | ggt | aaa | gat | tac | aag | 624 |
| Gly | Arg | Ile | Leu | Asp | Trp | Tyr | Lys | Ser | Ser | Thr | Gly | Lys | Asp | Tyr | Lys | |
| | | | 195 | | | | | 200 | | | | | 205 | | | |
| ggt | gaa | gcc | gac | cca | ggt | gtt | att | tcc | gtc | aag | aaa | atc | tac | aac | tac | 672 |
| Gly | Glu | Ala | Asp | Pro | Gly | Val | Ile | Ser | Val | Lys | Lys | Ile | Tyr | Asn | Tyr | |
| | 210 | | | | | 215 | | | | | 220 | | | | | |
| tac | aag | aag | tac | ggt | tac | aag | act | att | gtt | atg | ggt | gct | tct | ttc | aga | 720 |
| Tyr | Lys | Lys | Tyr | Gly | Tyr | Lys | Thr | Ile | Val | Met | Gly | Ala | Ser | Phe | Arg | |
| 225 | | | | | 230 | | | | | 235 | | | | | 240 | |
| agc | act | gac | gaa | atc | aaa | aac | ttg | gct | ggt | gtt | gac | tat | cta | aca | att | 768 |
| Ser | Thr | Asp | Glu | Ile | Lys | Asn | Leu | Ala | Gly | Val | Asp | Tyr | Leu | Thr | Ile | |
| | | | | 245 | | | | | 250 | | | | | 255 | | |
| tct | cca | gct | tta | ttg | gac | aag | ttg | atg | aac | agt | act | gaa | cct | ttc | cca | 816 |

```
Ser Pro Ala Leu Leu Asp Lys Leu Met Asn Ser Thr Glu Pro Phe Pro
            260                 265                 270 aga gtt ttg gac cct gtc tcc gct aag aag gaa gcc ggc gac aag att   864
Arg Val Leu Asp Pro Val Ser Ala Lys Lys Glu Ala Gly Asp Lys Ile
        275                 280                 285 tct tac atc agc gac gaa tct aaa ttc aga ttc gac ttg aat gaa gac   912
Ser Tyr Ile Ser Asp Glu Ser Lys Phe Arg Phe Asp Leu Asn Glu Asp
    290                 295                 300 gct atg gcc act gaa aaa ttg tcc gaa ggt atc aga aaa ttc tct gcc   960
Ala Met Ala Thr Glu Lys Leu Ser Glu Gly Ile Arg Lys Phe Ser Ala
305                 310                 315                 320 gat att gtt act cta ttc gac ttg att gaa aag aaa gtt acc gct taa  1008
Asp Ile Val Thr Leu Phe Asp Leu Ile Glu Lys Lys Val Thr Ala
            325                 330                 335

<210> SEQ ID NO 54
<211> LENGTH: 335
<212> TYPE: PRT
<213> ORGANISM: Saccharomyces cerevisiae

<400> SEQUENCE: 54

Met Ser Glu Pro Ala Gln Lys Lys Gln Lys Val Ala Asn Asn Ser Leu
1               5                   10                  15

Glu Gln Leu Lys Ala Ser Gly Thr Val Val Ala Asp Thr Gly Asp
            20                  25                  30

Phe Gly Ser Ile Ala Lys Phe Gln Pro Gln Asp Ser Thr Thr Asn Pro
        35                  40                  45

Ser Leu Ile Leu Ala Ala Ala Lys Gln Pro Thr Tyr Ala Lys Leu Ile
50                  55                  60

Asp Val Ala Val Glu Tyr Gly Lys Lys His Gly Lys Thr Thr Glu Glu
65                  70                  75                  80

Gln Val Glu Asn Ala Val Asp Arg Leu Leu Val Glu Phe Gly Lys Glu
                85                  90                  95

Ile Leu Lys Ile Val Pro Gly Arg Val Ser Thr Glu Val Asp Ala Arg
            100                 105                 110

Leu Ser Phe Asp Thr Gln Ala Thr Ile Glu Lys Ala Arg His Ile Ile
        115                 120                 125

Lys Leu Phe Glu Gln Glu Gly Val Ser Lys Glu Arg Val Leu Ile Lys
    130                 135                 140

Ile Ala Ser Thr Trp Glu Gly Ile Gln Ala Ala Lys Glu Leu Glu Glu
145                 150                 155                 160

Lys Asp Gly Ile His Cys Asn Leu Thr Leu Leu Phe Ser Phe Val Gln
                165                 170                 175

Ala Val Ala Cys Ala Glu Ala Gln Val Thr Leu Ile Ser Pro Phe Val
            180                 185                 190

Gly Arg Ile Leu Asp Trp Tyr Lys Ser Ser Thr Gly Lys Asp Tyr Lys
        195                 200                 205

Gly Glu Ala Asp Pro Gly Val Ile Ser Val Lys Lys Ile Tyr Asn Tyr
    210                 215                 220

Tyr Lys Lys Tyr Gly Tyr Lys Thr Ile Val Met Gly Ala Ser Phe Arg
225                 230                 235                 240

Ser Thr Asp Glu Ile Lys Asn Leu Ala Gly Val Asp Tyr Leu Thr Ile
                245                 250                 255

Ser Pro Ala Leu Leu Asp Lys Leu Met Asn Ser Thr Glu Pro Phe Pro
            260                 265                 270

Arg Val Leu Asp Pro Val Ser Ala Lys Lys Glu Ala Gly Asp Lys Ile
```

```
                      275                 280                 285
          Ser Tyr Ile Ser Asp Glu Ser Lys Phe Arg Phe Asp Leu Asn Glu Asp
              290                 295                 300

Ala Met Ala Thr Glu Lys Leu Ser Glu Gly Ile Arg Lys Phe Ser Ala
          305                 310                 315                 320

Asp Ile Val Thr Leu Phe Asp Leu Ile Glu Lys Lys Val Thr Ala
                          325                 330                 335

<210> SEQ ID NO 55
<211> LENGTH: 1005
<212> TYPE: DNA
<213> ORGANISM: Kluyveromyces marxianus
<220> FEATURE:
<221> NAME/KEY: CDS
<222> LOCATION: (1)..(1005)

<400> SEQUENCE: 55 atg tct gaa cca gct gct aag aaa caa aag ttc gcc aac tca ttg gaa       48
Met Ser Glu Pro Ala Ala Lys Lys Gln Lys Phe Ala Asn Ser Leu Glu
1               5                   10                  15 gcc ttg aag gct acc ggc acc gtt gtt gtt gcc gac act ggt gat ttc       96
Ala Leu Lys Ala Thr Gly Thr Val Val Val Ala Asp Thr Gly Asp Phe
                20                  25                  30 gaa tca att gcc aag ttc aca cca caa gac gcc acc acc aac cca tct      144
Glu Ser Ile Ala Lys Phe Thr Pro Gln Asp Ala Thr Thr Asn Pro Ser
            35                  40                  45 ttg att ttg gct gct gca aag caa gat gca tac gcc aag ttg atc gat      192
Leu Ile Leu Ala Ala Ala Lys Gln Asp Ala Tyr Ala Lys Leu Ile Asp
        50                  55                  60 gct gct gtc gaa tac ggt aag aag cac gga tca aac att gac gag caa      240
Ala Ala Val Glu Tyr Gly Lys Lys His Gly Ser Asn Ile Asp Glu Gln
65                  70                  75                  80 gtt gag att tcc gtc gac aag ctt ttg gtc gag ttt ggt act gcc atc      288
Val Glu Ile Ser Val Asp Lys Leu Leu Val Glu Phe Gly Thr Ala Ile
                85                  90                  95 ttg aag gtt gtt cca ggc aga gtc tcc acc gaa gtt gat gct aga ttg      336
Leu Lys Val Val Pro Gly Arg Val Ser Thr Glu Val Asp Ala Arg Leu
            100                 105                 110 tcc ttc gac aag gaa gcc act gtc aag aag gct ttg gaa atc atc aag      384
Ser Phe Asp Lys Glu Ala Thr Val Lys Lys Ala Leu Glu Ile Ile Lys
        115                 120                 125 cta tac gaa gcc gaa ggt atc tcc aag gaa aga gtg cta atc aag att      432
Leu Tyr Glu Ala Glu Gly Ile Ser Lys Glu Arg Val Leu Ile Lys Ile
    130                 135                 140 gcc tcc acc tgg gaa ggt atc caa gcc gca caa gag cta gag aag gat      480
Ala Ser Thr Trp Glu Gly Ile Gln Ala Ala Gln Glu Leu Glu Lys Asp
145                 150                 155                 160 cac ggt att cac gtc aac ttg acc ttg ttg ttc tct ttc tcc caa gcc      528
His Gly Ile His Val Asn Leu Thr Leu Leu Phe Ser Phe Ser Gln Ala
                165                 170                 175 gtt gct gct gct gag gcc aat gtc acc ttg atc tct cca ttt gtt ggt      576
Val Ala Ala Ala Glu Ala Asn Val Thr Leu Ile Ser Pro Phe Val Gly
            180                 185                 190 aga atc ttg gac tgg tac aag gcc aag acc ggt gaa act tac act gcc      624
Arg Ile Leu Asp Trp Tyr Lys Ala Lys Thr Gly Glu Thr Tyr Thr Ala
        195                 200                 205 gaa acc gac cca ggt gtc gaa tcc gtc aag aac atc tac aac tac tac      672
Glu Thr Asp Pro Gly Val Glu Ser Val Lys Asn Ile Tyr Asn Tyr Tyr
    210                 215                 220 aag aag cac ggc tac aag acc atc gtt atg ggt gct tcc ttc aga aac      720
```

| | | | | | | | | | | | | | | | |
|---|---|---|---|---|---|---|---|---|---|---|---|---|---|---|---|
|Lys|Lys|His|Gly|Tyr|Lys|Thr|Ile|Val|Met|Gly|Ala|Ser|Phe|Arg|Asn|
|225| | | |230| | | |235| | | |240| | | |

```
gtt ggt gaa atc aag gct ctt gcc ggt gtc gac tac ttg act att tct      768
Val Gly Glu Ile Lys Ala Leu Ala Gly Val Asp Tyr Leu Thr Ile Ser
        245                 250                 255 cca aag ttg ttg gac gaa ttg atg gcc tcc cag gac cct gtc cca caa      816
Pro Lys Leu Leu Asp Glu Leu Met Ala Ser Gln Asp Pro Val Pro Gln
    260                 265                 270 gtc ttg gac cct gaa tct gcc aag gat caa ggt tcc gga aga gtc tcc      864
Val Leu Asp Pro Glu Ser Ala Lys Asp Gln Gly Ser Gly Arg Val Ser
            275                 280                 285 ttc atc aac gac gaa tcc aag ttc aga ttc gag ttg aac gaa gac gcc      912
Phe Ile Asn Asp Glu Ser Lys Phe Arg Phe Glu Leu Asn Glu Asp Ala
290                 295                 300 atg gcc act gaa aag ttg tct gaa ggt atc aga aag ttc tct gcc gac      960
Met Ala Thr Glu Lys Leu Ser Glu Gly Ile Arg Lys Phe Ser Ala Asp
305                 310                 315                 320 atc gtc act ctg ttc gac ttg atc aag gct aag atc caa gct taa        1005
Ile Val Thr Leu Phe Asp Leu Ile Lys Ala Lys Ile Gln Ala
                325                 330

<210> SEQ ID NO 56
<211> LENGTH: 334
<212> TYPE: PRT
<213> ORGANISM: Kluyveromyces marxianus

<400> SEQUENCE: 56

Met Ser Glu Pro Ala Ala Lys Lys Gln Lys Phe Ala Asn Ser Leu Glu
1               5                   10                  15

Ala Leu Lys Ala Thr Gly Thr Val Val Ala Asp Thr Gly Asp Phe
            20                  25                  30

Glu Ser Ile Ala Lys Phe Thr Pro Gln Asp Ala Thr Thr Asn Pro Ser
        35                  40                  45

Leu Ile Leu Ala Ala Ala Lys Gln Asp Ala Tyr Ala Lys Leu Ile Asp
    50                  55                  60

Ala Ala Val Glu Tyr Gly Lys Lys His Gly Ser Asn Ile Asp Glu Gln
65                  70                  75                  80

Val Glu Ile Ser Val Asp Lys Leu Leu Val Glu Phe Gly Thr Ala Ile
                85                  90                  95

Leu Lys Val Val Pro Gly Arg Val Ser Thr Glu Val Asp Ala Arg Leu
            100                 105                 110

Ser Phe Asp Lys Glu Ala Thr Val Lys Lys Ala Leu Glu Ile Ile Lys
        115                 120                 125

Leu Tyr Glu Ala Glu Gly Ile Ser Lys Glu Arg Val Leu Ile Lys Ile
    130                 135                 140

Ala Ser Thr Trp Glu Gly Ile Gln Ala Ala Glu Leu Glu Lys Asp
145                 150                 155                 160

His Gly Ile His Val Asn Leu Thr Leu Leu Phe Ser Phe Ser Gln Ala
                165                 170                 175

Val Ala Ala Ala Glu Ala Asn Val Thr Leu Ile Ser Pro Phe Val Gly
            180                 185                 190

Arg Ile Leu Asp Trp Tyr Lys Ala Lys Thr Gly Glu Thr Tyr Thr Ala
        195                 200                 205

Glu Thr Asp Pro Gly Val Glu Ser Val Lys Asn Ile Tyr Asn Tyr Tyr
    210                 215                 220

Lys Lys His Gly Tyr Lys Thr Ile Val Met Gly Ala Ser Phe Arg Asn
225                 230                 235                 240
```

```
Val Gly Glu Ile Lys Ala Leu Ala Gly Val Asp Tyr Leu Thr Ile Ser
            245                 250                 255

Pro Lys Leu Leu Asp Glu Leu Met Ala Ser Gln Asp Pro Val Pro Gln
        260                 265                 270

Val Leu Asp Pro Glu Ser Ala Lys Asp Gln Gly Ser Gly Arg Val Ser
            275                 280                 285

Phe Ile Asn Asp Glu Ser Lys Phe Arg Phe Glu Leu Asn Glu Asp Ala
        290                 295                 300

Met Ala Thr Glu Lys Leu Ser Glu Gly Ile Arg Lys Phe Ser Ala Asp
305                 310                 315                 320

Ile Val Thr Leu Phe Asp Leu Ile Lys Ala Lys Ile Gln Ala
            325                 330

<210> SEQ ID NO 57
<211> LENGTH: 2110
<212> TYPE: DNA
<213> ORGANISM: Issatchenkia orientalis
<220> FEATURE:
<221> NAME/KEY: CDS
<222> LOCATION: (536)..(1360)

<400> SEQUENCE: 57
```

| | | | | |
|---|---|---|---|---|
| cccccctttt gccgagcctc tgcgcacgtt tcttttcct gcgtgtgcgc ccccccctct | | | | 60 |
| cggagaggga agcacaaact ccgtcggaga cacgcgcaaa agaaagata agcgagaaag | | | | 120 |
| ccctctgttt gaggacgcta tagaggacgc taccgagaag cgagaggatg ctcgagaatg | | | | 180 |
| tctgctgcag gggtcgtttc ttttggcgca gcgtcgtttc ttttgcggcc atgcggtgtt | | | | 240 |
| tgtcattctc aatggggagg gtgagccaag atagatatga cgttaaggat agagtgctgt | | | | 300 |
| tgatcaatag catatgtttg caacaaaca gtgactccgc taagaaatgc gtgtggattg | | | | 360 |
| caggggtata aataggaagg tgtgtcttac aattacagta ttctccatat agtatttatt | | | | 420 |
| ctagactata ctatttattc tagaataaat tacactacac tagactccac tagactcact | | | | 480 |
| acactacact ccattacact acactacact acactccatt acactacatt atacc atg | | | | 538 |
| | | | | Met<br>1 | |

```
tca gtt cca act ttt cga cta aca aac gag ctc acc gtc gtg aca ggc      586
Ser Val Pro Thr Phe Arg Leu Thr Asn Glu Leu Thr Val Val Thr Gly
      5                  10                  15 gcc agc ggc ggc att gcc cac gcc ctc gtg gag acg ctt ctg gtc tac      634
Ala Ser Gly Gly Ile Ala His Ala Leu Val Glu Thr Leu Leu Val Tyr
    20                  25                  30 ggg gcg ccg ctg gcg ctc gtg gac cgt aac atg gag gcg ttg cac cgc      682
Gly Ala Pro Leu Ala Leu Val Asp Arg Asn Met Glu Ala Leu His Arg
35                  40                  45 aca cgg gac gcc atg gtg cgt ttc tgt gtt gag gag gca aac att aag      730
Thr Arg Asp Ala Met Val Arg Phe Cys Val Glu Glu Ala Asn Ile Lys
50                  55                  60                  65 gag gag gat gtt cca aag atg gag tgc ttt aca tgt aat ata gga gac      778
Glu Glu Asp Val Pro Lys Met Glu Cys Phe Thr Cys Asn Ile Gly Asp
                70                  75                  80 gcg ggg gaa gtt gaa act cta ttt ggc gag ata tac aat gtc ttc caa      826
Ala Gly Glu Val Glu Thr Leu Phe Gly Glu Ile Tyr Asn Val Phe Gln
            85                  90                  95 cgg tac cca cta cac atg gtg aat tgt gca ggt tat tgc gag aac ttt      874
Arg Tyr Pro Leu His Met Val Asn Cys Ala Gly Tyr Cys Glu Asn Phe
        100                 105                 110 gcc gct gtc gac tat cca gca caa aat gcc cat gat ttg atg gga gtt      922
```

|    |    |    |    |    |    |    |    |    |    |    |    |    |      |
|----|----|----|----|----|----|----|----|----|----|----|----|----|------|
| Ala | Ala | Val | Asp | Tyr | Pro | Ala | Gln | Asn | Ala | His | Asp | Leu | Met | Gly | Val |
|     | 115 |     |     |     | 120 |     |     |     | 125 |

```
aac cta ttg ggt gcc ttt tat ctc tca caa tgt ttt gca aag cct ttg      970
Asn Leu Leu Gly Ala Phe Tyr Leu Ser Gln Cys Phe Ala Lys Pro Leu
130                 135                 140                 145 att gaa cat aac atc tca gga ggt tcg att gtc ctt att gca tca atg     1018
Ile Glu His Asn Ile Ser Gly Gly Ser Ile Val Leu Ile Ala Ser Met
                150                 155                 160 agt ggg aaa att gta aat acc ccg cag aat cag tgc atc tat aac gct     1066
Ser Gly Lys Ile Val Asn Thr Pro Gln Asn Gln Cys Ile Tyr Asn Ala
            165                 170                 175 agc aaa gcc ggc gtt att cat ttg gca aaa tct ctc gca gcg gaa tgg     1114
Ser Lys Ala Gly Val Ile His Leu Ala Lys Ser Leu Ala Ala Glu Trp
        180                 185                 190 ggc gcc ctc atg cac ccc att cga gtc aat acg ctc tcc ccc ggg tac     1162
Gly Ala Leu Met His Pro Ile Arg Val Asn Thr Leu Ser Pro Gly Tyr
    195                 200                 205 acc gcc acc cca tta acc aga aac gtg gtg agc ggc gac gcg tcg ctc     1210
Thr Ala Thr Pro Leu Thr Arg Asn Val Val Ser Gly Asp Ala Ser Leu
210                 215                 220                 225 gcc gcg gaa tgg aca aga cgt gtc ccc ctg ggg aga atg gcg cac ccg     1258
Ala Ala Glu Trp Thr Arg Arg Val Pro Leu Gly Arg Met Ala His Pro
                230                 235                 240 cgt gaa atg gcg ggc gcc gtt ctc ttt ctc ctt gca aac gac gca agt     1306
Arg Glu Met Ala Gly Ala Val Leu Phe Leu Leu Ala Asn Asp Ala Ser
            245                 250                 255 tct tac acc acg ggg gag gat gtt ctc gtt gat gga ggg tac tct gtg     1354
Ser Tyr Thr Thr Gly Glu Asp Val Leu Val Asp Gly Gly Tyr Ser Val
        260                 265                 270 tgg tga atggagggg acgagggaca ggggcgtcgc gacggccgcg ccgtgcaggg       1410
Trp cataataaac tatccactac acactggcac tctatagata ttccaaccac tcaacactag   1470
acgacactgt aacctataag taatactgta tatgctatct actacaatac accacacaca   1530
cactaggtta cacataacac catatcggat acagtgtata ccctccatct acatatggac   1590
accactttg gaagaataca tgactgtcta tgcgacggca gcgggttca aacggccgca    1650
cccacaacgc cgccaccgct acaagggtgc ccgtctcatt atcaacgacg aaatgcgcag   1710
ggtaaattcc ctccccgcag cgacgcgtcc gtccacgacg tacatgtcca ttgccgcccc   1770
tccctctctg cgtcctcctc gtaaatactg cgatatcact ggcctcccag cacactacac   1830
cgctccacat aatcaaatcc gatactttga cagtgaatgc tatcagctcg tgaaaaacat   1890
gccaccaggt gtcgatcagc agtacttatc ccttaggggt gctaacgtta tacttaaata   1950
gtaatactcg ttcgctagtc tattctacat atgtctttaa aaccatttta taccatgcca   2010
aaacgatact atatactata ctatactata ctatactata ctatattaca ctaacactct   2070
cgtataatgg ctctgagctt ctcgctaagc acagcgccct                         2110
```

<210> SEQ ID NO 58
<211> LENGTH: 274
<212> TYPE: PRT
<213> ORGANISM: Issatchenkia orientalis

<400> SEQUENCE: 58

```
Met Ser Val Pro Thr Phe Arg Leu Thr Asn Glu Leu Thr Val Val Thr
1               5                   10                  15

Gly Ala Ser Gly Gly Ile Ala His Ala Leu Val Glu Thr Leu Leu Val
            20                  25                  30
```

Tyr Gly Ala Pro Leu Ala Leu Val Asp Arg Asn Met Glu Ala Leu His
            35                  40                  45

Arg Thr Arg Asp Ala Met Val Arg Phe Cys Val Glu Glu Ala Asn Ile
 50                  55                  60

Lys Glu Glu Asp Val Pro Lys Met Glu Cys Phe Thr Cys Asn Ile Gly
 65                  70                  75                  80

Asp Ala Gly Glu Val Glu Thr Leu Phe Gly Glu Ile Tyr Asn Val Phe
                     85                  90                  95

Gln Arg Tyr Pro Leu His Met Val Asn Cys Ala Gly Tyr Cys Glu Asn
                100                 105                 110

Phe Ala Ala Val Asp Tyr Pro Ala Gln Asn Ala His Asp Leu Met Gly
            115                 120                 125

Val Asn Leu Leu Gly Ala Phe Tyr Leu Ser Gln Cys Phe Ala Lys Pro
130                 135                 140

Leu Ile Glu His Asn Ile Ser Gly Gly Ser Ile Val Leu Ile Ala Ser
145                 150                 155                 160

Met Ser Gly Lys Ile Val Asn Thr Pro Gln Asn Gln Cys Ile Tyr Asn
                165                 170                 175

Ala Ser Lys Ala Gly Val Ile His Leu Ala Lys Ser Leu Ala Ala Glu
            180                 185                 190

Trp Gly Ala Leu Met His Pro Ile Arg Val Asn Thr Leu Ser Pro Gly
        195                 200                 205

Tyr Thr Ala Thr Pro Leu Thr Arg Asn Val Val Ser Gly Asp Ala Ser
        210                 215                 220

Leu Ala Ala Glu Trp Thr Arg Arg Val Pro Leu Gly Arg Met Ala His
225                 230                 235                 240

Pro Arg Glu Met Ala Gly Ala Val Leu Phe Leu Leu Ala Asn Asp Ala
                245                 250                 255

Ser Ser Tyr Thr Thr Gly Glu Asp Val Leu Val Asp Gly Gly Tyr Ser
                260                 265                 270

Val Trp

<210> SEQ ID NO 59
<211> LENGTH: 3098
<212> TYPE: DNA
<213> ORGANISM: Issatchenkia orientalis
<220> FEATURE:
<221> NAME/KEY: CDS
<222> LOCATION: (1001)..(2098)

<400> SEQUENCE: 59
tcgtttgttg ttgtcccctt tgagttggtg aagatccggt tacaggataa gtccaaggcg      60
tccatgtata gcggtcccat tgatgttcta atgaagacag tcaaaaatga aggtatcttg     120
gccttgtata acggattaga ggcaacactg tggagacata ttgtatggaa tgccggctat     180
tttggtgtga ttttccaagt tcgtgacatg ttacccaagg caaaggacaa gacccagaaa     240
accatcaacg atttggtggg tggtatgatt ggtggtatcg ttggtactgc cttgaacatt     300
ccattcgatg ttgtcaaatc cagaatccaa agtgcaacca ttatggaagg tcaggtccgt     360
aaatacaatt ggacttggcc ctctcttggc attgtcttga gggaagaagg tgtctctgca     420
ttgtataaag gattccttcc aaaagtcctg agattgggtc caggtggtgg tattctactt     480
gttgtcttca caaactgtat ggacttcttt agaggccaat actatggaga caagaaatag     540
tagctgggtt cttcaccatc aggtttatac accctccacg acgtccattc tatactatac     600

-continued

```
tatgctattc gatgctattc gatgctatcc tgccctatct tatctaatct tatcttatct    660
tacaaaatta tatactttcc ttgtttcttt cacctcctcc tttatagatc aattgatttg    720
ataatacact tatacacatt gacgtctgtt gacatcttca tacaaaaaac cttaaaacat    780
agtgcaaagt cacgtgcacg ccttaaaaat gcagctgagc ccctttccca cttctctccc    840
ttcggatgcc ccacctgact attttcactt cccaattcga gcatcctcct ccagtccccg    900
cagactcaag agataagaaa ccttacagag actgttccca tcctcctatg ctcaacgtgt    960
cctgtatcta cattacacac cctctcgatt cgctacagct atg acc att gac cct     1015
                                             Met Thr Ile Asp Pro
                                              1               5 aca ctt gat tta aac aac ttg aaa gag gac aat ccc agt gtt gta ctt     1063
Thr Leu Asp Leu Asn Asn Leu Lys Glu Asp Asn Pro Ser Val Val Leu
             10              15              20 gag aaa atc ggg gaa atc cgc ttt gag gag aga cct gtt cct gaa atc     1111
Glu Lys Ile Gly Glu Ile Arg Phe Glu Glu Arg Pro Val Pro Glu Ile
         25              30              35 tcc gag cca aac tat gtc aag att gca atc aca cat act gga cta tgt     1159
Ser Glu Pro Asn Tyr Val Lys Ile Ala Ile Thr His Thr Gly Leu Cys
     40              45              50 gga tcc gat gtc cac tat tac gag cac ggt tct tgt gga tcc ttc aag     1207
Gly Ser Asp Val His Tyr Tyr Glu His Gly Ser Cys Gly Ser Phe Lys
 55              60              65 gtc gaa tct cca atg gtg tta ggc cat gaa tcg gca ggg ata att gtc     1255
Val Glu Ser Pro Met Val Leu Gly His Glu Ser Ala Gly Ile Ile Val
 70              75              80              85 caa gtt ggc gac agc gtt aca cgg ttg aag ccg gga gac cga gtt gca     1303
Gln Val Gly Asp Ser Val Thr Arg Leu Lys Pro Gly Asp Arg Val Ala
             90              95             100 tgc gaa cca ggt gtt ccc tca aga ctc tcc aag gaa tac aag gcc ggc     1351
Cys Glu Pro Gly Val Pro Ser Arg Leu Ser Lys Glu Tyr Lys Ala Gly
        105             110             115 aac tac aac ttg tgc ccc cac atg gcg ttt gca gca aca ccg ccc tac     1399
Asn Tyr Asn Leu Cys Pro His Met Ala Phe Ala Ala Thr Pro Pro Tyr
    120             125             130 gac ggc aca ctc tgc aga tac tat gta ttg ccg gag gat ttt gtc gtc     1447
Asp Gly Thr Leu Cys Arg Tyr Tyr Val Leu Pro Glu Asp Phe Val Val
135             140             145 aaa tta cca gat cat gtc tca cta gaa gaa ggt gcg ttg gtg gaa cct     1495
Lys Leu Pro Asp His Val Ser Leu Glu Glu Gly Ala Leu Val Glu Pro
150             155             160             165 cta tct gtt ggt gta cat gca aac aga cta att gat gtg aaa ttc gga     1543
Leu Ser Val Gly Val His Ala Asn Arg Leu Ile Asp Val Lys Phe Gly
            170             175             180 gat tcg atg gtg gtg ttt gga gca gga cca gtt gga ctt ctt gcc gct     1591
Asp Ser Met Val Val Phe Gly Ala Gly Pro Val Gly Leu Leu Ala Ala
        185             190             195 ggt gtc gcc aag gcg ttt ggc tgc gat aag gtt ctc att gtc gat att     1639
Gly Val Ala Lys Ala Phe Gly Cys Asp Lys Val Leu Ile Val Asp Ile
    200             205             210 gtg aat gag aaa tta gac ttt gca gtg caa cac aag ttg gca aca cat     1687
Val Asn Glu Lys Leu Asp Phe Ala Val Gln His Lys Leu Ala Thr His
215             220             225 tgt ttc aac tca aaa ggg aaa act ttt gaa gat ttg ctt gca tgt att     1735
Cys Phe Asn Ser Lys Gly Lys Thr Phe Glu Asp Leu Leu Ala Cys Ile
230             235             240             245 aaa gac atc tgg gac gag gac gaa ttg cca act tgt ggc atc gac gcc     1783
Lys Asp Ile Trp Asp Glu Asp Glu Leu Pro Thr Cys Gly Ile Asp Ala
            250             255             260
```

```
acg ggg aac cag tat tgc atc aac atg tgc att cga tcc cta gcc aag    1831
Thr Gly Asn Gln Tyr Cys Ile Asn Met Cys Ile Arg Ser Leu Ala Lys
            265                 270                 275 aag gga aga ttt gtg cag gtc ggg atg ggc ggc gac act ctg gac aag    1879
Lys Gly Arg Phe Val Gln Val Gly Met Gly Gly Asp Thr Leu Asp Lys
        280                 285                 290 ttc ccc ata gcg gcc gtt ttg gag aag gag ttg acg gtg aag ggc tcg    1927
Phe Pro Ile Ala Ala Val Leu Glu Lys Glu Leu Thr Val Lys Gly Ser
    295                 300                 305 ttt agg tac tct gtt gat gac tac aag tat tct gtc cag ttg ttg aag    1975
Phe Arg Tyr Ser Val Asp Asp Tyr Lys Tyr Ser Val Gln Leu Leu Lys
310                 315                 320                 325 gat ggg aaa atc aat gtt cgg cct ttg atc acc cat cgc ttc aag ttt    2023
Asp Gly Lys Ile Asn Val Arg Pro Leu Ile Thr His Arg Phe Lys Phe
                330                 335                 340 gaa cag gcc gtg gag gcg tat gag ttt tct aaa caa ggc aag agt atc    2071
Glu Gln Ala Val Glu Ala Tyr Glu Phe Ser Lys Gln Gly Lys Ser Ile
            345                 350                 355 aag atc atg atc gaa gga cct cca taa agagggtctg atggatcagt         2118
Lys Ile Met Ile Glu Gly Pro Pro
        360                 365 tggctcttat atatatataa tatatatata tatatatata tatagatgta tacaatatgt  2178
ctctttcata tacctatata tctacgtgtt tagcatttcc tatatacatg actctggttt  2238
tcatttcgtt tggttctcat tcctcttggc agcttcacta acaactggt cgtgttgttc   2298 gtcgtgtttt gccttgaaga atgtatagtg caacacaacg tcttcgatgt ttctcattgc  2358
cggatctctg gaaaactctg gatcgataaa gaaaaacaag ggcatatcaa cctcctcacc  2418
cttggccaac cgctgctctt caaagcagaa acactggatc ttgttgaagt aaggcgctac  2478
atgatcggga gtcactgagt atgtggccat gccagtaatg tccttgtcac ttatattctt  2538
ggctttgtag aaggccaagg cagtctctcc ggggacaaca taaacttctc tttgttgcgg  2598
tacaaacttc catggtaacg caccacttgt ctccgccgta aaggatacccc gcagtcttct  2658 ctctgtagct actggagtta gcttgtccct cgtgaacctg ctcttgtcgg tgattggtgt  2718 accacccat  ccagtacgtt gacaaattgc acgatacaag gggacactcg catacgataa  2778
tgcaaggaaa atcatcatca tggataacga ataataaatg gtggtttgcc tctcataccct  2838 cttctttct  ctatggtact tatctctcaa tgcttggaac tctgccaaag acatctttgg  2898
aagctccttc cggtttgctc gtggtgatac ctgatgttct gacgacccac caccaggaac  2958
ttcgtatttt gcaatacaac tggcatgtac atatctccta tgaagggcaa gtccgggaat  3018
cagcccaaca tcccgaaggg gcgcttgtat actagttctg aaaatccgcc ttaacatcac  3078
cgtacagaga caccttcacc                                             3098

<210> SEQ ID NO 60
<211> LENGTH: 365
<212> TYPE: PRT
<213> ORGANISM: Issatchenkia orientalis

<400> SEQUENCE: 60

Met Thr Ile Asp Pro Thr Leu Asp Leu Asn Asn Leu Lys Glu Asp Asn
1               5                   10                  15

Pro Ser Val Val Leu Glu Lys Ile Gly Glu Ile Arg Phe Glu Glu Arg
            20                  25                  30

Pro Val Pro Glu Ile Ser Glu Pro Asn Tyr Val Lys Ile Ala Ile Thr
        35                  40                  45
```

```
His Thr Gly Leu Cys Gly Ser Asp Val His Tyr Tyr Glu His Gly Ser
 50                  55                  60

Cys Gly Ser Phe Lys Val Glu Ser Pro Met Val Leu Gly His Glu Ser
 65                  70                  75                  80

Ala Gly Ile Ile Val Gln Val Gly Asp Ser Val Thr Arg Leu Lys Pro
                 85                  90                  95

Gly Asp Arg Val Ala Cys Glu Pro Gly Val Pro Ser Arg Leu Ser Lys
            100                 105                 110

Glu Tyr Lys Ala Gly Asn Tyr Asn Leu Cys Pro His Met Ala Phe Ala
        115                 120                 125

Ala Thr Pro Pro Tyr Asp Gly Thr Leu Cys Arg Tyr Tyr Val Leu Pro
130                 135                 140

Glu Asp Phe Val Val Lys Leu Pro Asp His Val Ser Leu Glu Glu Gly
145                 150                 155                 160

Ala Leu Val Glu Pro Leu Ser Val Gly Val His Ala Asn Arg Leu Ile
                165                 170                 175

Asp Val Lys Phe Gly Asp Ser Met Val Val Phe Gly Ala Gly Pro Val
            180                 185                 190

Gly Leu Leu Ala Ala Gly Val Ala Lys Ala Phe Gly Cys Asp Lys Val
        195                 200                 205

Leu Ile Val Asp Ile Val Asn Glu Lys Leu Asp Phe Ala Val Gln His
210                 215                 220

Lys Leu Ala Thr His Cys Phe Asn Ser Lys Gly Lys Thr Phe Glu Asp
225                 230                 235                 240

Leu Leu Ala Cys Ile Lys Asp Ile Trp Asp Glu Asp Leu Pro Thr
                245                 250                 255

Cys Gly Ile Asp Ala Thr Gly Asn Gln Tyr Cys Ile Asn Met Cys Ile
            260                 265                 270

Arg Ser Leu Ala Lys Lys Gly Arg Phe Val Gln Val Gly Met Gly Gly
        275                 280                 285

Asp Thr Leu Asp Lys Phe Pro Ile Ala Ala Val Leu Glu Lys Glu Leu
290                 295                 300

Thr Val Lys Gly Ser Phe Arg Tyr Ser Val Asp Asp Tyr Lys Tyr Ser
305                 310                 315                 320

Val Gln Leu Leu Lys Asp Gly Lys Ile Asn Val Arg Pro Leu Ile Thr
                325                 330                 335

His Arg Phe Lys Phe Glu Gln Ala Val Glu Ala Tyr Glu Phe Ser Lys
            340                 345                 350

Gln Gly Lys Ser Ile Lys Ile Met Ile Glu Gly Pro Pro
        355                 360                 365

<210> SEQ ID NO 61
<211> LENGTH: 3143
<212> TYPE: DNA
<213> ORGANISM: Issatchenkia orientalis
<220> FEATURE:
<221> NAME/KEY: CDS
<222> LOCATION: (1001)..(2143)

<400> SEQUENCE: 61
agtagatttc ccaaatcctg catgactcta gcaagaagac attagaaaag cagtgcgggg      60
aatgaaggaa cctttcattg tatttctttt ttttttttt  tttttttttt accgtttacg     120
actaaaataa ccccatggag agactatttt ggaatgacta ctaaagtggg aggaaaaaaa    180
aataacgagc tgcatatagt acgactcaac tggaactaga tggaactaga tggaactaaa    240
```

```
tggaacaaca aaagaatggg ctgtctatac tgtgtcatcc tttaacattt tttttccctt    300
tgtccattta tccttttaca tagtgcacag agagactgcc ttaatgacac tatttcagta    360
gactaaacgc attcgaccta gaatgttccg gcccggaagg aacggcacgg ccgagaacaa    420
acaaggagag agggagtcga aaagggaaa aaaaaagga aaaaaaaaa aggaaaaaaa       480 aaaaagaaa ggcccttagt tcctcttccc tttcttcccc cctccctgtg ttcaattccc     540
gcaaggacat gaacaccaca tcgtaaatac ctttccattt cttatttccc ttactccacc   600 ccagccccc ccatttttcg ctgcatttac ctccatttct gtccctctct ataagaggcg    660
ctgatctcaa tgcagtcaa tttcaatgtt tctttgtttt tccccatatt ggtgcataca    720
cattgttaat ctcttaattt aaaagtgcgc ttcctctaat ggtgttcttt tcatttaaat   780
aggtctaggt atcctttgtc tctccattct ttacttggtt ttattaaact tgctctctct   840
tgttttttac ttgtttttac ttgtctttac taatctttgc ttctttcctt tcttacttcc   900
ataactaata aacaatagac acgctggtcc atctactgat cattaccttc tgtttctatc   960
cattcgtaaa cataaaaaca agcacgactc caacattacc atg aaa ggc cta tta    1015
                                              Met Lys Gly Leu Leu
                                              1               5 tat tat gga aga gaa gag atc cgc tac tca gaa gac att ccc gaa cca    1063
Tyr Tyr Gly Arg Glu Glu Ile Arg Tyr Ser Glu Asp Ile Pro Glu Pro
         10                  15                  20 caa att aaa aac cca aac gac gtc aag gtc aag att gcc tat tgt ggc    1111
Gln Ile Lys Asn Pro Asn Asp Val Lys Val Lys Ile Ala Tyr Cys Gly
     25                  30                  35 atc tgt ggt act gat ttg cac gag ttt tta gat ggt cct att ttt ttc    1159
Ile Cys Gly Thr Asp Leu His Glu Phe Leu Asp Gly Pro Ile Phe Phe
         40                  45                  50 cca cag cca aat ggc cgt tcc gaa ata tcc ggt aaa aaa ttg cct ctt    1207
Pro Gln Pro Asn Gly Arg Ser Glu Ile Ser Gly Lys Lys Leu Pro Leu
 55                  60                  65 tgt cca ggt cat gaa ttt tcc ggt gtt att gaa gaa gtt ggc act ggt    1255
Cys Pro Gly His Glu Phe Ser Gly Val Ile Glu Glu Val Gly Thr Gly
 70                  75                  80                  85 gtc acc aag ttt caa agg gga gac cgt gtt gtt gtt gaa gca acg tcc    1303
Val Thr Lys Phe Gln Arg Gly Asp Arg Val Val Val Glu Ala Thr Ser
         90                  95                 100 cat tgc tcc gac aga gaa cgg tat aag gac gaa att gag gat aag gac    1351
His Cys Ser Asp Arg Glu Arg Tyr Lys Asp Glu Ile Glu Asp Lys Asp
        105                 110                 115 ctc tcc ttt tgt gca gcg tgt aag gca gaa aag cca aat tgc tgt aaa    1399
Leu Ser Phe Cys Ala Ala Cys Lys Ala Glu Lys Pro Asn Cys Cys Lys
        120                 125                 130 cgt ttg tcc ttt gtt gga tta ggt act gac cat ggt gcc ttt ggt caa    1447
Arg Leu Ser Phe Val Gly Leu Gly Thr Asp His Gly Ala Phe Gly Gln
    135                 140                 145 tat gtc gtt tat ggt gaa gac cat atc ttg aag att cca gat gat ttg    1495
Tyr Val Val Tyr Gly Glu Asp His Ile Leu Lys Ile Pro Asp Asp Leu
150                 155                 160                 165 cct ctt gac ttg gct gcc ttg gtg gaa cct cta tcg gtt gca tgg cac    1543
Pro Leu Asp Leu Ala Ala Leu Val Glu Pro Leu Ser Val Ala Trp His
            170                 175                 180 gct gtc agc ttg gcc aac ttt aaa ccg gga caa acg gca gtt gtt tta    1591
Ala Val Ser Leu Ala Asn Phe Lys Pro Gly Gln Thr Ala Val Val Leu
                185                 190                 195 gga ggc ggt cca att gga tta tgt act att ctt gca ttg aag ggc cat    1639
Gly Gly Gly Pro Ile Gly Leu Cys Thr Ile Leu Ala Leu Lys Gly His
```

```
              200                 205                 210
cag gct ggt aag att gtc tgt tcg gaa cct gca gct att aga aga gaa      1687
Gln Ala Gly Lys Ile Val Cys Ser Glu Pro Ala Ala Ile Arg Arg Glu
    215                 220                 225 ttg gct gaa aaa ttg gga gct gaa act ttc aat cca atg gat cat gaa      1735
Leu Ala Glu Lys Leu Gly Ala Glu Thr Phe Asn Pro Met Asp His Glu
230                 235                 240                 245 gac cct att gca gaa ttg aaa aac tta tta cct gaa act gaa ggc ttt      1783
Asp Pro Ile Ala Glu Leu Lys Asn Leu Leu Pro Glu Thr Glu Gly Phe
                250                 255                 260 acc gct tca ttt gat tgt tct ggt att cag aaa act ttt gat act tct      1831
Thr Ala Ser Phe Asp Cys Ser Gly Ile Gln Lys Thr Phe Asp Thr Ser
            265                 270                 275 atc gac gtt ttg ggt cca gga ggt tct gca gtt aat gtt gca att tgg      1879
Ile Asp Val Leu Gly Pro Gly Gly Ser Ala Val Asn Val Ala Ile Trp
        280                 285                 290 cct aat gtc cct atc caa tat gtc cca atg tgt ttg acc tat caa gag      1927
Pro Asn Val Pro Ile Gln Tyr Val Pro Met Cys Leu Thr Tyr Gln Glu
    295                 300                 305 aaa acc gct aca ggt tcc atg tgt tat gtc act aag gat ttc agg gaa      1975
Lys Thr Ala Thr Gly Ser Met Cys Tyr Val Thr Lys Asp Phe Arg Glu
310                 315                 320                 325 gtt ctt gat gcc att gca gca ggt ctc att gac cag aag tca atg agg      2023
Val Leu Asp Ala Ile Ala Ala Gly Leu Ile Asp Gln Lys Ser Met Arg
                330                 335                 340 ttg ttg gtg act ggt aaa gtt gaa gct aag gac gga atc gaa ggc ggg      2071
Leu Leu Val Thr Gly Lys Val Glu Ala Lys Asp Gly Ile Glu Gly Gly
            345                 350                 355 ttc atg caa ttg atc aac cac aag gaa aca aac gtc aag att ttg att      2119
Phe Met Gln Leu Ile Asn His Lys Glu Thr Asn Val Lys Ile Leu Ile
        360                 365                 370 gcg cca aac gga ctc gat atg tga tggagaatga ccatgttgtc catcattatg     2173
Ala Pro Asn Gly Leu Asp Met
    375                 380 tttgtcgttt gctctcattt gtctaagttg caacatgtaa tctcgtgcaa cactttcaac    2233
tttccttctt ctctttaact ttttcaattc ctgtattaat ctaattaatt taatgaactc    2293
tttataaagg taaagctaaa ccaagcgcaa aagtatcaat aataacctca aataaagtaa    2353
aaaattgaaa gaaataaacc atggggcgtg atattaacgg aacaaaatta ttatctgtgt    2413
agtcacatgt accgcgtcaa gtacttgcaa ataatcaaag tggtgtttaa acatcaccac    2473
catgcatcct tcttcctcta tgttgaagaa taccctattg gttagacgtt gttgatggcc    2533
aggatgcaag cttcgacccc tgtattaccg ccaattggat cagtgataag tttgcctaat    2593
tcaagcgata ttgcaatatt aaagtatgtc ggatcagtcg acaatcatga tggtgtgttc    2653
tgtggactgg agctatgtgg agccctggca tcaagtggta aaaacgacgg catcatcaat    2713
ggcattgagt atttccaagt cagtgtgcca aaaagtggct tatttgtacc attgagaaaa    2773
atacttggtt ggttatcaca tactcatact caaccacaac cacaaccaca accacaatca    2833
ttaccgcaat cacaaccact attacaaccg caattactac cccaaccaaa ctcggtatca    2893
atagagtcaa cttcttcagg gtctgttgct gctactaagg aaatagagga actaaagcga    2953
catatcattt cgcttgagaa acagctccta ctacgtgaaa atgacctgaa agagttagat    3013
atccagttgg acgagttgga tgcaactctg agatctaatg atgcacgatt ggccaggaag    3073
gaggagcgtt tcaatagata caaggttgaa aaggaggagg aaatctcaat gttgctaaca    3133
acaattgaat                                                           3143
```

<210> SEQ ID NO 62
<211> LENGTH: 380
<212> TYPE: PRT
<213> ORGANISM: Issatchenkia orientalis

<400> SEQUENCE: 62

```
Met Lys Gly Leu Leu Tyr Tyr Gly Arg Glu Glu Ile Arg Tyr Ser Glu
1               5                   10                  15
Asp Ile Pro Glu Pro Gln Ile Lys Asn Pro Asn Asp Val Lys Val Lys
            20                  25                  30
Ile Ala Tyr Cys Gly Ile Cys Gly Thr Asp Leu His Glu Phe Leu Asp
        35                  40                  45
Gly Pro Ile Phe Phe Pro Gln Pro Asn Gly Arg Ser Glu Ile Ser Gly
    50                  55                  60
Lys Lys Leu Pro Leu Cys Pro Gly His Glu Phe Ser Gly Val Ile Glu
65                  70                  75                  80
Glu Val Gly Thr Gly Val Thr Lys Phe Gln Arg Gly Asp Arg Val Val
                85                  90                  95
Val Glu Ala Thr Ser His Cys Ser Asp Arg Glu Arg Tyr Lys Asp Glu
            100                 105                 110
Ile Glu Asp Lys Asp Leu Ser Phe Cys Ala Ala Cys Lys Ala Glu Lys
        115                 120                 125
Pro Asn Cys Cys Lys Arg Leu Ser Phe Val Gly Leu Gly Thr Asp His
    130                 135                 140
Gly Ala Phe Gly Gln Tyr Val Val Tyr Gly Asp His Ile Leu Lys
145                 150                 155                 160
Ile Pro Asp Asp Leu Pro Leu Asp Leu Ala Ala Leu Val Glu Pro Leu
                165                 170                 175
Ser Val Ala Trp His Ala Val Ser Leu Ala Asn Phe Lys Pro Gly Gln
            180                 185                 190
Thr Ala Val Val Leu Gly Gly Gly Pro Ile Gly Leu Cys Thr Ile Leu
        195                 200                 205
Ala Leu Lys Gly His Gln Ala Gly Lys Ile Val Cys Ser Glu Pro Ala
    210                 215                 220
Ala Ile Arg Arg Glu Leu Ala Glu Lys Leu Gly Ala Glu Thr Phe Asn
225                 230                 235                 240
Pro Met Asp His Glu Asp Pro Ile Ala Glu Leu Lys Asn Leu Leu Pro
                245                 250                 255
Glu Thr Glu Gly Phe Thr Ala Ser Phe Asp Cys Ser Gly Ile Gln Lys
            260                 265                 270
Thr Phe Asp Thr Ser Ile Asp Val Leu Gly Pro Gly Gly Ser Ala Val
        275                 280                 285
Asn Val Ala Ile Trp Pro Asn Val Pro Ile Gln Tyr Val Pro Met Cys
    290                 295                 300
Leu Thr Tyr Gln Glu Lys Thr Ala Thr Gly Ser Met Cys Tyr Val Thr
305                 310                 315                 320
Lys Asp Phe Arg Glu Val Leu Asp Ala Ile Ala Ala Gly Leu Ile Asp
                325                 330                 335
Gln Lys Ser Met Arg Leu Leu Val Thr Gly Lys Val Glu Ala Lys Asp
            340                 345                 350
Gly Ile Glu Gly Gly Phe Met Gln Leu Ile Asn His Lys Glu Thr Asn
        355                 360                 365
Val Lys Ile Leu Ile Ala Pro Asn Gly Leu Asp Met
    370                 375                 380
```

-continued

<210> SEQ ID NO 63
<211> LENGTH: 2879
<212> TYPE: DNA
<213> ORGANISM: Issatchenkia orientalis
<220> FEATURE:
<221> NAME/KEY: CDS
<222> LOCATION: (1025)..(1882)

<400> SEQUENCE: 63

```
atctagaagg ttgggcaaaa tatgaacctc aaaatggtgt cattaacgat tccttcccat    60
tgtcagcatt agatagagag gtttattcaa ggggcgtctc aagaattatt ttgacccaag   120
taggtgaggg cccaactcaa acaaacgatg ttttaattga cttagagagc ggattgccaa   180
agtccaatta gacaaaccac cagttacatc aatattctat agactgtttc agttgtttgg   240
cactgcttta tatagtcaga aacttttcgc caatagataa tgttgtagat tttgtttttt   300
gtcgcattac aacagcatgg tttgttgtgg tcacaaaagt aatgttttct ttgctttact   360
atcaaattct acgcttaatc tccgtatttt accaagtaga tattaatgca atcgtgtttt   420
cggtgtatct ggttttagaa gctttattac atcaagaaaa gagcagccag ataacatttc   480
tgaacaaaaa aaaactgttt tttaaattac gaaaaacaga agttttaaa atagttgtag    540
tgtatgacat tgtcgttttg gcatccaatt tcacttttc aatcacaaca cgaattgcaa    600
cttcattcat acagaagaaa aaaaaagtt ggacaacatg cacacaacgt tgatgtctat    660
tacaaaattg aatggatgtg aatagtgatg acaaggtgat tctgactttg taaggaaaga   720
aaaaacatta tcatgaggaa aaactctacg tcatgttaaa tcttttgtac gtaaaggtta   780
tttctagatc tcgaacttga taggttactg acaaggtctt aatgcgggga ggtgtagttt   840
gtggcagata aggtgtcttg gctgtgagtg cgcttccggg aggtgttttc tcggagagac   900
tgaggtacat taatggttta tttcgcacga tattttacgg caaaagataa gtccgtcccc   960
gatgggtacg ccagtaagaa acacactcac tgctgcttag ttctttgccg caaaccaatt  1020
``` gtgt atg ata aaa aga gcc atg act atc gga aag cca att act tta aac    1069
     Met Ile Lys Arg Ala Met Thr Ile Gly Lys Pro Ile Thr Leu Asn
      1               5                  10                  15 aac gga aca aag atc cca ttc atg ggg tta ggt acc tgg gaa atc agt    1117
Asn Gly Thr Lys Ile Pro Phe Met Gly Leu Gly Thr Trp Glu Ile Ser
             20                  25                  30 aat gca gat gtg gtt gtt cgg gaa gca tta aat gtc ggc tat aga tgc    1165
Asn Ala Asp Val Val Val Arg Glu Ala Leu Asn Val Gly Tyr Arg Cys
         35                  40                  45 atc gat acc gct gtt ttg tat gga aat gag aag ttg tgc gga gat ggt    1213
Ile Asp Thr Ala Val Leu Tyr Gly Asn Glu Lys Leu Cys Gly Asp Gly
     50                  55                  60 att atc aaa tgg ttg gag tcc gat cct aac aat aag agg gaa gat gtg    1261
Ile Ile Lys Trp Leu Glu Ser Asp Pro Asn Asn Lys Arg Glu Asp Val
 65                  70                  75 tat tac att acc aag tta tgg aac cat cag aat gga tac gag aaa gcg    1309
Tyr Tyr Ile Thr Lys Leu Trp Asn His Gln Asn Gly Tyr Glu Lys Ala
 80                  85                  90                  95 aaa cgt gcc atc agg gag tgc ttt gaa aaa gtc aag ggg tta gga tac    1357
Lys Arg Ala Ile Arg Glu Cys Phe Glu Lys Val Lys Gly Leu Gly Tyr
                100                 105                 110 att gat tta ctt ttg atc cat tcg ccg acc gaa ggg cca aga atg agg    1405
Ile Asp Leu Leu Leu Ile His Ser Pro Thr Glu Gly Pro Arg Met Arg
            115                 120                 125

```
ttg gag act tgg aaa gcc atg caa gag gca gtt gac gag ggt atc gtc    1453
Leu Glu Thr Trp Lys Ala Met Gln Glu Ala Val Asp Glu Gly Ile Val
        130                 135                 140 aag tct att ggc gtt tct aac tat ggt att aag cat ttg caa gaa ttg    1501
Lys Ser Ile Gly Val Ser Asn Tyr Gly Ile Lys His Leu Gln Glu Leu
145                 150                 155 tta tca tgg gaa ggc act tat atc aag ccc gtt gcc aac gag atc gag    1549
Leu Ser Trp Glu Gly Thr Tyr Ile Lys Pro Val Ala Asn Glu Ile Glu
160                 165                 170                 175 gtt tct cct tgg tgt atg aga caa gaa cta tgt gac ttt act aaa aaa    1597
Val Ser Pro Trp Cys Met Arg Gln Glu Leu Cys Asp Phe Thr Lys Lys
                180                 185                 190 cac gat att gtg gtt att gcc tat gct ccg cta tca cac agt tat cgt    1645
His Asp Ile Val Val Ile Ala Tyr Ala Pro Leu Ser His Ser Tyr Arg
            195                 200                 205 ctc caa gat aag gac gct gtg gaa atc gca aag aaa aag aac gtt act    1693
Leu Gln Asp Lys Asp Ala Val Glu Ile Ala Lys Lys Lys Asn Val Thr
        210                 215                 220 gtt gcc caa gtc cta atc aga tgg tct cta cag aag ggg tac att cca    1741
Val Ala Gln Val Leu Ile Arg Trp Ser Leu Gln Lys Gly Tyr Ile Pro
225                 230                 235 atc ccg aaa aca aag acc cta gct aga ctt cct gta aat ttg gat gtt    1789
Ile Pro Lys Thr Lys Thr Leu Ala Arg Leu Pro Val Asn Leu Asp Val
240                 245                 250                 255 ttg agt ttc gag ttg agc act gac gaa atg aaa cag ctt gac cac cca    1837
Leu Ser Phe Glu Leu Ser Thr Asp Glu Met Lys Gln Leu Asp His Pro
                260                 265                 270 ttg gaa cac gat cca tcc gat tgg gag gtt aca atg tgt cca taa        1882
Leu Glu His Asp Pro Ser Asp Trp Glu Val Thr Met Cys Pro
            275                 280                 285 ccctcaccat atatgggta gccatacatt tgtaaaccat gtatctctct tgtgaaaccc    1942
ttctgaaacc cccttgtttt cttacagggt tggtccattt cctcctcctc ttcttcttct    2002
tcttttcccc ctttaaatca gataaatagt tacattgtgc atgcagtgtc gattttgttt    2062
tgaaatatgg tatctaacgg gatagtaaat cttctcactc aaggaaattt ccaatattt    2122 ttcttgcggg catttcctcc acctgcaaag aagtttggaa ttgtattata tgtcgacacg    2182
gtacttacag aaccgaacaa ctacacaagg atcacctgaa ggatgtcaga taccgagtct    2242
ctctttgacg gtgggttgtt tgaagaacct gaggagtttc aaagaaagga aattccttca    2302
cattttgcca aatacgaaag aaaataccaa acaccagagt tccatcattc tattgatgaa    2362
atccagctga ggttggttgg caaatccccc ctatgggggc acttgttatg gaatgcaggt    2422
acgtatactg ccaattacat tgaaaagcat cccaaagaag ttaggggaag aaggtggttg    2482
agtttggtgc agcgtctgca ctaccatcgt tactatgtgc cttgaacgga gcagagaggg    2542
tgatatgtac agactatcca gatccagatt tgttgtcgaa catcaagtac aacgttgaac    2602
atctggagta ttcgccggca caagagatca tagacgttga aggtttcatt tggggtaatc    2662
cggttgagga catttcccgc aaactaggcg gcaacggcaa ggccgacttc ctcattatga    2722
gtgacttggt gttcaaccac agcgagcacc acaaactcct caaatcatgc aaggaactca    2782
tccaaccact ggaggagggc aaacccagaa gtggtggtag atgcttggtt gtctggtcac    2842
cgcaccgacc agtgccaaag atggtggaaa acgattt                            2879

<210> SEQ ID NO 64
<211> LENGTH: 285
<212> TYPE: PRT
<213> ORGANISM: Issatchenkia orientalis
```

<400> SEQUENCE: 64

```
Met Ile Lys Arg Ala Met Thr Ile Gly Lys Pro Ile Thr Leu Asn Asn
1               5                   10                  15

Gly Thr Lys Ile Pro Phe Met Gly Leu Gly Thr Trp Glu Ile Ser Asn
            20                  25                  30

Ala Asp Val Val Arg Glu Ala Leu Asn Val Gly Tyr Arg Cys Ile
        35                  40                  45

Asp Thr Ala Val Leu Tyr Gly Asn Glu Lys Leu Cys Gly Asp Gly Ile
    50                  55                  60

Ile Lys Trp Leu Glu Ser Asp Pro Asn Asn Lys Arg Glu Asp Val Tyr
65                  70                  75                  80

Tyr Ile Thr Lys Leu Trp Asn His Gln Asn Gly Tyr Glu Lys Ala Lys
                85                  90                  95

Arg Ala Ile Arg Glu Cys Phe Glu Lys Val Lys Gly Leu Gly Tyr Ile
            100                 105                 110

Asp Leu Leu Leu Ile His Ser Pro Thr Glu Gly Pro Arg Met Arg Leu
        115                 120                 125

Glu Thr Trp Lys Ala Met Gln Glu Ala Val Asp Glu Gly Ile Val Lys
    130                 135                 140

Ser Ile Gly Val Ser Asn Tyr Gly Ile Lys His Leu Gln Glu Leu Leu
145                 150                 155                 160

Ser Trp Glu Gly Thr Tyr Ile Lys Pro Val Ala Asn Glu Ile Glu Val
                165                 170                 175

Ser Pro Trp Cys Met Arg Gln Glu Leu Cys Asp Phe Thr Lys Lys His
            180                 185                 190

Asp Ile Val Val Ile Ala Tyr Ala Pro Leu Ser His Ser Tyr Arg Leu
        195                 200                 205

Gln Asp Lys Asp Ala Val Glu Ile Ala Lys Lys Lys Asn Val Thr Val
    210                 215                 220

Ala Gln Val Leu Ile Arg Trp Ser Leu Gln Lys Gly Tyr Ile Pro Ile
225                 230                 235                 240

Pro Lys Thr Lys Thr Leu Ala Arg Leu Pro Val Asn Leu Asp Val Leu
                245                 250                 255

Ser Phe Glu Leu Ser Thr Asp Glu Met Lys Gln Leu Asp His Pro Leu
            260                 265                 270

Glu His Asp Pro Ser Asp Trp Glu Val Thr Met Cys Pro
        275                 280                 285
```

<210> SEQ ID NO 65
<211> LENGTH: 2873
<212> TYPE: DNA
<213> ORGANISM: Issatchenkia orientalis
<220> FEATURE:
<221> NAME/KEY: CDS
<222> LOCATION: (1001)..(1873)

<400> SEQUENCE: 65

| | |
|---|---|
| accacaatgc ggtatgcggt gaatggactg ctgctctcac tgattgtgct aaatggctca | 60 |
| atggaatggc gagaggcgca aggtatgatg caacatatca gaacgacact ccaattggtt | 120 |
| cttgttctaa cttgtacttg gctgattatt catacttcca acaggaagat gttagacaaa | 180 |
| cctacagaag gtatgttgaa gctcagatgg acgcatacct tcatgaaaag atgaatggat | 240 |
| gggttttttg gtgttggaaa actgaaaact tgattgagtg ggacttccaa aggttggttg | 300 |
| agttgaatat cattcctcag ccgttgaact ctagagaatt ctacaatcaa tgtggttatt | 360 |

```
gattcatctt actttctttt gaaacaaagg aaataggtag aaatcataaa accaacctaa      420
aaacatcaat caaaacaata atactttata ccttacatgc cggtttacct cattttatcc      480
agcatacttt tgctttcggg gggtttggtc taatcagata ttttgtctg tctttactat       540 taatatgcgt tctaaaaggg aacgattgac tgtataccct aataacttta tatttcataa      600
actagaaaaa aagactattt actatactcg gatatgcagt tgaatggttg acgcagttgc      660
tggagcctta gtagaccaga ctaacagtac ggtacgaaga cctgtaaaat agaactagcc      720
gtttctgtgt tgactaatct aggggaagaa aaaactaga cagacaattg catttttaagc     780 tgcagggttc cctttctgtg gtgaatctcc ggggtgagaa caatagaaat gggtttttagc    840 gattggcctg aaattgtctc gggcaggaga tatccttttgg gcattcatgc ttgcattaca    900
agtatataat tgaaagcttg caaccacaac ctattttttg caattagagg tcaggtagaa     960
acttttccac aatgtataac taaacatttc aatcctctca atg acg atc cct tca       1015
                                              Met Thr Ile Pro Ser
                                                1               5 tat cgt aca ctt aat tca ggt cac aaa ata cca agt att gca ttg ggt       1063
Tyr Arg Thr Leu Asn Ser Gly His Lys Ile Pro Ser Ile Ala Leu Gly
             10                  15                  20 gtc tat cag aca ccg cca cac gag act gca gca gtg gtg ttt gcc gcc       1111
Val Tyr Gln Thr Pro Pro His Glu Thr Ala Ala Val Val Phe Ala Ala
         25                  30                  35 tta gaa agt gga tat cgg cac att gat tgt gca cag ttt tat gaa aat       1159
Leu Glu Ser Gly Tyr Arg His Ile Asp Cys Ala Gln Phe Tyr Glu Asn
     40                  45                  50 gag gag gaa gca tgc cga ggt ata gca aaa tgg att gcc aaa gac ccc       1207
Glu Glu Glu Ala Cys Arg Gly Ile Ala Lys Trp Ile Ala Lys Asp Pro
 55                  60                  65 agc aga aac aag aga gag cat gtc ttc tac acg act aag atc ttt gac       1255
Ser Arg Asn Lys Arg Glu His Val Phe Tyr Thr Thr Lys Ile Phe Asp
 70                  75                  80                  85 cca gat cac ggt tac gca agg aca aac aaa gcc att gaa ctt tca ctt       1303
Pro Asp His Gly Tyr Ala Arg Thr Asn Lys Ala Ile Glu Leu Ser Leu
         90                  95                 100 gag aga gca aaa gaa att ggt tac att gat cta ctc tta ctt cat tct       1351
Glu Arg Ala Lys Glu Ile Gly Tyr Ile Asp Leu Leu Leu Leu His Ser
        105                 110                 115 cca cag tct gat tac gag aga aga cat ggt tcg tgg atg gcg ttt cag      1399
Pro Gln Ser Asp Tyr Glu Arg Arg His Gly Ser Trp Met Ala Phe Gln
        120                 125                 130 gag ttt gta gaa tca ggt aaa gtc aag agt atc ggc gtt tcc aat tat      1447
Glu Phe Val Glu Ser Gly Lys Val Lys Ser Ile Gly Val Ser Asn Tyr
    135                 140                 145 ggt att aaa cac ctc aag gaa tta ctt gaa tac cct gac ttg aaa acc      1495
Gly Ile Lys His Leu Lys Glu Leu Leu Glu Tyr Pro Asp Leu Lys Thr
150                 155                 160                 165 aag cca gca gtg aac caa ctc gaa ctt cat cca tgg ttg aca agg aat      1543
Lys Pro Ala Val Asn Gln Leu Glu Leu His Pro Trp Leu Thr Arg Asn
                170                 175                 180 gat ttg acc gcg tac act gcg aac cag ggt cta cta gtg gaa gct tat      1591
Asp Leu Thr Ala Tyr Thr Ala Asn Gln Gly Leu Leu Val Glu Ala Tyr
            185                 190                 195 acc ccg ttg gta agg gct agg aag atg gat gat ccc acc ctg ctc aaa      1639
Thr Pro Leu Val Arg Ala Arg Lys Met Asp Asp Pro Thr Leu Leu Lys
        200                 205                 210 gta gca gag gac cat aac aga aca cct gca cag atc ctc atc aat tgg      1687
Val Ala Glu Asp His Asn Arg Thr Pro Ala Gln Ile Leu Ile Asn Trp
```

```
                   215                 220                 225
tcg ctt tcc aag ggg ttt att cct ctt cca aag acc gcc aca gtt tca      1735
Ser Leu Ser Lys Gly Phe Ile Pro Leu Pro Lys Thr Ala Thr Val Ser
230                 235                 240                 245 aga ttg gca tct aac ttt gag gcc atg caa ttc caa cta tct aaa aaa      1783
Arg Leu Ala Ser Asn Phe Glu Ala Met Gln Phe Gln Leu Ser Lys Lys
                250                 255                 260 cag gtt gac acc cta gat gcc ctc aat gag ggc atg cac att tgc tgg      1831
Gln Val Asp Thr Leu Asp Ala Leu Asn Glu Gly Met His Ile Cys Trp
            265                 270                 275 aat cct agc act tat cct cta gat aat gag aga caa gct tag              1873
Asn Pro Ser Thr Tyr Pro Leu Asp Asn Glu Arg Gln Ala
        280                 285                 290 tcgatgtaag tacgtctata aagcccgtag gcatcacgta acagctatat gtgtcactct    1933
tctgtaacaa tcatgtatat gcattcatag gaatggaaac gtcaaaagga attggttgtt    1993
cgcctaagta atgtaaaacg tctcgggtat tacccgataa aagcgaggtc ttttttttc     2053 ttttcagatt atttgagttt tctataagaa gcagacattg ctttatcttc ctgtagcaat    2113
agattcattc ataccettgg atgtactctg tacaagctat acatttctct ctaaataaga    2173
taactctaac gtgtttactt ggacttgaag aagacagaca ttaggaagga aaaaaaagga    2233
tttttaattt catctcaaca aaaaatggcc aaaaaaagag aatgccccat tgtttagaa     2293 gatatcacct ctaatgatcc ttcatataca ttgacaatac cctgcaagca tttttatcac    2353
aagtcgtgca ttctttcatg gacctcaaaa tcagcatcta cctgtcctca gtgccgaaat    2413
gagctaacgt cattattcac gccagctgat cagaagacta taaagatcaa ccataaagta    2473
caggataaac tggttgactt gatcaataat cacccatctg aaccgtcgtc gtctatcatt    2533
tctacaaatg gactatcaca tatagaaatt aatacagaat cggctttatc aagaccaaac    2593
ggcccacttt tttcaaatac acaccaacag gtacaacaac agttaaacac aaatatcagg    2653
catttgtcta atcagcaatg cagtatttgc gataatacag tactcattac acaactgata    2713
atatgtccac agtgttcagg tttgtaccat cgctcatgtt gtgatggtct taattgcccc    2773
ttttgcgaag aatggatcga tgatttagct tgttcaaccg tgaccacaaa gaagaggaaa    2833
actttggatc gatcagctga tgatactcaa tactatacaa                          2873

<210> SEQ ID NO 66
<211> LENGTH: 290
<212> TYPE: PRT
<213> ORGANISM: Issatchenkia orientalis

<400> SEQUENCE: 66

Met Thr Ile Pro Ser Tyr Arg Thr Leu Asn Ser Gly His Lys Ile Pro
1               5                  10                  15

Ser Ile Ala Leu Gly Val Tyr Gln Thr Pro Pro His Glu Thr Ala Ala
            20                  25                  30

Val Val Phe Ala Ala Leu Glu Ser Gly Tyr Arg His Ile Asp Cys Ala
        35                  40                  45

Gln Phe Tyr Glu Asn Glu Glu Ala Cys Arg Gly Ile Ala Lys Trp
    50                  55                  60

Ile Ala Lys Asp Pro Ser Arg Asn Lys Arg Glu His Val Phe Tyr Thr
65                  70                  75                  80

Thr Lys Ile Phe Asp Pro Asp His Gly Tyr Ala Arg Thr Asn Lys Ala
                85                  90                  95

Ile Glu Leu Ser Leu Glu Arg Ala Lys Glu Ile Gly Tyr Ile Asp Leu
```

```
                    100                 105                 110
Leu Leu Leu His Ser Pro Gln Ser Asp Tyr Glu Arg Arg His Gly Ser
            115                 120                 125

Trp Met Ala Phe Gln Glu Phe Val Glu Ser Gly Lys Val Lys Ser Ile
130                 135                 140

Gly Val Ser Asn Tyr Gly Ile Lys His Leu Lys Glu Leu Leu Glu Tyr
145                 150                 155                 160

Pro Asp Leu Lys Thr Lys Pro Ala Val Asn Gln Leu Glu Leu His Pro
                165                 170                 175

Trp Leu Thr Arg Asn Asp Leu Thr Ala Tyr Thr Ala Asn Gln Gly Leu
            180                 185                 190

Leu Val Glu Ala Tyr Thr Pro Leu Val Arg Ala Arg Lys Met Asp Asp
        195                 200                 205

Pro Thr Leu Leu Lys Val Ala Glu Asp His Asn Arg Thr Pro Ala Gln
    210                 215                 220

Ile Leu Ile Asn Trp Ser Leu Ser Lys Gly Phe Ile Pro Leu Pro Lys
225                 230                 235                 240

Thr Ala Thr Val Ser Arg Leu Ala Ser Asn Phe Glu Ala Met Gln Phe
                245                 250                 255

Gln Leu Ser Lys Lys Gln Val Asp Thr Leu Asp Ala Leu Asn Glu Gly
            260                 265                 270

Met His Ile Cys Trp Asn Pro Ser Thr Tyr Pro Leu Asp Asn Glu Arg
        275                 280                 285

Gln Ala
    290

<210> SEQ ID NO 67
<211> LENGTH: 5331
<212> TYPE: DNA
<213> ORGANISM: Issatchenkia orientalis
<220> FEATURE:
<221> NAME/KEY: CDS
<222> LOCATION: (1001)..(1882)
<220> FEATURE:
<221> NAME/KEY: CDS
<222> LOCATION: (3469)..(4332)

<400> SEQUENCE: 67
taatatggga aagtccttgc gtggttgtgc acacttctct atttgacatc tagatttccc      60
caattgtgga caaattatac attgaagaca caaaaggggt atcactgaaa ttgatcactt     120
ttgcattgtt tgggaactta ttctattcaa tgtctctact attatctgag aattcattga     180
gaggcgggga agaatcaaag gagttttgga aggccgaatt gagttacttt ttaggggcaa     240
tcggaacagt attgtttgat tttattgcaa ttttacaatg gattcattat gacagccaca     300
gtaatcgtac caatcatatc caatctgtga ggttgaaagc ttacacccct aaatcattaa     360
aaagccagac aattcccaaa tcggtgccat tgatacattc acgtacatcg tccatgagag     420
atggtacaaa gatagatccc atcgaaatgg cggctagcgt caagtcaaca ttgtcacccc     480
agaatgtacg caaactcaat gagttcacac cattgtctcc tatggattta ttgctagatg     540
aacatatttc acgcagttat gtttcctcta ctgatacaaa actataccct cagaagaaga     600
gacctgatag tatcaagtct gtacacaggc acaacgagga cctgctaatg acattcgaag     660
aatagaagca gtcccaattt aaaccgtggc cgtggtaaca gccataactg tagccacaat     720
tggaaaattat ggatgtattg tctgatttgg acctccgggg cagggacaat ggacttggcc    780
aaagagtcga aaaaaatgtt caacagacga gataattggt ctttaattgt ctcggacatg     840
```

```
tgatttcctt aaaagtttaa tttcacaccc gcaggtttat ttatataaaa gtgtggccac    900
aagtcttggg aagatgaaca tcttgatatt catgtcccct ctcatttttct gagactggca   960 taagataagt agaaagcttt tgtaatcgaa taacatcata atg gca att gca acc     1015
                                              Met Ala Ile Ala Thr
                                              1               5 cac ctt aca ttg aat tca ggt tac cag att cca acc att gcg ttg ggt    1063
His Leu Thr Leu Asn Ser Gly Tyr Gln Ile Pro Thr Ile Ala Leu Gly
                10                  15                  20 gtc tac caa aca cca cca gag gag act gag aag atc gtt ctt gct gct    1111
Val Tyr Gln Thr Pro Pro Glu Glu Thr Glu Lys Ile Val Leu Ala Ala
            25                  30                  35 ttg gag gcc ggt tat cgc cat att gac agt gcc caa tac tac cac aac    1159
Leu Glu Ala Gly Tyr Arg His Ile Asp Ser Ala Gln Tyr Tyr His Asn
        40                  45                  50 gaa gaa gat gtt gca aag gca att gca aag tgg att gcc gaa gat cct    1207
Glu Glu Asp Val Ala Lys Ala Ile Ala Lys Trp Ile Ala Glu Asp Pro
    55                  60                  65 gct cac aac aaa agg gag gac att ttt tac acc acc aag atc tac gac    1255
Ala His Asn Lys Arg Glu Asp Ile Phe Tyr Thr Thr Lys Ile Tyr Asp
70                  75                  80                  85 caa gac cac ggg tat gag aag acc aaa aaa gct gtt gaa gtt tct ctt    1303
Gln Asp His Gly Tyr Glu Lys Thr Lys Lys Ala Val Glu Val Ser Leu
                90                  95                 100 gaa agg gca aag gac att gac tac atc gac ttg ctc cta ctc cat tcc    1351
Glu Arg Ala Lys Asp Ile Asp Tyr Ile Asp Leu Leu Leu Leu His Ser
            105                 110                 115 ccc caa tcc gac tac gaa agg aga cat ggc tcc tgg ttg gca ttc cag    1399
Pro Gln Ser Asp Tyr Glu Arg Arg His Gly Ser Trp Leu Ala Phe Gln
        120                 125                 130 gaa ttt gtg gag tcc ggc aag gtc aga agc atc ggt gtc tcc aac tac    1447
Glu Phe Val Glu Ser Gly Lys Val Arg Ser Ile Gly Val Ser Asn Tyr
    135                 140                 145 ggt gtc aag cac atc aag gag ttg ctt gaa tat ccc gac ttg aag att    1495
Gly Val Lys His Ile Lys Glu Leu Leu Glu Tyr Pro Asp Leu Lys Ile
150                 155                 160                 165 aaa ccc gcc gtc aac cag gtc gag ctt cat cca tgg ttg acc aga gag    1543
Lys Pro Ala Val Asn Gln Val Glu Leu His Pro Trp Leu Thr Arg Glu
                170                 175                 180 gac att gtg gac tat gct gcc aaa cac gga atc atc atc gag gcg tac    1591
Asp Ile Val Asp Tyr Ala Ala Lys His Gly Ile Ile Ile Glu Ala Tyr
            185                 190                 195 tct ccc ttg gta aga ggc cag aag atg gac gac cct acg ctt gtg aag    1639
Ser Pro Leu Val Arg Gly Gln Lys Met Asp Asp Pro Thr Leu Val Lys
        200                 205                 210 att gca gag aag tac aac aag act ccc gca cag atc ctc atc aac tgg    1687
Ile Ala Glu Lys Tyr Asn Lys Thr Pro Ala Gln Ile Leu Ile Asn Trp
    215                 220                 225 tcc tta tcc aag ggt tat att ccg ctt cca aaa aca agc aag gtg tct    1735
Ser Leu Ser Lys Gly Tyr Ile Pro Leu Pro Lys Thr Ser Lys Val Ser
230                 235                 240                 245 aga cta gct tct aac ctt gaa gca acg caa ttt gaa tta tcc aag gaa    1783
Arg Leu Ala Ser Asn Leu Glu Ala Thr Gln Phe Glu Leu Ser Lys Glu
                250                 255                 260 gac gtt gac atc ttg agt gca cta aac gaa aat ctc cac acc tgt tgg    1831
Asp Val Asp Ile Leu Ser Ala Leu Asn Glu Asn Leu His Thr Cys Trp
            265                 270                 275 gat cct act gtc tac cca cta gat aac gaa aag gaa gcc gaa aag aag    1879
Asp Pro Thr Val Tyr Pro Leu Asp Asn Glu Lys Glu Ala Glu Lys Lys
```

```
                280             285             290
taa atacgtacct tctgtactta atgtttagtt ttctttcaac tgaatccctg        1932
tgttattgga ttagtatttt cagggaatag ctctgacaga tccttacatt agtttctttg  1992
tagaagtgta gccttttttt tagcggaggt tgcgttttgt cttctcctgt ggaaacctcc  2052
tgaaggttct aagtgacact tgtatctgta tcgaactaag atgttaatcc attggctatg  2112
aatcaaaaca aacagaaagc aaagacgtga tgttaagcat tagtttatgt taaccctaac  2172
tgaaactcac gtggtaactg cagacagaat tatagcttcg ataggtttga atgacagcaa  2232
agggaaaaaa agttaaacta tagttgcagt gaagtcactc catagcggga ataaaatggt  2292
cgtaacaatg aaaagttaa actagaccac tgcaaaccgt tgatagtgac actttttgt    2352 tttcccatgc ttacgttgat acaagtttac aagcagttca atggcagcat gggtaacaga  2412
attctgggta aaccagtaat tcattagcaa aacaaaacct gcagtttact aaaagtttcc  2472
aaaacaaaaa ttttacccaa gattggaact tatactactt gaaccaaatg gacaattttt  2532
ttcttgtttc atagtcgtga gtgtcaagaa tccttttaaa atataaacag cccataggta  2592
gcttctaagt taaatcccg gtagtgaaaa ttatgaggta acatgaagtt aacaggatca   2652
agcccaaaaa acaagtacta ctgtaaacac catcttttg tgttttattt tagatcaaag    2712
cagtaacctt tacgggacat cccaggatta tttcttgcca atacaaagtt gtgttcagga  2772
aaaagtaaaa ttgtcaaata tatttcatat tgatagaaac aaaactctac tcgttctagc  2832
tttgctgttc ttcttattag ttctaccctc tgacctaaaa caacttgatt agataagctt  2892
taagttcctt tacattcatg acactcttag ataaagtatc caatttgcta ggcatttgaa  2952
caaatcacac catcacagtc acttgatacc acaaaacctt cataccataa atgtttcatc  3012
gtttcataag caaccaaaaa gaataaaacg gtcacagaag gctctagtc taatcaaaag   3072 tcaataactc taaggtccat tttacttagc acaataacaa cgataagcga ctaaaatata  3132
acgtactctt tttatactg tcggcatgaa tccggcttat actgaatttt gtgtagctag   3192
tccattacca tttccacctt ctgggcaaat atagttgaaa gccgtttgaa ttatgataga  3252
tttactctta atttcaccaa aaaaggttg ctctgaaaga gcaatagtta tagggttcag   3312
aaaatataag gtgagagtag tgggttgata acaaagagtg attaccttaa tagtgtaccc  3372
acgaagactt taaagggcc caagaatgcc cttatcattc gtttagtatt gatttaatgt   3432
ctgcaaattc agctacagct aaaaaacgta gtccta atg gca att gca acc cac    3486
                                        Met Ala Ile Ala Thr His
                                                            295 ctt aca ttg aat tca ggt tac cag att cca acc att gcg ttg ggt gtc    3534
Leu Thr Leu Asn Ser Gly Tyr Gln Ile Pro Thr Ile Ala Leu Gly Val
300             305                 310                 315 tat caa aca cca cca gag gag act gag aag atc gtt ctt gct gct ttg    3582
Tyr Gln Thr Pro Pro Glu Glu Thr Glu Lys Ile Val Leu Ala Ala Leu
                320                 325                 330 gag gcc ggt tat cgc cat att gac agt gcc caa tac tac cac aat gaa    3630
Glu Ala Gly Tyr Arg His Ile Asp Ser Ala Gln Tyr Tyr His Asn Glu
            335                 340                 345 gaa gat gtt gcc agg gca att gca aag tgg atc gcc aaa aat cca gct    3678
Glu Asp Val Ala Arg Ala Ile Ala Lys Trp Ile Ala Lys Asn Pro Ala
        350                 355                 360 cac aac aaa agg aag aat atc ttc tat act acg aag atc tat gac cag    3726
His Asn Lys Arg Lys Asn Ile Phe Tyr Thr Thr Lys Ile Tyr Asp Gln
    365                 370                 375 cat gta tat gag aaa acc aaa aaa gct gtt gaa gtt tct ctt gaa agg    3774
```

```
                His Val Tyr Glu Lys Thr Lys Lys Ala Val Glu Val Ser Leu Glu Arg
                380                 385                 390                 395 gca aag gac att gac tac atc gac ttg ctc cta ctc cat tcc ccc caa         3822
Ala Lys Asp Ile Asp Tyr Ile Asp Leu Leu Leu Leu His Ser Pro Gln
                400                 405                 410 tcc gac tac gaa agg aga cat ggc tcc tgg ttg gca ttc cag gaa ttt         3870
Ser Asp Tyr Glu Arg Arg His Gly Ser Trp Leu Ala Phe Gln Glu Phe
                415                 420                 425 gtg gag tcc ggc aag gtc aga agc atc ggt gtc tcc aac tat ggt gtc         3918
Val Glu Ser Gly Lys Val Arg Ser Ile Gly Val Ser Asn Tyr Gly Val
            430                 435                 440 aag cac atc aag gag ttg ctt gaa tat ccc gac ttg aag att aaa ccc         3966
Lys His Ile Lys Glu Leu Leu Glu Tyr Pro Asp Leu Lys Ile Lys Pro
            445                 450                 455 gcc gtc aac cag gtc gag ctt cat cca tgg ttg acc aga gag gac att         4014
Ala Val Asn Gln Val Glu Leu His Pro Trp Leu Thr Arg Glu Asp Ile
460                 465                 470                 475 gtg gac tat gct gcc aaa cac gga atc atc atc gag gcg tac tct ccc         4062
Val Asp Tyr Ala Ala Lys His Gly Ile Ile Ile Glu Ala Tyr Ser Pro
                480                 485                 490 ttg gtg aga ggc cag aag atg gac gac cct acg ctt gtg aag att gca         4110
Leu Val Arg Gly Gln Lys Met Asp Asp Pro Thr Leu Val Lys Ile Ala
                495                 500                 505 gag aag tac aac aag act ccc gca cag atc ctc atc aac tgg tcc tta         4158
Glu Lys Tyr Asn Lys Thr Pro Ala Gln Ile Leu Ile Asn Trp Ser Leu
            510                 515                 520 tcc aag ggt tat att cca ctt cca aat acg agc caa atc tct aga tta         4206
Ser Lys Gly Tyr Ile Pro Leu Pro Asn Thr Ser Gln Ile Ser Arg Leu
525                 530                 535 gcg tct aac cac gat gcc gca caa ttc gaa tta tcc aaa gaa gac att         4254
Ala Ser Asn His Asp Ala Ala Gln Phe Glu Leu Ser Lys Glu Asp Ile
540                 545                 550                 555 ggt act tta agt tct ctc aat gag cgc ctt cac acc tgt tgg gat cct         4302
Gly Thr Leu Ser Ser Leu Asn Glu Arg Leu His Thr Cys Trp Asp Pro
                560                 565                 570 acc ctc tac ccc ctt ggt gac gaa aag taa aacaacaaga attgatggta          4352
Thr Leu Tyr Pro Leu Gly Asp Glu Lys
                575                 580 tattggtaag gcggtgtaac ataccagtca gtaaatctat ccctactagc tttttttttc       4412
tatatattta cacaaaccaa cagctacatg tttcaataca taaacatgga gaaccgctcc       4472
cctttatatt ttttttttcc acacacacct tttatcttat cgctttacat tttcggtggc       4532
aaattgatta aaaaaagtac agaaatgctc agctccaaat agccttgaat tggggttgct       4592
tcctttctct gataaccatt tttcctttct caattgctag ctaacagtag caaaacaact       4652
agccctatac caaatgaaca ttcactcgtc agtattgaca tccgtagtcc tcttgctcgc       4712
ttcaattacg ggctccgatg ctaaggttca ttctgccagc atccacaaga atccgttcca       4772
agacaattat aaagatattt cctatctaga atatgttgac tccatcaaga acaagtatgt       4832
taacaatttt gtcaagaact tcaatgcacc ttttgtccca tttgttgaag atgcggtcat       4892
tgaggacact catgaactac ccttaaccaa ctatatgaat gcccaatact tcactgagat       4952
tcaacttggt acccctggcc agccattcaa ggtgattcta gacactgggt cttctaattt       5012
gtgggttcct tccacaaaat gtacatcttt ggcatgttat ttgcactcta aatatgatca       5072
cgatgcaagt tccacataca aacaaaatgg taccgattct ctatcagata tggttctggt       5132
tccttggaag gttttatttc acaagattta ctaactttttg gtgacttggt cattccagag      5192
```

-continued

```
caggatttcg ctgaggcaac aagtgaaccg ggcttggcgt ttgctttcgg aaaattcgac    5252
ggtattctag gtttagctta tgataccatc tcggtggaca aggttgttcc tccaatttac    5312
aatgccattg acaagggtc                                                 5331
```

<210> SEQ ID NO 68
<211> LENGTH: 293
<212> TYPE: PRT
<213> ORGANISM: Issatchenkia orientalis

<400> SEQUENCE: 68

```
Met Ala Ile Ala Thr His Leu Thr Leu Asn Ser Gly Tyr Gln Ile Pro
1               5                   10                  15

Thr Ile Ala Leu Gly Val Tyr Gln Thr Pro Pro Glu Thr Glu Lys
            20                  25                  30

Ile Val Leu Ala Ala Leu Glu Ala Gly Tyr Arg His Ile Asp Ser Ala
        35                  40                  45

Gln Tyr Tyr His Asn Glu Glu Asp Val Ala Lys Ala Ile Ala Lys Trp
    50                  55                  60

Ile Ala Glu Asp Pro Ala His Asn Lys Arg Glu Asp Ile Phe Tyr Thr
65                  70                  75                  80

Thr Lys Ile Tyr Asp Gln Asp His Gly Tyr Glu Lys Thr Lys Lys Ala
                85                  90                  95

Val Glu Val Ser Leu Glu Arg Ala Lys Asp Ile Asp Tyr Ile Asp Leu
            100                 105                 110

Leu Leu Leu His Ser Pro Gln Ser Asp Tyr Glu Arg Arg His Gly Ser
        115                 120                 125

Trp Leu Ala Phe Gln Glu Phe Val Glu Ser Gly Lys Val Arg Ser Ile
    130                 135                 140

Gly Val Ser Asn Tyr Gly Val Lys His Ile Lys Glu Leu Leu Glu Tyr
145                 150                 155                 160

Pro Asp Leu Lys Ile Lys Pro Ala Val Asn Gln Val Glu Leu His Pro
                165                 170                 175

Trp Leu Thr Arg Glu Asp Ile Val Asp Tyr Ala Ala Lys His Gly Ile
            180                 185                 190

Ile Ile Glu Ala Tyr Ser Pro Leu Val Arg Gly Gln Lys Met Asp Asp
        195                 200                 205

Pro Thr Leu Val Lys Ile Ala Glu Lys Tyr Asn Lys Thr Pro Ala Gln
    210                 215                 220

Ile Leu Ile Asn Trp Ser Leu Ser Lys Gly Tyr Ile Pro Leu Pro Lys
225                 230                 235                 240

Thr Ser Lys Val Ser Arg Leu Ala Ser Asn Leu Glu Ala Thr Gln Phe
                245                 250                 255

Glu Leu Ser Lys Glu Asp Val Asp Ile Leu Ser Ala Leu Asn Glu Asn
            260                 265                 270

Leu His Thr Cys Trp Asp Pro Thr Val Tyr Pro Leu Asp Asn Glu Lys
        275                 280                 285

Glu Ala Glu Lys Lys
    290
```

<210> SEQ ID NO 69
<211> LENGTH: 287
<212> TYPE: PRT
<213> ORGANISM: Issatchenkia orientalis

<400> SEQUENCE: 69

```
Met Ala Ile Ala Thr His Leu Thr Leu Asn Ser Gly Tyr Gln Ile Pro
  1               5                  10                  15
Thr Ile Ala Leu Gly Val Tyr Gln Thr Pro Glu Glu Thr Glu Lys
             20                  25                  30
Ile Val Leu Ala Ala Leu Glu Ala Gly Tyr Arg His Ile Asp Ser Ala
                 35                  40                  45
Gln Tyr Tyr His Asn Glu Glu Asp Val Ala Arg Ala Ile Ala Lys Trp
 50                  55                  60
Ile Ala Lys Asn Pro Ala His Asn Lys Arg Lys Asn Ile Phe Tyr Thr
 65                  70                  75                  80
Thr Lys Ile Tyr Asp Gln His Val Tyr Glu Lys Thr Lys Lys Ala Val
                 85                  90                  95
Glu Val Ser Leu Glu Arg Ala Lys Asp Ile Asp Tyr Ile Asp Leu Leu
                100                 105                 110
Leu Leu His Ser Pro Gln Ser Asp Tyr Glu Arg Arg His Gly Ser Trp
             115                 120                 125
Leu Ala Phe Gln Glu Phe Val Glu Ser Gly Lys Val Arg Ser Ile Gly
         130                 135                 140
Val Ser Asn Tyr Gly Val Lys His Ile Lys Glu Leu Leu Glu Tyr Pro
145                 150                 155                 160
Asp Leu Lys Ile Lys Pro Ala Val Asn Gln Val Glu Leu His Pro Trp
                 165                 170                 175
Leu Thr Arg Glu Asp Ile Val Asp Tyr Ala Ala Lys His Gly Ile Ile
                 180                 185                 190
Ile Glu Ala Tyr Ser Pro Leu Val Arg Gly Gln Lys Met Asp Asp Pro
             195                 200                 205
Thr Leu Val Lys Ile Ala Glu Lys Tyr Asn Lys Thr Pro Ala Gln Ile
         210                 215                 220
Leu Ile Asn Trp Ser Leu Ser Lys Gly Tyr Ile Pro Leu Pro Asn Thr
225                 230                 235                 240
Ser Gln Ile Ser Arg Leu Ala Ser Asn His Asp Ala Ala Gln Phe Glu
                 245                 250                 255
Leu Ser Lys Glu Asp Ile Gly Thr Leu Ser Ser Leu Asn Glu Arg Leu
             260                 265                 270
His Thr Cys Trp Asp Pro Thr Leu Tyr Pro Leu Gly Asp Glu Lys
         275                 280                 285

<210> SEQ ID NO 70
<211> LENGTH: 2963
<212> TYPE: DNA
<213> ORGANISM: Issatchenkia orientalis
<220> FEATURE:
<221> NAME/KEY: CDS
<222> LOCATION: (1001)..(1963)

<400> SEQUENCE: 70
ttttctctct gtctctttgt ttttttttc  caatctgatt tgacgtgcaa ggcaaagaca      60
tcacatgttt gagaatggca agagaagggg cgtggtagtg tataccaagc cggtgtagag     120
agtgtgattt tagagtgaat ccatccatga acacgagtag aggagatgta tgagcaaatc     180
cagggtgttt gtaatggtcc aagccgcaag gcggcgtaat ggaatgcaag aaacaaggga     240
cactaatgaa ggggtaagag gtgtctagtt gagaagtaca tartaaaaga tgaatagttg     300
agawgtacat rgtaaaagat gaatagttga gacaaatgaa ggtgtcaatg ttcctgataa     360
tgacactgca agraacaaat accgtgcagt tggaaggggg aaagagatgr ccgagataag     420
```

-continued

```
tgttgttgag gccaaaggat gttggaacct gctacaatag gagatggagc ggcctataac    480
tccggcgtgt ttgtgttgac agccctatac atcagccaat acgagagttt ggcatgtcct    540 ttaagggtt  tgctaccccc actcccgtaa tcatcgttaa aatcatcatc attgaaatca    600
ttataattaa cctcatcacc attcccacta ttatcacctt atattctcca ctccagggag    660
atgcatcgtt gtaaagggca tggctgtttg tttattttac ccgacaagcc aataccaaga    720
gcggacaaac cgcatcagaa tgcaacagaa ggttggagaa acgtgatgtc atttttccg     780 caaacggaga tctcgcacag cggtgagata taaaaggcgg agatgtggac accttcttta    840
tacaattccc ctctacttga ttgttccata ttcctaacat ctagttacaa ctctgaacat    900
cataattatt ttaaaattct caacccaact gcaattggat tgaactaaat caaattatat    960
caagttaaac caaactaaac tattttaaag cttaaacaca atg tcc caa gtc tac     1015
                                              Met Ser Gln Val Tyr
                                                1               5
```

| gtt act ttg aac aac ggt atc aag atc cct caa gtt ggc ttt gga tgc | 1063 |
|---|---|
| Val Thr Leu Asn Asn Gly Ile Lys Ile Pro Gln Val Gly Phe Gly Cys | |
| 10 15 20 | |

| tgg aaa ctt gtc aat gag gtt gca gct gac caa atc tac gag gcc atc | 1111 |
|---|---|
| Trp Lys Leu Val Asn Glu Val Ala Ala Asp Gln Ile Tyr Glu Ala Ile | |
| 25 30 35 | |

| aaa att gga tac aga ctg ttt gat ggt gcc caa gac tat ggt aac gag | 1159 |
|---|---|
| Lys Ile Gly Tyr Arg Leu Phe Asp Gly Ala Gln Asp Tyr Gly Asn Glu | |
| 40 45 50 | |

| aag gag att ggc cag ggc atc aag aga gca att aag gag gga att gtc | 1207 |
|---|---|
| Lys Glu Ile Gly Gln Gly Ile Lys Arg Ala Ile Lys Glu Gly Ile Val | |
| 55 60 65 | |

| aag agg gaa gac cta gtt gta gtt tcc aag cta tgg aac agt ttc cac | 1255 |
|---|---|
| Lys Arg Glu Asp Leu Val Val Val Ser Lys Leu Trp Asn Ser Phe His | |
| 70 75 80 85 | |

| gat ccc aag aat gtg gag gtt gcc atc aac aag gtt ttg tcg gac ttg | 1303 |
|---|---|
| Asp Pro Lys Asn Val Glu Val Ala Ile Asn Lys Val Leu Ser Asp Leu | |
| 90 95 100 | |

| gac ttg gat tac ctt gac atc ttt tac att cat ttc cca att gcg caa | 1351 |
|---|---|
| Asp Leu Asp Tyr Leu Asp Ile Phe Tyr Ile His Phe Pro Ile Ala Gln | |
| 105 110 115 | |

| aag ttt gtt cca att gag aag aag tac cca cct gga ttt tac tgt ggt | 1399 |
|---|---|
| Lys Phe Val Pro Ile Glu Lys Lys Tyr Pro Pro Gly Phe Tyr Cys Gly | |
| 120 125 130 | |

| gaa aat gga tgg gaa ttt gaa gat gtt cct ctc tct gtt act tgg aag | 1447 |
|---|---|
| Glu Asn Gly Trp Glu Phe Glu Asp Val Pro Leu Ser Val Thr Trp Lys | |
| 135 140 145 | |

| gca atg gag aat ttg gtt gac caa ggt aaa gtt aaa tcg att ggt atc | 1495 |
|---|---|
| Ala Met Glu Asn Leu Val Asp Gln Gly Lys Val Lys Ser Ile Gly Ile | |
| 150 155 160 165 | |

| tca aac tgc aat ggt gcc cta gtt cag gat ttg cta agg agc gcc aga | 1543 |
|---|---|
| Ser Asn Cys Asn Gly Ala Leu Val Gln Asp Leu Leu Arg Ser Ala Arg | |
| 170 175 180 | |

| atc aag cca cag ttg tta cag att gaa cac cat cca tac ctc gtt caa | 1591 |
|---|---|
| Ile Lys Pro Gln Leu Leu Gln Ile Glu His His Pro Tyr Leu Val Gln | |
| 185 190 195 | |

| cca agg ttg gtt aaa tac gca cag gat aac ggc atc cat gtt gta gca | 1639 |
|---|---|
| Pro Arg Leu Val Lys Tyr Ala Gln Asp Asn Gly Ile His Val Val Ala | |
| 200 205 210 | |

| tat tcc tcc ttt ggc ccg caa tca ttc ctt gaa ttg gac cat cca aag | 1687 |
|---|---|
| Tyr Ser Ser Phe Gly Pro Gln Ser Phe Leu Glu Leu Asp His Pro Lys | |
| 215 220 225 | |

| gct aag gat act gtg tca ttg ttt gaa cac gac acc atc aag gag att | 1735 |

```
Ala Lys Asp Thr Val Ser Leu Phe Glu His Asp Thr Ile Lys Glu Ile
230                 235                 240                 245 gca gcc aaa cat aat gtt tcc aca tcc aag gtg ttg ttg aga tgg gcc    1783
Ala Ala Lys His Asn Val Ser Thr Ser Lys Val Leu Leu Arg Trp Ala
                250                 255                 260 acc caa aat ggc gtt ttg gtt att cca aag tcc aac agg aag gag aga    1831
Thr Gln Asn Gly Val Leu Val Ile Pro Lys Ser Asn Arg Lys Glu Arg
            265                 270                 275 ctc ttg gag aac ttt tcg gtg aat gac ttc cag ttg gat gag gaa gat    1879
Leu Leu Glu Asn Phe Ser Val Asn Asp Phe Gln Leu Asp Glu Glu Asp
        280                 285                 290 atg aac aag atc acc ggt cta gac atg aat ctg aga ttc aac gac cca    1927
Met Asn Lys Ile Thr Gly Leu Asp Met Asn Leu Arg Phe Asn Asp Pro
    295                 300                 305 tgg aca tgg ggg gct gag att cca act ttt gtg taa atggtgttag         1973
Trp Thr Trp Gly Ala Glu Ile Pro Thr Phe Val
310                 315                 320 tctgatctaa tgacaactaa ttacgcactt acgactgtaa tgcctttatt tttctttata  2033
tttcccagcg tgttgttctt tcaaatatac gatgagtata aattaatttt acaaagcaga  2093
aacaacagga tctttagaaa cgtcactgta aacatcgaat cttctttgaa cactgaaggg  2153
aatatttctt ctcgtttctt caacaacgtc cttcttcagt tctgcataaa cgatggtttc  2213
ctcatggccg gcctcaacga ggatctcacc atctggatcg accaccatgc tatggccata  2273
agcctgatag ccgccctgtg ggttacgagc gggggaacac atcaacacgt agttttggtt  2333
gtcaatagct ctggcaacgg caaactttga ccagaattta ggacctgtca cggtattgaa  2393
tgcaccggga taagccataa taccagcgcc acgtctggct gcaatcatgg ccaattccgg  2453
gaacctgata tcatagcaaa tacctaagcc gaatctggtg tcgatttctg gaatgtcgaa  2513
aactgtaacc ttgttgcccg gttttaaaga atcagactcc ttgaacgtga ttccgcccgg  2573
aatagaaatg tcaaagaggt gcaccttacg atgcttggca acgatttccc ccttgggatt  2633
gaaaacaaga gaggtgttgt agataccgcc gtcattgtcg tcgatttccg gaatcgaacc  2693
tccaatgata gagacattgt acttttcgc ctgttcactt aaaaacgtgc tagtttcccc   2753
ctctgggata cgttctgcat aatttgcaaa ttggtctacg gcatatggag attggaaaca  2813
ttcaggtaga acaagaagtt gtggttttgg atcgtgttgg atcgccctct cgatgaattg  2873
ggtcactttg gcgagattgg ccttcttgtc tccaccacag tggaattgca gcagtgccac  2933
ttggagagtc ttggagagag taacggcaga                                   2963

<210> SEQ ID NO 71
<211> LENGTH: 320
<212> TYPE: PRT
<213> ORGANISM: Issatchenkia orientalis

<400> SEQUENCE: 71

Met Ser Gln Val Tyr Val Thr Leu Asn Asn Gly Ile Lys Ile Pro Gln
1               5                   10                  15

Val Gly Phe Gly Cys Trp Lys Leu Val Asn Glu Val Ala Ala Asp Gln
            20                  25                  30

Ile Tyr Glu Ala Ile Lys Ile Gly Tyr Arg Leu Phe Asp Gly Ala Gln
        35                  40                  45

Asp Tyr Gly Asn Glu Lys Glu Ile Gly Gln Gly Ile Lys Arg Ala Ile
    50                  55                  60

Lys Glu Gly Ile Val Lys Arg Glu Asp Leu Val Val Ser Lys Leu
65                  70                  75                  80
```

```
Trp Asn Ser Phe His Asp Pro Lys Asn Val Glu Val Ala Ile Asn Lys
                85                  90                  95

Val Leu Ser Asp Leu Asp Leu Asp Tyr Leu Asp Ile Phe Tyr Ile His
            100                 105                 110

Phe Pro Ile Ala Gln Lys Phe Val Pro Ile Glu Lys Lys Tyr Pro Pro
        115                 120                 125

Gly Phe Tyr Cys Gly Glu Asn Gly Trp Glu Phe Glu Asp Val Pro Leu
    130                 135                 140

Ser Val Thr Trp Lys Ala Met Glu Asn Leu Val Asp Gln Gly Lys Val
145                 150                 155                 160

Lys Ser Ile Gly Ile Ser Asn Cys Asn Gly Ala Leu Val Gln Asp Leu
                165                 170                 175

Leu Arg Ser Ala Arg Ile Lys Pro Gln Leu Leu Gln Ile Glu His His
            180                 185                 190

Pro Tyr Leu Val Gln Pro Arg Leu Val Lys Tyr Ala Gln Asp Asn Gly
        195                 200                 205

Ile His Val Val Ala Tyr Ser Ser Phe Gly Pro Gln Ser Phe Leu Glu
    210                 215                 220

Leu Asp His Pro Lys Ala Lys Asp Thr Val Ser Leu Phe Glu His Asp
225                 230                 235                 240

Thr Ile Lys Glu Ile Ala Ala Lys His Asn Val Ser Thr Ser Lys Val
                245                 250                 255

Leu Leu Arg Trp Ala Thr Gln Asn Gly Val Leu Val Ile Pro Lys Ser
            260                 265                 270

Asn Arg Lys Glu Arg Leu Leu Glu Asn Phe Ser Val Asn Asp Phe Gln
        275                 280                 285

Leu Asp Glu Glu Asp Met Asn Lys Ile Thr Gly Leu Asp Met Asn Leu
    290                 295                 300

Arg Phe Asn Asp Pro Trp Thr Trp Gly Ala Glu Ile Pro Thr Phe Val
305                 310                 315                 320

<210> SEQ ID NO 72
<211> LENGTH: 3966
<212> TYPE: DNA
<213> ORGANISM: Issatchenkia orientalis
<220> FEATURE:
<221> NAME/KEY: CDS
<222> LOCATION: (1201)..(2766)

<400> SEQUENCE: 72
aaagaacgag gttttactca aatccggtgt tgtgatggcc aagggagaat tggagacaga      60
ggataaacaa cggttgcaca gggccaagaa gagaaagcag cacatgcaac acaaggatga     120
ttctctgaag aagaagaagg tggaggtgaa gcagttatga agtgtaaaac acatatagcc     180
accctatagc tcgaattgtc taatctttgt acattattat atttctctct atctgtatag     240
gagagtagcc cacaacacag tccaaccaaa cataggctcc aacatctcgt agattctgtt     300
tggtttcggc ctcagagttg tccaggaaag agcagcatat gacgccaacg tggttcatat     360
gagtccctag tgtaacttaa tagcgcaaac tccgacaacg aggagacact gacgtgccct     420
gttcaaggaa ttacatacag ccacttgtcc gagatgtaga accattggtc aacacgactc     480
tctgtagcaa ggggcaaaga cactagtgtt tctcaaggat acacttgtac atagacaaac     540
tagttgataa acaaatactc aaacgcatat acgcttactg gccttaatac tacagtaaac     600
gtgctccccg aatccccgaa cacaaggtcg aaccggctac tctatccctg cctttgcccc     660
```

```
tcctccctag cccattcacc ccgtcaatgc agacaccctc tttggacttc ccctgttggc    720
cctcctaagg cacccccccc cccaccccc c ctttcttcc ccgcaatacc caaacttatc    780
gccgcgtacc cgttttccta agtttggtgc tatttcgctt acacacccct cacgtgctct    840
tacctctagc tcctctttct tgacacatca cacccccccc gtctccgaat accgaaaata    900
gaaaaagcca ccccgggtg caaagttccg gagatctcgg ccctcagtgg accggctcat     960
gccacgcact ggaaccccac actgtacccg ttaccggtga tgactctttg taattttca   1020 gtggatgcta ctcaacaaaa accaagggg gaagtgcaca tgcttactaa accccgggag   1080
aagggaagtg tctggaattt acacttctag gggggacat ttcttcacgt ggatataaaa    1140
gcaaacaccc attcctacca gagaggttac aattagactt ccaatatccc acttttata    1200
```

| | | | | |
|---|---|---|---|---|
| atg ttg tcc ctc tct aaa cag tca aga aac ttt ttc aaa ttg aac tat | | | | 1248 |
| Met Leu Ser Leu Ser Lys Gln Ser Arg Asn Phe Phe Lys Leu Asn Tyr | | | | |
| 1               5                   10                  15 | | | | |

```
ttt tca gtc acc caa ata gca aaa atg tct gca act tcc gtc act ttc    1296
Phe Ser Val Thr Gln Ile Ala Lys Met Ser Ala Thr Ser Val Thr Phe
             20                  25                  30 cca att atc aac gaa act tac caa cag cca acc ggg ctt ttc atc aac    1344
Pro Ile Ile Asn Glu Thr Tyr Gln Gln Pro Thr Gly Leu Phe Ile Asn
         35                  40                  45 aat gaa ttt gtt agt gca aag tca ggt aag act ttt gat gtt aac acc    1392
Asn Glu Phe Val Ser Ala Lys Ser Gly Lys Thr Phe Asp Val Asn Thr
 50                  55                  60 cca att gat gag tct ctc att tgt aaa gtc caa cag gcc gat gct gaa    1440
Pro Ile Asp Glu Ser Leu Ile Cys Lys Val Gln Gln Ala Asp Ala Glu
65                  70                  75                  80 gat gtt gaa att gcc gtt caa gca gca tct aaa gct tac aag act tgg    1488
Asp Val Glu Ile Ala Val Gln Ala Ala Ser Lys Ala Tyr Lys Thr Trp
                 85                  90                  95 aga ttt aca ccg cca aat gaa aga ggc aga tac ttg aac aaa ttg gcc    1536
Arg Phe Thr Pro Pro Asn Glu Arg Gly Arg Tyr Leu Asn Lys Leu Ala
             100                 105                 110 gat ttg atg gac gaa aag aga gac tta ctt gcc aaa att gaa tcc ctt    1584
Asp Leu Met Asp Glu Lys Arg Asp Leu Leu Ala Lys Ile Glu Ser Leu
         115                 120                 125 gat aat ggt aag gcc tta cat tgt gca aaa ttc gat gtc aat ctt gtc    1632
Asp Asn Gly Lys Ala Leu His Cys Ala Lys Phe Asp Val Asn Leu Val
130                 135                 140 att gaa tat ttc aga tac tgt gca ggt tac tgt gat aaa atc gat ggt    1680
Ile Glu Tyr Phe Arg Tyr Cys Ala Gly Tyr Cys Asp Lys Ile Asp Gly
145                 150                 155                 160 aga aca att aca acc gat gta gaa cat ttt acc tac act aga aag gaa    1728
Arg Thr Ile Thr Thr Asp Val Glu His Phe Thr Tyr Thr Arg Lys Glu
                 165                 170                 175 cct tta ggt gtc tgt ggt gca att aca cct tgg aac ttc cca ttg ctg    1776
Pro Leu Gly Val Cys Gly Ala Ile Thr Pro Trp Asn Phe Pro Leu Leu
             180                 185                 190 atg ttt gct tgg aaa atc ggc ccg gct tta gca acc ggt aat acc att    1824
Met Phe Ala Trp Lys Ile Gly Pro Ala Leu Ala Thr Gly Asn Thr Ile
         195                 200                 205 atc ttg aag cct gcc agt gca aca cct cta tca aac ctc ttt act tgt    1872
Ile Leu Lys Pro Ala Ser Ala Thr Pro Leu Ser Asn Leu Phe Thr Cys
210                 215                 220 acc ttg atc aag gag gcg ggc att cca gcc ggt gtt gtt aat gtt gtt    1920
Thr Leu Ile Lys Glu Ala Gly Ile Pro Ala Gly Val Val Asn Val Val
225                 230                 235                 240 cca ggt tcc ggt aga ggc tgt ggt aac tcc att tta caa cat cct aaa    1968
Pro Gly Ser Gly Arg Gly Cys Gly Asn Ser Ile Leu Gln His Pro Lys
```

```
                    Pro Gly Ser Gly Arg Gly Cys Gly Asn Ser Ile Leu Gln His Pro Lys
                                    245                 250                 255 att aag aag gtt gcg ttt acc gga tct aca gaa gtt ggt aaa act gtt         2016
Ile Lys Lys Val Ala Phe Thr Gly Ser Thr Glu Val Gly Lys Thr Val
                260                 265                 270 atg aag gaa tgt gct aat tcc atc aaa aag gtt act ctc gaa ttg ggt         2064
Met Lys Glu Cys Ala Asn Ser Ile Lys Lys Val Thr Leu Glu Leu Gly
            275                 280                 285 ggt aag tct cca aac att gtt ttc aaa gac tgt aac gtt gaa caa acc         2112
Gly Lys Ser Pro Asn Ile Val Phe Lys Asp Cys Asn Val Glu Gln Thr
        290                 295                 300 att caa aat ttg att act ggt att ttc ttc aat ggt ggt gaa gtc tgt         2160
Ile Gln Asn Leu Ile Thr Gly Ile Phe Phe Asn Gly Gly Glu Val Cys
305                 310                 315                 320 tgt gct ggt tct aga att tac att gaa gca acc gat gag aaa tgg tat         2208
Cys Ala Gly Ser Arg Ile Tyr Ile Glu Ala Thr Asp Glu Lys Trp Tyr
                325                 330                 335 act gaa ttc ttg acc aaa ttc aag gag act gtt gaa aaa tta aag att         2256
Thr Glu Phe Leu Thr Lys Phe Lys Glu Thr Val Glu Lys Leu Lys Ile
            340                 345                 350 ggt aac cca ttt gaa gag ggt gtt ttc caa ggt gca caa acc act cca         2304
Gly Asn Pro Phe Glu Glu Gly Val Phe Gln Gly Ala Gln Thr Thr Pro
        355                 360                 365 gat caa ttc caa act gtc ttg gac tac atc acc gct gct aac gaa tcc         2352
Asp Gln Phe Gln Thr Val Leu Asp Tyr Ile Thr Ala Ala Asn Glu Ser
370                 375                 380 agc ttg aaa cta tta act ggt ggt aaa aga att ggc aat aag gga tac         2400
Ser Leu Lys Leu Leu Thr Gly Gly Lys Arg Ile Gly Asn Lys Gly Tyr
385                 390                 395                 400 ttt gtt gag cca act atc ttc tac gat gtt cct caa aat tcc aag tta         2448
Phe Val Glu Pro Thr Ile Phe Tyr Asp Val Pro Gln Asn Ser Lys Leu
                405                 410                 415 act caa gaa gaa atc ttt ggt cca gtt gct gtt gtt tta cct ttc aag         2496
Thr Gln Glu Glu Ile Phe Gly Pro Val Ala Val Val Leu Pro Phe Lys
            420                 425                 430 tcc act gaa gaa ttg att gaa aag gca aat gat tcc gat ttt ggc tta         2544
Ser Thr Glu Glu Leu Ile Glu Lys Ala Asn Asp Ser Asp Phe Gly Leu
        435                 440                 445 ggt tcc ggt att cac act gaa gat ttc aac aag gca att tgg gtt tcc         2592
Gly Ser Gly Ile His Thr Glu Asp Phe Asn Lys Ala Ile Trp Val Ser
450                 455                 460 gaa agg ctt gaa gca ggt tct gtt tgg atc aac act tac aat gat ttc         2640
Glu Arg Leu Glu Ala Gly Ser Val Trp Ile Asn Thr Tyr Asn Asp Phe
465                 470                 475                 480 cac cca gct gct cca ttc ggt ggt tac aag gaa tcc ggt att ggc aga         2688
His Pro Ala Ala Pro Phe Gly Gly Tyr Lys Glu Ser Gly Ile Gly Arg
                485                 490                 495 gaa atg ggt att gaa gct ttc gac aac tat act caa acc aag tta gtt         2736
Glu Met Gly Ile Glu Ala Phe Asp Asn Tyr Thr Gln Thr Lys Leu Val
            500                 505                 510 aga gct aga gtt aac aag cca gct ttt tag atgccccggg tctaaaataa          2786
Arg Ala Arg Val Asn Lys Pro Ala Phe
        515                 520 aaatcaatac caatcccctt gtttgcatta tgtattttga aaatatgtat ataggtcctc      2846
tcactttcct ttgacttttc taatctctac tattcagata attgatttat cagaatggtg      2906
tatttattta tattgttggt cttaaaattt gaaataagta caataacaaa ataaaaaata      2966 aagttttca aagcttaaat ttcggagttg ccatttcgg ccaaatatga ttttctctta       3026
```

```
aaaagtttat acctagttat cttatttgtc atcagctaaa acataggaaa atctgccttt    3086
gagaaggcta cattctccat cttatcttaa tattctttgt agcagtcaaa tcagaagcaa    3146
tacagtgttt cattgagtta ctaagggatg ggttttgttt gaagttactc tagtatttta    3206
agacatctct aaaagatata atctctggtc ttaagaccaa gctgtataat tcccccaaac    3266
tttgaataca aagtagtatg tgatgaaata attgtctcgg atgctgccaa acatggcctg    3326
aaaatcgggt gaaaattgca cctaaaagat cagcacatat atatatatga tactttaaac    3386
aatgtagatg ttaactataa cattgatatt ctcaaattgg ttctcaaaag tggaacacat    3446
ttgtcgttgc ttttgattgc ttgattgcaa ataactgtat ataccctacgt caagcactaa    3506 tacaccgtct ttgtttcaag tgtgctaatt aaaattaatt atgcctgcat ataccaaaca    3566
ggttgtgact attgactggt gttcttcctt tccgggcaaa gtcttgattc tattaggaaa    3626
aattaaacaa ttattctgta cttgatgttt gtggaaatga taaacctaat agttatacta    3686
actgctttga gtataatggc aagaatcgga gtcaatgaat attatttttc tatcattagc    3746
cgtagtgata taatttgaaa aaggacaaat aactagaagt cacttttctg ggaaccatcc    3806
catcatagca tagatttgga tattacttgc ctcaatgcgt gaccgttact aaaatcccaa    3866
gactacttat actgtagtta tacgatcat ttaaattggc aactaaatct gcgagcaaaa    3926
attgttaagc tttgtaactg tgtagtttga agagtctgaa                         3966
```

```
<210> SEQ ID NO 73
<211> LENGTH: 521
<212> TYPE: PRT
<213> ORGANISM: Issatchenkia orientalis

<400> SEQUENCE: 73
```

Met Leu Ser Leu Ser Lys Gln Ser Arg Asn Phe Phe Lys Leu Asn Tyr
1               5                   10                  15

Phe Ser Val Thr Gln Ile Ala Lys Met Ser Ala Thr Ser Val Thr Phe
            20                  25                  30

Pro Ile Ile Asn Glu Thr Tyr Gln Gln Pro Thr Gly Leu Phe Ile Asn
        35                  40                  45

Asn Glu Phe Val Ser Ala Lys Ser Gly Lys Thr Phe Asp Val Asn Thr
    50                  55                  60

Pro Ile Asp Glu Ser Leu Ile Cys Lys Val Gln Gln Ala Asp Ala Glu
65                  70                  75                  80

Asp Val Glu Ile Ala Val Gln Ala Ala Ser Lys Ala Tyr Lys Thr Trp
                85                  90                  95

Arg Phe Thr Pro Pro Asn Glu Arg Gly Arg Tyr Leu Asn Lys Leu Ala
            100                 105                 110

Asp Leu Met Asp Glu Lys Arg Asp Leu Leu Ala Lys Ile Glu Ser Leu
        115                 120                 125

Asp Asn Gly Lys Ala Leu His Cys Ala Lys Phe Asp Val Asn Leu Val
    130                 135                 140

Ile Glu Tyr Phe Arg Tyr Cys Ala Gly Tyr Cys Asp Lys Ile Asp Gly
145                 150                 155                 160

Arg Thr Ile Thr Thr Asp Val Glu His Phe Thr Tyr Thr Arg Lys Glu
                165                 170                 175

Pro Leu Gly Val Cys Gly Ala Ile Thr Pro Trp Asn Phe Pro Leu Leu
            180                 185                 190

Met Phe Ala Trp Lys Ile Gly Pro Ala Leu Ala Thr Gly Asn Thr Ile
        195                 200                 205

| | | | | | | | | | | | |
|---|---|---|---|---|---|---|---|---|---|---|---|
| Ile | Leu | Lys | Pro | Ala | Ser | Ala | Thr | Pro | Leu | Ser | Asn | Leu | Phe | Thr | Cys |
| 210 | | | | 215 | | | | | 220 | | |

Ile Leu Lys Pro Ala Ser Ala Thr Pro Leu Ser Asn Leu Phe Thr Cys
  210                 215                 220

Thr Leu Ile Lys Glu Ala Gly Ile Pro Ala Gly Val Val Asn Val Val
225                 230                 235                 240

Pro Gly Ser Gly Arg Gly Cys Gly Asn Ser Ile Leu Gln His Pro Lys
                245                 250                 255

Ile Lys Lys Val Ala Phe Thr Gly Ser Thr Glu Val Gly Lys Thr Val
                260                 265                 270

Met Lys Glu Cys Ala Asn Ser Ile Lys Lys Val Thr Leu Glu Leu Gly
            275                 280                 285

Gly Lys Ser Pro Asn Ile Val Phe Lys Asp Cys Asn Val Glu Gln Thr
290                 295                 300

Ile Gln Asn Leu Ile Thr Gly Ile Phe Phe Asn Gly Gly Glu Val Cys
305                 310                 315                 320

Cys Ala Gly Ser Arg Ile Tyr Ile Glu Ala Thr Asp Glu Lys Trp Tyr
                325                 330                 335

Thr Glu Phe Leu Thr Lys Phe Lys Glu Thr Val Glu Lys Leu Lys Ile
                340                 345                 350

Gly Asn Pro Phe Glu Glu Gly Val Phe Gln Gly Ala Gln Thr Thr Pro
                355                 360                 365

Asp Gln Phe Gln Thr Val Leu Asp Tyr Ile Thr Ala Ala Asn Glu Ser
370                 375                 380

Ser Leu Lys Leu Leu Thr Gly Gly Lys Arg Ile Gly Asn Lys Gly Tyr
385                 390                 395                 400

Phe Val Glu Pro Thr Ile Phe Tyr Asp Val Pro Gln Asn Ser Lys Leu
                405                 410                 415

Thr Gln Glu Glu Ile Phe Gly Pro Val Ala Val Leu Pro Phe Lys
                420                 425                 430

Ser Thr Glu Glu Leu Ile Glu Lys Ala Asn Asp Ser Asp Phe Gly Leu
                435                 440                 445

Gly Ser Gly Ile His Thr Glu Asp Phe Asn Lys Ala Ile Trp Val Ser
450                 455                 460

Glu Arg Leu Glu Ala Gly Ser Val Trp Ile Asn Thr Tyr Asn Asp Phe
465                 470                 475                 480

His Pro Ala Ala Pro Phe Gly Tyr Lys Glu Ser Gly Ile Gly Arg
                485                 490                 495

Glu Met Gly Ile Glu Ala Phe Asp Asn Tyr Thr Gln Thr Lys Leu Val
                500                 505                 510

Arg Ala Arg Val Asn Lys Pro Ala Phe
                515                 520

<210> SEQ ID NO 74
<211> LENGTH: 3179
<212> TYPE: DNA
<213> ORGANISM: Issatchenkia orientalis
<220> FEATURE:
<221> NAME/KEY: CDS
<222> LOCATION: (1052)..(2182)

<400> SEQUENCE: 74
gatttggacc tacaaggtgc tgtaaagagt atgaacactt ctggggagga ggaatggaac     60
agtgatgacg atgatgatga agaaagtgac gaaagtaacg aaagtgatta ctattcttac    120
gatgaaggcg aagaaacaga tgatagtgag ggagcccaag agggagagga agacgaaaat    180
gaacgaatca ttgaagctct aagtagtggt gttggtgaac tcaagatgga ctcttttaggt   240

-continued

```
aattatattc ttgaatagtt gtgtaaagcg aatatgcaaa tagatttgtt ttataattat    300
gcatctcttt gaaagaggtt tagaggcaaa gttcttgcat acaatattgt gattgtttta    360
atgtcattct tgattttcat aaagagatta aaaaaaaaaa aaaaaaactt ataaaattga    420
gtagaaccat ttatatataa gacaaagatt gtctgtatta gtcctcaaca cactaaacct    480
tacatactta gggtaaattt gctaatagag tgatatgttc atgagaactc caacgacaac    540
acaaccacct atttgcacaa caaacaccat tgtcgcacgc tgcgcgccct agaagtagaa    600
agaaagggaa atgacattaa gagaatcata ccccgtgccc gtaacgccga aaaaatcaca    660
ccccgtcccc cacaccttaa aacctcaacc gcttaacacc gccacaccct ttctctttat    720
aaacgccgtt tgcattactc attcttctta taaaccgcac cccccaaaac gcggaatagc    780
ttcaaccccc caatcagata tgagtttccc gggaaacccg cttttcccga cagccccaca    840
aggggttggt ctataaaaga ggacgttttc cccgtcatcg agattgaaga ttcttacagg    900
cccatttatt caaattggag ttgattcttc ttgtctttac tttctttctc tcttttttctt   960 ccttttttaa tattatcttt tgtcaagcct ggttccctaa gttgaactct cttttcttgt   1020
gatcctccta tatagatacg ccttgccaaa t atg ttt gca tca acc ttc aga      1072
                                   Met Phe Ala Ser Thr Phe Arg
                                    1               5
```

| | | | | | | | | | | | | | | | |
|---|---|---|---|---|---|---|---|---|---|---|---|---|---|---|---|
| agt | caa | gct | gta | aga | gct | gca | aga | ttt | act | aga | ttc | caa | tcc | act | ttt | 1120 |
| Ser | Gln | Ala | Val | Arg | Ala | Ala | Arg | Phe | Thr | Arg | Phe | Gln | Ser | Thr | Phe | |
| | 10 | | | | 15 | | | | | 20 | | | | | | |

```
gcc att cct gag aag caa atg ggt gtt atc ttt gaa act cat ggt ggt     1168
Ala Ile Pro Glu Lys Gln Met Gly Val Ile Phe Glu Thr His Gly Gly
     25              30                  35 cct tta caa tac aag gaa att cca gtt cca aaa cca aaa cca act gaa     1216
Pro Leu Gln Tyr Lys Glu Ile Pro Val Pro Lys Pro Lys Pro Thr Glu
40              45                  50                  55 att tta atc aat gtt aaa tac tct ggt gtc tgc cat acc gat tta cac     1264
Ile Leu Ile Asn Val Lys Tyr Ser Gly Val Cys His Thr Asp Leu His
                 60                  65                  70 gca tgg aaa ggt gac tgg cca tta cca gca aag tta ccc cta gtt ggt     1312
Ala Trp Lys Gly Asp Trp Pro Leu Pro Ala Lys Leu Pro Leu Val Gly
             75                  80                  85 ggt cac gaa ggt gcg ggc att gtt gtt gcg aaa ggt tct gca gtt acc     1360
Gly His Glu Gly Ala Gly Ile Val Val Ala Lys Gly Ser Ala Val Thr
         90                  95                 100 aac ttt gag att ggc gat tat gct ggt att aag tgg tta aac ggt tca     1408
Asn Phe Glu Ile Gly Asp Tyr Ala Gly Ile Lys Trp Leu Asn Gly Ser
    105                 110                 115 tgt atg tca tgt gaa ttc tgt gaa caa ggt gat gaa tct aac tgt gaa     1456
Cys Met Ser Cys Glu Phe Cys Glu Gln Gly Asp Glu Ser Asn Cys Glu
120                 125                 130                 135 cat gcc gat ttg agt ggt tat act cat gat ggt tct ttc caa caa tat     1504
His Ala Asp Leu Ser Gly Tyr Thr His Asp Gly Ser Phe Gln Gln Tyr
                140                 145                 150 gcc act gct gac gct att caa gct gca aag atc cca aag ggt acc gac     1552
Ala Thr Ala Asp Ala Ile Gln Ala Ala Lys Ile Pro Lys Gly Thr Asp
            155                 160                 165 tta tct gaa gtt gcg cca att tta tgt gct ggt gtt act gtc tat aaa     1600
Leu Ser Glu Val Ala Pro Ile Leu Cys Ala Gly Val Thr Val Tyr Lys
        170                 175                 180 gct ttg aaa act gct gat tta aga gca ggt caa tgg gtt gcg att tct    1648
Ala Leu Lys Thr Ala Asp Leu Arg Ala Gly Gln Trp Val Ala Ile Ser
    185                 190                 195 ggt gcc gct ggt ggt cta ggt tct ctt gct gtc caa tat gca aag gca    1696
```

```
Gly Ala Ala Gly Gly Leu Gly Ser Leu Ala Val Gln Tyr Ala Lys Ala
200                 205                 210                 215 atg ggt cta aga gtt tta ggt atc gat ggt ggt gaa ggt aaa aag gaa    1744
Met Gly Leu Arg Val Leu Gly Ile Asp Gly Gly Glu Gly Lys Lys Glu
                    220                 225                 230 ctt ttt gaa caa tgt ggt ggt gat gtg ttt atc gat ttc acc aga tac    1792
Leu Phe Glu Gln Cys Gly Gly Asp Val Phe Ile Asp Phe Thr Arg Tyr
                235                 240                 245 cca aga gat gca cct gaa aag atg gtt gct gat att aag gct gca act    1840
Pro Arg Asp Ala Pro Glu Lys Met Val Ala Asp Ile Lys Ala Ala Thr
            250                 255                 260 aac ggt ttg ggt cca cac ggt gtt atc aat gtc tct gtc tcc cca gct    1888
Asn Gly Leu Gly Pro His Gly Val Ile Asn Val Ser Val Ser Pro Ala
        265                 270                 275 gct atc tct caa tca tgt gac tat gtt aga gca act ggt aag gtt gtc    1936
Ala Ile Ser Gln Ser Cys Asp Tyr Val Arg Ala Thr Gly Lys Val Val
280                 285                 290                 295 ctt gtc ggt atg cca tct ggt gct gtc tgt aag tct gat gtc ttc act    1984
Leu Val Gly Met Pro Ser Gly Ala Val Cys Lys Ser Asp Val Phe Thr
                    300                 305                 310 cat gtt gtt aaa tcc tta caa att aaa ggt tct tat gtt ggt aac aga    2032
His Val Val Lys Ser Leu Gln Ile Lys Gly Ser Tyr Val Gly Asn Arg
                315                 320                 325 gca gat acc aga gaa gct ttg gaa ttc ttt aat gaa ggt aag gtc aga    2080
Ala Asp Thr Arg Glu Ala Leu Glu Phe Phe Asn Glu Gly Lys Val Arg
            330                 335                 340 tct cca atc aag gtt gtc cca tta tct act tta cct gaa att tac gaa    2128
Ser Pro Ile Lys Val Val Pro Leu Ser Thr Leu Pro Glu Ile Tyr Glu
345                 350                 355 ttg atg gag caa ggt aag att tta ggt aga tac gtt gtt gat act tct    2176
Leu Met Glu Gln Gly Lys Ile Leu Gly Arg Tyr Val Val Asp Thr Ser
360                 365                 370                 375 aaa taa tgaagatgaa gaaaacagca aactttttat gactacccccc aaccatctaa    2232
Lys cgatttatga tctatatata gctttctaga acatccattt atttattcac ttactcatgt   2292
atttatatta tataatacaa aataactaat tacaatgtgt acatttttt  ttttcattac   2352 cataatgtat gcgttgagcc tcttgcacct tctttattag gaaatcagtt gaaaaatttc   2412
cggattgtct ttattattgg cccatttttt tttggtcaca cctttatttt tgtacacttc   2472
tcgggcaaag caaaaactat agtaccggat aggcctttat aaaactccag tgtgtatgat   2532
tttagttggt gtgccatcta cacgttctct tagtttcttt atcatgtcac agaaagcaag   2592
catgcaaacc cttacaaaaa ataacaacat acaaatgcct aaacaactgg actataatga   2652
tggtgagtca gttacgaaaa gagcaagtgg gttaatacga tttcgtaagg acagtctga    2712 ggaagactac aattttcaaa aggagcagtt ctggtccacg ggtcctttag tacagaatca   2772
cacatttgtg actgaatttg ttgaaaagtt tattgaaaac acaattagtg aagattattc   2832
aatcacagat agatcgaaaa tagaacgtga acaatcata cacggattgg agaagctgta    2892
ttttcaaagg gaatatgagc gatgtctaaa agatgttcaa ctattgaagg acaatatcga   2952
taagttcaat cctaatttgg atcttaatga aaagaattta taatgagctg aatttatttt   3012
cttggatgtg catcaaaaag atccatgaga gtaacgaaaa gaaactgggg gaaatctaat   3072
aatttacaat ttcaatatac acttctatat cctttaatgt aatggcttta taaataaaca   3132
cgaacttcta cagcaccgac gtttcttttt cttaccagct cctcttc                 3179
```

```
<210> SEQ ID NO 75
<211> LENGTH: 376
<212> TYPE: PRT
<213> ORGANISM: Issatchenkia orientalis

<400> SEQUENCE: 75

Met Phe Ala Ser Thr Phe Arg Ser Gln Ala Val Arg Ala Ala Arg Phe
1               5                   10                  15

Thr Arg Phe Gln Ser Thr Phe Ala Ile Pro Glu Lys Gln Met Gly Val
            20                  25                  30

Ile Phe Glu Thr His Gly Gly Pro Leu Gln Tyr Lys Glu Ile Pro Val
        35                  40                  45

Pro Lys Pro Lys Pro Thr Glu Ile Leu Ile Asn Val Lys Tyr Ser Gly
    50                  55                  60

Val Cys His Thr Asp Leu His Ala Trp Lys Gly Asp Trp Pro Leu Pro
65                  70                  75                  80

Ala Lys Leu Pro Leu Val Gly Gly His Glu Gly Ala Gly Ile Val Val
                85                  90                  95

Ala Lys Gly Ser Ala Val Thr Asn Phe Glu Ile Gly Asp Tyr Ala Gly
            100                 105                 110

Ile Lys Trp Leu Asn Gly Ser Cys Met Ser Cys Glu Phe Cys Glu Gln
        115                 120                 125

Gly Asp Glu Ser Asn Cys Glu His Ala Asp Leu Ser Gly Tyr Thr His
130                 135                 140

Asp Gly Ser Phe Gln Gln Tyr Ala Thr Ala Asp Ala Ile Gln Ala Ala
145                 150                 155                 160

Lys Ile Pro Lys Gly Thr Asp Leu Ser Glu Val Ala Pro Ile Leu Cys
                165                 170                 175

Ala Gly Val Thr Val Tyr Lys Ala Leu Lys Thr Ala Asp Leu Arg Ala
            180                 185                 190

Gly Gln Trp Val Ala Ile Ser Gly Ala Ala Gly Gly Leu Gly Ser Leu
        195                 200                 205

Ala Val Gln Tyr Ala Lys Ala Met Gly Leu Arg Val Leu Gly Ile Asp
210                 215                 220

Gly Gly Glu Gly Lys Lys Glu Leu Phe Glu Gln Cys Gly Gly Asp Val
225                 230                 235                 240

Phe Ile Asp Phe Thr Arg Tyr Pro Arg Asp Ala Pro Glu Lys Met Val
                245                 250                 255

Ala Asp Ile Lys Ala Ala Thr Asn Gly Leu Gly Pro His Gly Val Ile
            260                 265                 270

Asn Val Ser Val Ser Pro Ala Ala Ile Ser Gln Ser Cys Asp Tyr Val
        275                 280                 285

Arg Ala Thr Gly Lys Val Val Leu Val Gly Met Pro Ser Gly Ala Val
290                 295                 300

Cys Lys Ser Asp Val Phe Thr His Val Val Lys Ser Leu Gln Ile Lys
305                 310                 315                 320

Gly Ser Tyr Val Gly Asn Arg Ala Asp Thr Arg Glu Ala Leu Glu Phe
                325                 330                 335

Phe Asn Glu Gly Lys Val Arg Ser Pro Ile Lys Val Val Pro Leu Ser
            340                 345                 350

Thr Leu Pro Glu Ile Tyr Glu Leu Met Glu Gln Gly Lys Ile Leu Gly
        355                 360                 365

Arg Tyr Val Val Asp Thr Ser Lys
    370                 375
```

<210> SEQ ID NO 76
<211> LENGTH: 696
<212> TYPE: DNA
<213> ORGANISM: Escherichia coli
<220> FEATURE:
<221> NAME/KEY: CDS
<222> LOCATION: (1)..(696)

<400> SEQUENCE: 76

```
atg tta gaa gat ctc aaa cgc cag gta tta gaa gcc aac ctg gcg ctg        48
Met Leu Glu Asp Leu Lys Arg Gln Val Leu Glu Ala Asn Leu Ala Leu
1               5                   10                  15 cca aaa cac aac ctg gtc acg ctc aca tgg ggc aac gtc agc gcc gtt        96
Pro Lys His Asn Leu Val Thr Leu Thr Trp Gly Asn Val Ser Ala Val
            20                  25                  30 gat cgc gag cgc ggc gtc ttt gtg atc aaa cct tcc ggc gtc gat tac       144
Asp Arg Glu Arg Gly Val Phe Val Ile Lys Pro Ser Gly Val Asp Tyr
        35                  40                  45 agc gtc atg acc gct gac gat atg gtc gtg gtt agc atc gaa acc ggt       192
Ser Val Met Thr Ala Asp Asp Met Val Val Val Ser Ile Glu Thr Gly
    50                  55                  60 gaa gtg gtt gaa ggt acg aaa aag ccc tcc tcc gac acg cca act cac       240
Glu Val Val Glu Gly Thr Lys Lys Pro Ser Ser Asp Thr Pro Thr His
65                  70                  75                  80 cgg ctg ctc tat cag gca ttc ccc tcc att ggc ggc att gtg cat acg       288
Arg Leu Leu Tyr Gln Ala Phe Pro Ser Ile Gly Gly Ile Val His Thr
                85                  90                  95 cac tcg cgc cac gcc acc atc tgg gcg cag gcg ggt cag tcg att cca       336
His Ser Arg His Ala Thr Ile Trp Ala Gln Ala Gly Gln Ser Ile Pro
            100                 105                 110 gca acc ggc acc acc cac gcc gac tat ttc tac ggc acc att ccc tgc       384
Ala Thr Gly Thr Thr His Ala Asp Tyr Phe Tyr Gly Thr Ile Pro Cys
        115                 120                 125 acc cgc aaa atg acc gac gca gaa atc aac ggc gaa tat gag tgg gaa       432
Thr Arg Lys Met Thr Asp Ala Glu Ile Asn Gly Glu Tyr Glu Trp Glu
    130                 135                 140 acc ggt aac gtc atc gta gaa acc ttt gaa aaa cag ggt atc gat gca       480
Thr Gly Asn Val Ile Val Glu Thr Phe Glu Lys Gln Gly Ile Asp Ala
145                 150                 155                 160 gcg caa atg ccc ggc gtt ctg gtc cat tcc cac ggc ccg ttt gca tgg       528
Ala Gln Met Pro Gly Val Leu Val His Ser His Gly Pro Phe Ala Trp
                165                 170                 175 ggc aaa aat gcc gaa gat gcg gtg cat aac gcc atc gtg ctg gaa gag       576
Gly Lys Asn Ala Glu Asp Ala Val His Asn Ala Ile Val Leu Glu Glu
            180                 185                 190 gtc gct tat atg ggg ata ttc tgc cgt cag tta gcg ccg cag tta ccg       624
Val Ala Tyr Met Gly Ile Phe Cys Arg Gln Leu Ala Pro Gln Leu Pro
        195                 200                 205 gat atg cag caa acg ctg ctg gat aaa cac tat ctg cgt aag cat ggc       672
Asp Met Gln Gln Thr Leu Leu Asp Lys His Tyr Leu Arg Lys His Gly
    210                 215                 220 gcg aag gca tat tac ggg cag taa                                       696
Ala Lys Ala Tyr Tyr Gly Gln
225                 230
```

<210> SEQ ID NO 77
<211> LENGTH: 231
<212> TYPE: PRT
<213> ORGANISM: Escherichia coli

<400> SEQUENCE: 77

```
Met Leu Glu Asp Leu Lys Arg Gln Val Leu Glu Ala Asn Leu Ala Leu
1               5                   10                  15

Pro Lys His Asn Leu Val Thr Leu Thr Trp Gly Asn Val Ser Ala Val
                20                  25                  30

Asp Arg Glu Arg Gly Val Phe Val Ile Lys Pro Ser Gly Val Asp Tyr
            35                  40                  45

Ser Val Met Thr Ala Asp Asp Met Val Val Ser Ile Glu Thr Gly
    50                  55                  60

Glu Val Val Glu Gly Thr Lys Lys Pro Ser Ser Asp Thr Pro Thr His
65                  70                  75                  80

Arg Leu Leu Tyr Gln Ala Phe Pro Ser Ile Gly Gly Ile Val His Thr
                85                  90                  95

His Ser Arg His Ala Thr Ile Trp Ala Gln Ala Gly Gln Ser Ile Pro
            100                 105                 110

Ala Thr Gly Thr Thr His Ala Asp Tyr Phe Tyr Gly Thr Ile Pro Cys
            115                 120                 125

Thr Arg Lys Met Thr Asp Ala Glu Ile Asn Gly Glu Tyr Glu Trp Glu
            130                 135                 140

Thr Gly Asn Val Ile Val Glu Thr Phe Glu Lys Gln Gly Ile Asp Ala
145                 150                 155                 160

Ala Gln Met Pro Gly Val Leu Val His Ser His Gly Pro Phe Ala Trp
                165                 170                 175

Gly Lys Asn Ala Glu Asp Ala Val His Asn Ala Ile Val Leu Glu Glu
            180                 185                 190

Val Ala Tyr Met Gly Ile Phe Cys Arg Gln Leu Ala Pro Gln Leu Pro
            195                 200                 205

Asp Met Gln Gln Thr Leu Leu Asp Lys His Tyr Leu Arg Lys His Gly
            210                 215                 220

Ala Lys Ala Tyr Tyr Gly Gln
225                 230

<210> SEQ ID NO 78
<211> LENGTH: 729
<212> TYPE: DNA
<213> ORGANISM: Artificial Sequence
<220> FEATURE:
<223> OTHER INFORMATION: Codon optimized L. plantarum araD
<220> FEATURE:
<221> NAME/KEY: CDS
<222> LOCATION: (1)..(729)

<400> SEQUENCE: 78 atg ttg gaa gca tta aag caa gaa gtt tac gaa gct aat atg cag ttg      48
Met Leu Glu Ala Leu Lys Gln Glu Val Tyr Glu Ala Asn Met Gln Leu
1               5                   10                  15 cca aaa tta ggt tta gtt act ttc acc tgg ggt aat gtt tct ggt att     96
Pro Lys Leu Gly Leu Val Thr Phe Thr Trp Gly Asn Val Ser Gly Ile
                20                  25                  30 gat aga gag aaa ggt ttg ttc gtt atc aag cca tca ggt gtc gac tat    144
Asp Arg Glu Lys Gly Leu Phe Val Ile Lys Pro Ser Gly Val Asp Tyr
            35                  40                  45 ggt gaa ctt aag cca tcc gat tta gtt gtt gtc aat tta caa ggt gaa    192
Gly Glu Leu Lys Pro Ser Asp Leu Val Val Val Asn Leu Gln Gly Glu
    50                  55                  60 gtt gtt gaa ggt aaa tta aac cca tct tct gat aca cct acc cac act    240
Val Val Glu Gly Lys Leu Asn Pro Ser Ser Asp Thr Pro Thr His Thr
65                  70                  75                  80 gtt tta tat aac gca ttt cca aac atc ggt ggt atc gtt cat acc cat    288
```

```
Val Leu Tyr Asn Ala Phe Pro Asn Ile Gly Gly Ile Val His Thr His
            85              90              95 tcc cca tgg gcc gtc gca tac gca gct gca caa atg gac gtc cct gca      336
Ser Pro Trp Ala Val Ala Tyr Ala Ala Ala Gln Met Asp Val Pro Ala
        100             105             110 atg aac acc acc cac gct gat acc ttc tac ggt gat gtc cct gca gct      384
Met Asn Thr Thr His Ala Asp Thr Phe Tyr Gly Asp Val Pro Ala Ala
            115             120             125 gac gca ttg act aag gaa gaa att gaa gca gac tac gag ggt aat acc      432
Asp Ala Leu Thr Lys Glu Glu Ile Glu Ala Asp Tyr Glu Gly Asn Thr
        130             135             140 ggt aaa act att gtc aag acc ttt caa gaa aga ggt tta gat tac gaa      480
Gly Lys Thr Ile Val Lys Thr Phe Gln Glu Arg Gly Leu Asp Tyr Glu
145             150             155             160 gcc gtt cca gct tct ttg gtc tct caa cat ggt cct ttc gca tgg ggt      528
Ala Val Pro Ala Ser Leu Val Ser Gln His Gly Pro Phe Ala Trp Gly
                165             170             175 cca aca cca gct aaa gca gtt tat aat gct aag gtt tta gag gtt gtc      576
Pro Thr Pro Ala Lys Ala Val Tyr Asn Ala Lys Val Leu Glu Val Val
            180             185             190 gca gag gaa gac tat cac acc gca caa ttg acc aga gct tcc tcc gaa      624
Ala Glu Glu Asp Tyr His Thr Ala Gln Leu Thr Arg Ala Ser Ser Glu
        195             200             205 ctt cca caa tac ttg tta gat aag cac tat tta aga aag cac ggt gct      672
Leu Pro Gln Tyr Leu Leu Asp Lys His Tyr Leu Arg Lys His Gly Ala
    210             215             220 tct gct tat tac ggt caa aac aat gca cat tcc aag gat cac gct gtt      720
Ser Ala Tyr Tyr Gly Gln Asn Asn Ala His Ser Lys Asp His Ala Val
225             230             235             240 aga aag taa                                                          729
Arg Lys <210> SEQ ID NO 79
<211> LENGTH: 242
<212> TYPE: PRT
<213> ORGANISM: Artificial Sequence
<220> FEATURE:
<223> OTHER INFORMATION: Synthetic Construct

<400> SEQUENCE: 79

Met Leu Glu Ala Leu Lys Gln Glu Val Tyr Glu Ala Asn Met Gln Leu
1               5                   10                  15

Pro Lys Leu Gly Leu Val Thr Phe Thr Trp Gly Asn Val Ser Gly Ile
            20                  25                  30

Asp Arg Glu Lys Gly Leu Phe Val Ile Lys Pro Ser Gly Val Asp Tyr
        35                  40                  45

Gly Glu Leu Lys Pro Ser Asp Leu Val Val Val Asn Leu Gln Gly Glu
    50                  55                  60

Val Val Glu Gly Lys Leu Asn Pro Ser Ser Asp Thr Pro Thr His Thr
65                  70                  75                  80

Val Leu Tyr Asn Ala Phe Pro Asn Ile Gly Gly Ile Val His Thr His
            85                  90                  95

Ser Pro Trp Ala Val Ala Tyr Ala Ala Ala Gln Met Asp Val Pro Ala
            100                 105                 110

Met Asn Thr Thr His Ala Asp Thr Phe Tyr Gly Asp Val Pro Ala Ala
        115                 120                 125

Asp Ala Leu Thr Lys Glu Glu Ile Glu Ala Asp Tyr Glu Gly Asn Thr
    130                 135                 140
```

| | | | | | | | | | | | | | |
|---|---|---|---|---|---|---|---|---|---|---|---|---|---|
|Gly|Lys|Thr|Ile|Val|Lys|Thr|Phe|Gln|Glu|Arg|Gly|Leu|Asp|Tyr|Glu|
|145| | | |150| | | |155| | | |160| | | |

Ala Val Pro Ala Ser Leu Val Ser Gln His Gly Pro Phe Ala Trp Gly
            165                 170                 175

Pro Thr Pro Ala Lys Ala Val Tyr Asn Ala Lys Val Leu Glu Val Val
                180                 185                 190

Ala Glu Glu Asp Tyr His Thr Ala Gln Leu Thr Arg Ala Ser Ser Glu
            195                 200                 205

Leu Pro Gln Tyr Leu Leu Asp Lys His Tyr Leu Arg Lys His Gly Ala
        210                 215                 220

Ser Ala Tyr Tyr Gly Gln Asn Asn Ala His Ser Lys Asp His Ala Val
225                 230                 235                 240

Arg Lys

```
<210> SEQ ID NO 80
<211> LENGTH: 1425
<212> TYPE: DNA
<213> ORGANISM: Artificial Sequence
<220> FEATURE:
<223> OTHER INFORMATION: Codon optimized L. plantarum araA
<220> FEATURE:
<221> NAME/KEY: CDS
<222> LOCATION: (1)..(1425)

<400> SEQUENCE: 80
```

| | | | | | | | | | | | | | | | | |
|---|---|---|---|---|---|---|---|---|---|---|---|---|---|---|---|---|
|atg|tta|tcc|gtt|cca|gat|tac|gaa|ttt|tgg|ttc|gtc|act|ggt|tct|caa| 48|
|Met|Leu|Ser|Val|Pro|Asp|Tyr|Glu|Phe|Trp|Phe|Val|Thr|Gly|Ser|Gln| |
|1| | | |5| | | | |10| | | | |15| | | cac ttg tac ggt gaa gaa caa ctt aag tct gtc gct aag gat gca caa     96
His Leu Tyr Gly Glu Glu Gln Leu Lys Ser Val Ala Lys Asp Ala Gln
            20                  25                  30 gac atc gca gac aag tta aac gct tct ggt aag ttg cca tac aag gtt    144
Asp Ile Ala Asp Lys Leu Asn Ala Ser Gly Lys Leu Pro Tyr Lys Val
        35                  40                  45 gtc ttc aag gat gtt atg act acc gca gaa tct atc act aac ttt atg    192
Val Phe Lys Asp Val Met Thr Thr Ala Glu Ser Ile Thr Asn Phe Met
    50                  55                  60 aag gaa gtt aat tac aac gat aag gtt gct ggt gtt att acc tgg atg    240
Lys Glu Val Asn Tyr Asn Asp Lys Val Ala Gly Val Ile Thr Trp Met
65                  70                  75                  80 cat acc ttc tct cca gct aaa aac tgg att aga ggt aca gaa ttg ttg    288
His Thr Phe Ser Pro Ala Lys Asn Trp Ile Arg Gly Thr Glu Leu Leu
                85                  90                  95 caa aag cca ttg tta cac ctt gct act caa tat ttg aac aac att cca    336
Gln Lys Pro Leu Leu His Leu Ala Thr Gln Tyr Leu Asn Asn Ile Pro
            100                 105                 110 tac gca gat att gat ttt gat tat atg aac ttg aac caa tct gct cac    384
Tyr Ala Asp Ile Asp Phe Asp Tyr Met Asn Leu Asn Gln Ser Ala His
        115                 120                 125 ggt gac aga gaa tat gca tat atc aat gca aga tta caa aag cat aac    432
Gly Asp Arg Glu Tyr Ala Tyr Ile Asn Ala Arg Leu Gln Lys His Asn
    130                 135                 140 aag att gtt tac ggt tat tgg ggt gat gaa gat gtt caa gaa caa att    480
Lys Ile Val Tyr Gly Tyr Trp Gly Asp Glu Asp Val Gln Glu Gln Ile
145                 150                 155                 160 gct aga tgg gaa gat gtt gca gtt gca tac aat gaa tct ttt aag gtt    528
Ala Arg Trp Glu Asp Val Ala Val Ala Tyr Asn Glu Ser Phe Lys Val
                165                 170                 175 aag gtc gca aga ttc ggt gat act atg aga aac gtc gca gtt act gaa    576
Lys Val Ala Arg Phe Gly Asp Thr Met Arg Asn Val Ala Val Thr Glu

```
                     180                 185                  190
ggt gat aag gtt gaa gct caa att aag atg ggt tgg act gtt gac tac       624
Gly Asp Lys Val Glu Ala Gln Ile Lys Met Gly Trp Thr Val Asp Tyr
        195                 200                 205 tac ggt att ggt gat ttg gtt gag gaa att aat aag gtt tcc gat gct       672
Tyr Gly Ile Gly Asp Leu Val Glu Glu Ile Asn Lys Val Ser Asp Ala
    210                 215                 220 gat gtc gat aag gaa tac gca gat tta gaa tcc aga tac gaa atg gtc       720
Asp Val Asp Lys Glu Tyr Ala Asp Leu Glu Ser Arg Tyr Glu Met Val
225                 230                 235                 240 caa ggt gat aat gac gcc gat act tac aag cat tcc gtc aga gtt caa       768
Gln Gly Asp Asn Asp Ala Asp Thr Tyr Lys His Ser Val Arg Val Gln
        245                 250                 255 ctt gct caa tac tta ggt atc aag aga ttt ttg gaa aga ggt ggt tac       816
Leu Ala Gln Tyr Leu Gly Ile Lys Arg Phe Leu Glu Arg Gly Gly Tyr
    260                 265                 270 act gct ttc act act aat ttc gaa gat tta tgg ggt atg gaa caa tta       864
Thr Ala Phe Thr Thr Asn Phe Glu Asp Leu Trp Gly Met Glu Gln Leu
275                 280                 285 cca ggt ctt gca tcc caa tta tta att aga gat ggt tat ggt ttc ggt       912
Pro Gly Leu Ala Ser Gln Leu Leu Ile Arg Asp Gly Tyr Gly Phe Gly
        290                 295                 300 gca gaa ggt gac tgg aag act gca gca tta ggt aga gtc atg aag att       960
Ala Glu Gly Asp Trp Lys Thr Ala Ala Leu Gly Arg Val Met Lys Ile
305                 310                 315                 320 atg tct cac aac aaa caa acc gct ttt atg gag gat tat act tta gat      1008
Met Ser His Asn Lys Gln Thr Ala Phe Met Glu Asp Tyr Thr Leu Asp
        325                 330                 335 tta aga cac ggt cac gaa gca att tta ggt tcc cac atg ctt gaa gtt      1056
Leu Arg His Gly His Glu Ala Ile Leu Gly Ser His Met Leu Glu Val
    340                 345                 350 gat cca tcc att gct tct gat aaa cca aga gtt gaa gtt cac cca tta      1104
Asp Pro Ser Ile Ala Ser Asp Lys Pro Arg Val Glu Val His Pro Leu
355                 360                 365 gat atc ggt ggt aaa gac gac cca gct aga tta gtt ttt act ggt tct      1152
Asp Ile Gly Gly Lys Asp Asp Pro Ala Arg Leu Val Phe Thr Gly Ser
        370                 375                 380 gag ggt gaa gct att gat gtt act gtc gca gac ttt aga gat ggt ttt      1200
Glu Gly Glu Ala Ile Asp Val Thr Val Ala Asp Phe Arg Asp Gly Phe
385                 390                 395                 400 aag atg att tcc tac gct gtt gac gca aac aag cca gag gct gaa aca      1248
Lys Met Ile Ser Tyr Ala Val Asp Ala Asn Lys Pro Glu Ala Glu Thr
        405                 410                 415 cca aat ttg cca gtc gcc aag caa ttg tgg acc cca aag atg ggt tta      1296
Pro Asn Leu Pro Val Ala Lys Gln Leu Trp Thr Pro Lys Met Gly Leu
    420                 425                 430 aag aag ggt gct tta gaa tgg atg caa gct ggt ggt cac cat act           1344
Lys Lys Gly Ala Leu Glu Trp Met Gln Ala Gly Gly His His Thr
435                 440                 445 atg tta tct ttc tct tta act gaa gaa caa atg gaa gat tat gct act      1392
Met Leu Ser Phe Ser Leu Thr Glu Glu Gln Met Glu Asp Tyr Ala Thr
        450                 455                 460 atg gtt ggt atg acc aaa gcc ttc tta aag tag                          1425
Met Val Gly Met Thr Lys Ala Phe Leu Lys
465                 470
```

<210> SEQ ID NO 81
<211> LENGTH: 474
<212> TYPE: PRT
<213> ORGANISM: Artificial Sequence
<220> FEATURE:
<223> OTHER INFORMATION: Synthetic Construct

<400> SEQUENCE: 81

```
Met Leu Ser Val Pro Asp Tyr Glu Phe Trp Phe Val Thr Gly Ser Gln
1               5                   10                  15

His Leu Tyr Gly Glu Glu Gln Leu Lys Ser Val Ala Lys Asp Ala Gln
            20                  25                  30

Asp Ile Ala Asp Lys Leu Asn Ala Ser Gly Lys Leu Pro Tyr Lys Val
        35                  40                  45

Val Phe Lys Asp Val Met Thr Thr Ala Glu Ser Ile Thr Asn Phe Met
50                  55                  60

Lys Glu Val Asn Tyr Asn Asp Lys Val Ala Gly Val Ile Thr Trp Met
65                  70                  75                  80

His Thr Phe Ser Pro Ala Lys Asn Trp Ile Arg Gly Thr Glu Leu Leu
                85                  90                  95

Gln Lys Pro Leu Leu His Leu Ala Thr Gln Tyr Leu Asn Asn Ile Pro
            100                 105                 110

Tyr Ala Asp Ile Asp Phe Asp Tyr Met Asn Leu Asn Gln Ser Ala His
        115                 120                 125

Gly Asp Arg Glu Tyr Ala Tyr Ile Asn Ala Arg Leu Gln Lys His Asn
130                 135                 140

Lys Ile Val Tyr Gly Tyr Trp Gly Asp Glu Asp Val Gln Glu Gln Ile
145                 150                 155                 160

Ala Arg Trp Glu Asp Val Ala Val Ala Tyr Asn Glu Ser Phe Lys Val
                165                 170                 175

Lys Val Ala Arg Phe Gly Asp Thr Met Arg Asn Val Ala Val Thr Glu
            180                 185                 190

Gly Asp Lys Val Glu Ala Gln Ile Lys Met Gly Trp Thr Val Asp Tyr
        195                 200                 205

Tyr Gly Ile Gly Asp Leu Val Glu Glu Ile Asn Lys Val Ser Asp Ala
210                 215                 220

Asp Val Asp Lys Glu Tyr Ala Asp Leu Glu Ser Arg Tyr Glu Met Val
225                 230                 235                 240

Gln Gly Asp Asn Asp Ala Asp Thr Tyr Lys His Ser Val Arg Val Gln
                245                 250                 255

Leu Ala Gln Tyr Leu Gly Ile Lys Arg Phe Leu Glu Arg Gly Gly Tyr
            260                 265                 270

Thr Ala Phe Thr Thr Asn Phe Glu Asp Leu Trp Gly Met Glu Gln Leu
        275                 280                 285

Pro Gly Leu Ala Ser Gln Leu Leu Ile Arg Asp Gly Tyr Gly Phe Gly
290                 295                 300

Ala Glu Gly Asp Trp Lys Thr Ala Ala Leu Gly Arg Val Met Lys Ile
305                 310                 315                 320

Met Ser His Asn Lys Gln Thr Ala Phe Met Glu Asp Tyr Thr Leu Asp
                325                 330                 335

Leu Arg His Gly His Glu Ala Ile Leu Gly Ser His Met Leu Glu Val
            340                 345                 350

Asp Pro Ser Ile Ala Ser Asp Lys Pro Arg Val Glu Val His Pro Leu
        355                 360                 365

Asp Ile Gly Gly Lys Asp Pro Ala Arg Leu Val Phe Thr Gly Ser
370                 375                 380

Glu Gly Glu Ala Ile Asp Val Thr Val Ala Asp Phe Arg Asp Gly Phe
385                 390                 395                 400
```

```
Lys Met Ile Ser Tyr Ala Val Asp Ala Asn Lys Pro Glu Ala Glu Thr
                405                 410                 415

Pro Asn Leu Pro Val Ala Lys Gln Leu Trp Thr Pro Lys Met Gly Leu
            420                 425                 430

Lys Lys Gly Ala Leu Glu Trp Met Gln Ala Gly Gly His His Thr
        435                 440                 445

Met Leu Ser Phe Ser Leu Thr Glu Glu Gln Met Glu Asp Tyr Ala Thr
    450                 455                 460

Met Val Gly Met Thr Lys Ala Phe Leu Lys
465                 470

<210> SEQ ID NO 82
<211> LENGTH: 1482
<212> TYPE: DNA
<213> ORGANISM: Artificial Sequence
<220> FEATURE:
<223> OTHER INFORMATION: Codon optimized B. licheniformis araA
<220> FEATURE:
<221> NAME/KEY: CDS
<222> LOCATION: (1)..(1482)

<400> SEQUENCE: 82 atg atc caa gca aag acc cac gtc ttc tgg ttc gtc aca ggt tcc caa      48
Met Ile Gln Ala Lys Thr His Val Phe Trp Phe Val Thr Gly Ser Gln
1               5                   10                  15 cac tta tac ggt gaa gaa gca gtt caa gaa gtc gaa gaa cac tcc aag      96
His Leu Tyr Gly Glu Glu Ala Val Gln Glu Val Glu Glu His Ser Lys
                20                  25                  30 atg atc tgt aac ggt tta aac gat ggt gat tta aga ttt caa gtt gaa     144
Met Ile Cys Asn Gly Leu Asn Asp Gly Asp Leu Arg Phe Gln Val Glu
            35                  40                  45 tac aag gct gtc gct act tcc tta gac ggt gtc aga aag ttg ttc gaa     192
Tyr Lys Ala Val Ala Thr Ser Leu Asp Gly Val Arg Lys Leu Phe Glu
        50                  55                  60 gaa gct aac aga gat gaa gaa tgt gcc ggt att att acc tgg atg cat     240
Glu Ala Asn Arg Asp Glu Glu Cys Ala Gly Ile Ile Thr Trp Met His
65                  70                  75                  80 acc ttc tct cct gca aag atg tgg att cca ggt tta tct gaa ttg aac     288
Thr Phe Ser Pro Ala Lys Met Trp Ile Pro Gly Leu Ser Glu Leu Asn
                85                  90                  95 aag cca tta ttg cac ttt cac act caa ttt aac aga gac atc cct tgg     336
Lys Pro Leu Leu His Phe His Thr Gln Phe Asn Arg Asp Ile Pro Trp
                100                 105                 110 gac aag att gat atg gac ttc atg aat atc aac caa tct gct cac ggt     384
Asp Lys Ile Asp Met Asp Phe Met Asn Ile Asn Gln Ser Ala His Gly
            115                 120                 125 gac aga gaa tac ggt ttt atc ggt gct aga ttg ggt atc cca aga aag     432
Asp Arg Glu Tyr Gly Phe Ile Gly Ala Arg Leu Gly Ile Pro Arg Lys
        130                 135                 140 gtc atc gcc ggt tac tgg gaa gat aga gaa gtt aaa aga tcc att gat     480
Val Ile Ala Gly Tyr Trp Glu Asp Arg Glu Val Lys Arg Ser Ile Asp
145                 150                 155                 160 aaa tgg atg tcc gcc gct gtt gct tac atc gaa tca aga cac att aag     528
Lys Trp Met Ser Ala Ala Val Ala Tyr Ile Glu Ser Arg His Ile Lys
                165                 170                 175 gtt gct aga ttt ggt gat aat atg aga aat gtt gct gtt act gaa ggt     576
Val Ala Arg Phe Gly Asp Asn Met Arg Asn Val Ala Val Thr Glu Gly
                180                 185                 190 gat aag att gaa gct caa att caa ctt ggt tgg tca gtt gat ggc tac     624
Asp Lys Ile Glu Ala Gln Ile Gln Leu Gly Trp Ser Val Asp Gly Tyr
```

```
            195                 200                 205
ggt att ggt gat tta gtt acc gaa atc aat gca gtc tct gaa caa tcc      672
Gly Ile Gly Asp Leu Val Thr Glu Ile Asn Ala Val Ser Glu Gln Ser
210                 215                 220 tta tcc gaa tta att tcc gaa tac gaa gaa tta tac gag tgg cca gaa      720
Leu Ser Glu Leu Ile Ser Glu Tyr Glu Glu Leu Tyr Glu Trp Pro Glu
225                 230                 235                 240 ggt gaa gct gct aga gaa tct gtt aag gaa caa gca aga att gaa ctt      768
Gly Glu Ala Ala Arg Glu Ser Val Lys Glu Gln Ala Arg Ile Glu Leu
                245                 250                 255 ggt tta aag aga ttt ctt tct tct ggt ggt tat acc gca ttt acc act      816
Gly Leu Lys Arg Phe Leu Ser Ser Gly Gly Tyr Thr Ala Phe Thr Thr
            260                 265                 270 acc ttc gaa gac tta cac ggt atg aag caa tta cct ggt tta gca gtt      864
Thr Phe Glu Asp Leu His Gly Met Lys Gln Leu Pro Gly Leu Ala Val
        275                 280                 285 caa aga ctt atg gct gaa ggt tac ggt ttc ggt ggt gaa ggt gac tgg      912
Gln Arg Leu Met Ala Glu Gly Tyr Gly Phe Gly Gly Glu Gly Asp Trp
290                 295                 300 aag acc gct gct ttg gtc aga atg atg aag atg atg gct ggt ggt aag      960
Lys Thr Ala Ala Leu Val Arg Met Met Lys Met Met Ala Gly Gly Lys
305                 310                 315                 320 gaa act tct ttc atg gaa gat tac acc tac cac ttc gaa cca ggt aat     1008
Glu Thr Ser Phe Met Glu Asp Tyr Thr Tyr His Phe Glu Pro Gly Asn
                325                 330                 335 gaa atg att tta ggt tcc cac atg tta gaa gtt tgc cct tct atc gct     1056
Glu Met Ile Leu Gly Ser His Met Leu Glu Val Cys Pro Ser Ile Ala
            340                 345                 350 gag cac aag cca aga atc gaa gtt cat cct tta tct atg ggt gca aag     1104
Glu His Lys Pro Arg Ile Glu Val His Pro Leu Ser Met Gly Ala Lys
        355                 360                 365 gat gac cca gct aga tta gtc ttc gat ggt att gca ggt cca gca gtt     1152
Asp Asp Pro Ala Arg Leu Val Phe Asp Gly Ile Ala Gly Pro Ala Val
370                 375                 380 aac gtc tcc tta atc gac ctt ggt ggt aga ttc aga tta gtt att aat     1200
Asn Val Ser Leu Ile Asp Leu Gly Gly Arg Phe Arg Leu Val Ile Asn
385                 390                 395                 400 aag gtc gaa gct gtt aag gtt cca cat gat atg cct aat cta cca gtt     1248
Lys Val Glu Ala Val Lys Val Pro His Asp Met Pro Asn Leu Pro Val
                405                 410                 415 gct aga gtt tta tgg aag cca caa cct tcc ttg aga act tcc gct gaa     1296
Ala Arg Val Leu Trp Lys Pro Gln Pro Ser Leu Arg Thr Ser Ala Glu
            420                 425                 430 gcc tgg att ttg gca ggt ggt gcc cat cac acc tgt ttg tct tat caa     1344
Ala Trp Ile Leu Ala Gly Gly Ala His His Thr Cys Leu Ser Tyr Gln
        435                 440                 445 ttg act gca gaa caa atg tta gac tgg gct gaa atg tcc ggt att gaa     1392
Leu Thr Ala Glu Gln Met Leu Asp Trp Ala Glu Met Ser Gly Ile Glu
450                 455                 460 gct gtc tta atc aac aga gat act act att ctt aat ctt aga aac gaa     1440
Ala Val Leu Ile Asn Arg Asp Thr Thr Ile Leu Asn Leu Arg Asn Glu
465                 470                 475                 480 ctt aag tgg tcc gaa gca gct tac aga ttg aga aag ttt tag             1482
Leu Lys Trp Ser Glu Ala Ala Tyr Arg Leu Arg Lys Phe
                485                 490

<210> SEQ ID NO 83
<211> LENGTH: 493
<212> TYPE: PRT
<213> ORGANISM: Artificial Sequence
```

<220> FEATURE:
<223> OTHER INFORMATION: Synthetic Construct

<400> SEQUENCE: 83

```
Met Ile Gln Ala Lys Thr His Val Phe Trp Phe Val Thr Gly Ser Gln
1               5                   10                  15

His Leu Tyr Gly Glu Glu Ala Val Gln Val Glu Glu His Ser Lys
            20                  25                  30

Met Ile Cys Asn Gly Leu Asn Asp Gly Asp Leu Arg Phe Gln Val Glu
            35                  40                  45

Tyr Lys Ala Val Ala Thr Ser Leu Asp Gly Val Arg Lys Leu Phe Glu
        50                  55                  60

Glu Ala Asn Arg Asp Glu Glu Cys Ala Gly Ile Ile Thr Trp Met His
65                  70                  75                  80

Thr Phe Ser Pro Ala Lys Met Trp Ile Pro Gly Leu Ser Glu Leu Asn
                85                  90                  95

Lys Pro Leu Leu His Phe His Thr Gln Phe Asn Arg Asp Ile Pro Trp
            100                 105                 110

Asp Lys Ile Asp Met Asp Phe Met Asn Ile Asn Gln Ser Ala His Gly
        115                 120                 125

Asp Arg Glu Tyr Gly Phe Ile Gly Ala Arg Leu Gly Ile Pro Arg Lys
    130                 135                 140

Val Ile Ala Gly Tyr Trp Glu Asp Arg Glu Val Lys Arg Ser Ile Asp
145                 150                 155                 160

Lys Trp Met Ser Ala Ala Val Ala Tyr Ile Glu Ser Arg His Ile Lys
                165                 170                 175

Val Ala Arg Phe Gly Asp Asn Met Arg Asn Val Ala Val Thr Glu Gly
            180                 185                 190

Asp Lys Ile Glu Ala Gln Ile Gln Leu Gly Trp Ser Val Asp Gly Tyr
        195                 200                 205

Gly Ile Gly Asp Leu Val Thr Glu Ile Asn Ala Val Ser Glu Gln Ser
    210                 215                 220

Leu Ser Glu Leu Ile Ser Glu Tyr Glu Glu Leu Tyr Glu Trp Pro Glu
225                 230                 235                 240

Gly Glu Ala Ala Arg Glu Ser Val Lys Glu Gln Ala Arg Ile Glu Leu
                245                 250                 255

Gly Leu Lys Arg Phe Leu Ser Ser Gly Gly Tyr Thr Ala Phe Thr Thr
            260                 265                 270

Thr Phe Glu Asp Leu His Gly Met Lys Gln Leu Pro Gly Leu Ala Val
        275                 280                 285

Gln Arg Leu Met Ala Glu Gly Tyr Gly Phe Gly Glu Gly Asp Trp
    290                 295                 300

Lys Thr Ala Ala Leu Val Arg Met Met Lys Met Ala Gly Gly Lys
305                 310                 315                 320

Glu Thr Ser Phe Met Glu Asp Tyr Thr Tyr His Phe Glu Pro Gly Asn
                325                 330                 335

Glu Met Ile Leu Gly Ser His Met Leu Glu Val Cys Pro Ser Ile Ala
            340                 345                 350

Glu His Lys Pro Arg Ile Glu Val His Pro Leu Ser Met Gly Ala Lys
        355                 360                 365

Asp Asp Pro Ala Arg Leu Val Phe Asp Gly Ile Ala Gly Pro Ala Val
    370                 375                 380

Asn Val Ser Leu Ile Asp Leu Gly Gly Arg Phe Arg Leu Val Ile Asn
385                 390                 395                 400
```

```
Lys Val Glu Ala Val Lys Val Pro His Asp Met Pro Asn Leu Pro Val
            405                 410                 415
Ala Arg Val Leu Trp Lys Pro Gln Pro Ser Leu Arg Thr Ser Ala Glu
        420                 425                 430
Ala Trp Ile Leu Ala Gly Gly Ala His His Thr Cys Leu Ser Tyr Gln
    435                 440                 445
Leu Thr Ala Glu Gln Met Leu Asp Trp Ala Glu Met Ser Gly Ile Glu
450                 455                 460
Ala Val Leu Ile Asn Arg Asp Thr Thr Ile Leu Asn Leu Arg Asn Glu
465                 470                 475                 480
Leu Lys Trp Ser Glu Ala Ala Tyr Arg Leu Arg Lys Phe
                485                 490
```

<210> SEQ ID NO 84
<211> LENGTH: 3134
<212> TYPE: DNA
<213> ORGANISM: Issatchenkia orientalis
<220> FEATURE:
<221> NAME/KEY: CDS
<222> LOCATION: (1001)..(2134)

<400> SEQUENCE: 84

```
atgtatttgg agatttcgaa aagagtttgt atagagtctg taattgggtg tgtatttcaa      60
gacccacttt aaactgcgcc attaggagag ggagaggggg ggggggggg gaagacggt       120
gaagtgtata caggatcgaa gaatagaagt tgtgtgtgtg ttttattacc cgtttcgatg     180
ggattcccag aagtggatac tatactgtct gcaatgcact acactctaaa aaagtattat     240
acattaccat acattagcaa atcaccaata ctctgcactg tttcagtgtg tgcacattgc     300
tacccaattg ggaaattgca gggaaaatga gaccccccct ccattccgta ttacgtaaga     360
caatatcagg gctgccgaat tcggcagaaa agccgagccg gccgagtcct cttgcacgga     420
gtgtgtccga aaagggcagc tctgcagtgg gggagaggag gtcgcacgtc tatgcggtgt     480
tggcatggcc tgtgcgtgta cctgtcccct ccctgggcat cccccactgc gcgccttctc     540
cattgggcgc tgcgggcact ccgcgccgtt aatacaggag gggggggggg aaagcttaag     600
attagagcgg gtacagtcag tgggtgtatt gaccccattt ctgtcagtat aaaccccccg     660
ttgagccgcc ggtttggttg tttatggata aaattttttt tccccgcatg gagaagattg     720
aggggagaa ggaatgggaa aaaggccaga gccatctcca cagcggaatc cgaccgttaa     780
tggggtgaaa caccccacc aggtagagca ggaagaatgg ggaaacaagg tggagagatg     840
gtcattgttg ggaatagtgg gaaatgaggg gggaagagaa tgactataaa atgggaaggg     900
ggtccaagtt atccaagcag tccatttaga gaagggaaaa taaagctata gatagaaacc     960
aaccaaacaa ccaaacaatt aaacaaacaa ttaaacgaac atg tta tcc aag acc     1015
                                              Met Leu Ser Lys Thr
                                              1               5
atc act gct gca ttg agg ggc aat aca act cgt act gca ttc aga atc     1063
Ile Thr Ala Ala Leu Arg Gly Asn Thr Thr Arg Thr Ala Phe Arg Ile
            10                  15                  20
aat gcc att aga agt tta gcg atc cca gct att cca gag aca caa aag     1111
Asn Ala Ile Arg Ser Leu Ala Ile Pro Ala Ile Pro Glu Thr Gln Lys
        25                  30                  35
ggt gtt atc ttt tat gag aac gga ggt gaa cta ttt tac aag gac att     1159
Gly Val Ile Phe Tyr Glu Asn Gly Gly Glu Leu Phe Tyr Lys Asp Ile
    40                  45                  50
cca gtt cca aag cca aag cca aat gag att ttg gtg aat gtc aag tat     1207
```

-continued

```
Pro Val Pro Lys Pro Lys Pro Asn Glu Ile Leu Val Asn Val Lys Tyr
     55                  60                  65 tct ggt gtt tgt cat acc gat tta cac gca tgg aaa ggt gac tgg cct      1255
Ser Gly Val Cys His Thr Asp Leu His Ala Trp Lys Gly Asp Trp Pro
 70                  75                  80                  85 ttg gcg acc aag ttg cca ttg gtt ggt gga cat gaa ggt gcc gga gtt      1303
Leu Ala Thr Lys Leu Pro Leu Val Gly Gly His Glu Gly Ala Gly Val
                 90                  95                 100 gtt gtt gct aag ggg gac aat gtc acc aac ttt gaa att ggc gat tat      1351
Val Val Ala Lys Gly Asp Asn Val Thr Asn Phe Glu Ile Gly Asp Tyr
             105                 110                 115 gcc ggt atc aag tgg ttg aat ggt tca tgt atg ggg tgt gaa ttt tgc      1399
Ala Gly Ile Lys Trp Leu Asn Gly Ser Cys Met Gly Cys Glu Phe Cys
         120                 125                 130 caa caa ggt gca gag cca aac tgt cca cag gcc gac ttg agt ggt tac      1447
Gln Gln Gly Ala Glu Pro Asn Cys Pro Gln Ala Asp Leu Ser Gly Tyr
     135                 140                 145 acc cat gac ggg tcc ttt caa caa tat gcc act gcc gat gct gtt cag      1495
Thr His Asp Gly Ser Phe Gln Gln Tyr Ala Thr Ala Asp Ala Val Gln
150                 155                 160                 165 gca gcc aag att cct cag ggc act gat ttg gct caa gtt gcg cca att      1543
Ala Ala Lys Ile Pro Gln Gly Thr Asp Leu Ala Gln Val Ala Pro Ile
                 170                 175                 180 tta tgt gca ggt att act gtc tat aag gct tta aag act gca gaa tta      1591
Leu Cys Ala Gly Ile Thr Val Tyr Lys Ala Leu Lys Thr Ala Glu Leu
             185                 190                 195 aga cca ggt caa tgg gtt gcc att tct ggt gct gct gga ggt tta ggt      1639
Arg Pro Gly Gln Trp Val Ala Ile Ser Gly Ala Ala Gly Gly Leu Gly
         200                 205                 210 tct ctt gct gtt caa tat gcc aag gcc atg ggt ttg aga gtt ttg ggt      1687
Ser Leu Ala Val Gln Tyr Ala Lys Ala Met Gly Leu Arg Val Leu Gly
     215                 220                 225 att gat ggt ggt gag gag aag ggc aag ttt gca aag tct ctt gga gct      1735
Ile Asp Gly Gly Glu Glu Lys Gly Lys Phe Ala Lys Ser Leu Gly Ala
230                 235                 240                 245 gaa gtt ttc att gat ttc acc aaa tcc aag gac att gtc aag gat atc      1783
Glu Val Phe Ile Asp Phe Thr Lys Ser Lys Asp Ile Val Lys Asp Ile
                 250                 255                 260 caa gag gcc acc aat ggt ggt cca cat ggt gtc att aat gtt tct gtt      1831
Gln Glu Ala Thr Asn Gly Gly Pro His Gly Val Ile Asn Val Ser Val
             265                 270                 275 tct cca gct gct att tct caa agt acc cag tat gtc aga acc ttg ggt      1879
Ser Pro Ala Ala Ile Ser Gln Ser Thr Gln Tyr Val Arg Thr Leu Gly
         280                 285                 290 aag gtt gtc ctt gtt gga tta cca gcg cat gct gta tgc gag tct tcg      1927
Lys Val Val Leu Val Gly Leu Pro Ala His Ala Val Cys Glu Ser Ser
     295                 300                 305 gtt ttc gac cat gtt gtc aag tcg att caa att aga ggc tct tat gtt      1975
Val Phe Asp His Val Val Lys Ser Ile Gln Ile Arg Gly Ser Tyr Val
310                 315                 320                 325 ggt aac agg gaa gat act agt gag gct att gat ttt ttc acc agg ggt      2023
Gly Asn Arg Glu Asp Thr Ser Glu Ala Ile Asp Phe Phe Thr Arg Gly
                 330                 335                 340 tta gtg aag tca cca att aag att gtt ggt ttg agt gag ttg cca aag      2071
Leu Val Lys Ser Pro Ile Lys Ile Val Gly Leu Ser Glu Leu Pro Lys
             345                 350                 355 atc tat gaa ttg atg gag caa ggt aag att tta ggc aga tat gtt gtt      2119
Ile Tyr Glu Leu Met Glu Gln Gly Lys Ile Leu Gly Arg Tyr Val Val
         360                 365                 370
```

```
gac act tcg aaa tga tgggctgact tgggtgtact ggtgtgacgt ttttatgtgt    2174
Asp Thr Ser Lys
    375 atattgatat gcatggggga tgtatagtga tgaggagtag agtatataac gaaatgaaat    2234 gaaataatat gatatgataa gataagatga gatcaaatac gataatataa gatgcgacat    2294 gaggagttca atgtagcata ctacacgatg ctgcagtaca actctgatac gctagactat    2354 actatacaaa actgtagtac actatacgtt agtgtagtat ccagaaacaa cactgcttta    2414 tagtacaata caactctata atactatagt atactatgcc aaaccacgta ataccataat    2474 atgctccacg acatggtaca atgtgctata cttcatacta ttataccata tatactccga    2534 tatattattg atatactatt ttatactata ataccatacc acacaacact acattacaac    2594 gagcaacctt accataaatg tcagttatgt ggcccggaga ctctctcgag gagcgtgttc    2654 acctcgttgt agacgttctg cacatcctct ccgagcaggg cacgtgctcc catagtggga    2714 ggggcctctt ccaagggcga cccgcggcgc cccgcaccaa gaagcgcctg ttccttgagc    2774 gcatgtgcaa tattgagaag ggtgtctatg ctgcgaagaa cggtgtctgt gtcggcagca    2834 gcagcagcgg cgtctgctcc ctgggcggaa cgtgtcttcc ccgctaaggg gagcacagca    2894 agaatatcat gtaatgcagc aagagcattc tgagttgaag tatcgatttt cgatgccata    2954 ttgtatgtgt attgtattaa gtgtgtattg tcttaagtgt gtaagagaca tttatttgtg    3014 tcaacaatag cgacgccact gaaaacctca aatatcgtat ttattaatcc ccttcccccc    3074 agcgcagatc gtcccgtcga tttctattgt ttgggcatta tcagcgacgc gacggcgacg    3134

<210> SEQ ID NO 85
<211> LENGTH: 377
<212> TYPE: PRT
<213> ORGANISM: Issatchenkia orientalis

<400> SEQUENCE: 85

Met Leu Ser Lys Thr Ile Thr Ala Ala Leu Arg Gly Asn Thr Thr Arg
1               5                   10                  15

Thr Ala Phe Arg Ile Asn Ala Ile Arg Ser Leu Ala Ile Pro Ala Ile
            20                  25                  30

Pro Glu Thr Gln Lys Gly Val Ile Phe Tyr Glu Asn Gly Gly Glu Leu
        35                  40                  45

Phe Tyr Lys Asp Ile Pro Val Pro Lys Pro Lys Pro Asn Glu Ile Leu
    50                  55                  60

Val Asn Val Lys Tyr Ser Gly Val Cys His Thr Asp Leu His Ala Trp
65                  70                  75                  80

Lys Gly Asp Trp Pro Leu Ala Thr Lys Leu Pro Leu Val Gly Gly His
                85                  90                  95

Glu Gly Ala Gly Val Val Ala Lys Gly Asp Asn Val Thr Asn Phe
            100                 105                 110

Glu Ile Gly Asp Tyr Ala Gly Ile Lys Trp Leu Asn Gly Ser Cys Met
        115                 120                 125

Gly Cys Glu Phe Cys Gln Gln Gly Ala Glu Pro Asn Cys Pro Gln Ala
    130                 135                 140

Asp Leu Ser Gly Tyr Thr His Asp Gly Ser Phe Gln Gln Tyr Ala Thr
145                 150                 155                 160

Ala Asp Ala Val Gln Ala Ala Lys Ile Pro Gln Gly Thr Asp Leu Ala
                165                 170                 175

Gln Val Ala Pro Ile Leu Cys Ala Gly Ile Thr Val Tyr Lys Ala Leu
            180                 185                 190
```

```
Lys Thr Ala Glu Leu Arg Pro Gly Gln Trp Val Ala Ile Ser Gly Ala
            195                 200                 205
Ala Gly Leu Gly Ser Leu Ala Val Gln Tyr Ala Lys Ala Met Gly
    210                 215                 220
Leu Arg Val Leu Gly Ile Asp Gly Gly Glu Lys Gly Lys Phe Ala
225                 230                 235                 240
Lys Ser Leu Gly Ala Glu Val Phe Ile Asp Phe Thr Lys Ser Lys Asp
                245                 250                 255
Ile Val Lys Asp Ile Gln Glu Ala Thr Asn Gly Gly Pro His Gly Val
            260                 265                 270
Ile Asn Val Ser Val Ser Pro Ala Ala Ile Ser Gln Ser Thr Gln Tyr
        275                 280                 285
Val Arg Thr Leu Gly Lys Val Val Leu Val Gly Leu Pro Ala His Ala
    290                 295                 300
Val Cys Glu Ser Ser Val Phe Asp His Val Val Lys Ser Ile Gln Ile
305                 310                 315                 320
Arg Gly Ser Tyr Val Gly Asn Arg Glu Asp Thr Ser Glu Ala Ile Asp
                325                 330                 335
Phe Phe Thr Arg Gly Leu Val Lys Ser Pro Ile Lys Ile Val Gly Leu
            340                 345                 350
Ser Glu Leu Pro Lys Ile Tyr Glu Leu Met Glu Gln Gly Lys Ile Leu
        355                 360                 365
Gly Arg Tyr Val Val Asp Thr Ser Lys
    370                 375
```

<210> SEQ ID NO 86
<211> LENGTH: 1596
<212> TYPE: DNA
<213> ORGANISM: Bacteroides thetaiotaomicron
<220> FEATURE:
<221> NAME/KEY: CDS
<222> LOCATION: (1)..(1596)

<400> SEQUENCE: 86

```
atg aaa tta gat gca aaa tca acc atc gag aca ggt aaa gct atc ctt    48
Met Lys Leu Asp Ala Lys Ser Thr Ile Glu Thr Gly Lys Ala Ile Leu
1               5                   10                  15 ggc ata gaa ctc ggt tct aca cga ata aaa gct gtt ctg att gac cag    96
Gly Ile Glu Leu Gly Ser Thr Arg Ile Lys Ala Val Leu Ile Asp Gln
            20                  25                  30 gaa aac aaa cct atc gct caa ggc agc cac aca tgg gaa aat caa ctg    144
Glu Asn Lys Pro Ile Ala Gln Gly Ser His Thr Trp Glu Asn Gln Leu
        35                  40                  45 gtc aac gga ctt tgg act tac agc att gat gcc atc tgg tcc gga ctg    192
Val Asn Gly Leu Trp Thr Tyr Ser Ile Asp Ala Ile Trp Ser Gly Leu
    50                  55                  60 caa gat tgc tac gcc gac ctc cgc tcc aac gtg aag aaa tta tac gac    240
Gln Asp Cys Tyr Ala Asp Leu Arg Ser Asn Val Lys Lys Leu Tyr Asp
65                  70                  75                  80 aca gag atc gaa aca ctg gca gcc atc ggt gtc agc gcc atg atg cat    288
Thr Glu Ile Glu Thr Leu Ala Ala Ile Gly Val Ser Ala Met Met His
                85                  90                  95 ggt tac atg cct ttc aat gaa aaa gaa gaa atc ctc gtg cct ttc cgc    336
Gly Tyr Met Pro Phe Asn Glu Lys Glu Glu Ile Leu Val Pro Phe Arg
            100                 105                 110 act tgg aga aat acc aat aca ggc cgt gct gcg gca gaa tta tcc gaa    384
Thr Trp Arg Asn Thr Asn Thr Gly Arg Ala Ala Ala Glu Leu Ser Glu
        115                 120                 125
```

```
tta ttt gtc tat aac atc cct ttg aga tgg agc att tct cat ttg tac      432
Leu Phe Val Tyr Asn Ile Pro Leu Arg Trp Ser Ile Ser His Leu Tyr
130                 135                 140 cag gct att ctg gac aac gaa gcg cac gtc aaa gac atc aag ttc ctg      480
Gln Ala Ile Leu Asp Asn Glu Ala His Val Lys Asp Ile Lys Phe Leu
145                 150                 155                 160 aca act ctt gca ggt tat gta cat tgg cag ata aca ggc gaa aag gtg      528
Thr Thr Leu Ala Gly Tyr Val His Trp Gln Ile Thr Gly Glu Lys Val
                165                 170                 175 ttg ggc att ggt gac gca tcg ggt atg ctc ccc ata gat ccg act acc      576
Leu Gly Ile Gly Asp Ala Ser Gly Met Leu Pro Ile Asp Pro Thr Thr
                180                 185                 190 aac aac tat tcc gcc gaa atg gtg gcc aaa ttc aac aat ctg att gct      624
Asn Asn Tyr Ser Ala Glu Met Val Ala Lys Phe Asn Asn Leu Ile Ala
            195                 200                 205 tcg aaa gaa tac agt tgg aaa ctg gaa gac att ctg ccc aaa gta ttg      672
Ser Lys Glu Tyr Ser Trp Lys Leu Glu Asp Ile Leu Pro Lys Val Leu
        210                 215                 220 tcg gct ggt gaa aat gcc ggt gtc ctc aca ccg gaa ggc tgt aaa aaa      720
Ser Ala Gly Glu Asn Ala Gly Val Leu Thr Pro Glu Gly Cys Lys Lys
225                 230                 235                 240 ctc gat gca tcc ggt cat ctg aag gca gga ata ccg gtc tgc cca ccg      768
Leu Asp Ala Ser Gly His Leu Lys Ala Gly Ile Pro Val Cys Pro Pro
                245                 250                 255 gaa gga gac gca ggc acc ggc atg gta gca acc aac gcc gtc aag caa      816
Glu Gly Asp Ala Gly Thr Gly Met Val Ala Thr Asn Ala Val Lys Gln
                260                 265                 270 cgc acc ggc aac gta tcg gca ggt act tct tct ttc tct atg atc gta      864
Arg Thr Gly Asn Val Ser Ala Gly Thr Ser Ser Phe Ser Met Ile Val
            275                 280                 285 ttg gaa aaa gaa ttg tcg aag cca tac gaa atg atc gac atg gtc acc      912
Leu Glu Lys Glu Leu Ser Lys Pro Tyr Glu Met Ile Asp Met Val Thr
        290                 295                 300 act ccc gac gga agc ctc gta gcc atg gta cat tgc aac aac tgt act      960
Thr Pro Asp Gly Ser Leu Val Ala Met Val His Cys Asn Asn Cys Thr
305                 310                 315                 320 tcg gat ctt aac gca tgg gtc aac ctg ttc aaa gaa tac cag gaa ctt     1008
Ser Asp Leu Asn Ala Trp Val Asn Leu Phe Lys Glu Tyr Gln Glu Leu
                325                 330                 335 ctg ggt ata cct gta gat atg gat gaa ctc tat ggc aaa ctt tat aac     1056
Leu Gly Ile Pro Val Asp Met Asp Glu Leu Tyr Gly Lys Leu Tyr Asn
                340                 345                 350 att gcc ctt acc ggt gat acc gat tgc ggt ggt ctc ctc tcc tac aac     1104
Ile Ala Leu Thr Gly Asp Thr Asp Cys Gly Gly Leu Leu Ser Tyr Asn
            355                 360                 365 tac att tca ggc gaa cct gtt acg gga ctt gcc gag gga aga cct ttg     1152
Tyr Ile Ser Gly Glu Pro Val Thr Gly Leu Ala Glu Gly Arg Pro Leu
        370                 375                 380 ttc gta cgt tcg gcc aat gac aag ttc aac ctt gca aac ttt atg cgg     1200
Phe Val Arg Ser Ala Asn Asp Lys Phe Asn Leu Ala Asn Phe Met Arg
385                 390                 395                 400 gct cat ttg tac gcc tca gtc gga gtt ctc aag att ggc aac gac atc     1248
Ala His Leu Tyr Ala Ser Val Gly Val Leu Lys Ile Gly Asn Asp Ile
                405                 410                 415 ttg ttc aac gaa gaa aag atc aaa gtc gac aga atc aca ggt cac gga     1296
Leu Phe Asn Glu Glu Lys Ile Lys Val Asp Arg Ile Thr Gly His Gly
                420                 425                 430 gga ttg ttc aga acc aaa gga gtc ggt caa aga gta ctt gca gca gcc     1344
Gly Leu Phe Arg Thr Lys Gly Val Gly Gln Arg Val Leu Ala Ala Ala
```

-continued

```
               435                 440                 445
atc aac tcg ccc ata tct gtt atg gaa aca gcc ggt gaa ggc ggt gca      1392
Ile Asn Ser Pro Ile Ser Val Met Glu Thr Ala Gly Glu Gly Gly Ala
    450                 455                 460 tgg gga att gcc ctg ctg ggt tct tac ctg gta aac aat aaa aag ggt      1440
Trp Gly Ile Ala Leu Leu Gly Ser Tyr Leu Val Asn Asn Lys Lys Gly
465                 470                 475                 480 caa tct ctt gcc gat ttc ctg gat gaa agt gta ttt gtc agc gat gct      1488
Gln Ser Leu Ala Asp Phe Leu Asp Glu Ser Val Phe Val Ser Asp Ala
                485                 490                 495 ggt gtc gag gta tca ccc aca ccc gaa gat gta gcc ggc ttc aac aca      1536
Gly Val Glu Val Ser Pro Thr Pro Glu Asp Val Ala Gly Phe Asn Thr
            500                 505                 510 tac atc gaa agc tac aag gca ggt ttg cct ata gaa gaa gca gcc gtc      1584
Tyr Ile Glu Ser Tyr Lys Ala Gly Leu Pro Ile Glu Glu Ala Ala Val
        515                 520                 525 aaa ttc aaa taa                                                      1596
Lys Phe Lys
    530

<210> SEQ ID NO 87
<211> LENGTH: 3347
<212> TYPE: DNA
<213> ORGANISM: Issatchenkia orientalis
<220> FEATURE:
<221> NAME/KEY: CDS
<222> LOCATION: (1001)..(2347)

<400> SEQUENCE: 87
gttttgattc atcaaggtct gagaaatctt ctgcatcgac tgttaacaga aaaaatacga      60
tatcggggtc tcctaatatc gaaggttccc cacaaacgtc aatgcacagt ggcagtctga     120
ttgttggagg atcacaagtt cagcagcccc atattgatcc gaagaagtta cgtaagatta     180
gcgaaactgt tccttatatg ttaagacacg agactatccg tagcaaacaa gctaaattgg     240
aagagttgga acgtcaaagt gccttagaat taagcagaag agcagcggaa cttgaacgca     300
aggccaagga attgaagatg cgtgaaacaa tgttgcgtga acgtttagct aaggccaacg     360
gcagcggcag tctctccttg tcaaacacag ccgacagtaa aggggcgtct tctatacgtt     420
ccaatgtctc agaaaaccga agagagagag cttcatacag cgtccaaact accactagtg     480
aatacgaaga taccgttgaa gacaacgacg gatctgctgc ttagcttggg atctatgtac     540
tgactttgta tgtacctata aatctacact ctatacctca acttgaacta catgggctgt     600
tttctaggaa acaatcagct atacgcgtgg ctgtcctctt acttaacttc atgtttccct     660
ggtacttgtc ttgttctact gtcccacgga tacaggatgc agacaacaac actcttcttc     720
gggtggtaaa caaccttggt agaacagtgt aagaccagca cagtgcaatc ttagtatcat     780
tgcatccgtg tggggaaacg gcaaattcta cattgaagcg ttcctgtttt ttttttgtg      840 gcacaaacaa aggagaaggt gcttttcgt tggttcataa gaacggttat ttctgtggtg     900
aattgccacc tggctttctc ctttagaagc tagctttgtg tgtttccagt atcttgattt     960
tctgtgtaga dacaaacaat agccaagagc cactccaaaa atg tct cct tca caa     1015
                                              Met Ser Pro Ser Gln
                                                1               5 att aac gtt gac aac tta tct aat tgg act gaa gaa ttc aaa tct gac     1063
Ile Asn Val Asp Asn Leu Ser Asn Trp Thr Glu Glu Phe Lys Ser Asp
         10                  15                  20 gcc aag act caa atc ggg ggt tct gta ttg caa cat tcc aac att gat     1111
Ala Lys Thr Gln Ile Gly Gly Ser Val Leu Gln His Ser Asn Ile Asp
```

```
                   25                  30                  35
gag gtc ttg att aac aga gat gca gaa atc gcc aac aag cat atc ttc      1159
Glu Val Leu Ile Asn Arg Asp Ala Glu Ile Ala Asn Lys His Ile Phe
         40                  45                  50 aac cac aag att gaa att gaa ggt cta cct gtc atg gat cag aag gct      1207
Asn His Lys Ile Glu Ile Glu Gly Leu Pro Val Met Asp Gln Lys Ala
 55                  60                  65 tct ggt aga tgt tgg ttg ttt gca tcg act aac ttg atg cgt gtt act      1255
Ser Gly Arg Cys Trp Leu Phe Ala Ser Thr Asn Leu Met Arg Val Thr
 70                  75                  80                  85 gca atg aag aaa tac aat ttg aag gaa atc aag ctt tcc cca tcg tat      1303
Ala Met Lys Lys Tyr Asn Leu Lys Glu Ile Lys Leu Ser Pro Ser Tyr
                 90                  95                 100 ttg ttt ttc tat gac aaa ttg gaa aga gca aac tat ttc ctt gaa caa      1351
Leu Phe Phe Tyr Asp Lys Leu Glu Arg Ala Asn Tyr Phe Leu Glu Gln
            105                 110                 115 atc atc gac act cat aag gaa cca atc gat tca aga ttg gtt caa tat      1399
Ile Ile Asp Thr His Lys Glu Pro Ile Asp Ser Arg Leu Val Gln Tyr
        120                 125                 130 ttc ctg acc aat cca gtt gaa gat ggt ggt caa ttc acc atg atg gca      1447
Phe Leu Thr Asn Pro Val Glu Asp Gly Gly Gln Phe Thr Met Met Ala
135                 140                 145 caa att gct acc aaa tac ggt gtt gtt cct gat caa gtc tac cca gat      1495
Gln Ile Ala Thr Lys Tyr Gly Val Val Pro Asp Gln Val Tyr Pro Asp
150                 155                 160                 165 tct ttc aac aca acc act tcg agg att atg aac aga tta gtc aac cac      1543
Ser Phe Asn Thr Thr Thr Ser Arg Ile Met Asn Arg Leu Val Asn His
                170                 175                 180 aga tta cgt tct tat gca atg act tta cgt aac gct cta gat gaa ggt      1591
Arg Leu Arg Ser Tyr Ala Met Thr Leu Arg Asn Ala Leu Asp Glu Gly
            185                 190                 195 aaa gat gta atg tcc ttg aag aat gag atg caa aaa gaa att tat cgt      1639
Lys Asp Val Met Ser Leu Lys Asn Glu Met Gln Lys Glu Ile Tyr Arg
        200                 205                 210 ttg cta aca atg ttc ctt ggt aac cca cca aag cca aac gaa gag ttt      1687
Leu Leu Thr Met Phe Leu Gly Asn Pro Pro Lys Pro Asn Glu Glu Phe
215                 220                 225 gtc tgg gaa ttc acc gat aaa gat ggt aaa tat gaa tct att aaa act      1735
Val Trp Glu Phe Thr Asp Lys Asp Gly Lys Tyr Glu Ser Ile Lys Thr
230                 235                 240                 245 aca cca tta aaa tat gca act gaa gtt ttg gat ttc cat gct cca gaa      1783
Thr Pro Leu Lys Tyr Ala Thr Glu Val Leu Asp Phe His Ala Pro Glu
                250                 255                 260 tat gtt tcc ttg tta aat gac cca aga aat aag tat aac aag atg gtt      1831
Tyr Val Ser Leu Leu Asn Asp Pro Arg Asn Lys Tyr Asn Lys Met Val
            265                 270                 275 caa gtt gaa aga tta ggt aat gtt gct ggt ggc gaa cca gtt gca tac      1879
Gln Val Glu Arg Leu Gly Asn Val Ala Gly Gly Glu Pro Val Ala Tyr
        280                 285                 290 tta aac tta gaa att gaa aag tta tct caa gct gtt gtt aac aga atc      1927
Leu Asn Leu Glu Ile Glu Lys Leu Ser Gln Ala Val Val Asn Arg Ile
295                 300                 305 aaa aat aac aaa cca gtt ttc ttt ggt acc gat aca cct aaa ttt atg      1975
Lys Asn Asn Lys Pro Val Phe Phe Gly Thr Asp Thr Pro Lys Phe Met
310                 315                 320                 325 gat aaa agt aga ggt att atg gat atc aat tta tgg gac tat gag tta      2023
Asp Lys Ser Arg Gly Ile Met Asp Ile Asn Leu Trp Asp Tyr Glu Leu
                330                 335                 340 tta ggt tat gat gtc cgt acc atg tca aag aag gaa aga gtt gtt ttt      2071
```

| | | | | | | | | | | | | |
|---|---|---|---|---|---|---|---|---|---|---|---|---|
| Leu | Gly | Tyr | Asp | Val | Arg | Thr | Met | Ser | Lys | Lys | Glu | Arg | Val | Val | Phe |
| | | | 345 | | | | | 350 | | | | | 355 | | |

```
ggt gat tct tta atg acc cac gct atg ttg att act gca gtg cac gtt    2119
Gly Asp Ser Leu Met Thr His Ala Met Leu Ile Thr Ala Val His Val
        360                 365                 370 gat gaa aat ggc aaa cct gtc aga tac aga gtc gaa aac agt tgg ggt    2167
Asp Glu Asn Gly Lys Pro Val Arg Tyr Arg Val Glu Asn Ser Trp Gly
    375                 380                 385 acc aag agt ggt caa gaa ggt tat tac aca atg acc caa gaa tat ttt    2215
Thr Lys Ser Gly Gln Glu Gly Tyr Tyr Thr Met Thr Gln Glu Tyr Phe
390                 395                 400                 405 gaa gag tac gtt tat caa gta gtc att gaa aag agt gaa ttt gct gcc    2263
Glu Glu Tyr Val Tyr Gln Val Val Ile Glu Lys Ser Glu Phe Ala Ala
            410                 415                 420 cta aac ctc gat gtt tcc att ctg gag gat aaa gaa cca gtc gtc ttg    2311
Leu Asn Leu Asp Val Ser Ile Leu Glu Asp Lys Glu Pro Val Val Leu
                425                 430                 435 cca cct tat gac cct atg ggt gca ctt gct tta taa attgattttg         2357
Pro Pro Tyr Asp Pro Met Gly Ala Leu Ala Leu
            440                 445 tagggggaa   aaaaaggaaa   aagagacatc   acaagtcaat   gtgatttagc   aagttatttt    2417
tagcttacat  tgaaggttat   cttcttaaag   ctctcccaac   gtatgtccaa   caagtttggg    2477
tatcaaaact  atgtaatcct   tttagataaa   aaacaatagt   actaaatacg   cttttattag    2537
accctggcaa  gctgtaaact   tagcaaaaag   agttagctcc   taacaactgt   accagcacta    2597
ttactgttgt  tgaaaattgc   gatctctctt   ccaaatttgg   cgagcaatga   agtttcacca    2657
aatcgtggag  ttttaaaaaa   acattgtga    tacggttctg   gttttctaca   acttttcttt    2717
tccctctctt  gactgctttg   ctggcactgg   ttgacaatct   cattctgaga   atcggacctg    2777
ttactccttt  ctctctgtct   aaataaaaaa   aagataaggc   agaaaattag   aaaactagga    2837
agcatgaatt  ttacctgggt   attcaaaatt   ttgctgtgtt   tgatattttc   aaatcgtatc    2897
aatgccatag  gcaataagga   ctttgctaac   aaagactacc   taatggtaga   agtaaagggg    2957
gattatgatt  tacataacat   acaagaatta   catccagatt   gggaatatga   atatgaaatt    3017
gactttctag  ataattttca   tgtgtttagt   atgaagaaag   accatcagtt   aatagaaaag    3077
ttttcaaagt  acacatctat   caaagagctc   ttgcaaggtg   acaaaaaatt   aattaaacgt    3137
gaagattatg  attttttgag   tagtttgaat   gataacaatg   ttacaggtgt   tcatttacta    3197
tcgaggaaac  aactagtaaa   acgtttccct   gttcccgtat   catatgggaa   agacgtacct    3257
gttctacatt  ctcgagagaa   cacaaacgtt   gattcaagct   tagatgaaat   agctcaagtt    3317
gcagaagaat  ttggtattaa   tgatccaatc                                          3347

<210> SEQ ID NO 88
<211> LENGTH: 448
<212> TYPE: PRT
<213> ORGANISM: Issatchenkia orientalis

<400> SEQUENCE: 88
```

| Met | Ser | Pro | Ser | Gln | Ile | Asn | Val | Asp | Asn | Leu | Ser | Asn | Trp | Thr | Glu |
|---|---|---|---|---|---|---|---|---|---|---|---|---|---|---|---|
| 1 | | | | 5 | | | | | 10 | | | | | 15 | |

| Glu | Phe | Lys | Ser | Asp | Ala | Lys | Thr | Gln | Ile | Gly | Gly | Ser | Val | Leu | Gln |
|---|---|---|---|---|---|---|---|---|---|---|---|---|---|---|---|
| | | | 20 | | | | | 25 | | | | | 30 | | |

| His | Ser | Asn | Ile | Asp | Glu | Val | Leu | Ile | Asn | Arg | Asp | Ala | Glu | Ile | Ala |
|---|---|---|---|---|---|---|---|---|---|---|---|---|---|---|---|
| | | 35 | | | | | 40 | | | | | 45 | | | |

| Asn | Lys | His | Ile | Phe | Asn | His | Lys | Ile | Glu | Ile | Glu | Gly | Leu | Pro | Val |
|---|---|---|---|---|---|---|---|---|---|---|---|---|---|---|---|

-continued

```
              50                  55                  60
Met Asp Gln Lys Ala Ser Gly Arg Cys Trp Leu Phe Ala Ser Thr Asn
 65                  70                  75                  80

Leu Met Arg Val Thr Ala Met Lys Lys Tyr Asn Leu Lys Glu Ile Lys
                 85                  90                  95

Leu Ser Pro Ser Tyr Leu Phe Phe Tyr Asp Lys Leu Glu Arg Ala Asn
                100                 105                 110

Tyr Phe Leu Glu Gln Ile Ile Asp Thr His Lys Glu Pro Ile Asp Ser
                115                 120                 125

Arg Leu Val Gln Tyr Phe Leu Thr Asn Pro Val Glu Asp Gly Gly Gln
130                 135                 140

Phe Thr Met Met Ala Gln Ile Ala Thr Lys Tyr Gly Val Val Pro Asp
145                 150                 155                 160

Gln Val Tyr Pro Asp Ser Phe Asn Thr Thr Ser Arg Ile Met Asn
                165                 170                 175

Arg Leu Val Asn His Arg Leu Arg Ser Tyr Ala Met Thr Leu Arg Asn
                180                 185                 190

Ala Leu Asp Glu Gly Lys Asp Val Met Ser Leu Lys Asn Glu Met Gln
                195                 200                 205

Lys Glu Ile Tyr Arg Leu Leu Thr Met Phe Leu Gly Asn Pro Pro Lys
210                 215                 220

Pro Asn Glu Glu Phe Val Trp Glu Phe Thr Asp Lys Asp Gly Lys Tyr
225                 230                 235                 240

Glu Ser Ile Lys Thr Thr Pro Leu Lys Tyr Ala Thr Glu Val Leu Asp
                245                 250                 255

Phe His Ala Pro Glu Tyr Val Ser Leu Leu Asn Asp Pro Arg Asn Lys
                260                 265                 270

Tyr Asn Lys Met Val Gln Val Glu Arg Leu Gly Asn Val Ala Gly Gly
                275                 280                 285

Glu Pro Val Ala Tyr Leu Asn Leu Glu Ile Glu Lys Leu Ser Gln Ala
290                 295                 300

Val Val Asn Arg Ile Lys Asn Asn Lys Pro Val Phe Phe Gly Thr Asp
305                 310                 315                 320

Thr Pro Lys Phe Met Asp Lys Ser Arg Gly Ile Met Asp Ile Asn Leu
                325                 330                 335

Trp Asp Tyr Glu Leu Leu Gly Tyr Asp Val Arg Thr Met Ser Lys Lys
                340                 345                 350

Glu Arg Val Val Phe Gly Asp Ser Leu Met Thr His Ala Met Leu Ile
                355                 360                 365

Thr Ala Val His Val Asp Glu Asn Gly Lys Pro Val Arg Tyr Arg Val
370                 375                 380

Glu Asn Ser Trp Gly Thr Lys Ser Gly Gln Gly Tyr Tyr Thr Met
385                 390                 395                 400

Thr Gln Glu Tyr Phe Glu Glu Tyr Val Tyr Gln Val Val Ile Glu Lys
                405                 410                 415

Ser Glu Phe Ala Ala Leu Asn Leu Asp Val Ser Ile Leu Glu Asp Lys
                420                 425                 430

Glu Pro Val Val Leu Pro Pro Tyr Asp Pro Met Gly Ala Leu Ala Leu
                435                 440                 445
```